US012600760B2

(12) United States Patent
Maus

(10) Patent No.: US 12,600,760 B2
(45) Date of Patent: Apr. 14, 2026

(54) CHIMERIC ANTIGEN RECEPTORS TARGETING CD79B AND CD19

(71) Applicant: The General Hospital Corporation, Boston, MA (US)

(72) Inventor: Marcela V. Maus, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 1117 days.

(21) Appl. No.: 17/312,744

(22) PCT Filed: Dec. 13, 2019

(86) PCT No.: PCT/US2019/066357
§ 371 (c)(1),
(2) Date: Jun. 10, 2021

(87) PCT Pub. No.: WO2020/124021
PCT Pub. Date: Jun. 18, 2020

(65) Prior Publication Data
US 2022/0047636 A1      Feb. 17, 2022

Related U.S. Application Data

(60) Provisional application No. 62/888,795, filed on Aug. 19, 2019, provisional application No. 62/779,346, filed on Dec. 13, 2018.

(51) Int. Cl.
| | |
|---|---|
| *A61K 35/17* | (2025.01) |
| *A61K 35/00* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/705* | (2006.01) |
| *C07K 14/725* | (2006.01) |
| *C07K 16/28* | (2006.01) |
| *C12N 5/0783* | (2010.01) |

(52) U.S. Cl.
CPC .......... *C07K 14/7051* (2013.01); *A61K 40/11* (2025.01); *A61K 40/31* (2025.01); *A61K 40/421* (2025.01); *A61K 40/4211* (2025.01); *A61P 35/00* (2018.01); *C07K 14/70517* (2013.01); *C07K 14/70521* (2013.01); *C07K 14/70578* (2013.01); *C07K 16/2803* (2013.01); *C12N 5/0636* (2013.01); *A61K 2239/13* (2023.05); *A61K 2239/28* (2023.05); *A61K 2239/29* (2023.05); *A61K 2239/31* (2023.05); *A61K 2239/38* (2023.05); *A61K 2239/48* (2023.05)

(58) Field of Classification Search
CPC .......... C07K 14/7051; C07K 14/70578; A61K 40/11; A61K 40/31; A61K 40/421; A61K 40/4211; A61K 2239/28; C12N 5/0636
See application file for complete search history.

(56) References Cited

U.S. PATENT DOCUMENTS

| | | | |
|---|---|---|---|
| 8,088,378 B2 | 1/2012 | Chen et al. | |
| 8,691,531 B2 | 4/2014 | Chen et al. | |
| 2009/0028856 A1* | 1/2009 | Chen ...................... A61P 35/00 | |
| | | | 435/69.6 |
| 2014/0271635 A1* | 9/2014 | Brogdon ............ C07K 16/2803 | |
| | | | 536/23.53 |
| 2016/0362472 A1* | 12/2016 | Bitter ..................... A61K 40/36 | |
| 2017/0051308 A1 | 2/2017 | Morgan et al. | |
| 2018/0162939 A1 | 6/2018 | Ma et al. | |
| 2020/0207852 A1 | 7/2020 | Maus et al. | |
| 2020/0247887 A1 | 8/2020 | Chen et al. | |

FOREIGN PATENT DOCUMENTS

| | | |
|---|---|---|
| JP | 2015-092865 A | 5/2015 |
| JP | 2015-528298 A | 9/2015 |
| WO | WO 2009/012268 A1 | 1/2009 |
| WO | WO 2014/011521 A1 | 1/2014 |
| WO | WO 2015/142675 A2 | 9/2015 |
| WO | WO 2016/126608 A1 | 8/2016 |
| WO | WO 2016/164731 A2 | 10/2016 |
| WO | WO 2016/187216 A1 | 11/2016 |
| WO | WO 2016/210293 A1 | 12/2016 |
| WO | WO 2017/015427 A1 | 1/2017 |
| WO | WO 2018/226958 A1 | 12/2018 |
| WO | WO 2020/124021 A1 | 6/2020 |

OTHER PUBLICATIONS

Chu et al., Targeting CAR T Resistance Due to CD19 Loss with CD79b-Specific CAR T Cells in B-Cell Malignancies. Blood. Nov. 2018; 132(Supplement 1):1662.
Ding et al., Targeting CD79b for Chimeric Antigen Receptor T-Cell Therapy of B-Cell Lymphomas. Target Oncol. Jun. 2020;15(3):365-375.
Dorman et al., Therapeutic potential of an anti-CD79b antibody-drug conjugate, anti-CD79b-vc-MMAE, for the treatment of non-Hodgkin lymphoma. Blood. Sep. 24, 2009;114(13):2721-9. doi: 10.1182/blood-2009-02-205500. Epub Jul. 24, 2009.

(Continued)

*Primary Examiner* — Jeremy C Flinders
*Assistant Examiner* — Masudur Rahman
(74) *Attorney, Agent, or Firm* — Wolf, Greenfield & Sacks, P.C.

(57) ABSTRACT

Described herein are upfront methods for treating a patient suffering from a cancer. The method includes administering to the patient a therapeutically effective amount of an anti-cancer therapy including a chimeric antigen receptor (CAR) including an extracellular domain including a CD79b-binding domain and a CD19-binding domain, wherein the patient has not been previously treated for the cancer. The invention accordingly also relates to methods of producing and utilizing, e.g., T cells including CARs having an extracellular domain that binds CD79b and CD19.

11 Claims, 60 Drawing Sheets
Specification includes a Sequence Listing.

(56) References Cited

OTHER PUBLICATIONS

Fesnak et al., Engineered T cells: the promise and challenges of cancer immunotherapy. Nat Rev Cancer. Aug. 23, 2016;16(9):566-81. doi: 10.1038/nrc.2016.97.

Haso et al., Anti-CD22-chimeric antigen receptors targeting B-cell precursor acute lymphoblastic leukemia. Blood. Feb. 14, 2013;121(7):1165-74. doi: 10.1182/blood-2012-06-438002. Epub Dec. 14, 2012.

Mardiros et al., T cells expressing CD123-specific chimeric antigen receptors exhibit specific cytolytic effector functions and antitumor effects against human acute myeloid leukemia. Blood. Oct. 31, 2013;122(18):3138-48. doi: 10.1182/blood-2012-12-474056. Epub Sep. 12, 2013.

Mehta et al., Development and Integration of Antibody-Drug Conjugate in Non-Hodgkin Lymphoma. Curr Oncol Rep. Sep. 2015;17(9):41.

Nakagawa et al., Development of next-generation adoptive immunotherapy using cytotoxic T-lymphocyte(CTL) expressing chimeric antigen-receptor(CAR). Drug Delivery System. Jan. 30, 2013;28(1):35-44.

OrmhØj et al., Chimeric Antigen Receptor T Cells Targeting CD79b Show Efficacy in Lymphoma with or without Cotargeting CD19. Clin Cancer Res. Dec. 1, 2019;25(23):7046-7057. doi: 10.1158/1078-0432.CCR-19-1337. Epub Aug. 22, 2019. Erratum in: Clin Cancer Res. May 15, 2024;30(10):2286.

Pfeifer et al., Anti-CD22 and anti-CD79B antibody drug conjugates are active in different molecular diffuse large B-cell lymphoma subtypes. Leukemia. Jul. 2015;29(7):1578-86. doi: 10.1038/leu.2015.48. Epub Feb. 24, 2015.

Zah et al., T Cells Expressing CD19/CD20 Bispecific Chimeric Antigen Receptors Prevent Antigen Escape by Malignant B Cells. Cancer Immunol Res. Jun. 2016;4(6):498-508. doi: 10.1158/2326-6066.CIR-15-0231. Epub Apr. 8, 2016. Author manuscript, 22 pages.

* cited by examiner

CHIMERIC ANTIGEN RECEPTORS TARGETING CD79B AND CD19

RELATED APPLICATIONS

The present invention is a national stage filing under 35 U.S.C. § 371 of international PCT application PCT/US2019/066357, filed Dec. 13, 2019, which claims priority under 35 U.S.C. § 119 (e) to U.S. provisional patent application No. 62/888,795, filed Aug. 19, 2019 and U.S. provisional patent application No. 62/779,346, filed Dec. 13, 2018, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created on Jun. 8, 2021, is named M105370016US02-SEQ-RE, and is 85,916 bytes in size.

BACKGROUND OF THE INVENTION

This invention relates to chimeric antigen receptors and methods of using the same, including upfront or first line cancer treatments.

Non-Hodgkin lymphoma (NHL) is a large group of B cell malignancies accounting for about 4% of all tumors (CA Cancer J Clin 2017; 67(1):7-30). Standard treatment for most subtypes of NHL involves a combination of therapies including rituximab and chemotherapy. Despite improvements in available therapies, NHLs carry a uniformly poor prognosis in the relapsed/refractory (r/r) setting.

Adoptive immunotherapy utilizing T cells genetically modified to express a chimeric antigen receptor (CAR) has shown great efficacy as treatment of CD19-positive B cell malignancies. Approximately, 80% of NHL subtypes are derived from the B cell linage and retain expression of B cell markers, including CD19 and CD20 after malignant transformation. These surface antigens represent key targets for antibody-based therapeutics and CAR T cell therapy. In lymphoma, CAR19 therapy has a reported overall response rate in the 60-80% range, with approximately 40% of patients achieving long-term complete remission (N Engl J Med 2017; 377(26):2545-54; N Engl J Med 2017; 377(8):783-4; J Clin Oncol 2015; 33(6):540-9; Sci Transl Med 2016; 8(355):355ra116). Recently, these response rates led to the approval of two CAR19 products, axicabtagene ciloleucel, which bears a CD28 co-stimulatory domain, and tisagenlecleucel, which bears a 4-1 BB co-stimulatory domain, for the treatment of r/r diffuse large B cell lymphoma (DLBCL). In addition, the tisagenlecleucel product has also been approved as treatment for children and young adults with r/r B cell acute lymphoblastic leukemia (ALL). However, clinical data reporting disease relapse due to CD19 antigen loss in both ALL and lymphoma patients are now emerging (N Engl J Med 2017; 377(26):2545-54; Cancer Discov 2015; 5(12):1282-95; Blood 2016; 127(20):2406-10; Haematologica 2018; 103(5):e215-e8), highlighting an unmet clinical need for targeting novel surface antigens.

CD79b is part of the B cell receptor (BCR) signaling complex, and a critical receptor for the successful development and maintenance of mature B cells (Appl Immunohistochem Mol Morphol 2001; 9(2):97-106). CD79b expression is restricted to the B cell linage, and high expression is maintained on most subtypes of NHL, including mantle cell lymphoma (MCL), DLBCL, Burkitt's lymphoma (BL), and follicular lymphoma (FL) (Appl Immunohistochem Mol Morphol 2001; 9(2):97-106; Haematologica 1999; 84(5):413-8; Leukemia 1996; 10(12):1966-70). Indeed, targeting CD79b with antibody-drug conjugates or bi-specific T-cell engagers (BiTEs) has been shown to be safe, well tolerated, and demonstrated early signs of efficacy (Leukemia 2015; 29(7):1578-86; Lancet Oncol 2015; 16(6):704-15).

Chimeric antigen receptors (CARs) provide a way to direct, e.g., a cytotoxic T cell response to target cells expressing a selected target antigen, most often a tumor antigen or a tumor-associated antigen. CARs are an adaptation of the T cell receptor, in which the antigen binding domain is replaced with the antigen binding domain of an antibody that specifically binds the target antigen. Engagement of the target antigen on the surface of a target cell by a CAR expressed on a T cell (a "CAR T cell") promotes killing of the target cell.

Mantle cell lymphoma (MCL) is an example of a cancer showing an aggressive clinical course with high resistance to currently available therapies in many patients. Despite recent advantages in treatment, MCL remains an incurable disease. Adoptive immunotherapy utilizing T cells genetically modified to express a chimeric antigen receptor (CAR) has shown tremendous potential as treatment for CD19$^+$ B cell malignancies. However, treatment failures due to antigen-escape have been descried in patients receiving CD19 CAR therapy.

New approaches to treating cancers such as B cell malignancies, including MCL, are needed.

SUMMARY OF THE INVENTION

Described herein are chimeric antigen receptor (CAR) polypeptides targeting CD79b and CD19, compositions thereof, and related methods of use, e.g., for the treatment of cancer.

In one aspect, the invention features a first line or upfront method for treating a patient suffering from a cancer. In general, the method includes administering to the patient a therapeutically effective amount of an anti-cancer therapy including a chimeric antigen receptor (CAR) including an extracellular domain including a CD79b-binding domain and a CD19-binding domain, wherein the patient has not been previously treated for the cancer. In some embodiments, the CD79b-binding domain includes an antibody, or an antigen binding fragment thereof. In some embodiments, the CD79b-binding domain includes a single chain variable fragment (scFv). In other embodiments, the CD19-binding domain includes an antibody, or an antigen binding fragment thereof. In other embodiments, the CD19-binding domain includes an scFv. In still further embodiments, the CD79b-binding domain is positioned N-terminal to the CD19-binding domain. And in yet other embodiments, the CD19-binding domain is positioned N-terminal to the CD79b-binding domain.

Accordingly, in other aspects, the invention features a CAR including an extracellular domain including a CD79b-binding domain and a CD19-binding domain. In some embodiments, the CD79b-binding domain of the CAR includes an antibody, or an antigen binding fragment thereof, e.g., a single chain variable fragment (scFv). In some embodiments, the CD19-binding domain of the CAR includes an antibody, or an antigen binding fragment thereof, e.g., an scFv. In some embodiments, the CD79b-binding domain is positioned N-terminal to the CD19- binding domain. In other embodiments, the CD19-binding domain is positioned N-terminal to the CD79b-binding domain. In further embodiments, the CD79b-binding domain and the CD19-binding domain are connected by a linker sequence. Such a linker sequence includes the amino acid sequence of SEQ ID NO: 7, 20, 21, 22, or 23, or an amino acid sequence having at least 90% sequence identity (e.g., 90%, 91%, 92%, 93%, 94%, 95%, 96%, 97%, 98%, or 99% sequence identity) to the amino acid sequence of SEQ ID NO: 7, 20, 21, 22, or 23.

In other embodiments, the CAR includes a transmembrane domain (e.g., a hinge/transmembrane domain) and an intracellular signaling domain. In certain embodiments, the CAR further includes one or more co-stimulatory domains.

In some embodiments, the hinge/transmembrane domain includes the hinge/transmembrane domain of an immunoglobulin-like protein (e.g., IgA, IgD, IgE, IgG, or IgM), CD28, CD8, or 4-1 BB. In particular embodiments, the hinge/transmembrane domain includes the hinge/transmembrane domain of CD8, optionally including the amino acid sequence of SEQ ID NO: 11, or an amino acid sequence having at least 90% sequence identity (e.g., 90%, 91%, 92%, 93%, 94%, 95%, 96%, 97%, 98%, or 99% sequence identity) to the amino acid sequence of SEQ ID NO: 11.

In some embodiments, the intracellular signaling domain includes the intracellular signaling domain of TCRζ, FcRγ, FcRβ, CD3γ, CD3θ, CD3δ, CD3ε, CD3η, CD3ζ, CD22, CD79a, CD79b, or CD66d. In particular embodiments, the intracellular signaling domain includes the intracellular signaling domain of CD3ζ, optionally including the amino acid sequence of SEQ ID NO: 13, or an amino acid sequence having at least 90% sequence identity (e.g., 90%, 91%, 92%, 93%, 94%, 95%, 96%, 97%, 98%, or 99% sequence identity) to the amino acid sequence of SEQ ID NO: 13.

In further embodiments, the co-stimulatory domain includes the co-stimulatory domain of 4-1 BB, CD27, CD28, or OX40. In particular embodiments, the co-stimulatory domain includes the co-stimulatory domain of 4-1BB, optionally including the amino acid sequence of SEQ ID NO: 12, or an amino acid sequence having at least 90% sequence identity (e.g., 90%, 91%, 92%, 93%, 94%, 95%, 96%, 97%, 98%, or 99% sequence identity) to the amino acid sequence of SEQ ID NO: 12.

In some embodiments, the CD79b-binding domain includes a heavy chain variable domain (VH) including the amino acid sequence of SEQ ID NO: 9, or an amino acid sequence having at least 90% sequence identity (e.g., 90%, 91%, 92%, 93%, 94%, 95%, 96%, 97%, 98%, or 99% sequence identity) to the amino acid sequence of SEQ ID NO: 9; and a light chain variable domain (VL) including the amino acid sequence of SEQ ID NO: 8, or an amino acid sequence having at least 90% sequence identity (e.g., 90%, 91%, 92%, 93%, 94%, 95%, 96%, 97%, 98%, or 99% sequence identity) to the amino acid sequence of SEQ ID NO: 8. In some embodiments, the CD79b-binding domain includes the amino acid sequence of SEQ ID NO: 10, or an amino acid sequence having at least 90% (e.g., 90%, 91%, 92%, 93%, 94%, 95%, 96%, 97%, 98%, or 99% sequence identity) sequence identity to the amino acid sequence of SEQ ID NO: 10.

In further embodiments, the CD19-binding domain includes a VH including the amino acid sequence of SEQ ID NO: 5, or an amino acid sequence having at least 90% sequence identity (e.g., 90%, 91%, 92%, 93%, 94%, 95%, 96%, 97%, 98%, or 99% sequence identity) to the amino acid sequence of SEQ ID NO: 5; and a VL including the amino acid sequence of SEQ ID NO: 4, or an amino acid sequence having at least 90% sequence identity (e.g., 90%, 91%, 92%, 93%, 94%, 95%, 96%, 97%, 98%, or 99% sequence identity) to the amino acid sequence of SEQ ID NO: 4. In some embodiments, the CD19-binding domain includes the amino acid sequence of SEQ ID NO: 6, or an amino acid sequence having at least 90% sequence identity (e.g., 90%, 91%, 92%, 93%, 94%, 95%, 96%, 97%, 98%, or 99% sequence identity) to the amino acid sequence of SEQ ID NO: 6.

In certain embodiments, the CAR includes the amino acid sequence of SEQ ID NO: 1, 2, 24, or 25, or an amino acid sequence having at least 90% sequence identity (e.g., 90%, 91%, 92%, 93%, 94%, 95%, 96%, 97%, 98%, or 99% sequence identity) to the amino acid sequence of SEQ ID NO: 1, 2, 24, or 25.

In another aspect, the invention features a polynucleotide encoding the CAR of the preceding aspect. In some embodiments, the polynucleotide further includes a suicide gene. In some embodiments, the polynucleotide further includes a sequence encoding a signal sequence.

In another aspect, the invention features a vector including the polynucleotide of the preceding aspect.

In another aspect, the invention features an immune cell including the CAR, the polynucleotide, and/or the vector of any one of the preceding aspects. In some embodiments, the immune cell is a T cell or a natural killer (NK) cell. In further embodiments, the immune cell is a human cell.

In another aspect, the invention features a pharmaceutical composition including the polynucleotide, the vector, and/or the immune cell of any one of the preceding aspects and a pharmaceutically acceptable carrier.

In another aspect, the invention features a method of treating a cancer in a subject in need thereof, the method including administering the polynucleotide, the vector, the immune cell, and/or the pharmaceutical composition of any one of the preceding aspects to the subject.

In some embodiments, the cancer is a lymphoma or a leukemia. In particular embodiments, the cancer is mantle cell lymphoma (MCL), diffuse large B-cell lymphoma (DLBCL), primary mediastinal B-cell lymphoma (PMBCL), chronic lymphocytic leukemia (CLL), small lymphocytic lymphoma (SLL), follicular lymphoma, or transformed follicular lymphoma. In some embodiments, the cancer includes cells expressing CD19. In some embodiments, the cancer includes cells expressing CD79b. In further embodiments, the subject is resistant to anti-CD19 therapy.

In another aspect, the invention features a method of treating a subject who has relapsed with CD19-negative lymphoma after receiving anti-CD19 CAR therapy, the method comprising administering the polynucleotide, the vector, the immune cell, and/or the pharmaceutical composition of any one of the preceding aspects to the subject.

Complete remission has been observed in about 40% of lymphoma patients treated with anti-CD19 CAR T cells, but disease relapse can occur due to antigen escape. We have designed a CAR against CD79b, an antigen widely expressed in B cell lymphomas. We showed that targeting CD79b as a single antigen or in combination with CD19 using CAR T cells is effective in vitro and in vivo in xenograft and patient derived xenograft (PDX) lymphoma models. We further demonstrate that CAR T cells targeting CAR79b in a monospecific or bispecific configuration with CD19-targeting are able to clear CD19+"upfront" lymphomas, heterogeneous tumors containing CD19+ and CD19− cells, and "relapsed" CD19-negative tumors. These results provide a rationale for clinical evaluation of CAR79b and CAR79b-19 T cells in patients.

Definitions

For convenience, the meaning of some terms and phrases used in the specification, examples, and appended claims, are provided below. Unless stated otherwise, or implicit from the context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan et al. (eds.), John Wiley and Sons, Inc., 2003 (ISBN 0471142735, 9780471142737), the contents of each of which are incorporated by reference herein in their entireties.

The terms "decrease," "reduced," "reduction," or "inhibit" are all used herein to mean a decrease by a statistically significant amount. In some embodiments, "reduce," "reduction," "decrease," or "inhibit" typically mean a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. Where applicable, a decrease can be down to a level accepted as within the range of normal for an individual without a given disorder.

The terms "increased," "increase," "enhance," or "activate" are all used herein to mean an increase by a statically significant amount. In some embodiments, the terms "increased," "increase," "enhance," or "activate" can mean an increase of at least 10% as compared to a reference level, for example, an increase of at least about 20%, or at least about 30%, or at least about 40%, or at least about 50%, or at least about 60%, or at least about 70%, or at least about 80%, or at least about 90%, or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal, or game animal. Primates include, for example, chimpanzees, cynomologous monkeys, spider monkeys, and macaques, e.g., Rhesus. Rodents include, for example, mice, rats, woodchucks, ferrets, rabbits, and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish, and salmon. In some embodiments, the subject is a mammal, e.g., a primate, e.g., a human. The terms, "individual," "patient," and "subject" are used interchangeably herein.

In various embodiments, the subject is a mammal. The mammal can be a human, non-human primate, mouse, rat, dog, cat, horse, or cow, but is not limited to these examples. Mammals other than humans can be advantageously used as subjects that represent animal models of disease, e.g., cancer. A subject can be male or female, which can be an adult, child, or infant.

A subject can be one who has been previously diagnosed with or identified as suffering from or having a condition in need of treatment (e.g., lymphoma, leukemia, or another type of cancer, among others) or one or more complications related to such a condition, and optionally, have already undergone treatment for the condition or the one or more complications related to the condition. Alternatively, a subject can also be one who has not been previously diagnosed as having such condition or related complications. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

A "disease" is a state of health of an animal, for example, a human, wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "tumor antigen" and "cancer antigen" are used interchangeably to refer to antigens that are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those that are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, and 3, defined by immunity; MART-1/Melan-A, gp100, carcinoembryonic antigen (CEA), HER2, mucins (i.e., MUC-1), prostate-specific antigen (PSA), and prostatic acid phosphatase (PAP). In addition, viral proteins such as some encoded by hepatitis B (HBV), Epstein-Barr (EBV), and human papilloma (HPV) have been shown to be important in the development of hepatocellular carcinoma, lymphoma, and cervical cancer, respectively.

As used herein, the term "chimeric" refers to the product of the fusion of portions of at least two or more different polynucleotide molecules. In one embodiment, the term "chimeric" refers to a gene expression element produced through the manipulation of known elements or other polynucleotide molecules.

In some embodiments, "activation" can refer to the state of a T cell that has been sufficiently stimulated to induce detectable cellular proliferation. In some embodiments activation can refer to induced cytokine production. In other embodiments, activation can refer to detectable effector functions. At a minimum, an "activated T cell" as used herein is a proliferative T cell.

As used herein, the terms "specific binding" and "specifically binds" refer to a physical interaction between two molecules, compounds, cells and/or particles wherein first entity binds to the second, target, entity with greater specificity and affinity than it binds to a third entity which is a non-target. In some embodiments, specific binding can refer to an affinity of the first entity for the second target, entity, which is at least 10 times, at least 50 times, at least 100 times, at least 500 times, at least 1000 times or greater than the affinity for the third non-target entity under the same conditions. A reagent specific for a given target is one that exhibits specific binding for that target under the conditions of the assay being utilized. A non-limiting example includes an antibody or a ligand, which recognizes and binds with a cognate binding partner (for example, a stimulatory and/or costimulatory molecule present on a T cell) protein.

A "stimulatory ligand," as used herein, refers to a ligand that when present on an antigen presenting cell (APC, e.g., a macrophage, a dendritic cell, a B-cell, an artificial APC, and the like) can specifically bind with a cognate binding partner (referred to herein as a "stimulatory molecule" or "co-stimulatory molecule") on a T cell, thereby mediating a primary response by the T cell, including, but not limited to, proliferation, activation, initiation of an immune response, and the like. Stimulatory ligands are well-known in the art and encompass, inter alia, a MHC Class I molecule loaded with a peptide, an anti-CD3 antibody, a superagonist anti-CD28 antibody, and a superagonist anti-CD2 antibody.

A "stimulatory molecule," as the term is used herein, means a molecule on a T cell that specifically binds with a cognate stimulatory ligand present on an antigen presenting cell.

"Co-stimulatory ligand," as the term is used herein, includes a molecule on an APC that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, 4-1 BBL, OX40L, CD7, B7-1 (CD80), B7-2 (CD86), PD-L1, PD-L2, inducible COStimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll-like receptor and a ligand that specifically binds with B7-H3. A co-stimulatory ligand also can include, but is not limited to, an antibody that specifically binds with a co-stimulatory molecule present on a T cell, such as, but not limited to, CD27, CD28, 4-1 BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

For example, 4-1 BBL is a type 2 transmembrane glycoprotein belonging to the TNFR/TNF ligand superfamily. 4-1 BBL is a co-stimulatory ligand that binds receptor 4-1 BB (CD137) expressed on T cell. 4-1 BBL is expressed on professional APCs including dendritic cells, macrophages, and activated B cells. 4-1 BBL sequences are known for a number of species, e.g., human 4-1 BBL, also known as TNFSF9 (NCBI Gene ID: 8744) polypeptide (e.g., NCBI Ref Seq NP_003802.1) and mRNA (e.g., NCBI Ref Seq NM_003811.3). 4-1 BBL can refer to human 4-1 BBL, including naturally occurring variants, molecules, and alleles thereof. In some embodiments of any of the aspects, e.g., in veterinary applications, 4-1BBL can refer to the 4-1BBL of, e.g., dog, cat, cow, horse, pig, and the like. Homologs and/or orthologs of human 4-1BBL are readily identified for such species by one of skill in the art, e.g., using the NCBI ortholog search function or searching available sequence data for a given species for sequence similar to a reference 4-1 BBL sequence.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA, a Toll-like receptor, CD27, CD28, 4-1 BB, OX40, CD30, CD40, PD-1, ICOS, lymphocyte function-associated antigen-1 (LFA-1), CD2, CD7, LIGHT, NKG2C, B7-H3, and CD83.

In one embodiment, the term "engineered" and its grammatical equivalents as used herein can refer to one or more human-designed alterations of a nucleic acid, e.g., the nucleic acid within an organism's genome. In another embodiment, engineered can refer to alterations, additions, and/or deletion of genes. An "engineered cell" can refer to a cell with an added, deleted and/or altered gene. The term "cell" or "engineered cell" and their grammatical equivalents as used herein can refer to a cell of human or nonhuman animal origin.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may or may not be part of a single contiguous polynucleotide molecule and may or may not be adjacent. For example, a promoter is operably linked to a gene of interest if the promoter regulates or mediates transcription of the gene of interest in a cell.

In various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of ordinary skill will recognize that individual substitutions, deletions, or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure. Variants of the sequences provided herein (see, e.g., Example 2) are included in the present invention.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g., ligand-mediated receptor activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, a polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to an assay known in the art or described below herein. A functional fragment can comprise conservative substitutions of the sequences disclosed herein.

In some embodiments, a polypeptide described herein can be a variant of a polypeptide or molecule as described herein (see, e.g., the sequences in Example 2). In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions, or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence (see, e.g., the sequences of Example 12). The degree of homology (percent identity) between a native and a mutant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are each herein incorporated by reference in their entireties. Any cysteine residue not involved in maintaining the proper conformation of a polypeptide also can be substituted, generally with serine, to improve the oxidative stability of the molecule and prevent aberrant crosslinking. Conversely, cysteine bond(s) can be added to a polypeptide to improve its stability or facilitate oligomerization.

As used herein, the term "DNA" is defined as deoxyribonucleic acid. The term "polynucleotide" is used herein interchangeably with "nucleic acid" to indicate a polymer of nucleosides. Typically a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However, the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e., the succession of letters used as abbreviations for bases) that biochemically characterizes a specific nucleic acid. A polynucleotide sequence presented herein is presented in a 5' to 3' direction unless otherwise indicated. The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide." Exemplary modifications include glycosylation and palmitoylation.

Polypeptides can be purified from natural sources, produced using recombinant DNA technology or synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

In some embodiments, a nucleic acid encoding a polypeptide as described herein (e.g., a CAR polypeptide) is comprised by a vector. In some of the aspects described herein, a nucleic acid sequence encoding a given polypeptide as described herein, or any module thereof, is operably linked to a vector. The term "vector," as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3' UTR or "trailer" sequences, as well as intervening sequences (introns) between individual coding segments (exons).

As used herein, a "signal peptide" or "signal sequence" refers to a peptide at the N-terminus of a newly synthesized protein that serves to direct a nascent protein into the endoplasmic reticulum. In some embodiments, the signal peptide is a CD8 signal sequence. The CD8 signal sequence can correspond to, comprise, or comprise an amino acid sequence having at least 80%, at least 85%, at least 90%, at least 91%, at least 92%, at least 93%, at least 94%, at least 95%, at least 96%, at least 97%, at least 98%, at least 99% or greater sequence identity to the amino acid sequence of MALPVTALLLPLALLLHAARP (SEQ ID NO: 3).

As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of non-essential viral genes. The vector and/or particle may be utilized for the purpose of transferring nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra-chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g., acute lymphoblastic leukemia or other cancer, disease, or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier, e.g., a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier in which the active ingredient would not be found to occur in nature.

As used herein, the term "administering" refers to the placement of a therapeutic or pharmaceutical composition as disclosed herein into a subject by a method or route which results in at least partial delivery of the agent at a desired site. Pharmaceutical compositions comprising agents as disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the technology.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined within the description of the various aspects and embodiments of the technology of the following.

BRIEF DESCRIPTION OF THE DRAWINGS

FIG. 1A shows a bar graph showing the percent CD79b and CD19 expression on human B cell tumor cell lines determined by flow cytometry. FIG. 1B shows percent CD79b and CD19 expression on MCL-patient-derived xenografts determined by flow cytometry (mean±SEM shown, *<0.05, t test). FIG. 1C shows percent CD79b and CD19 expression on circulating tumor cells obtained from MCL patients, gated as CD3-CD20+CD5+ (n=6 patients, mean±SEM shown, **<0.0001, t test). MM: multiple myeloma, BL: Burkitt's lymphoma, DLBCL: diffuse large B cell lymphoma, MCL: mantle cell lymphoma. FIG. 1D shows two second-generation chimeric antigen receptors against CD79b were constructed, utilizing a humanized antibody-derived single-chain variable fragment with a light-heavy (CAR79b (L/H), middle) or heavy-light (CAR79b (H/L), bottom) chain configuration. A second-generation CAR against CD19 was included as a control (CAR19, top). FIG. 1E shows cytotoxicity of CAR T cells after overnight co-culture with target cells at different effector-target ratios (n=2 healthy donors, mean±SEM shown, <0.01, ***<0.001, ANOVA). FIG. 1F shows effector cytokine production measured in collected cell culture supernatants after overnight co-culture of CAR T cells and target cells at a 1:1 ratio. Cytokine analysis was performed using a Luminex array (n=2 healthy donors, mean+SEM shown).

FIG. 2A shows mean fluorescent intensity (MFI), determined by flow cytometry, of CD79b and CD19 surface expression on human tumor B cell lines or mantle cell lymphoma patient derived xenografts. MM: multiple myeloma, BL: Burkitt's lymphoma, DLBCL: diffuse large B cell lymphoma, MCL: mantle cell lymphoma. Peripheral blood mononuclear cells from 6 patients diagnosed with MCL were evaluated for CD19 and CD79b expression using flow cytometry. Malignant B cells were gated as CD3-CD20+CD5+. FIG. 2B shows CD19 and CD79b surface staining on one MCL donor with bright CD79b expression. The CD3-CD20+CD5+CD19+CD79b+ cells are clearly defined as a kappa+ population. FIG. 2C shows CD19 and CD79b surface staining on one MCL donor with dim CD79b expression. The CD3-CD20+CD5+CD19+ CD79b+ cells are not clearly defined as either kappa or lambda+. Dim expression of CD79b could not be clearly resolved by the chosen flourochrome thereby giving the impression of being CD79b negative.

FIG. 3A shows a representative flow plot of human T cells transduced with a chimeric antigen receptor, and transduction efficiency after 10 days of culture (n=3 healthy donors, mean+SEM shown). FIG. 3B shows the activation of Jurkat reporter (NFAT-Luc) T cells, based on luciferase activity, transduced with different CAR constructs and co-cultured overnight with target cells, anti-CD3/CD28 Dynabeads as positive control, or media as negative control (n=3, mean+SEM shown). FIG. 3C shows TNFa production measured by Luminex in collected cell culture supernatants after overnight co-culture of CAR T cells and target cells at a 1:1 ratio (n=2 healthy donors, mean+SEM shown, *<0.001, **<0.0001 by Anova).

FIG. 4A shows a schematic overview of xenograft experiment: NSG mice were engrafted with 1 e6 Jeko-1 (CBG-GFP+) cells and tumor development was monitored with biolumi-nescent imaging. At day 0, mice were grouped according to tumor burden and injected with 2e6 CAR79b (L/H), CAR19 or untransduced control T cells (UTD). FIG. 4B shows representative bioluminescent images of tumor burden over-time for one experiment. FIG. 4C shows average radiance [p/s/cm2/sr] FLUX, of groups of mice at different time points (n=9-10 mice per group, mean±SEM shown, p=NS, two-way ANOVA). FIG. 4D shows absolute numbers of CAR T cells in blood, quantified by flow cytometry and Trucount beads (mean±SEM shown, p=NS, ANOVA). FIG. 4E shows the persistence of CAR T cells in bone marrow, 14 days after infusion of UTDs, CAR19, or CAR79b (L/H) determined by flow cytometry (n=9-10 mice per group, mean±SEM shown, p=NS, ANOVA). Graphs are represen-tative of two experiments with two different healthy donor T cells. NS; Non-significant.

FIG. 5A shows a schematic overview of patient derived xenograft experiment: NSG mice received an IV injection of $1×10^6$ MCL-patient-derived cells (DFBL-98848-V3) in the tail vein. Tumor development was moni-tored by bioluminescent imaging. At day 0, mice were grouped according to tumor burden and received a single IV dose of $3×10^6$ CAR79b, CAR19, or UTD control cells. FIG. 5B shows representative bioluminescent images of tumor growth overtime. FIG. 5C shows average radiance [p/s/cm2/sr] FLUX, of whole mice in the different treatment groups overtime (n=4-5 mice per group, mean+SEM shown, p=NS, two-way ANOVA). FIG. 5D shows a Kaplan-Meier survival curve of groups of mice receiving UTDs, CAR79b (L/H), or CAR19. FIG. 5E shows persistence of CAR T cells in the bone marrow of mice 66 days after CAR T cell injection (n=4-5 mice per group, mean±SEM shown, p=NS, ANOVA). Graphs are representative of T cells from one healthy donor. NS; non-significant.

FIG. 6A shows representative histograms showing CD19 and CD79b surface expression, determined by flow cytometry, on parental Jeko-1 cells and Jeko-1 cells with CRISPR/Cas9 mediated knockout of CD19. FIG. 6B shows the mean fluorescent intensity (MFI) of surface CD19 and CD79b on parental Jeko-1 cells and CD19 knockout cell lines. FIG. 6C shows a comparison of long-term growth of parental Jeko-1 and CD19 negative Jeko-1 clones. FIG. 6D shows a representative histograms of surface CD19 and CD79b expression, determined by flow cytometry, on parental Jeko-1 or CD19 negative Jeko-1 clones at day 14 and 21 of culturing.

FIG. 7A shows an efficient knockdown of CD19 was achieved in Jeko-1 cells with two different CD19 directed shRNAs. FIG. 7B shows a flow cytometric analysis of CD19 and CD79b surface expression on Jeko-1 cells after shRNA mediated CD19 knockdown. The graphs are representative of two indepen-dent experiments (one shown).

FIG. 8A shows a schematic illustration of the in vivo experiment: NSG mice received an IV injection of a total of 1e6 Jeko-1 CD19 negative CBG-GFP (F12 clone 5) tumor cells. Tumor engraftment was established with BLI imaging. At day 0, mice were grouped according to BLI expression and given a single dose of 2e6 CAR19, CAR79b (L/H) or UTD controls cells. FIG. 8B shows a representative biolumines-cent images of CD19 negative tumor growth overtime. FIG. 8C shows the average radiance [p/s] FLUX, of whole mice in different treatment groups over time (n=10 mice pr. group, mean±SEM shown, two-way ANOVA). Graphs are based on experiments with T cells from two different healthy donors.

FIG. 9A is a schematic diagram of the bispecific CAR constructs targeting CD79b and CD19. FIG. 9B is a graph showing activation of CAR T cells. FIG. 9C is a graph showing results of a cytotoxicity assay, whereby the GFP+ cells are the viable tumor cells remaining after co-culture with the indicated CAR constructs. Jeko-1 wild type cells are GFP+, CD19+ and CD79b+. Jeko-1 F12 cells have been knocked out for CD19 but are CD79b+ and GFP+. FIG. 9D and FIG. 9E are a series of a graphs showing in vitro effector function of CAR T cells. FIG. 9D is a graph showing killing of Jeko-1 cells by CAR T cells. FIG. 9E is a graph showing cytokine production by CD79b CAR T cells. n=2 healthy donors, mean±standard error of the mean (S.E.M.) shown;  <0.01, * <0.001. FIG. 9F and FIG. 9G are a series of graphs showing cytokine production by bispecific CAR T cells.

FIG. 10A shows CD19 and CD79b expression in Jeko-1 cells that have been knocked out for CD19 with various combinations of CRISPR/Cas9 guides, labeled F12 clone 5, G1 clone 4, G2 clone 2. FIG. 10B indicates the mean fluorescence of intensity (MFI) of surface expression of CD19 and CD79b in the indicated Jeko cell lines described.

FIG. 12A shows two second-generation chimeric antigen receptors were constructed, targeting both CD79b and CD19 in either a CD19-CD79b (CAR19-79b, top) or a CD79b-CD19 (CAR79b-19, bottom) configuration. FIG. 12B shows a schematic illustration of the experiment: NSG mice received an IV injection of a total of $1×10^6$ Jeko-1 CD19-negative (F12 clone 5) and parental Jeko-1 tumor cells, mixed in a 1:1 ratio, into the tail vein. Tumor engraftment was established with BLI. At day 0, mice were grouped according to BLI and given a single dose of 2e6 CAR19-79b, CAR79b-19, CAR19, CAR79b (L/H), or UTD control cells. FIG. 12C shows representative bioluminescent images of tumor growth overtime from one experiment. FIG. 12D shows the average radiance [p/s/cm2/sr] FLUX, of whole mice in different treatment groups over time (n=8 mice per group, mean±SEM shown, **<0.01, p=NS, two-way ANOVA). FIG. 12E shows the persistence of CD3+mCherry+ cells in peripheral blood 14 days post CART injection (n=4 mice per group, mean±SEM shown). Graphs are based on experiments with T cells from two different healthy donors, one shown as representative. NS; non-significant.

FIG. 13A shows tandem CAR transduction efficiency of human T cells across multiple donors (n=3, healthy donors, mean+SEM shown, ANOVA). FIG. 13B shows luciferace activity of Jurkat reporter (NFAT-Luc) T cells, transduced with different CAR constructs, after overnight co-culture with target cells, anti-CD3/CD28 Dynabeads as positive control, or media as negative control (n=3 mean+SEM, ANOVA compared to UTD, *<0.05, <0.01, *<0.001, ****<0.0001). FIG. 13C shows degranulation of CAR T cells in response to parental Jeko-1 or CD19 negative Jeko-1 (F12 clone 5) cells established by CRISPR/Cas9-mediated knockout of CD19. Effector cytokine production measured in cell culture supernatants of CAR T cells stimulated with (as is shown in FIG. 13D) parental Jeko-1 or (as is shows in FIG. 13E) CD19 negative (F12 clone 5) Jeko-1 cells. Cytokine analysis was performed using a Luminex array (n=3 healthy donors, mean+SEM shown, *<0.05<0.01, *<0.001, ****<0.0001, ANOVA of each condition compared to UTD).

FIG. 14A shows a schematic representation of the experimental design: NSG mice received an IV injection of 1e6 CD19 negative Jeko-1 tumor cells and tumor engraftment established by BLI. 7 days after initial tumor injection, mice received a single dose of CAR19, CAR79b, CAR79b-19, or untransduced control T (UTD) cells. FIG. 14B shows a representative bioluminescent images of tumor growth overtime. FIG. 14C shows the average radiance [p/s/cm2/sr] FLUX, of whole mice in different treatment groups over time (n=8 mice per group, mean±SEM shown, p=NS, **<0.01, two-way ANOVA).

FIG. 15A shows a schematic illustration of the experimental design indicating tumor cells, timeline, dose, and imaging time points. Mice were grouped according to tumor engraftment and before injection with a single dose of 2e6 CAR19, CAR79b, CAR79b-19 or untransduced control T (UTD) cells. FIG. 15B shows a representative bioluminescent images of tumor growth over time. FIG. 15C shows the average radiance [p/s/cm2/sr] FLUX, of whole mice in different treatment groups overtime (n=3-4 mice per group, mean±SEM shown, p=NS, two-way ANOVA). FIG. 15D shows the presence of CD3+mCherry+ cells in peripheral blood at day 14 post CAR T cell injection (n=3-4 mice per group, mean±SEM shown). Graphs are representative of T cells from one healthy donor.

FIG. 16A shows a schematic representation of the experimental design: NSG mice received an IV injection of 1e6 Jeko-1 tumor cells and tumor engraftment established by BLI. 7 days after initial tumor injection, mice received a single dose of 1e6 or 0.5e6 of CAR19, CAR79b, CAR79b-19, or untransduced control T (UTD) cells. FIG. 16B shows the tumor burden shown as bioluminescent signal quantified per animal every week overtime. Each line represents one mouse (n=8 mice per group). FIG. 16C shows the detection of CD3+mCherry+ cells in whole blood at day 14 post CAR T cell injection (n=8mice per group, mean±SEM shown).

DETAILED DESCRIPTION OF THE INVENTION

Figure 1A:
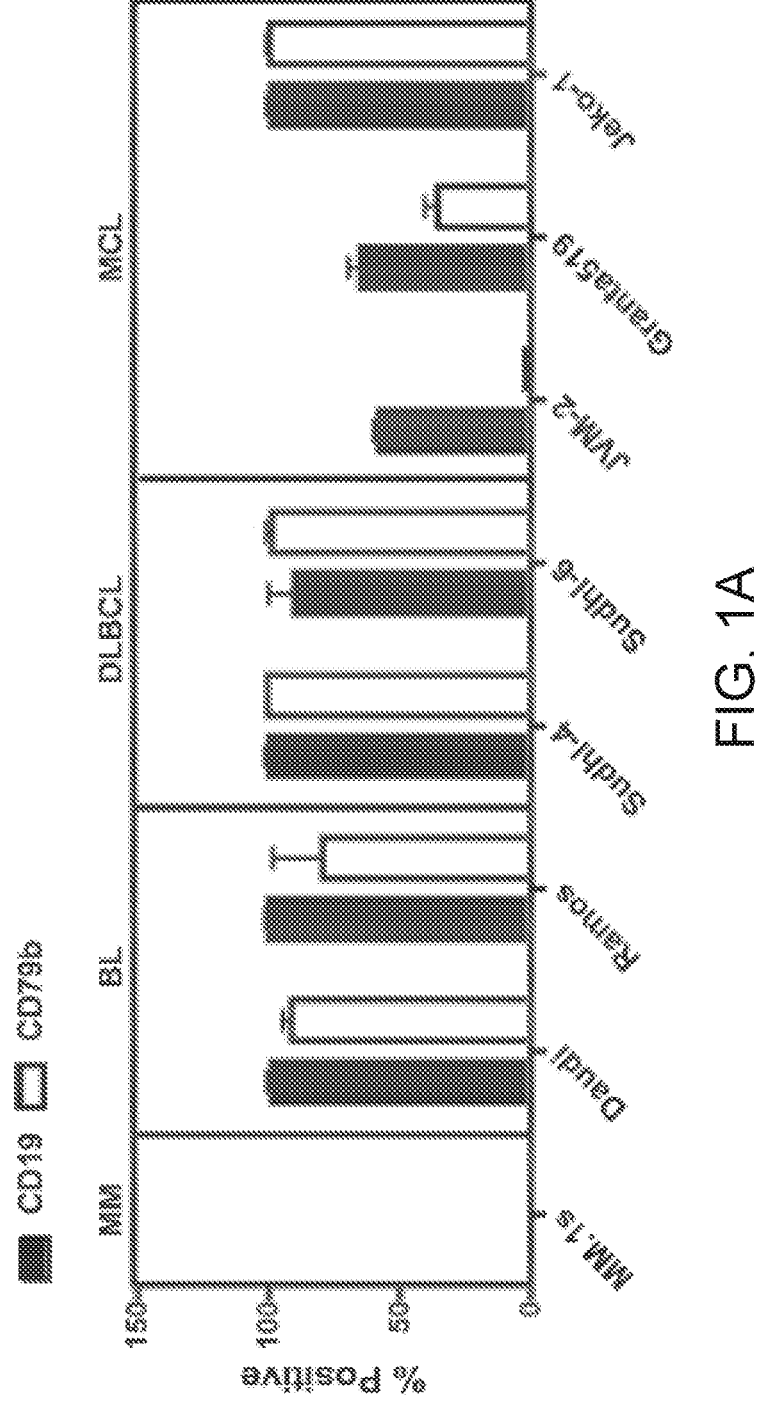
FIG. 1A-FIG. 1F show CD79b CAR T cells demonstrate potent effector functions in vitro against CD79b-positive lymphoma cell lines.

Described herein are bispecific chimeric antigen receptors (CARs) directed against CD79b and CD19, which can be used, for example, in the prevention and treatment of cancer, as described herein (for example, lymphoma, e.g., mantle cell lymphoma (MCL) and other non-Hodgkin lymphomas (NHLs), diffuse large B-cell lymphoma (DLBCL), primary mediastinal B-cell lymphoma (PMBCL), chronic lymphocytic leukemia (CLL), small lymphocytic lymphoma (SLL), follicular lymphoma, and transformed follicular lymphoma). The bispecific CARs described herein can advantageously be used, e.g., to reduce the possibility for tumor escape by loss of target antigen. In particular, a CAR that binds two different tumor-associated antigens or factors (such as CD79b and CD19) will not lose effectiveness if one or the other of the antigens or factors is down-regulated by targeted cells. Similarly, the CD79b CAR can advantageously be used in the treatment of subjects who have previously been treated with CD19 CARs, but have experienced a CD19-negative relapse.

Embodiments of the technology described herein relate to the discovery that CD79b is expressed on cancer cells, including lymphoma cells. Accordingly, CARs directed against CD79b and CD19 are an efficient therapeutic to treat cancer, for example, lymphoma, e.g., MCL and other NHLs, DLBCL, PMBCL, CLL, SLL, follicular lymphoma, and transformed follicular lymphoma.

Accordingly, one aspect of the invention described herein relates to a CAR polypeptide comprising (a) an extracellular domain comprising sequences that specifically bind to CD79b and sequences that specifically bind to CD19 (e.g., single chain antibody sequences; scFv), (b) a hinge and transmembrane domain, and (c) an intracellular signaling domain. Optionally, the CAR polypeptide also includes a co-stimulatory domain, as described herein.

Considerations for use in making and using these and other aspects of the technology are described in the following.

Chimeric Antigen Receptors

The technology described herein provides improved CARs for use in immunotherapy. The following discusses CARs and the various improvements.

The terms "chimeric antigen receptor" or "CAR" or "CARs" as used herein refer to engineered T cell receptors, which graft a ligand or antigen specificity onto, e.g., T cells (for example naïve T cells, central memory T cells, effector memory T cells, or combinations thereof) or natural killer (NK) cells. CARs are also known as artificial T-cell receptors, chimeric T-cell receptors, or chimeric immunoreceptors.

A CAR places a chimeric extracellular target-binding domain that specifically binds a target, e.g., a polypeptide expressed on the surface of a cell to be targeted for a T cell response onto a construct including a transmembrane domain, and intracellular domain(s) (including signaling domains) of a T cell receptor molecule. In one embodiment, the chimeric extracellular target-binding domain comprises the antigen-binding domain(s) of an antibody that specifically binds an antigen expressed on a cell to be targeted for a T cell response. In another embodiment, the chimeric extracellular target-binding domain comprises the antigen-binding domain(s) of a first antibody that specifically binds a first antigen expressed on a cell to be targeted by a T cell response, and also the antigen-binding domain(s) of a second antibody that specifically binds to a second antigen expressed on a cell to be targeted by a T cell response. The properties of the intracellular signaling domain(s) of the CAR can vary as known in the art and as disclosed herein, but the chimeric target/antigen-binding domains(s) render the receptor sensitive to signaling activation when the chimeric target/antigen binding domain binds the target/antigen on the surface of a targeted cell.

With respect to intracellular signaling domains, so-called "first-generation" CARs include those that solely provide CD3zeta (CD3) signals upon antigen binding. So-called "second-generation" CARs include those that provide both co-stimulation (e.g., CD28 or CD137) and activation (CD3) domains, and so-called "third-generation" CARs include those that provide multiple costimulatory (e.g., CD28 and CD137) domains and activation domains (e.g., CD3). In various embodiments, the CAR is selected to have high affinity or avidity for the target/antigen. For example, antibody-derived target or antigen binding domains will generally have higher affinity and/or avidity for the target antigen than would a naturally-occurring T cell receptor. This property, combined with the high specificity one can select for an antibody provides highly specific T cell targeting by CAR T cells.

As used herein, a "CAR T cell" or "CAR-T" refers to a T cell which expresses a CAR. When expressed in a T cell, CARs have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape.

As used herein, the term "extracellular target binding domain" refers to a polypeptide found on the outside of the cell sufficient to facilitate binding to a target. The extracellular target binding domain will specifically bind to its binding partner. In general, the extracellulartarget-binding domain can include an antigen-binding domain of an antibody or a ligand, which recognizes and binds with a cognate binding partner protein. In this context, a ligand is a molecule which binds specifically to a portion of a protein and/or receptor. The cognate binding partner of a ligand useful in the methods and compositions described herein can generally be found on the surface of a cell. Ligand:cognate partner binding can result in the alteration of the ligand-bearing receptor, or activate a physiological response, for example, the activation of a signaling pathway or cascade. In one embodiment, the ligand can be non-native to the genome. Optionally, the ligand has a conserved function across at least two species.

Antibody Reagents

In various embodiments, the CARs described herein comprise an antibody reagent or an antigen-binding domain thereof as an extracellular target-binding domain.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g., de Wildt et al., Eur J. Immunol. 26(3):629-639, 1996; which is incorporated by reference herein in its entirety)), as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like. Fully human antibody binding domains can be selected, for example, from phage display libraries using methods known to those of ordinary skill in the art.

The VH and VL regions can be further subdivided into regions of hypervariability, termed "complementarity determining regions" ("CDRs"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia et al., J. Mol. Biol. 196:901-917, 1987; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, and FR4.

In one embodiment, the antibody or antibody reagent is not a human antibody or antibody reagent, (i.e., the antibody or antibody reagent is mouse), but has been humanized. A "humanized antibody or antibody reagent" refers to a non-human antibody or antibody reagent that has been modified at the protein sequence level to increase its similarity to antibody or antibody reagent variants produced naturally in humans. One approach to humanizing antibodies employs the grafting of murine or other non-human CDRs onto human antibody frameworks.

In one embodiment, a CAR's extracellular target binding domain comprises or consists essentially of a single-chain Fv (scFv) fragment created by fusing the VH and VL domains of an antibody, generally a monoclonal antibody, via a flexible linker peptide. In various embodiments, the scFv is fused to a transmembrane domain and to a T cell receptor intracellular signaling domain, e.g., an engineered intracellular signaling domain as described herein.

Antibody binding domains and ways to select and clone them are well known to those of ordinary skill in the art.

In one embodiment, the extracellular domain of the CAR polypeptide comprises (i) an antibody reagent or an antigen-binding domain thereof as an extracellular target-binding domain, which is directed against CD79b, and (ii) an antibody reagent or an antigen-binding domain thereof as an extracellular target-binding domain, which is directed against CD19.

In some embodiments, the CD79b-binding domain of the CAR polypeptide comprises an scFv. In some embodiments, the anti-CD79b scFv comprises a VH corresponding to, comprising, or comprising an amino acid sequence having at least 80%, at least 85%, at least 90%, at least 91%, at least 92%, at least 93%, at least 94%, at least 95%, at least 96%, at least 97%, at least 98%, at least 99% or greater sequence identity to the amino acid sequence of SEQ ID NO: 9. In some embodiments, the anti-CD79b scFv comprises a VL corresponding to, comprising, or comprising an amino acid sequence having at least 80%, at least 85%, at least 90%, at least 91%, at least 92%, at least 93%, at least 94%, at least 95%, at least 96%, at least 97%, at least 98%, at least 99% or greater sequence identity to the amino acid sequence of SEQ ID NO: 8 or 16. The VH of the anti-CD79b scFv can be positioned N-terminal to the VL, or the VL can be positioned N-terminal to the VH. The VL and VH domains can optionally be connected via a linker, e.g., a linker of SEQ ID NO: 7, 20, 21, 22, or 23. In one embodiment, the VL and VH are connected by a linker of SEQ ID NO: 7. In some embodiments, the anti-CD79b scFv corresponds to, comprises, or comprises an amino acid sequence having at least 80%, at least 85%, at least 90%, at least 91%, at least 92%, at least 93%, at least 94%, at least 95%, at least 96%, at least 97%, at least 98%, at least 99% or greater sequence identity to the amino acid sequence of SEQ ID NO: 10 or 17.

In some embodiments, the CD19-binding domain of the CAR polypeptide comprises an scFv. In some embodiments, the anti-CD19 scFv comprises a VH corresponding to, comprising, or comprising an amino acid sequence having at least 80%, at least 85%, at least 90%, at least 91%, at least 92%, at least 93%, at least 94%, at least 95%, at least 96%, at least 97%, at least 98%, at least 99% or greater sequence identity to the amino acid sequence of SEQ ID NO: 5. In some embodiments, the anti-CD19 scFv comprises a VL corresponding to, comprising, or comprising an amino acid sequence having at least 80%, at least 85%, at least 90%, at least 91%, at least 92%, at least 93%, at least 94%, at least 95%, at least 96%, at least 97%, at least 98%, at least 99% or greater sequence identity to the amino acid sequence of SEQ ID NO: 4. The VH of the anti-CD19 scFv can be positioned N-terminal to the VL, or the VL can be positioned N-terminal to the VH. The VL and VH domains can optionally be connected via a linker, e.g., a linker of SEQ ID NO: 7, 20, 21, 22, or 23. In one embodiment, the VL and VH are connected by a linker of SEQ ID NO: 7. In some embodiments, the anti-CD19 scFv corresponds to, comprises, or comprises an amino acid sequence having at least 80%, at least 85%, at least 90%, at least 91%, at least 92%, at least 93%, at least 94%, at least 95%, at least 96%, at least 97%, at least 98%, at least 99% or greater sequence identity to the amino acid sequence of SEQ ID NO: 6.

Furthermore, the CD79b-binding domain and CD19-binding domains may optionally be connected by a linker, e.g., a linker of SEQ ID NO: 7, 20, 21, 22, or 23. In one embodiment, the CD79b and CD19-binding domains are connected by a linker of SEQ ID NO: 7. The CD79b-binding domain may be positioned N-terminal to the CD19-binding domain, or the CD19-binding domain may be positioned N-terminal to the CD79b-binding domain.

In one embodiment, the CAR polypeptide comprises one or more mutations within its coding region, to generate a variant sequence as described herein. One skilled in the art will be capable of introducing mutations into the nucleic acid sequence of a gene or gene product using standard techniques. For example, point mutations can be introduced via site-directed point mutagenesis, a PCR technique. Site-directed mutagenesis kits are commercially available, for instance, through New England Biolabs; Ipswich, MA Non-limiting examples of alternative methods to introduce point mutations to the nucleic acid sequence of a gene or gene product include cassette mutagenesis or whole plasmid mutagenesis.

Target/Antigen

In general, any cell-surface moiety can be targeted by a CAR. Most often, the target will be a cell-surface polypep-tide differentially or preferentially expressed on a cell one wishes to target for a T cell response. In this regard, tumor antigens or tumor-associated antigens provide attractive targets, providing a means to target tumor cells while avoiding or at least limiting collateral damage to non-tumor cells or tissues. CARs directed against CD79b and CD19 are described herein.

CD79b is a protein associated with the B cell receptor (BCR) complex and can be found on many B cell malig-nancies. CD79b interacts with CD79a and is involved in the initiation of the signal transduction cascade activated by the BCR. CD79b sequences are known for a number of species, e.g., human CD79b (NCBI Gene ID: 974) polypeptide (e.g., UniProtKB: P40259) and DNA (e.g., NCBI Reference Sequence: NG_007368.1). CD79b can refer to human CD79b, including naturally occurring variants, molecules, and alleles thereof. In some embodiments of any of the aspects, e.g., in veterinary applications, CD79b can refer to the CD79b of, e.g., cat, dog, cow, horse, pig, and the like. Homologs and/or orthologs of human CD79b are readily identified for such species by one of skill in the art, e.g., using the NCBI ortholog search function or searching avail-able sequence data for a given species for sequence similar to a reference CD79b sequence.

CD19 is a transmembrane protein expressed in all B lineage cells, except for plasma cells, and in follicular dendritic cells. CD19 sequences are known for a number of species, e.g., human CD19 (NCBI Gene ID: 930) polypep-tide (e.g., NCBI GenBank Accession No.: AAB60697.1) and DNA (e.g., NCBI GenBank Accession No.: AH005421.2). CD19 can refer to human CD19, including naturally occur-ring variants, molecules, and alleles thereof. In some embodiments of any of the aspects, e.g., in veterinary applications, CD19 can refer to the CD19 of, e.g., cat, dog, cow, horse, pig, and the like. Homologs and/or orthologs of human CD19 are readily identified for such species by one of skill in the art, e.g., using the NCBI ortholog search function or searching available sequence data for a given species for sequence similar to a reference CD19 sequence.

Non-limiting examples of additional tumor antigens or tumor-associated antigens include CEA, Immature laminin receptor, TAG-72, HPV E6 and E7, BING-4, Calcium-activated chloride channel 2, Cyclin B1, 9D7, Ep-CAM, EphA3, Her2/neu, Telomerase, Mesotheliun, SAP-1, Sur-vivin, BAGE family, CAGE family, GAGE family, MAGE family, SAGE family, XAGE family, NY-ESO-1/LAGE-1, PRAME, SSX-2, Melan-A/MART-1, Gp100/pmel17, Tyro-sinase, TRP-1/-2, MC1R, BRCA1/2, CDK4, MART-2, p53, Ras, MUC1, and TGF-βRII. CARs against one or more of these antigens can be used in combination with a CAR against CD79b and CD19 as described herein, as determined to be appropriate by those of skill in the art.

Hinge and Transmembrane Domains

The binding domain of the CAR is optionally followed by one or more "hinge domains," which plays a role in posi-tioning the target binding domain away from the effector cell surface to enable proper cell/cell contact, target binding and activation. A CAR optionally comprises one or more hinge domains between the binding domain and the transmem-brane (TM) domain. The hinge domain may be derived either from a natural, synthetic, semi-synthetic, or recom-binant source. The hinge domain can include the amino acid sequence of a naturally occurring immunoglobulin hinge region or an altered immunoglobulin hinge region. Illustra-tive hinge domains suitable for use in the CARs described herein include the hinge region derived from the extracel-lular regions of type 1 membrane proteins such as CD8 (e.g., CD8a), CD4, CD28, 4-1 BB, and CD7, which may be wild-type hinge regions from these molecules or may be altered. In some embodiments, the hinge region is derived from the hinge region of an immunoglobulin-like protein (e.g., IgA, IgD, IgE, IgG, or IgM), CD28, 4-1 BB, or CD8. In one embodiment, the hinge domain comprises a CD8a hinge region.

As used herein, "transmembrane domain" (TM domain) refers to the generally hydrophobic region of the CAR which crosses the plasma membrane of a cell. The TM domain can be the transmembrane region or fragment thereof of a transmembrane protein (for example a Type I transmembrane protein or other transmembrane protein), an artificial hydrophobic sequence, or a combination thereof. While specific examples are provided herein and used in the examples, other transmembrane domains will be apparent to those of skill in the art and can be used in connection with alternate embodiments of the technology. A selected transmembrane region or fragment thereof would preferably not interfere with the intended function of the CAR. As used in relation to a transmembrane domain of a protein or polypeptide, "fragment thereof" refers to a portion of a transmembrane domain that is sufficient to anchor or attach a protein to a cell surface.

In one embodiment, the transmembrane domain or fragment thereof of any of the CAR polypeptides described herein comprises a transmembrane domain selected from the transmembrane domain of CD8 or 4-1 BB. In an alternate embodiment of any aspect, the transmembrane domain or fragment thereof of the CAR described herein comprises a transmembrane domain selected from the transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7Ra, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1(CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Lyl08), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

CD8 is an antigen preferentially found on the cell surface of cytotoxic T lymphocytes. CD8 mediates cell-cell interactions within the immune system, and acts as a T cell co-receptor. CD8 consists of an alpha (CD8a) and beta (CD8b) chain. CD8a sequences are known for a number of species, e.g., human CD8a, (NCBI Gene ID: 925) polypeptide (NCBI Ref Seq NP_001139345.1) and mRNA (e.g., NCBI Ref Seq NM_000002.12). CD8 can refer to human CD8, including naturally occurring variants, molecules, and alleles thereof. In some embodiments of any of the aspects, e.g., in veterinary applications, CD8 can refer to the CD8 of, e.g., dog, cat, cow, horse, pig, and the like. Homologs and/or orthologs of human CD8 are readily identified for such species by one of skill in the art, e.g., using the NCBI ortholog search function or searching available sequence data for a given species for sequence similar to a reference CD8 sequence.

As used herein, a "hinge/transmembrane domain" refers to a domain comprising both a hinge domain and a transmembrane domain. In one embodiment, the hinge/transmembrane domain of a CAR or fragment thereof is derived from or comprises the hinge/transmembrane domain of CD8. In one embodiment, the CD8 hinge and transmembrane sequence comprises the sequence of SEQ ID NO: 11, or comprises a sequence with at least 80%, at least 85%, at least 90%, at least 91%, at least 92%, at least 93%, at least 94%, at least 95%, at least 96%, at least 97%, at least 98%, at least 99%, or at least 100% sequence identity to the sequence of SEQ ID NO: 11.

Co-Stimulatory Domain

Each CAR described herein can optionally comprise one or more intracellular domain of a co-stimulatory molecule, or co-stimulatory domain. As used herein, the term "co-stimulatory domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70. In some embodiments, the co-stimulatory domain comprises the co-stimulatory domain of CD27, CD28, OX40, or 4-1 BB. In one embodiment, the co-stimulatory domain is the co-stimulatory domain of 4-1 BB.

4-1 BB is a membrane receptor protein, also known as CD137, which is a member of the tumor necrosis factor (TNF) receptor superfamily. 4-1 BB is expressed on activated T lymphocytes. 4-1 BB sequences are known for a number of species, e.g., human 4-1BB, also known as TNFRSF9 (NCBI Gene ID: 3604) and mRNA (NCBI Reference Sequence: NM_001561.5). 4-1BB can refer to human 4-1BB, including naturally occurring variants, molecules, and alleles thereof. In some embodiments of any of the aspects, e.g., in veterinary applications, 4-1BB can refer to the 4-1BB of, e.g., dog, cat, cow, horse, pig, and the like. Homologs and/or orthologs of human 4-1 BB are readily identified for such species by one of skill in the art, e.g., using the NCBI ortholog search function or searching available sequence data for a given species for sequence similar to a reference 4-1 BB sequence.

Accordingly, in one embodiment, the CAR polypeptide further comprises an intracellular domain. As used herein, an "intracellular domain" refers to a sequence fully comprised within a cell. In one embodiment, the intracellular domain refers to the intracellular domain of a receptor. An intracellular domain can interact with the interior of a cell. With respect to the intracellular domain of a receptor, the intracellular domain can function to relay a signal transduced. An intracellular domain of a receptor can comprise enzymatic activity.

In one embodiment, the co-stimulatory domain is the co-stimulatory domain of 4-1 BB. In one embodiment, the 4-1BB co-stimulatory domain comprises the sequence of SEQ ID NO: 12; or comprises at least 80%, at least 85%, at least 90%, at least 95%, at least 96%, at least 97%, at least 98%, at least 99%, or at least 100% sequence identity SEQ ID NO: 12.

Intracellular Signaling Domain

CARs as described herein comprise an intracellular signaling domain. An "intracellular signaling domain," refers to the part of a CAR polypeptide that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited following antigen binding to the extracellular CAR domain.

CD3 is a T cell co-receptor that facilitates T lymphocytes activation when simultaneously engaged with the appropriate co-stimulation (e.g., binding of a co-stimulatory molecule). A CD3 complex consists of 4 distinct chains; mammal CD3 consists of a CD3γ chain, a CD3δ chain, and two CD3ε chains. These chains associate with a molecule known as the T cell receptor (TCR) and the CD3(to generate an activation signal in T lymphocytes. A complete TCR complex comprises a TCR, CD3ζ, and the complete CD3 complex.

In some embodiments of any aspect, a CAR polypeptide described herein comprises an intracellular signaling domain that comprises an Immunoreceptor Tyrosine-based Activation Motif or ITAM from CD3 zeta (CD3ζ), ITAM-mutated CD3ζ, CD3η, or CD3δ. In some embodiments of any aspect, the ITAM comprises three motifs of ITAM of CD3ζ (ITAM3). In some embodiments of any aspect, the three motifs of ITAM of CD3(are mutated.

ITAMS are known as a primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Non-limiting examples of ITAM containing intracellular signaling domains that are of particular use in the technology include those derived from TCRζ, FcRγ, FcRβ, CD3γ, CD3δ, CD3δ, CD3ε, CD3η, CD3ζ, CD22, CD79a, CD79b, and CD66d.

One skilled in the art will be capable of introducing mutations into the nucleic acid sequence of a gene or gene product, for example ITAM, using standard techniques. For example, point mutations can be introduced via site-directed point mutagenesis, a PCR technique. Site-directed mutagenesis kits are commercially available, for instance, through New England Biolabs; Ipswich, MA Non-limiting examples of alternative methods to introduce point mutations to the nucleic acid sequence of a gene or gene product include cassette mutagenesis or whole plasmid mutagenesis.

In one embodiment, the ITAM utilized in the CAR is based on alternatives to CD3ζ, including mutated ITAMs from CD3ζ (which contains 3 ITAM motifs), truncations of CD3ζ, and alternative splice variants known as CD3ε, CD3η, CD3δ, and artificial constructs engineered to express fusions between CD3ε, CD3η, or CD36 and CD3ζ

In some embodiments, a CAR polypeptide described herein comprises the intracellular signaling domain of CD3ζ (including variants of CD3ζ, e.g., ITAM-mutated CD3ζ), CD3η, or CD3δ. In particular embodiments, a CAR polypeptide described herein comprises the intracellular signaling domain of CD3ζ. In one embodiment, the CD3(intracellular signaling domain corresponds to the amino acid sequence of SEQ ID NO: 13; or comprises the sequence of SEQ ID NO: 13; or comprises a sequence with at least 80%, at least 85%, at least 90%, at least 91%, at least 92%, at least 93%, at least 94%, at least 95%, at least 96%, at least 97%, at least 98%, at least 99%, or at least 100% sequence identity to the sequence of SEQ ID NO: 13.

A more detailed description of CARs and CAR T cells can be found in Maus et al., Blood 123:2624-2635, 2014; Reardon et al., Neuro-Oncology 16:1441-1458, 2014;

Hoyos et al., Haematologica 97:1622, 2012; Byrd et al., J. Clin. Oncol. 32:3039-3047, 2014; Maher et al., Cancer Res. 69:4559-4562, 2009; and Tamada et al., Clin. Cancer Res. 18:6436-6445, 2012; each of which is incorporated by reference herein in its entirety.

In one embodiment, the CAR polypeptide further comprises a CD8 signal sequence. In one embodiment, the CD8 signal sequence corresponds to the amino acid sequence of SEQ ID NO: 3; or comprises SEQ ID NO: 3; or comprises a sequence with at least 80%, at least 85%, at least 90%, at least 91%, at least 92%, at least 93%, at least 94%, at least 95%, at least 96%, at least 97%, at least 98%, at least 99%, or at least 100% sequence identity to a SEQ ID NO: 3.

In one embodiment, the CAR further comprises a linker domain. As used herein "linker domain" refers to an oligo- or polypeptide region from about 2 to 100 amino acids, 5 to 50 amino acids, 10 to 15 amino acids, 15 to 20 amino acids, or 18 to 20 amino acids in length, which links together any of the domains/regions of the CAR as described herein, and includes any suitable linkers known in the art. In some embodiment, linkers can include or be composed of flexible residues such as glycine and serine so that the adjacent protein domains are free to move relative to one another. For instance, linker sequences useful for the invention include, but are not limited to, glycine/serine linkers, e.g., GGGSGGGSGGGS (SEQ ID NO: 21) and Gly4Ser (G4S) linkers such as (G4S)3 (GGGGSGGGGSGGGGS (SEQ ID NO: 20)) and (G4S)4 (GGGGSGGGGSGGGGSGGGGS (SEQ ID NO: 7)); the linker sequence of GST-SGSGKPGSGEGSTKG (SEQ ID NO: 22) as described by Whitlow et al., Protein Eng. 6(8):989-95, 1993, which is incorporated herein by reference in its entirety; the linker sequence of GGSSRSSSSGGGGSGGGG (SEQ ID NO: 23) as described by Andris-Widhopf et al., Cold Spring Harb. Protoc. 2011(9), 2011, which is incorporated herein by reference in its entirety; as well as linker sequences with added functionalities, e.g., an epitope tag or an encoding sequence containing Cre-Lox recombination site as described by Sblattero et al., Nat. Biotechnol. 18(1):75-80, 2000, which is incorporated herein by reference in its entirety.

Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. In one embodiment, the linker region is T2A derived from Thosea asigna virus. Non-limiting examples of linkers include linkers derived from Thosea asigna virus, and a linker derived from the internal ribosomal entry site (IRES) sequence.

In one embodiment, a CAR as described herein further comprises a reporter molecule, e.g., to permit for non-invasive imaging (e.g., positron-emission tomography PET scan). In a bispecific CAR that includes a reporter molecule, the first extracellular binding domain and the second extracellular binding domain can include different or the same reporter molecule. In a bispecific CAR T cell, the first CAR and the second CAR can express different or the same reporter molecule. In another embodiment, a CAR as described herein further comprises a reporter molecule (for example, hygromycin phosphotransferase (hph)) that can be imaged alone or in combination with a substrate or chemical (for example 9-[4-[$^{18}$F]fluoro-3-(hydroxymethyl)butyl]guanine ([$^{18}$F]FHBG)). In another embodiment, a CAR as described herein further comprises nanoparticles at can be readily imaged using non-invasive techniques (e.g., gold nanoparticles (GNP) functionalized with $^{64}$Cu$^{2+}$). Labeling of CAR T cells for non-invasive imaging is reviewed, for example in Bhatnagar et al., Integr. Biol. (Camb) 5(1):231-238, 2013, and Keu et al., Sci. Transl. Med. 9(373), 2017, which are incorporated herein by reference in their entireties.

GFP and mCherry are demonstrated herein as fluorescent tags useful for imaging a CAR expressed on a T cell (e.g., a CAR T cell). It is expected that essentially any fluorescent protein known in the art can be used as a fluorescent tag for this purpose. For clinical applications, the CAR need not include a fluorescent tag or fluorescent protein.

Another aspect of the invention relates to a CAR polypeptide comprising a sequence having at least 80%, at least 85%, at least 90%, at least 91%, at least 92%, at least 93%, at least 94%, at least 95%, at least 96%, at least 97%, at least 98%, at least 99%, or 100% sequence identity with a sequence selected from SEQ ID NO: 1, 2, 14, 15, 24, 25, 26, or 27. Another aspect of the invention relates to a CAR polypeptide comprising a sequence selected from SEQ ID NO: 1, 2, 14, 15, 24, 25, 26, or 27.

Another aspect of the invention described herein relates to a polypeptide complex comprising two or more (e.g., two or more, three or more, four or more, five or more, six or more, seven or more, eight or more, nine or more, or ten or more) of any of the CAR polypeptides described herein. In one embodiment, the polypeptide complex comprises three of any of the CAR polypeptides described herein.

Nucleic Acids and Cells

In some embodiments, any of the CAR polypeptides described herein are encoded by a polynucleotide comprised, e.g., in a viral vector. Optionally, a polynucleotide encoding a CAR polypeptide as described herein can be codon-optimized to enhance expression or stability. Codon optimization may be performed in according to any standard methods known in the art.

Retroviruses, such as lentiviruses, provide a convenient platform for delivery of nucleic acid sequences encoding a gene, or chimeric gene of interest. A selected nucleic acid sequence can be inserted into a vector and packaged in retroviral particles using techniques known in the art. The recombinant virus can then be isolated and delivered to cells, e.g. in vitro or ex vivo. Retroviral systems are well known in the art and are described in, for example, U.S. Pat. No. 5,219,740; Kurth and Bannert (2010) "Retroviruses: Molecular Biology, Genomics and Pathogenesis" Calster Academic Press (ISBN:978-1-90455-55-4); and Hu and Pathak Pharmacological Reviews 2000 52:493-512; which are incorporated by reference herein in their entirety. Lentiviral system for efficient DNA delivery can be purchased from OriGene; Rockville, MD In alternative embodiments, the CAR polypeptide of any of the CARs described herein are expressed in the mammalian cell via transfection or electroporation of an expression vector comprising nucleic acid encoding the CAR. Transfection or electroporation methods are known in the art.

Efficient expression of the CAR polypeptide of any of the CAR polypeptides described herein can be assessed using standard assays that detect the mRNA, DNA, or gene product of the nucleic acid encoding the CAR. For example, RT-PCR, FACS, northern blotting, western blotting, ELISA, or immunohistochemistry.

In one embodiment, the CAR polypeptide of any of the CAR polypeptides described herein is constitutively expressed. In one embodiment, the CAR polypeptide of any of the CAR polypeptides described herein is encoded by recombinant nucleic acid sequence.

Another aspect of the invention relates to a mammalian cell comprising any of the CAR polypeptides described herein; or a nucleic acid encoding any of the CAR polypeptides described herein. In one embodiment, the mammalian cell comprises an antibody, antibody reagent, antigen-binding portion thereof, or any of the CAR polypeptides described herein, or a nucleic acid encoding such an antibody, antibody reagent, antigen-binding portion thereof, or any of the CAR polypeptides described herein. The mammalian cell or tissue can be of human, primate, hamster, rabbit, rodent, cow, pig, sheep, horse, goat, dog, or cat origin, but any other mammalian cell may be used. In a preferred embodiment of any aspect, the mammalian cell is human.

In one embodiment, the cell is a T cell. In alternate embodiments of any aspect, the cell is an immune cell. As used herein, "immune cell" refers to a cell that plays a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. In some embodiments, the cell is a T cell; a NK cell; a NKT cell; lymphocytes, such as B cells and T cells; and myeloid cells, such as monocytes, macrophages, eosinophils, mast cells, basophils, and granulocytes.

In one embodiment, the cell is obtained from an individual having or diagnosed as having cancer, a plasma cell disorder, or autoimmune disease. T cells can be obtained from a subject using standard techniques known in the field, for example, T cells are isolated from peripheral blood taken from a patient. Immune cells can also be obtained from allogeneic donors, which are non-genetically identical individuals of the same species as the intended recipients of the cells.

Immune cells (e.g., human immune cells) that can be used in the invention include autologous cells, obtained from the subject to whom the cells are later to be administered, after ex vivo modification and expansion. For example, the immune cells can be obtained from an individual having or diagnosed as having cancer, an autoimmune disease, or a plasma cell disorder. Immune cells can also be obtained from allogeneic donors, which are non-genetically identical individuals of the same species as the intended recipients of the cells. Immune cells useful for the invention include T cells and NK cells.

Methods for obtaining T cells and NK are known in the art and can be useful for the engineered immune cells described herein. T cells and NK cells are typically obtained from peripheral blood that is collected from a subject by, e.g., venipuncture or withdrawal through an implanted port or catheter. Optionally, the blood can be obtained by a process including leukapheresis, in which white cells are obtained from the blood of a subject, while other blood components are returned to the subject. Blood or leukapheresis product (fresh or cryopreserved) is processed to enrich for T cells or NK cells using methods known in the art. For example, density gradient centrifugation (using, e.g., Ficoll) and/or counter-flow centrifugal elutriation can be carried out to enrich for mononuclear cells (including T cells or NK cells). In one example, for T cells, a T cell stimulation step employing, e.g., CD3/CD28 antibodies coated on magnetic beads or artificial antigen presenting cells (aAPCs) expressing, e.g., cell surface-bound anti-CD3 and anti-CD28 antibody fragments (see below), can further be carried out in order to stimulate T cells and to deplete other cells, e.g., B cells. The T cells of enriched T cell preparations can then be subject to genetic modification.

As an alternative to peripheral blood, tissues including bone marrow, lymph nodes, spleen, and tumors can be used as a source for T cells and NK cells. The T cells and NK cells can be of human, primate, hamster, rabbit, rodent, cow, pig, sheep, horse, goat, dog, or cat origin, but any other mammalian cell may be used. In a certain embodiments of any aspect, the T or NK cell is human.

An immune cell, e.g., a T cell or NK cell, can be engineered to comprise any of the CAR polypeptides described herein (e.g., the CAR polypeptide of SEQ ID NO: 1, 2, 14, 15, 24, 25, 26, or 27); or a nucleic acid encoding any of the CAR polypeptides described herein (e.g., a nucleic acid encoding the CAR polypeptide of SEQ ID NO: 1, 2, 14, 15, 24, 25, 26, or 27). In further embodiments, a CAR polypeptide described herein is comprised in a lentiviral vector. The lentiviral vector is used to express the CAR polypeptide in a cell using infection standard techniques. In preferred embodiments, anti-CD79b CARs described herein, for example, with either a light-heavy (CAR79b (L/H)) or a heavy-light (CAR79b (H/L)) single-chain variable fragment (scFv) configuration, are synthesized and cloned into a third-generation lentiviral backbone under control of human EF1α promoter.

The invention furthermore provides compositions and methods for treating and preventing diseases and conditions including, e.g., cancer, autoimmune diseases or disorders, or plasma cell diseases or disorders. These methods include the use of an immune cell (e.g., a T cell or an NK cell) including a CAR polypeptide, or a nucleic acid encoding said CAR, as described herein, and administering the modified immune cell to a subject to treat, e.g., cancer. In some embodiments of any of the aspect, the modified immune cell (e.g., a T cell or an NK cell including one or more additional modification as described herein) is stimulated and/or activated prior to administration to the subject.

Therapeutic Methods

The invention further provides methods and compositions for use treating a disease or disorder, e.g., cancer, using the CAR polypeptides described herein.

"Cancer" as used herein can refer to a hyperproliferation of cells whose unique trait—loss of normal cellular control—results in unregulated growth, lack of differentiation, local tissue invasion, and metastasis, and can be, for example, lymphoma, leukemia, multiple myeloma, or a solid tumor. In one example, the cancer is a non-Hodgkin lymphoma. In certain examples, the cancer is any type of B cell malignancy. Non-limiting examples of B cell malignancies include diffuse large B-cell lymphoma (DLBCL), follicular lymphoma, transformed follicular lymphoma, chronic lymphocytic leukemia (CLL), small lymphocytic lymphoma (SLL), mantle cell lymphoma (MCL), marginal zone lymphoma, Burkitt's lymphoma, hairy cell leukemia (HCL), Hodgkin's lymphoma, Nodular lymphocyte predominant Hodgkin's lymphoma, mucosa-associated lymphatic tissue lymphoma (MALT), lymphoplasmacytic lymphoma, nodal marginal zone B cell lymphoma, splenic marginal zone lymphoma, intravascular large B-cell lymphoma, primary effusion lymphoma, lymphomatoid granulomatosis, primary central nervous system lymphoma, ALK-positive large B-cell lymphoma, plasmablastic lymphoma, large B-cell lymphoma arising in HHV8-associated multicentric Castleman's disease, primary mediastinal B-cell lymphoma (PMBCL), and unclassifiable B-cell lymphomas.

Non-limiting examples of leukemia include acute myeloid leukemia (AML), chronic myeloid leukemia (CML), acute lymphocytic leukemia (ALL), and chronic lymphocytic leukemia (CLL). In one embodiment, the cancer is ALL or CLL. Non-limiting examples of solid tumors include adrenocortical tumor, alveolar soft part sarcoma, carcinoma, chondrosarcoma, colorectal carcinoma, desmoid tumors, desmoplastic small round cell tumor, endocrine tumors, endodermal sinus tumor, epithelioid hemangioendothelioma, Ewing sarcoma, germ cell tumors (solid tumor), giant cell tumor of bone and soft tissue, hepatoblastoma, hepatocellular carcinoma, melanoma, nephroma, neuroblastoma, non-rhabdomyosarcoma soft tissue sarcoma (NRSTS), osteosarcoma, paraspinal sarcoma, renal cell carcinoma, retinoblastoma, rhabdomyosarcoma, synovial sarcoma, and Wilms tumor. Solid tumors can be found in bones, muscles, or organs, and can be sarcomas or carcinomas. It is contemplated that any aspect of the invention described herein can be used to treat all types of cancers, including cancers not listed in the instant application. As used herein, the term "tumor" refers to an abnormal growth of cells or tissues, e.g., of malignant type or benign type.

As used herein, an "autoimmune disease or disorder" is characterized by the inability of one's immune system to distinguish between a foreign cell and a healthy cell. This results in one's immune system targeting one's healthy cells for programmed cell death. Non-limiting examples of an autoimmune disease or disorder include inflammatory arthritis, type 1 diabetes mellitus, multiples sclerosis, psoriasis, inflammatory bowel diseases, SLE, and vasculitis, allergic inflammation, such as allergic asthma, atopic dermatitis, and contact hypersensitivity, rheumatoid arthritis, multiple sclerosis (MS), systemic lupus erythematosus, Graves' disease (overactive thyroid), Hashimoto's thyroiditis (underactive thyroid), chronic graft vs. host disease, hemophilia with antibodies to coagulation factors, celiac disease, Crohn's disease and ulcerative colitis, Guillain-Barre syndrome, primary biliary sclerosis/cirrhosis, sclerosing cholangitis, autoimmune hepatitis, Raynaud's phenomenon, scleroderma, Sjogren's syndrome, Goodpasture's syndrome, Wegener's granulomatosis, polymyalgia rheumatica, temporal arteritis/giant cell arteritis, chronic fatigue syndrome CFS), psoriasis, autoimmune Addison's Disease, ankylosing spondylitis, acute disseminated encephalomyelitis, antiphospholipid antibody syndrome, aplastic anemia, idiopathic thrombocytopenic purpura, Myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, Wegener's granulomatosis and fibromyalgia (FM).

In one embodiment, the mammalian cell is obtained for a patient having an immune system disorder that results in abnormally low activity of the immune system, or immune deficiency disorders, which hinders one's ability to fight a foreign cell (i.e., a virus or bacterial cell).

A plasma cell is a white blood cell produces from B lymphocytes which function to generate and release antibodies needed to fight infections. As used herein, a "plasma cell disorder or disease" is characterized by abnormal multiplication of a plasma cell. Abnormal plasma cells are capable of "crowding out" healthy plasma cells, which results in a decreased capacity to fight a foreign object, such as a virus or bacterial cell. Non-limiting examples of plasma cell disorders include amyloidosis, Waldenstrom's macroglobulinemia, osteosclerotic myeloma (POEMS syndrome), monoclonal gammopathy of unknown significance (MGUS), and plasma cell myeloma.

One aspect of the invention described herein relates to a method to a method of treating cancer, a plasma cell disorder, amyloidosis, or an autoimmune disease in a subject, the method comprising: engineering a T cell to comprise any of the CAR polypeptides described herein on the T cell surface; administering the engineered T cell to the subject.

Another aspect of the invention described herein relates to a method of treating cancer, a plasma cell disorder, or an autoimmune disease in a subject, the method comprising administering a cell comprising any of the CAR polypeptides described herein, or a nucleic acid encoding any of the CAR polypeptides described herein.

In one embodiment, the method further comprises activating or stimulating the CAR-T prior to administering the cell to the subject, e.g., according to a method as described elsewhere herein.

In one embodiment, the cancer comprises cells expressing the tumor antigen CD79b. In another embodiment, the cancer comprises cells expressing the tumor antigen CD19. In further embodiments, the cancer comprises cells expressing both of the tumor antigens CD79b and CD19.

Administration

In some embodiments, the methods described herein relate to treating a subject having or diagnosed as having cancer, a plasma cell disease or disorder, or an autoimmune disease or disorder with a mammalian cell comprising any of the CAR polypeptides described herein, or a nucleic acid encoding any of the CAR polypeptides described herein. As used herein, a "CAR T cell as described herein" refers to a mammalian cell comprising any of the CAR polypeptides described herein, or a nucleic acid encoding any of the CAR polypeptides described herein. As used herein, a "condition" refers to a cancer, a plasma cell disease or disorder, or an autoimmune disease or disorder. Subjects having a condition can be identified by a physician using current methods of diagnosing the condition. Symptoms and/or complications of the condition, which characterize these conditions and aid in diagnosis are well known in the art and include but are not limited to, fatigue, persistent infections, and persistent bleeding. Tests that may aid in a diagnosis of, e.g. the condition, but are not limited to, blood screening and bone marrow testing, and are known in the art for a given condition. A family history for a condition, or exposure to risk factors for a condition can also aid in determining if a subject is likely to have the condition or in making a diagnosis of the condition.

The compositions described herein can be administered to a subject having or diagnosed as having a condition. In some embodiments, the methods described herein comprise administering an effective amount of activated CAR T cells described herein to a subject in order to alleviate a symptom of the condition. As used herein, "alleviating a symptom of the condition" is ameliorating any condition or symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. In one embodiment, the compositions described herein are administered systemically or locally. In a preferred embodiment, the compositions described herein are administered intravenously. In another embodiment, the compositions described herein are administered at the site of the tumor.

The term "effective amount" as used herein refers to the amount of activated CAR T cells needed to alleviate at least one or more symptom of the disease or disorder, and relates to a sufficient amount of the cell preparation or composition to provide the desired effect. The term "therapeutically effective amount" therefore refers to an amount of activated CAR T cells that is sufficient to provide a particular anti-condition effect when administered to a typical subject. An effective amount as used herein, in various contexts, would also include an amount sufficient to delay the development of a symptom of the disease, alter the course of a symptom disease (for example, but not limited to, slowing the progression of a condition), or reverse a symptom of the condition. Thus, it is not generally practicable to specify an exact "effective amount." However, for any given case, an appropriate "effective amount" can be determined by one of ordinary skill in the art using only routine experimentation.

Effective amounts, toxicity, and therapeutic efficacy can be evaluated by standard pharmaceutical procedures in cell cultures or experimental animals. The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of activated CAR T cells, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for bone marrow testing, among others. The dosage can be determined by a physician and adjusted, as necessary, to suit observed effects of the treatment.

In one aspect of the invention, the technology described herein relates to a pharmaceutical composition comprising activated CAR T cells as described herein, and optionally a pharmaceutically acceptable carrier. The active ingredients of the pharmaceutical composition at a minimum comprise activated CAR T cells as described herein. In some embodiments, the active ingredients of the pharmaceutical composition consist essentially of activated CAR T cells as described herein. In some embodiments, the active ingredients of the pharmaceutical composition consist of activated CAR T cells as described herein. Pharmaceutically acceptable carriers for cell-based therapeutic formulation include saline and aqueous buffer solutions, Ringer's solution, and serum component, such as serum albumin, HDL and LDL. The terms such as "excipient," "carrier," "pharmaceutically acceptable carrier" or the like are used interchangeably herein.

In some embodiments, the pharmaceutical composition comprising activated CAR T cells as described herein can be a parenteral dose form. Since administration of parenteral dosage forms typically bypasses the patient's natural defenses against contaminants, the components apart from the CAR T cells themselves are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Any of these can be added to the activated CAR T cells preparation prior to administration.

Suitable vehicles that can be used to provide parenteral dosage forms of activated CAR T cells as disclosed within are well known to those skilled in the art. Examples include, without limitation: saline solution; glucose solution; aqueous vehicles including but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Dosage

"Unit dosage form" as the term is used herein refers to a dosage for suitable one administration. By way of example a unit dosage form can be an amount of therapeutic disposed in a delivery device, e.g., a syringe or intravenous drip bag. In one embodiment, a unit dosage form is administered in a single administration. In another, embodiment more than one unit dosage form can be administered simultaneously.

In some embodiments, the activated CAR T cells described herein are administered as a monotherapy, i.e., another treatment for the condition is not concurrently administered to the subject.

A pharmaceutical composition comprising the T cells described herein can generally be administered at a dosage of $10^4$ to $10^9$ cells/kg body weight, in some instances $10^5$ to $10^6$ cells/kg body weight, including all integer values within those ranges. If necessary, T cell compositions can also be administered multiple times at these dosages. The cells can be administered by using infusion techniques that are commonly known in immunotherapy (see, e.g., Rosenberg et al., New Engl. J. Med. 319:1676, 1988).

In certain aspects, it may be desired to administer activated CAR T cells to a subject and then subsequently redraw blood (or have an apheresis performed), activate T cells therefrom as described herein, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

Modes of administration can include, for example intravenous (i.v.) injection or infusion. The compositions described herein can be administered to a patient transarterially, intratumorally, intranodally, or intramedullary. In some embodiments, the compositions of T cells may be injected directly into a tumor, lymph node, or site of infection. In one embodiment, the compositions described herein are administered into a body cavity or body fluid (e.g., ascites, pleural fluid, peritoneal fluid, or cerebrospinal fluid).

In a particular exemplary aspect, subjects may undergo leukapheresis, wherein leukocytes are collected, enriched, or depleted ex vivo to select and/or isolate the cells of interest, e.g., T cells. These T cell isolates can be expanded by contact with an artificial antigen presenting cell (aAPC), e.g., an aAPC expressing anti-CD28 and anti-CD3 CDRs, and treated such that one or more CAR constructs of the invention may be introduced, thereby creating a CAR T cell. Subjects in need thereof can subsequently undergo standard treatment with high dose chemotherapy followed by peripheral blood stem cell transplantation. Following or concurrent with the transplant, subjects can receive an infusion of the expanded CAR T cells. In one embodiment, expanded cells are administered before or following surgery.

In some embodiments, lymphodepletion is performed on a subject prior to administering one or more CAR T cell as described herein. In such embodiments, the lymphodepletion can comprise administering one or more of melphalan, cytoxan, cyclophosphamide, and fludarabine.

The dosage of the above treatments to be administered to a patient will vary with the precise nature of the condition being treated and the recipient of the treatment. The scaling of dosages for human administration can be performed according to art-accepted practices.

In some embodiments, a single treatment regimen is required. In others, administration of one or more subsequent doses or treatment regimens can be performed. For example, after treatment biweekly for three months, treatment can be repeated once per month, for six months or a year or longer. In some embodiments, no additional treatments are administered following the initial treatment.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further cells, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

Combinational Therapy

The activated CAR T cells described herein can be used in combination with other known agents and therapies. In one embodiment, the subject is administered an anti-CD19 therapy and an anti-CD79b therapy. In another embodiment, the subject is further administered an anti-BCMA therapy. Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The activated CAR T cells described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed. The CAR T therapy and/or other therapeutic agents, procedures, or modalities can be administered during periods of active disorder, or during a period of remission or less active disease. The CAR T therapy can be administered before another treatment, concurrently with the treatment, post-treatment, or during remission of the disorder.

When administered in combination, the activated CAR T cells and the additional agent (e.g., second or third agent), or all, can be administered in an amount or dose that is higher, lower or the same as the amount or dosage of each agent used individually, e.g., as a monotherapy. In certain embodiments, the administered amount or dosage of the activated CAR T cells, the additional agent (e.g., second or third agent), or all, is lower (e.g., at least 20%, at least 30%, at least 40%, or at least 50%) than the amount or dosage of each agent used individually. In other embodiments, the amount or dosage of the activated CAR T cells, the additional agent (e.g., second or third agent), or all, that results in a desired effect (e.g., treatment of cancer) is lower (e.g., at least 20%, at least 30%, at least 40%, or at least 50% lower) than the amount or dosage of each agent individually required to achieve the same therapeutic effect. In further embodiments, the activated CAR T cells described herein can be used in a treatment regimen in combination with surgery, chemotherapy, radiation, an mTOR pathway inhibitor, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, rapamycin, mycophenolic acid, steroids, FR901228, cytokines, or a peptide vaccine, such as that described in Izumoto et al., J. Neurosurg. 108:963-971, 2008.

In one embodiment, the activated CAR T cells described herein can be used in combination with a checkpoint inhibitor. Exemplary checkpoint inhibitors include anti-PD-1 inhibitors (Nivolumab, MK-3475, Pembrolizumab, Pidilizumab, AMP-224, AMP-514), anti-CTLA4 inhibitors (Ipilimumab and Tremelimumab), anti-PDL1 inhibitors (Atezolizumab, Avelomab, MSB0010718C, MEDI4736, and MPDL3280A), and anti-TIM3 inhibitors.

In one embodiment, the activated CAR T cells described herein can be used in combination with a chemotherapeutic agent. Exemplary chemotherapeutic agents include an anthracycline (e.g., doxorubicin (e.g., liposomal doxorubicin)), a *vinca* alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide). General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®). Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®). Exemplary mTOR inhibitors include, e.g., temsirolimus; ridaforolimus (formally known as deferolimus, (IR,2R,45)-4-[(2R)-2 [(1R, 95,125,15R,16E,18R,19R,21R,235,24E,26E,28Z,305,325, 35R)-1,18-dihydroxy-19,30-dimethoxy-15,17,21,23,29,35-hexamethyl-2,3,10,14,20-pentaoxo-11,36-dioxa-4-azatricyclo[30.3.1.04'9]hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RADOOI); rapamycin (AY22989, Sirolimus®); simapimod (CAS 164301-51-3); emsirolimus, (5-{2,4-Bis[(35,)-3-methylmorpholin-4-yl]pyrido[2,3-(i]pyrimidin-7-yl}-2- methoxyphenyl)methanol (AZD8055); 2-Amino-8-[iraw5,-4-(2-hydroxyethoxy)cyclohexyl]-6-(6-methoxy-3-pyridinyl)-4-methyl-pyrido[2,3-JJpyrimidin-7(8H)-one (PF04691502, CAS 1013101-36-4); and N2-[1,4-dioxo-4-[[4-(4-oxo-8-phenyl-4H-1-benzopyran-2-yl)morpholinium-4-yl]methoxy]butyl]-L-arginylglycyl-L-a-aspartylL-serine, inner salt (SF1126, CAS 936487-67-1), and XL765. Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics). Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin. Exemplary *vinca* alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®). Exemplary proteosome inhibitors include bortezomib (Velcade®); carfilzomib (PX-171-007, (5)-4-Methyl-N-((5)-1-(((5)-4-methyl-1-((R)-2-methyloxiran-2-yl)-1-oxopentan-2-yl)amino)-1-oxo-3-phenylpropan-2-yl)-2-((5,)-2-(2-morpholinoacetamido)-4-phenylbutanamido)-pentanamide); marizomib (NPT0052); ixazomib citrate (MLN-9708); delanzomib (CEP-18770); and O-Methyl-N-[(2-methyl-5-thiazolyl)carbonyl]-L-seryl-O-methyl-N-[(IIS')-2-[(2R)-2-methyl-2-oxiranyl]-2-oxo-1-(phenylmethyl)ethyl]-L-serinamide (ONX-0912).

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed., St. Louis, Mosby-Year Book, 2003).

In an embodiment, activated CAR T cells described herein are administered to a subject in combination with a molecule that decreases the activity and/or level of a molecule targeting GITR and/or modulating GITR functions, a molecule that decreases the Treg cell population, an mTOR inhibitor, a GITR agonist, a kinase inhibitor, a non-receptor tyrosine kinase inhibitor, a CDK4 inhibitor, and/or a BTK inhibitor.

Efficacy

The efficacy of activated CAR T cells in, e.g., the treatment of a condition described herein, or to induce a response as described herein (e.g., a reduction in cancer cells) can be determined by the skilled clinician. However, a treatment is considered "effective treatment," as the term is used herein, if one or more of the signs or symptoms of a condition described herein is altered in a beneficial manner, other clinically accepted symptoms are improved, or even ameliorated, or a desired response is induced, e.g., by at least 10% following treatment according to the methods described herein. Efficacy can be assessed, for example, by measuring a marker, indicator, symptom, and/or the incidence of a condition treated according to the methods described herein or any other measurable parameter appropriate. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

Efficacy can also be measured by a failure of an individual to worsen as assessed by hospitalization, or need for medical interventions (i.e., progression of the disease is halted). Methods of measuring these indicators are known to those of skill in the art and/or are described herein.

Treatment includes any treatment of a disease in an individual or an animal (some non-limiting examples include a human or an animal) and includes: (1) inhibiting the disease, e.g., preventing a worsening of symptoms (e.g., pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy of a given approach can be assessed in animal models of a condition described herein, for example, treatment of lymphoma as described herein. When using an experimental animal model, efficacy of treatment is evidenced when a statistically significant change in a marker is observed.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

All such modifications are intended to be included within the scope of the appended claims.

The invention is further described in the following numbered paragraphs:

1. A chimeric antigen receptor (CAR) comprising an extracellular domain comprising a CD79b-binding domain and a CD19-binding domain.

2. The CAR of paragraph 1, wherein the CD79b-binding domain comprises an antibody, or an antigen binding fragment thereof.

3. The CAR of paragraph 1 or 2, wherein the CD79b-binding domain comprises a single chain variable fragment (scFv).

4. The CAR of any one of paragraphs 1-3, wherein the CD19-binding domain comprises an antibody, or an antigen binding fragment thereof.

5. The CAR of any one of paragraphs 1-4, wherein the CD19-binding domain comprises an scFv.

6. The CAR of any one of paragraphs 1-5, wherein the CD79b-binding domain is positioned N-terminal to the CD19-binding domain.

7. The CAR of any one of paragraphs 1-5, wherein the CD19-binding domain is positioned N-terminal to the CD79b-binding domain.

8. The CAR of any one of paragraphs 1-7, wherein the CD79b-binding domain and the CD19– binding domain are connected by a linker sequence, optionally comprising the amino acid sequence of SEQ ID NO: 7, 20, 21, 22, or 23.

9. The CAR of any one of paragraphs 1-8, wherein the CAR comprises a transmembrane domain and an intracellular signaling domain.

10. The CAR of any one of paragraphs 1-9, wherein the CAR further comprises one or more co-stimulatory domains.

11. The CAR of paragraph 9 or 10, wherein the transmembrane domain comprises a hinge/transmembrane domain.

12. The CAR of paragraph 11, wherein the hinge/transmembrane domain comprises the hinge/transmembrane domain of an immunoglobulin-like protein, CD28, CD8, or 4-1 BB.

13. The CAR of paragraph 11 or 12, wherein the hinge/transmembrane domain comprises the hinge/transmembrane domain of CD8, optionally comprising the amino acid sequence of SEQ ID NO: 11.

14. The CAR of any one of paragraphs 9-13, wherein the intracellular signaling domain comprises the intracellular signaling domain of TCRζ, FcRγ, FcRβ, CD3γ, CD3δ, CD3δ, CD3ε, CD3η, CD3ζ, CD22, CD79a, CD79b, or CD66d.

15. The CAR of paragraph 14, wherein the intracellular signaling domain comprises the intracellular signaling domain of CD3ζ, optionally comprising the amino acid sequence of SEQ ID NO: 13.

16. The CAR of any one of paragraphs 10-15, wherein the co-stimulatory domain comprises the co-stimulatory domain of 4-1BB, CD27, CD28, or OX40.

17. The CAR of paragraph 16, wherein the co-stimulatory domain comprises the co-stimulatory domain of 4-1BB, optionally comprising the amino acid sequence of SEQ ID NO: 12.

18. The CAR of any one of paragraphs 1-17, wherein the CD79b-binding domain comprises a heavy chain variable domain (VH) comprising an amino acid sequence having at least 90% sequence identity to the amino acid sequence of SEQ ID NO: 9 and a light chain variable domain (VL) comprising an amino acid sequence having at least 90% sequence identity to the amino acid sequence of SEQ ID NO: 8.

19. The CAR of paragraph 18, wherein the VH comprises the amino acid sequence of SEQ ID NO: 9 and the VL comprises the amino acid sequence of SEQ ID NO: 8.

20. The CAR of any one of paragraphs 1-19, wherein the CD79b-binding domain comprises an amino acid sequence having at least 90% sequence identity to the amino acid sequence of SEQ ID NO: 10.

21. The CAR of paragraph 20, wherein the CD79b-binding domain comprises the amino acid sequence of SEQ ID NO: 10.

22. The CAR of any one of paragraphs 1-21, wherein the CD19-binding domain comprises a VH comprising an amino acid sequence having at least 90% sequence identity to the amino acid sequence of SEQ ID NO: 5 and a VL comprising an amino acid sequence having at least 90% sequence identity to the amino acid sequence of SEQ ID NO: 4.

23. The CAR of paragraph 22, wherein the VH comprises the amino acid sequence of SEQ ID NO: 5 and the VL comprises the amino acid sequence of SEQ ID NO: 4.

24. The CAR of any one of paragraphs 1-23, wherein the CD19-binding domain comprises an amino acid sequence having at least 90% sequence identity to the amino acid sequence of SEQ ID NO: 6.

25. The CAR of paragraph 24, wherein the CD19-binding domain comprises the amino acid sequence of SEQ ID NO: 6.

26. The CAR of any one of paragraphs 1-25, wherein the CAR comprises an amino acid sequence having at least 90% sequence identity to the amino acid sequence of SEQ ID NO: 1, 2, 24, or 25.

27. The CAR of paragraph 26, wherein the CAR comprises the amino acid sequence of SEQ ID NO: 1, 2, 24, or 25.

28. A polynucleotide encoding the CAR of any one of paragraphs 1-27.

29. The polynucleotide of paragraph 28, further comprising a suicide gene.

30. The polynucleotide of paragraph 28 or 29, further comprising a sequence encoding a signal sequence.

31. A vector comprising the polynucleotide of any one of paragraphs 28-30.

32. An immune cell comprising the CAR of any one of paragraphs 1-27, the polynucleotide of any one of paragraphs 28-30, and/or the vector of paragraph 31.

33. The immune cell of paragraph 32, wherein the immune cell is a T cell or a natural killer (NK) cell.

34. The immune cell of paragraph 32 or 33, wherein the immune cell is a human cell.

35. A pharmaceutical composition comprising the polynucleotide of any one of paragraphs 28-30, the vector of paragraph 31, and/or the immune cell of any one of paragraphs 32-34 and a pharmaceutically acceptable carrier.

36. A method of treating a cancer in a subject in need thereof, the method comprising administering the polynucleotide of any one of paragraphs 28-30, the vector of paragraph 31, the immune cell of any one of paragraphs 32-34, and/or the pharmaceutical composition of paragraph 35 to the subject.

37. The method of paragraph 36, wherein the cancer is a lymphoma or a leukemia.

38. The method of paragraph 36 or 37, wherein the cancer is mantle cell lymphoma (MCL), diffuse large B-cell lymphoma (DLBCL), primary mediastinal B-cell lymphoma (PMBCL), chronic lymphocytic leukemia (CLL), small lymphocytic lymphoma (SLL), follicular lymphoma, or transformed follicular lymphoma.

39. The method of any one of paragraphs 36-38, wherein the cancer comprises cells expressing CD19.

40. The method of any one of paragraphs 36-39, wherein the cancer comprises cells expressing CD79b.

41. The method of any one of paragraphs 36-40, wherein the subject is resistant to anti-CD19 therapy.

42. A method of treating a subject who has relapsed with CD19-negative lymphoma after receiving anti-CD19 CAR therapy, the method comprising administering the polynucleotide of any one of paragraphs 28-30, the vector of paragraph 31, the immune cell of any one of paragraphs 32-34, and/or the pharmaceutical composition of paragraph 35 to the subject.

The invention is still further described in the following numbered paragraphs:

1. A method for treating a patient suffering from a cancer, the method comprising administering to the patient a therapeutically effective amount of an anti-cancer therapy comprising a chimeric antigen receptor (CAR) comprising an extracellular domain comprising a CD79b-binding domain and a CD19– binding domain, wherein the patient has not been previously treated for the cancer.

2. The method of paragraph 1, wherein the CD79b-binding domain comprises an antibody, or an antigen binding fragment thereof.

3. The method paragraph 1 or 2, wherein the CD79b-binding domain comprises a single chain variable fragment (scFv).

4. The method any one of paragraphs 1-3, wherein the CD19-binding domain comprises an antibody, or an antigen binding fragment thereof.

5. The method any one of paragraphs 1-4, wherein the CD19-binding domain comprises an scFv.

6. The method any one of paragraphs 1-5, wherein the CD79b-binding domain is positioned N-terminal to the CD19-binding domain.

7. The method of any one of paragraphs 1-5, wherein the CD19-binding domain is positioned N-terminal to the CD79b-binding domain.

8. The method of any one of paragraphs 1-7, wherein the CD79b-binding domain and the CD19– binding domain are connected by a linker sequence, optionally comprising the amino acid sequence of SEQ ID NO: 7, 20, 21, 22, or 23.

9. The method of any one of paragraphs 1-8, wherein the CAR comprises a transmembrane domain and an intracellular signaling domain.

10. The method of any one of paragraphs 1-9, wherein the CAR further comprises one or more co-stimulatory domains.

11. The method of paragraph 9 or 10, wherein the transmembrane domain comprises a hinge/transmembrane domain.

12. The method of paragraph 11, wherein the hinge/transmembrane domain comprises the hinge/transmembrane domain of an immunoglobulin-like protein, CD28, CD8, or 4-1 BB.

13. The method of paragraph 11 or 12, wherein the hinge/transmembrane domain comprises the hinge/transmembrane domain of CD8, optionally comprising the amino acid sequence of SEQ ID NO: 11.

14. The method of any one of paragraphs 9-13, wherein the intracellular signaling domain comprises the intracellular signaling domain of TCRζ, FcRγ, FcRβ, CD3γ, CD3δ, CD3δ, CD3ε, CD3η, CD3ζ, CD22, CD79a, CD79b, or CD66d.

15. The method of paragraph 14, wherein the intracellular signaling domain comprises the intracellular signaling domain of CD3ζ, optionally comprising the amino acid sequence of SEQ ID NO: 13.

16. The method of any one of paragraphs 10-15, wherein the co-stimulatory domain comprises the co-stimulatory domain of 4-1 BB, CD27, CD28, or OX40.

17. The method of paragraph 16, wherein the co-stimulatory domain comprises the co-stimulatory domain of 4-1BB, optionally comprising the amino acid sequence of SEQ ID NO: 12.

18. The method of any one of paragraphs 1-17, wherein the CD79b-binding domain comprises a heavy chain variable domain (VH) comprising an amino acid sequence having at least 90% sequence identity to the amino acid sequence of SEQ ID NO: 9 and a light chain variable domain (VL) comprising an amino acid sequence having at least 90% sequence identity to the amino acid sequence of SEQ ID NO: 8.

19. The method of paragraph 18, wherein the VH comprises the amino acid sequence of SEQ ID NO: 9 and the VL comprises the amino acid sequence of SEQ ID NO: 8.

20. The method of any one of paragraphs 1-19, wherein the CD79b-binding domain comprises an amino acid sequence having at least 90% sequence identity to the amino acid sequence of SEQ ID NO: 10.

21. The method of paragraph 20, wherein the CD79b-binding domain comprises the amino acid sequence of SEQ ID NO: 10.

22. The method of any one of paragraphs 1-21, wherein the CD19-binding domain comprises a VH comprising an amino acid sequence having at least 90% sequence identity to the amino acid sequence of SEQ ID NO: 5 and a VL comprising an amino acid sequence having at least 90% sequence identity to the amino acid sequence of SEQ ID NO: 4.

23. The method of paragraph 22, wherein the VH comprises the amino acid sequence of SEQ ID NO: 5 and the VL comprises the amino acid sequence of SEQ ID NO: 4.

24. The method of any one of paragraphs 1-23, wherein the CD19-binding domain comprises an amino acid sequence having at least 90% sequence identity to the amino acid sequence of SEQ ID NO: 6.

25. The method of paragraph 24, wherein the CD19-binding domain comprises the amino acid sequence of SEQ ID NO: 6.

26. The method of any one of paragraphs 1-25, wherein the CAR comprises an amino acid sequence having at least 90% sequence identity to the amino acid sequence of SEQ ID NO: 1, 2, 24, or 25.

27. The method of paragraph 26, wherein the CAR comprises the amino acid sequence of SEQ ID NO: 1, 2, 24, or 25.

28. The method of paragraph 1, wherein the cancer is a lymphoma or a leukemia.

29. The method of paragraph 32, wherein the cancer is mantle cell lymphoma (MCL), diffuse large B-cell lymphoma (DLBCL), primary mediastinal B-cell lymphoma (PMBCL), chronic lymphocytic leukemia (CLL), small lymphocytic lymphoma (SLL), follicular lymphoma, or transformed follicular lymphoma.

30. The method of any one of paragraphs 28-29, wherein the cancer comprises cells expressing CD19.

31. The method of any one of paragraphs 28-30, wherein the cancer comprises cells expressing CD79b.

32. The method of paragraphs 2-31, wherein the CD79b-binding domain and the CD19-binding domain, with either a light-heavy (CAR79b (L/H)) or a heavy-light (CAR79b (H/L)) single-chain variable fragment (scFv) configuration are expressed from a polynucleotide under control of a human EF1α promoter.

33. The method of paragraph 32, wherein the polynucleotide comprises a lentiviral backbone.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

EXAMPLES

Herein, we describe the development of a CAR product targeting CD79b. We initially confirmed expression of CD79b on patient-derived xenografts (PDX) and malignant cells in blood from MCL patients. We show that loss of CD19 at the DNA and RNA level does not interfere with CD79b surface expression, further supporting the use of CD79b as an alternative CAR T cell target in CD19-negative lymphomas. Importantly, we demonstrate potent antitumor effects of anti-CD79b CAR T cells, comparable to anti-CD19 CAR T cells, in vitro and in vivo, with prolonged remission in both cell line-based and patient-derived xenograft lymphoma models. Finally, anti-CD79b CAR T cells alone or arranged in a bi-specific format with an anti-CD19 CAR is able to eliminate CD19-positive, CD19-negative, and mixed CD19– expressing lymphomas in vivo.

As discussed herein, T cells have been engineered to express a chimeric antigen receptor (CAR) against CD19 have recently been FDA-approved for the treatment of relapsed or refractory large B cell lymphoma. Despite the success and curative potential of CD19 CAR T cells, several reports describing disease relapse due to antigen loss are now emerging.

As is described below, we developed a CAR construct directed against CD79b, a critical receptor for successful B cell development that remains highly expressed in several subtypes of B cell lymphoma, including mantle cell lymphoma (MCL). We tested CAR T cells directed against CD79b alone or in combination with CD19 targeting in a single construct, against cell line- and patient-derived xenograft models.

Furthermore, we demonstrate CAR79b antigen-specific recognition and cytotoxicity against a panel of cell lines and patient-derived xenograft models of MCL. Importantly, we show that downregulation of CD19 does not influence surface expression of CD79b and that anti-CD79b CAR T cells alone or arranged in a dual-targeting format with a CD19 single-chain variable fragment (scFv) are able to recognize and eliminate CD19-positive, CD19-negative, and mixed CD19+/CD19– B cell lymphoma.

Our findings demonstrate that CAR T cells targeting CD79b alone or in combination have promise for treating and preventing CD19 antigen escape in B cell lymphomas. CD79b can be targeted with CAR T cells, and this antigen is retained on B cell lymphoma cell lines independent of loss of CD19. Primary human T cells transduced with CARs targeting CD79b alone or in a tandem CAR format with anti-CD19 eradicate CD19-positive, CD19-negative, and mixed CD19-expressing lymphoma cells in a xenograft model.

The following are examples of the methods and compositions of the invention. It is understood that various other embodiments may be practiced, given the description provided herein.

Example 1. CD79b is Expressed on Human Lymphoma Subtypes and MCL Patient Cells

Figure 1B:
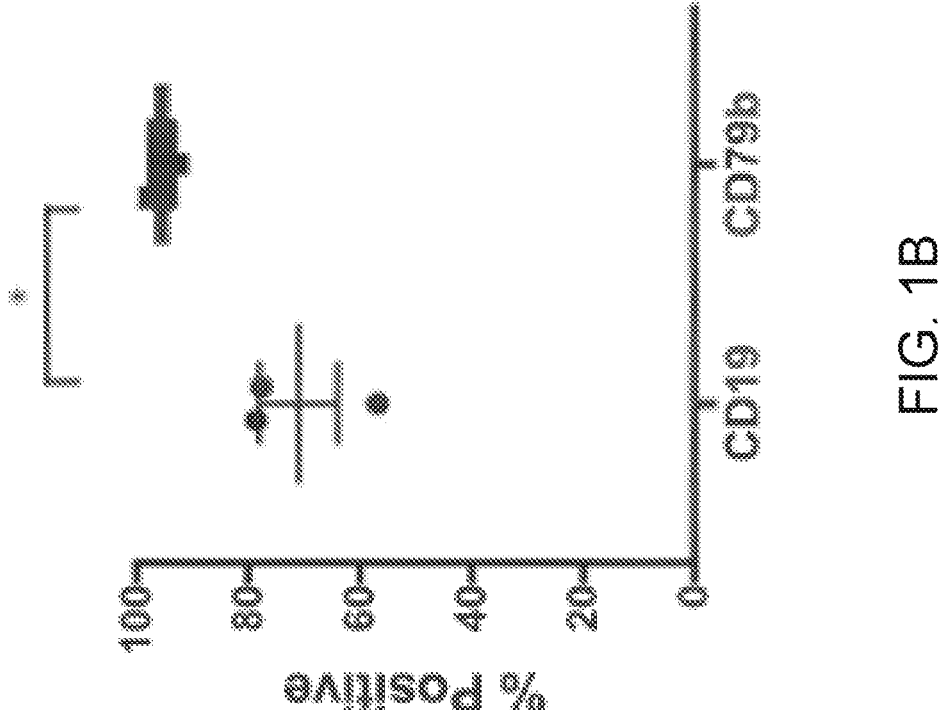
Figure 1C:
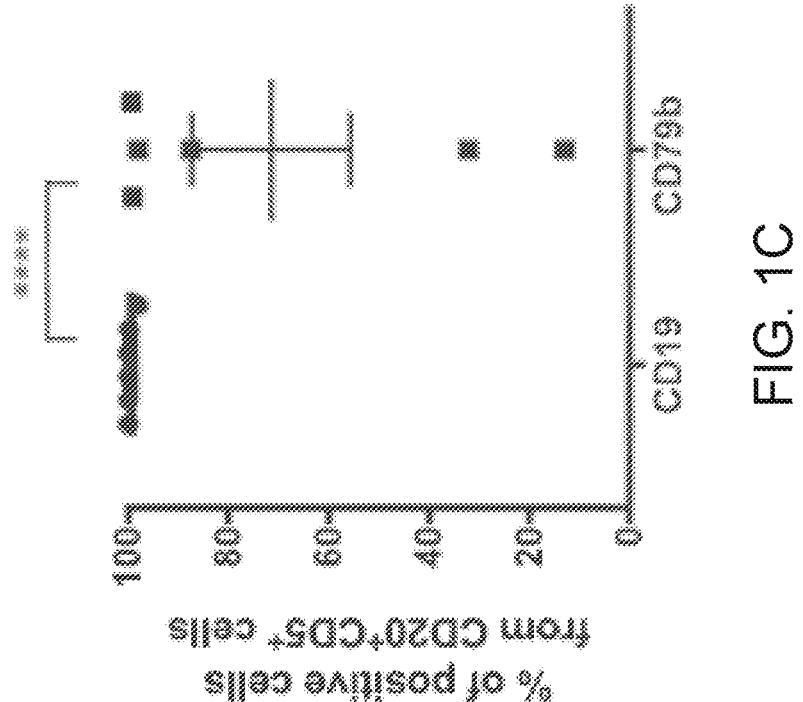
Figure 2A:
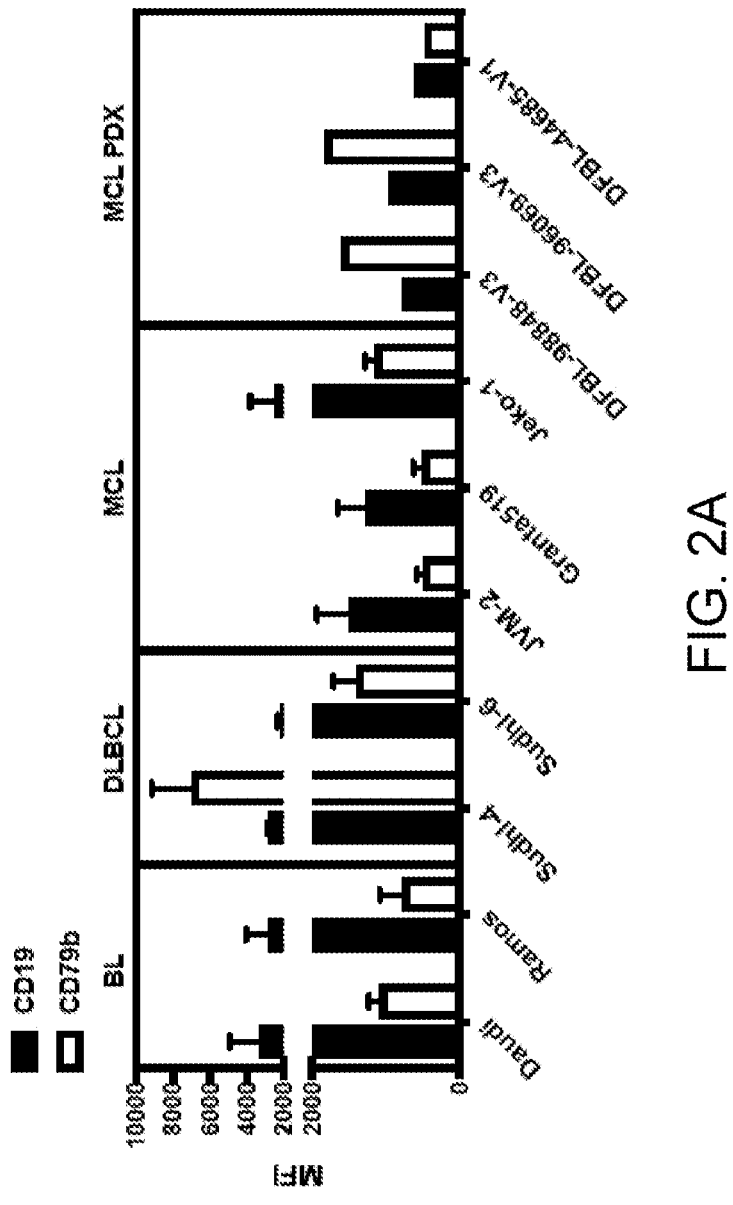
FIG. 2A-FIG. 2C show CD79b and CD19 expression on human lymphomas.
Figure 2B:
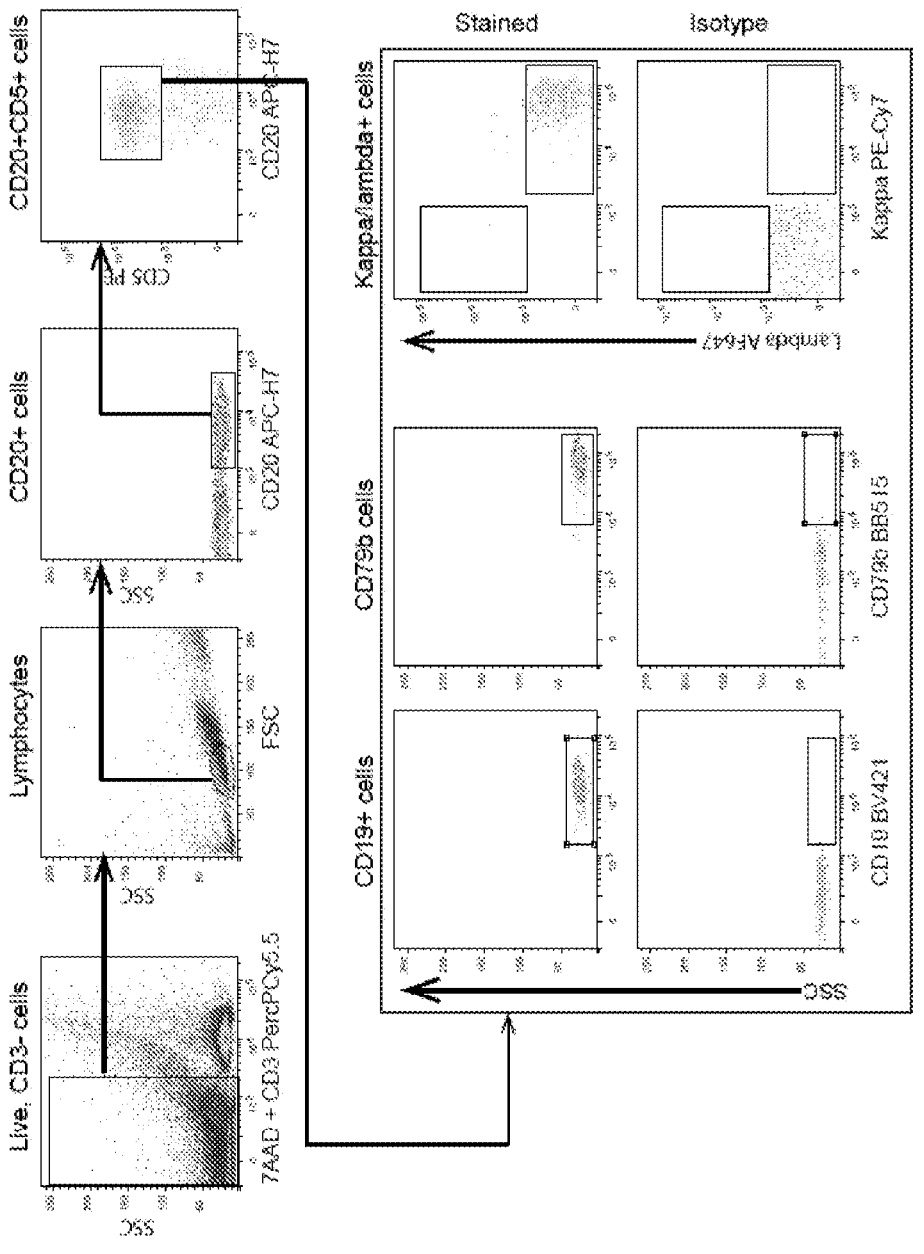
Figure 2C:
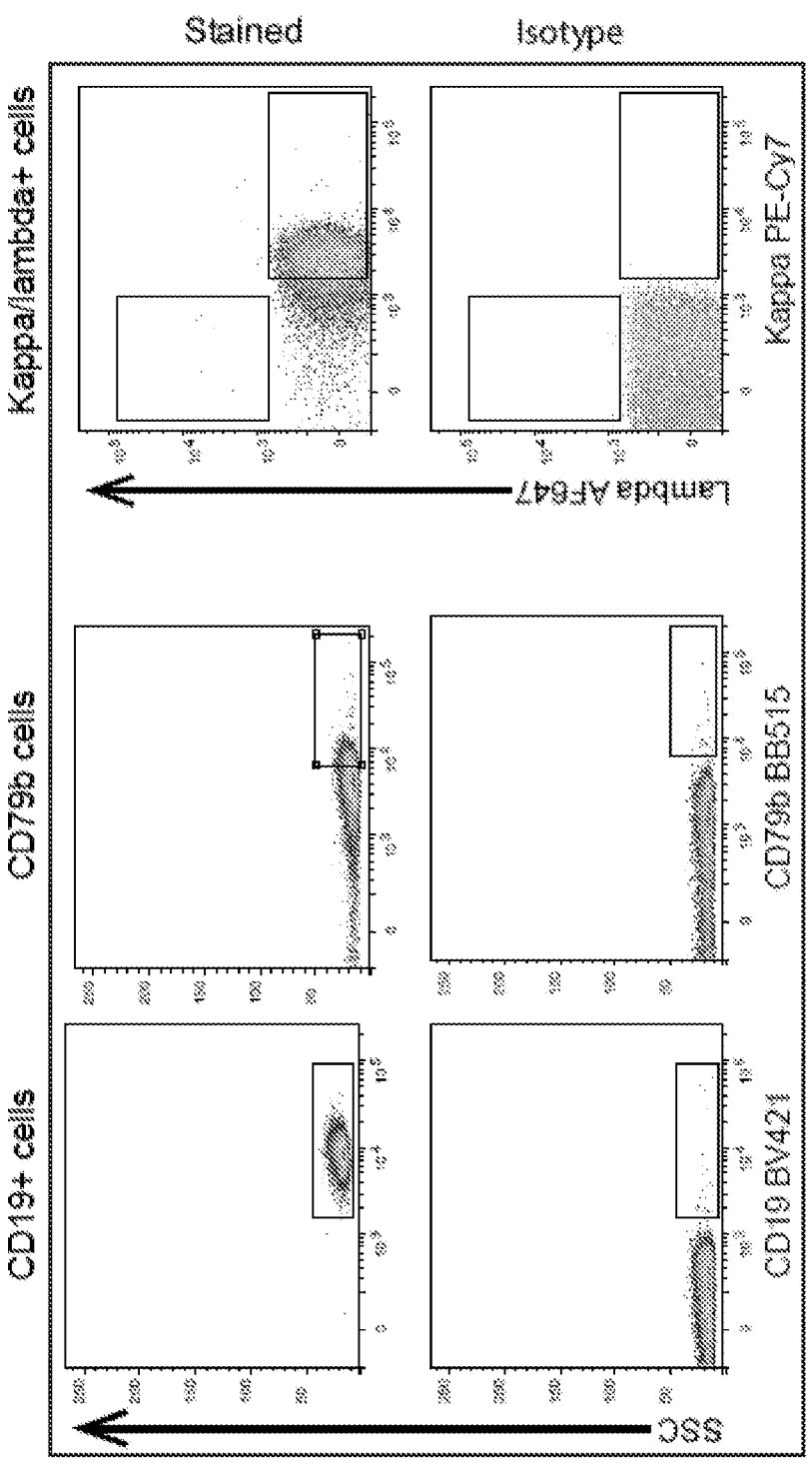

Expression of CD19 and CD79b on B cell tumor lines and MCL-patient-derived xenografts was evaluated by flow cytometry. CD79b and CD19 were expressed on human BL, DLBCL, and MCL, but not multiple myeloma as expected (FIG. 1A and FIG. 2A). In addition, CD79b expression has been reported in patients diagnosed with follicular lymphoma both at presentation and relapse (Blood 2009; 114 (13):2721-9). We noted a high frequency and homogeneity of CD79b-positive cells in the MCL PDX samples, to a greater degree than for CD19 (FIG. 1B). Next, we evaluated the expression of CD79b and CD19 on malignant cells in blood from six patients diagnosed with MCL (FIG. 1C). Malignant cells were gated as CD3-CD20+CD5+B cells, and expression was analyzed by flow cytometry (FIG. 2B and FIG. 2C). All malignant cells expressed CD19, but unlike in the PDX models, the frequency CD79b-positive malignant cells appeared to be more variable.

Example 2. Design of Anti-CD79b CAR Constructs

Figure 1D:
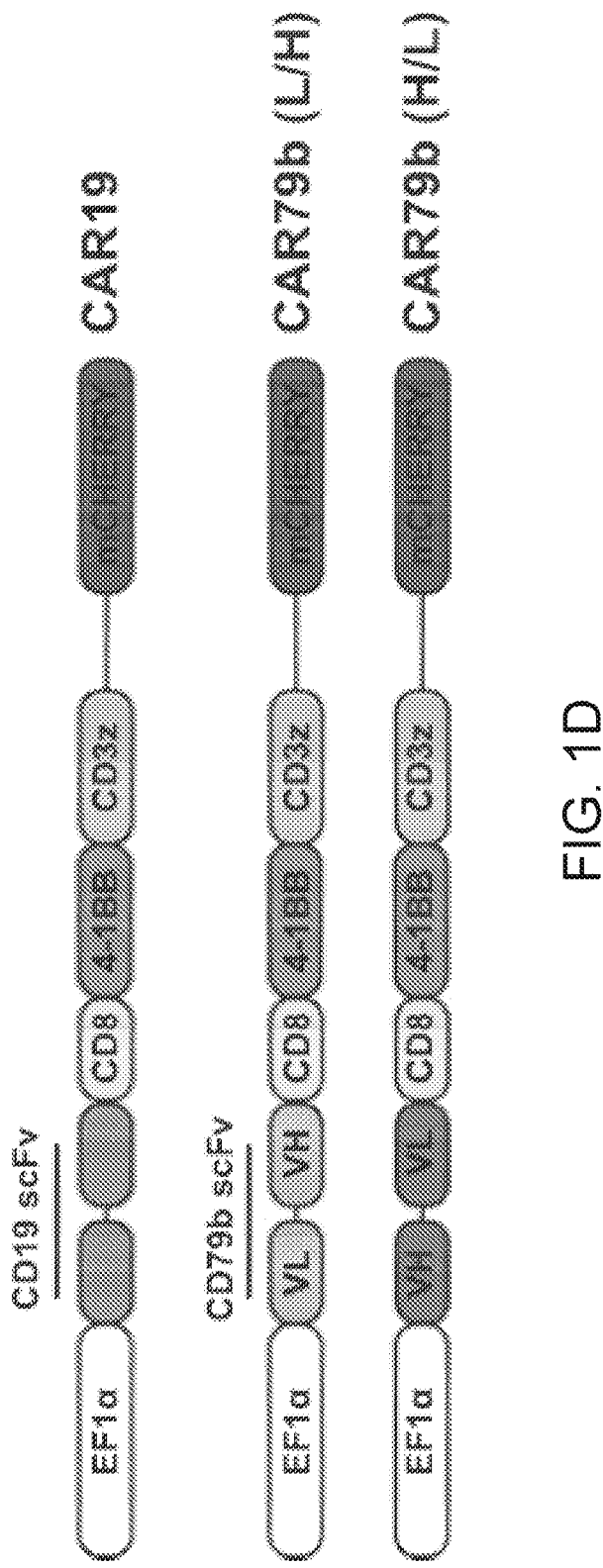
Figure 3A:
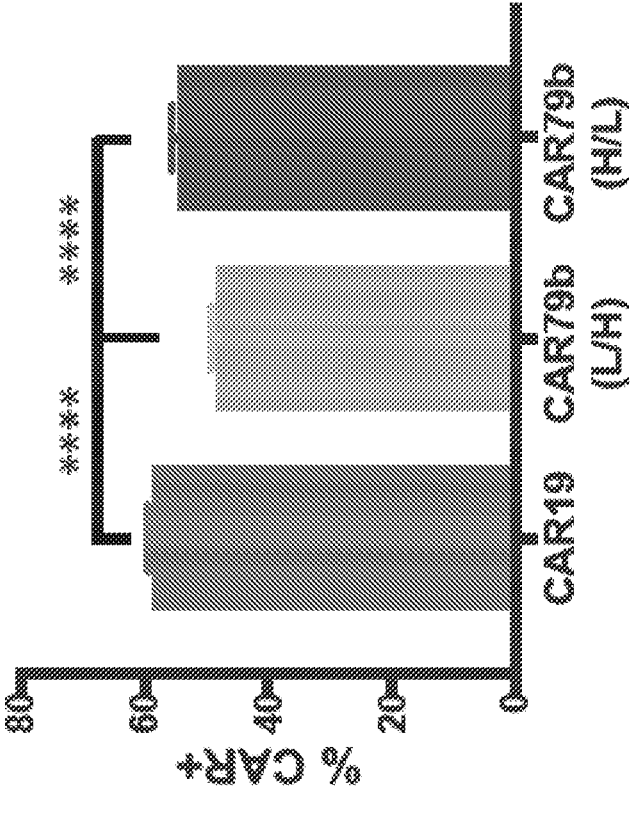
FIG. 3A-FIG. 3C shows transduction efficiency and in vitro activation of CAR T cells.
Figure 3A:
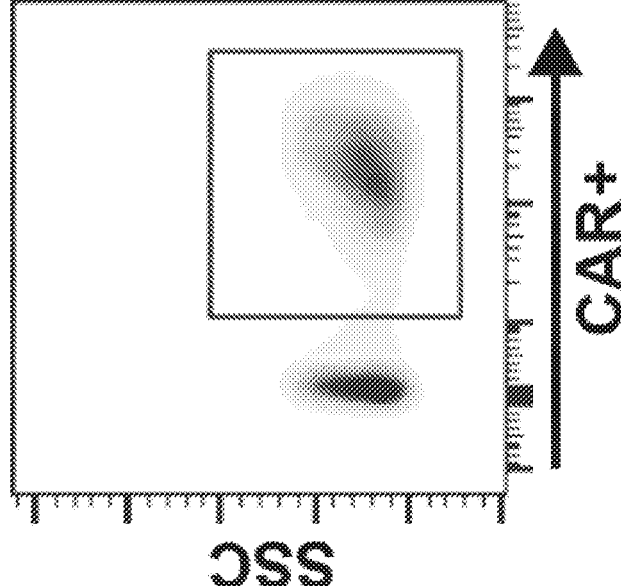

We designed two second-generation CAR constructs directed against CD79b. Both constructs included an anti-CD79b scFv connected via a CD8 hinge and transmembrane domain to an intracellular 4-1 BB signaling domain and a CD3 zeta activation domain (FIG. 1D). The scFv was synthesized in a light-heavy (L/H) or a heavy-light (H/L) orientation of the variable domains generating CAR79b (L/H) or CAR79b (H/L) CAR T cells. For comparison, we generated a CAR19, and used the same hinge, transmembrane, and signaling domains as in the CD79b CARs. In order to determine transduction efficiency easily, we incorporated an mCherry fluorescent protein, separated from the CARsequence by a T2A element. High transduction efficiencies of activated human T cells were routinely obtained using a third-generation, self-inactivating lentiviral vector system (FIG. 3A). We observed similar transduction efficiency across multiple donors for CAR19 compared to CAR79b (L/H) and CAR79b (H/L).

Example 3. CD79b CAR T Cells have Potent Effector Functions In Vitro

Figure 1E:
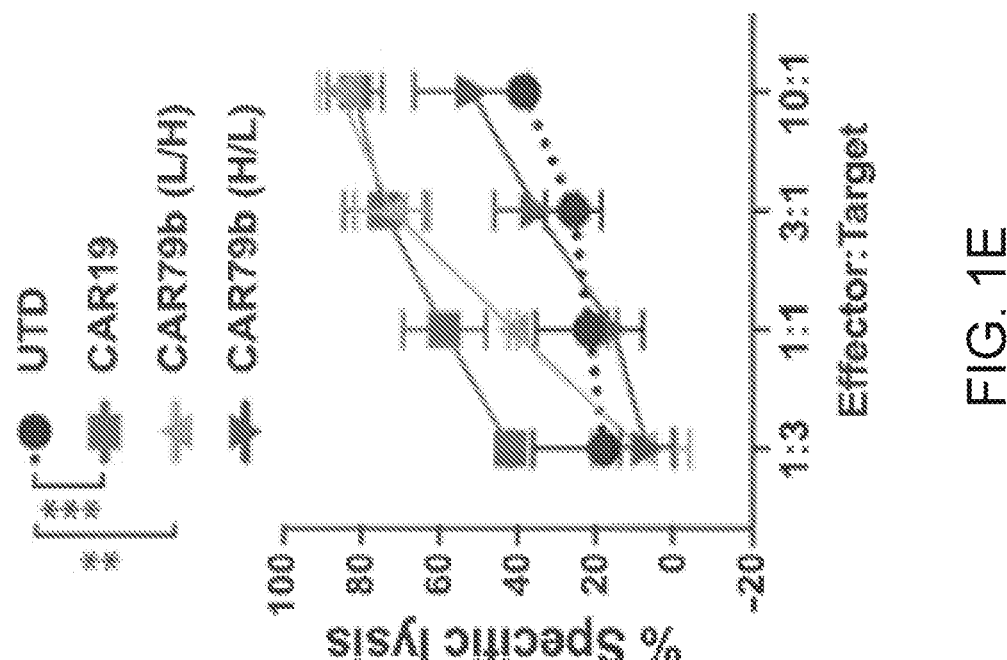
Figure 1F:
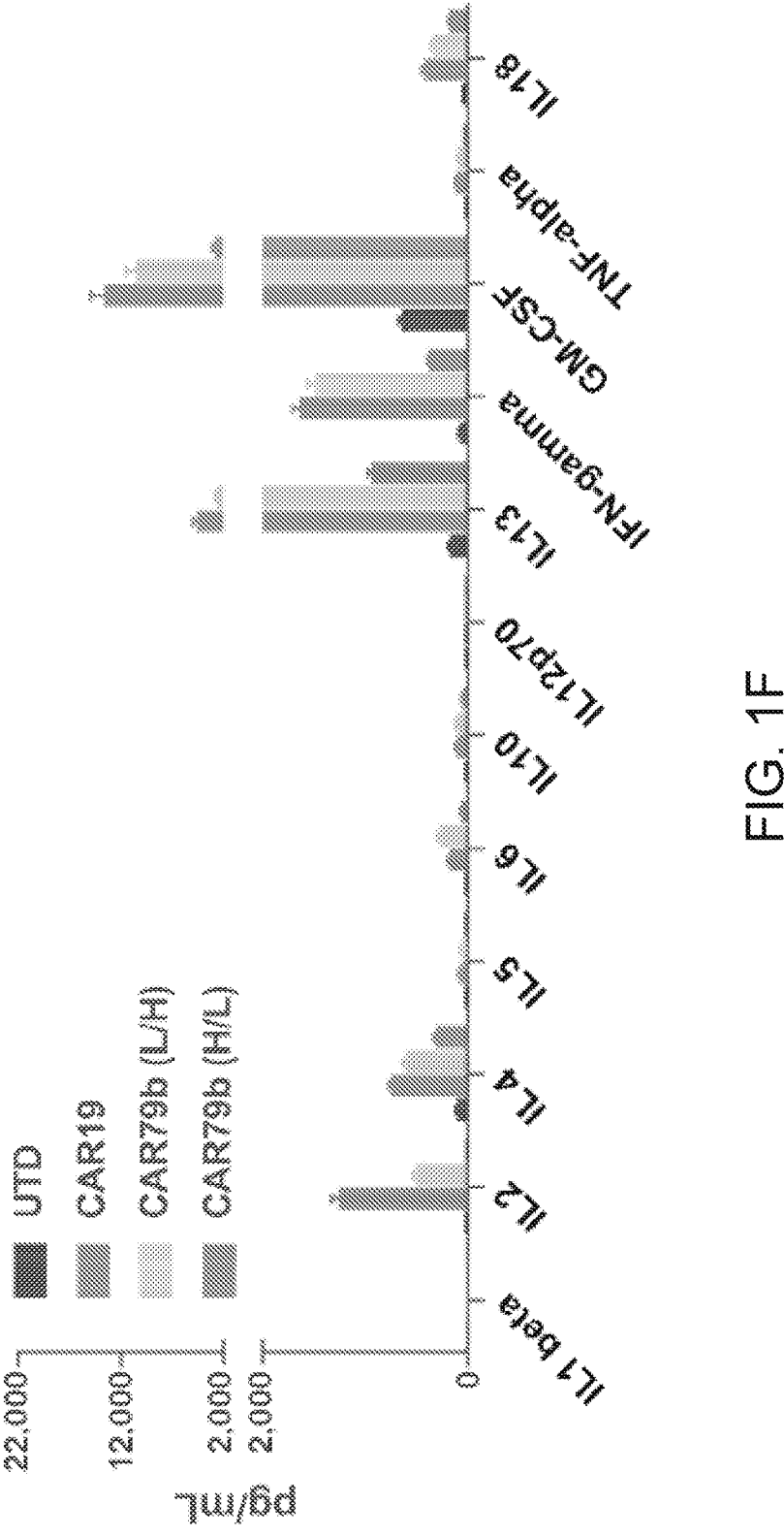
Figure 3B:
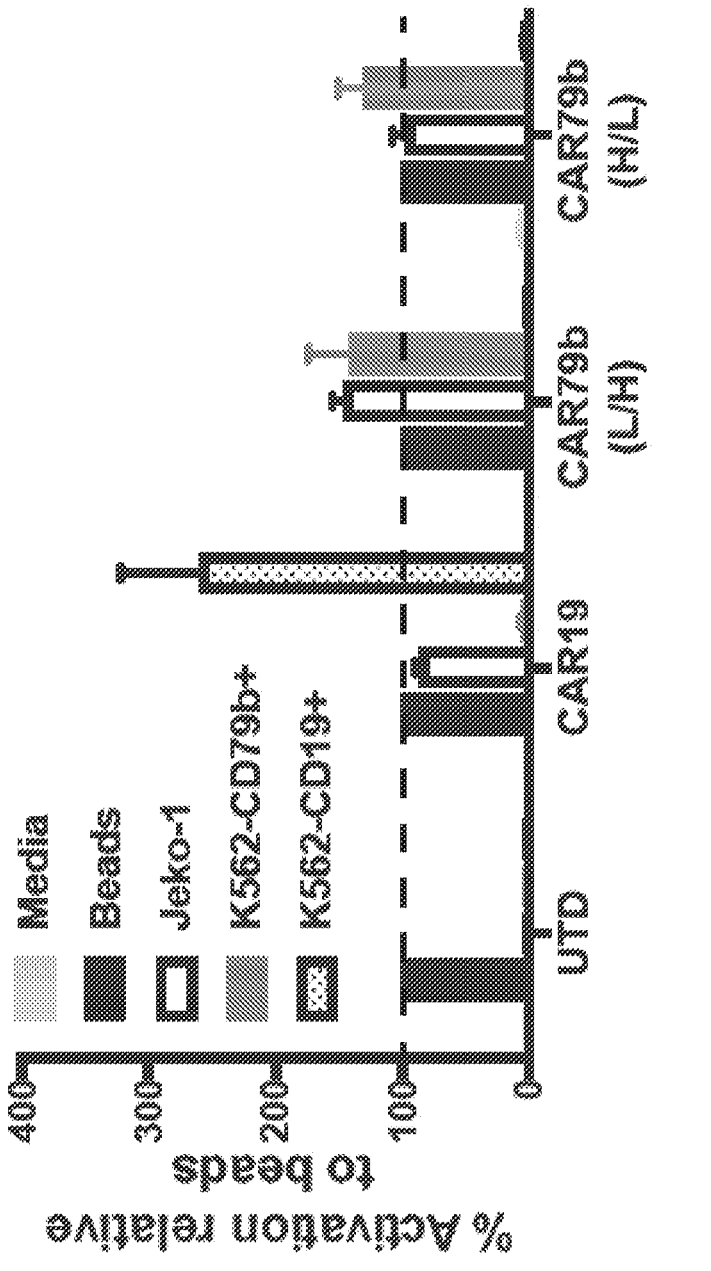
Figure 3C:
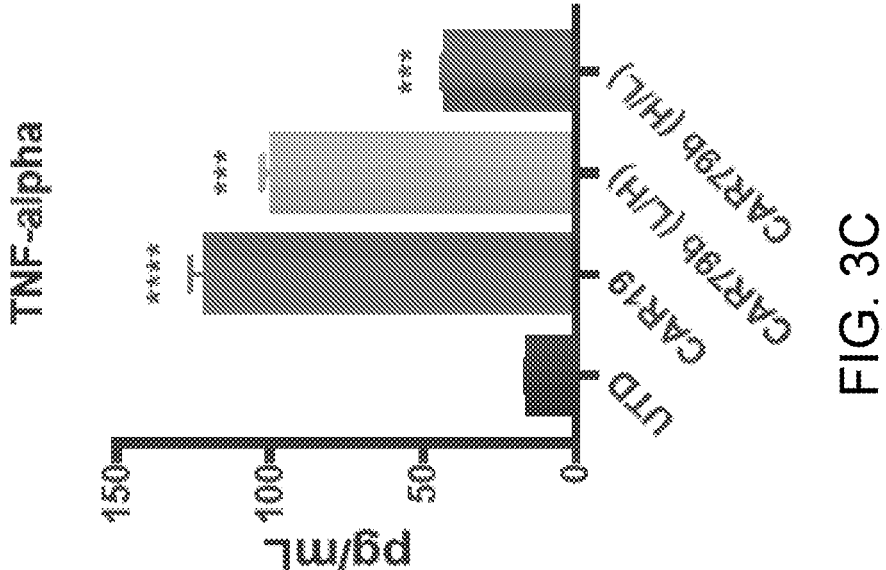

We designed a series of in vitro experiments to test the efficacy of the anti-CD79b CAR T cells. First, the ability of CAR T cells to be activated in response to antigen was tested. The different CAR constructs were transduced into the Jurkat-NFAT reporter T cell line. After transduction, Jurkat-NFAT cells were co-cultured with the MCL cell line Jeko-1, K562 transduced to express either CD19 or CD79b, anti-CD3/CD28 Dynabeads for positive control, or media for negative control. NFAT mediated luminescence demonstrated activation of Jurkat T cells in response to antigen-specific stimulation (FIG. 3B). We noted comparable levels of activation between CAR19 and CD79b CAR T cells in response to the CD19-positive MCL tumor cell line Jeko-1. Luminescent signal was only observed when CD79b CAR T cells were stimulated with K562–CD79b+ but not K562–CD19+, indicating that activation was antigen-specific. To evaluate the cytotoxic efficacy of the anti-CD79b CAR T cells, we performed tumor lysis assays against Jeko-1 transduced to express luciferase. CAR T cells were co-cultured overnight with tumor cells at various effector-target ratios (FIG. 1E). Only anti-CD79b CAR T cells bearing the L/H scFv configuration showed increased cytotoxicity compared to untransduced T cells. Importantly, the ability of CAR79b (L/H) T cells to lyse tumor cells was comparable to CAR19. Next, we analyzed the production of cytokines from CAR T cells in response to antigen-specific stimulation. CAR T cells were co-cultured overnight with either Jeko-1 cells, anti-CD3/CD28 Dynabeads as a positive control, or media as a negative control. The pattern of cytokine production in response to Jeko-1 cells—especially with upregulation of Th1 cytokines IL-2, IFN-$\gamma$, GM-CSF and TNF$\alpha$—was similar among different groups of CAR T cells (FIG. 1F and FIG. 3C). In general, CAR19 produced slightly higher levels of cytokines compared to the CD79b CAR T cells. The levels of cytokine production correlating to optimal CAR-mediated killing is not known. Consistent with the cytotoxicity assays, CAR79b with the H/L configuration produced the lowest levels of cytokines in response to antigen. Together this set of in vitro experiments demonstrated superior antigen-specific effector functions of CAR79b (L/H) compared to CAR79b (H/L).

Figure 4A:
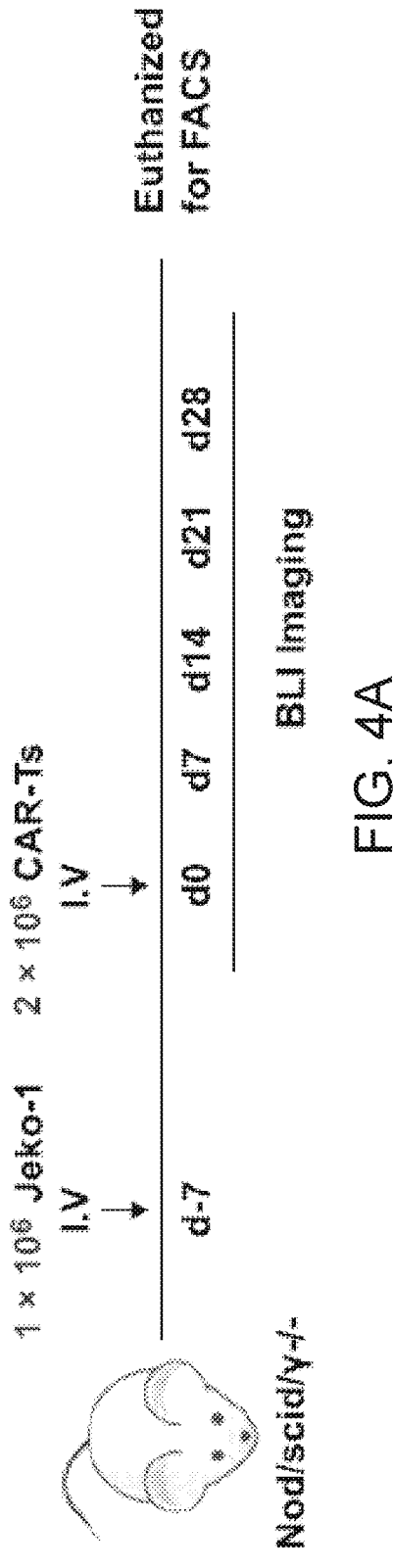
FIG. 4A-FIG. 4E show CAR79b (L/H) induced tumor clearance and persistence in an MCL xenograft model.
Figure 4B:
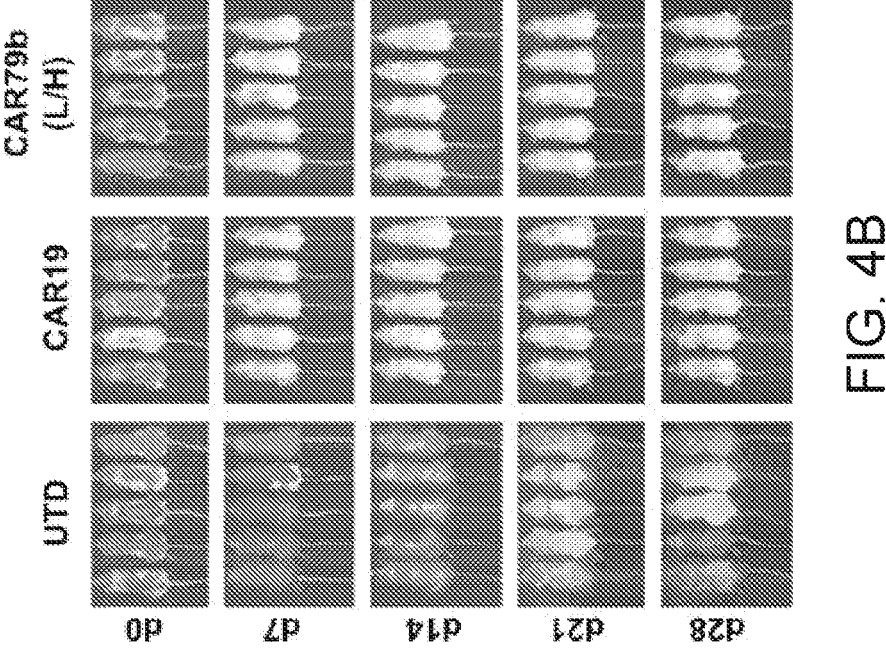
Figure 4C:
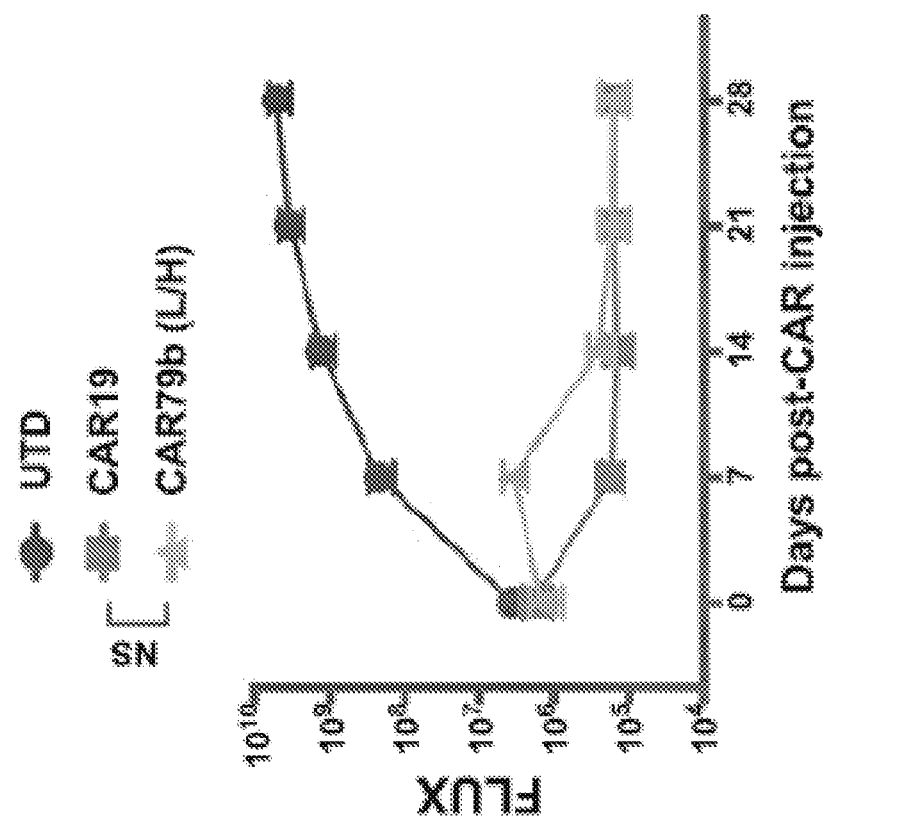
Figure 4D:
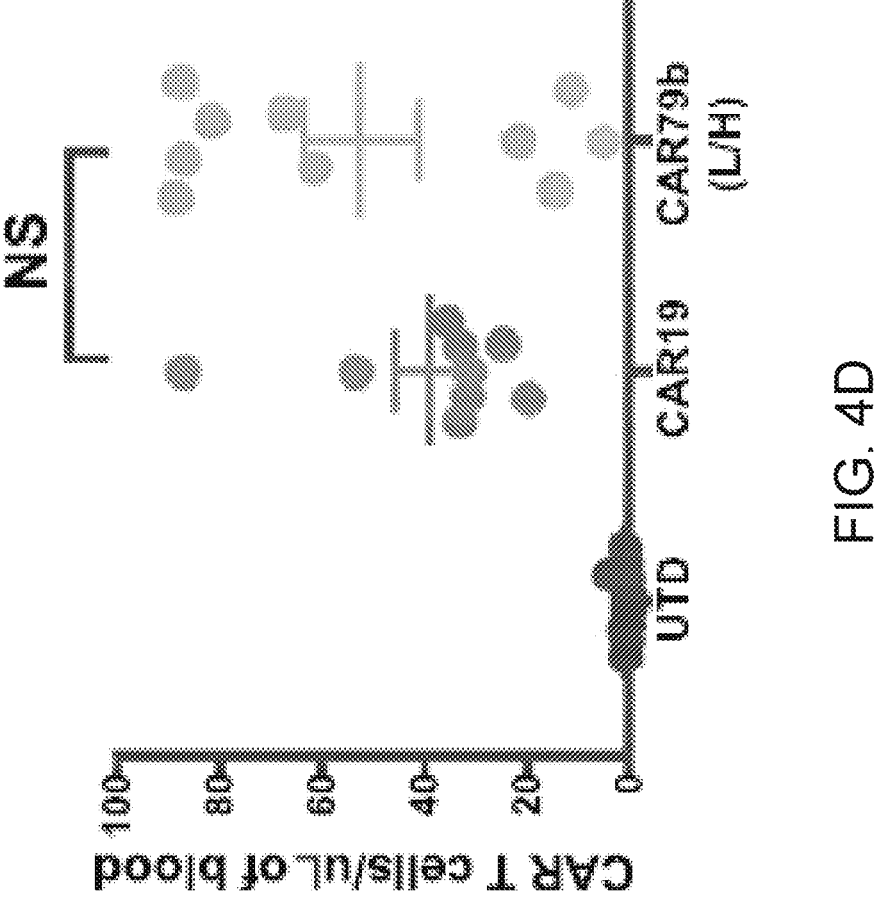
Figure 4E:
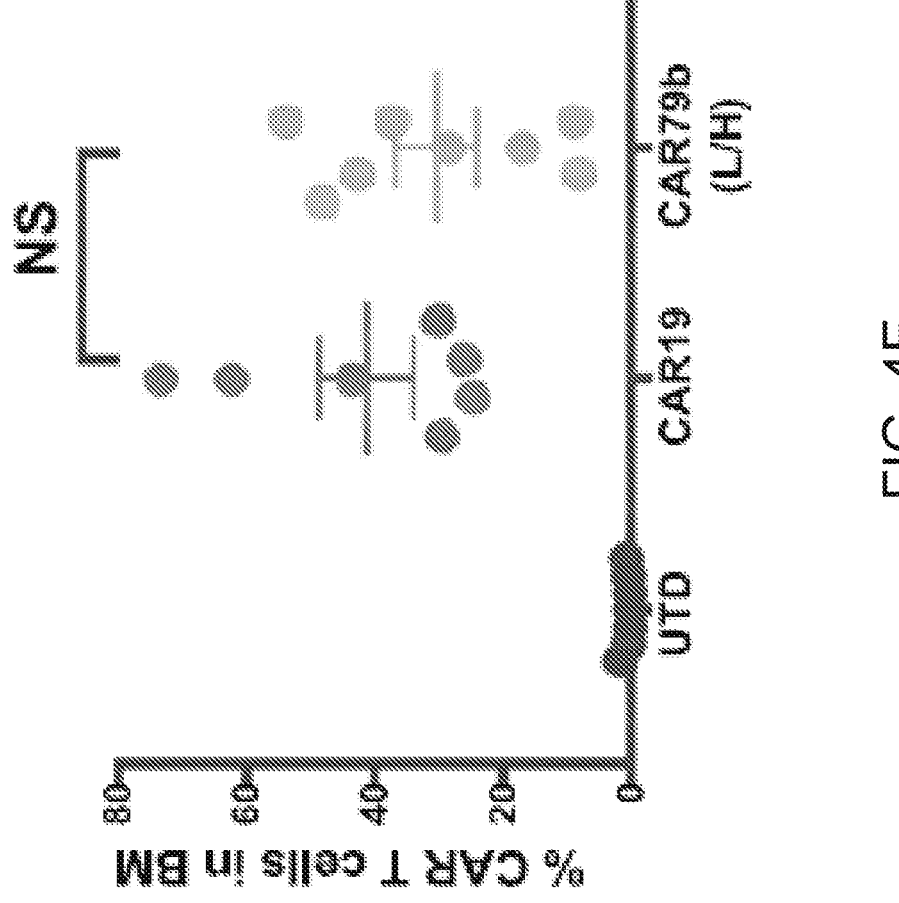
Figure 5A:
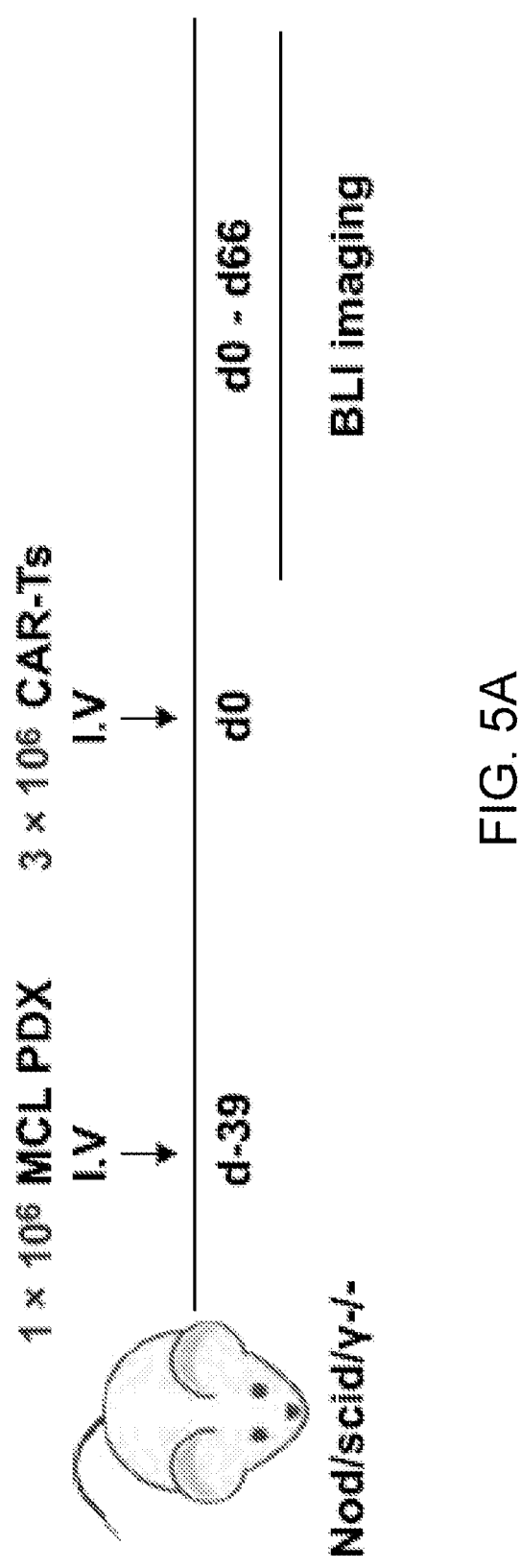
FIG. 5A-FIG. 5E show CAR79b (L/H) mediates tumor clearance and prolongs survival in an MCL-patient-derived xenograft model.
Figure 5B:
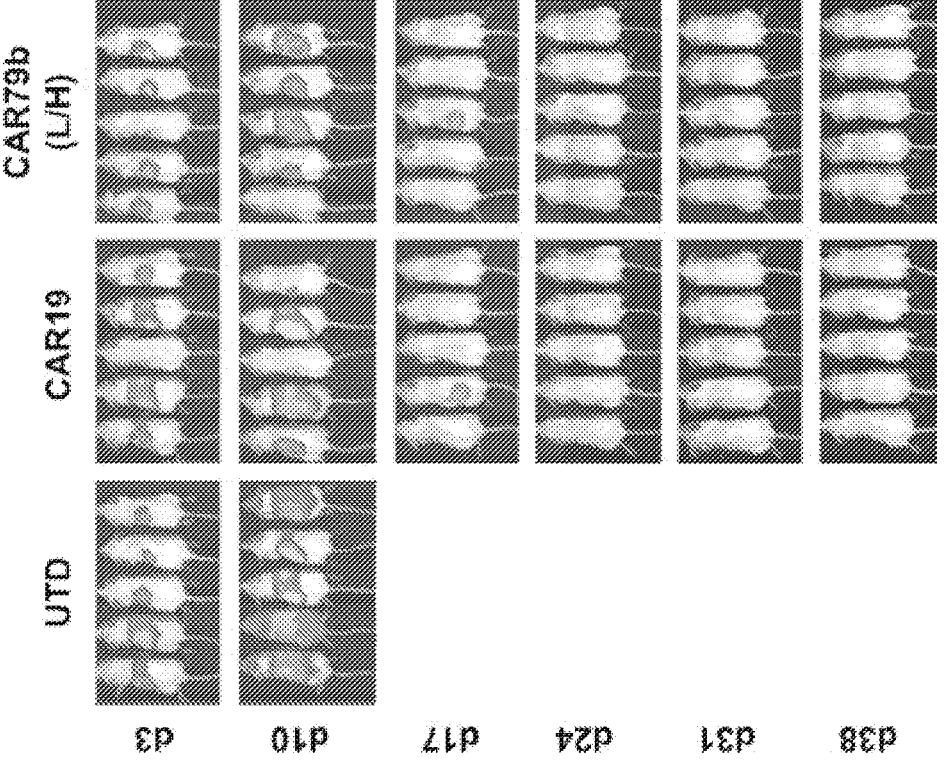
Figure 5C:
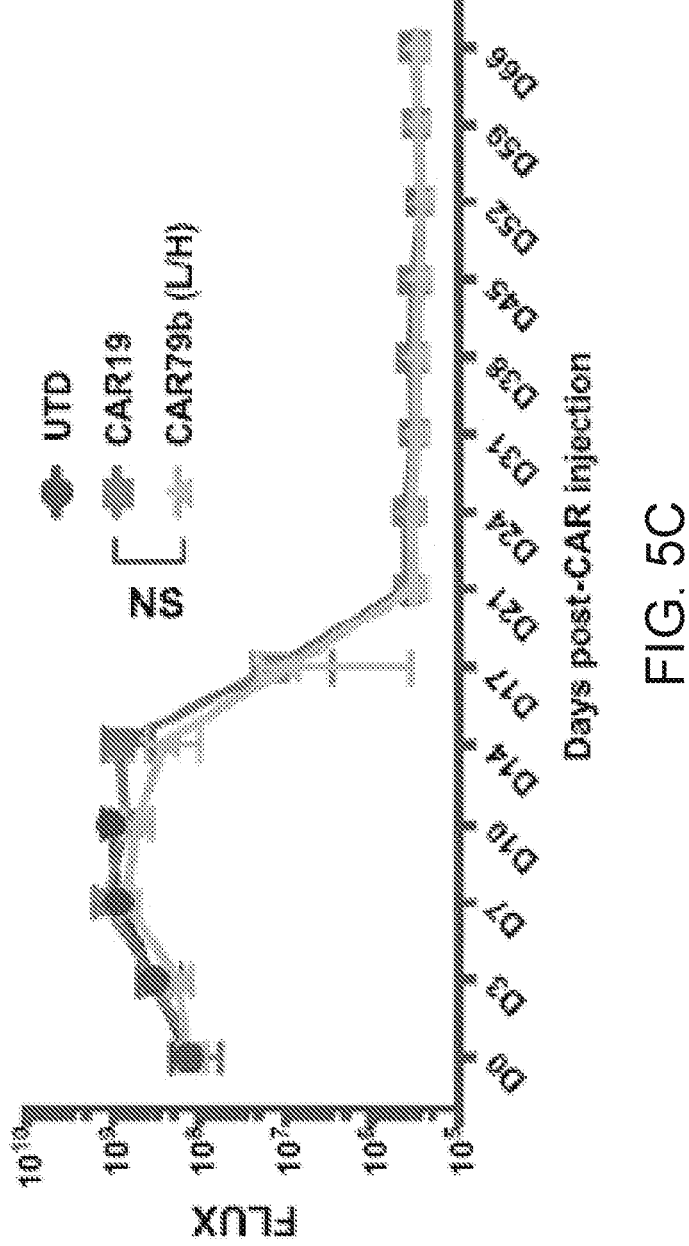
Figure 5D:
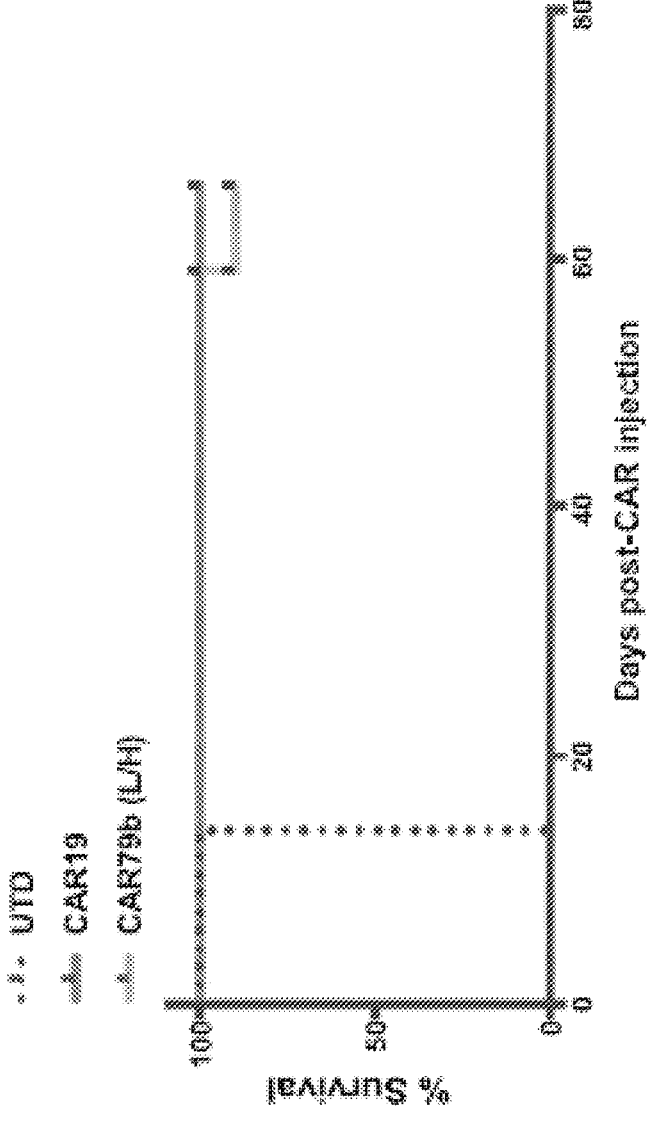
Figure 5E:
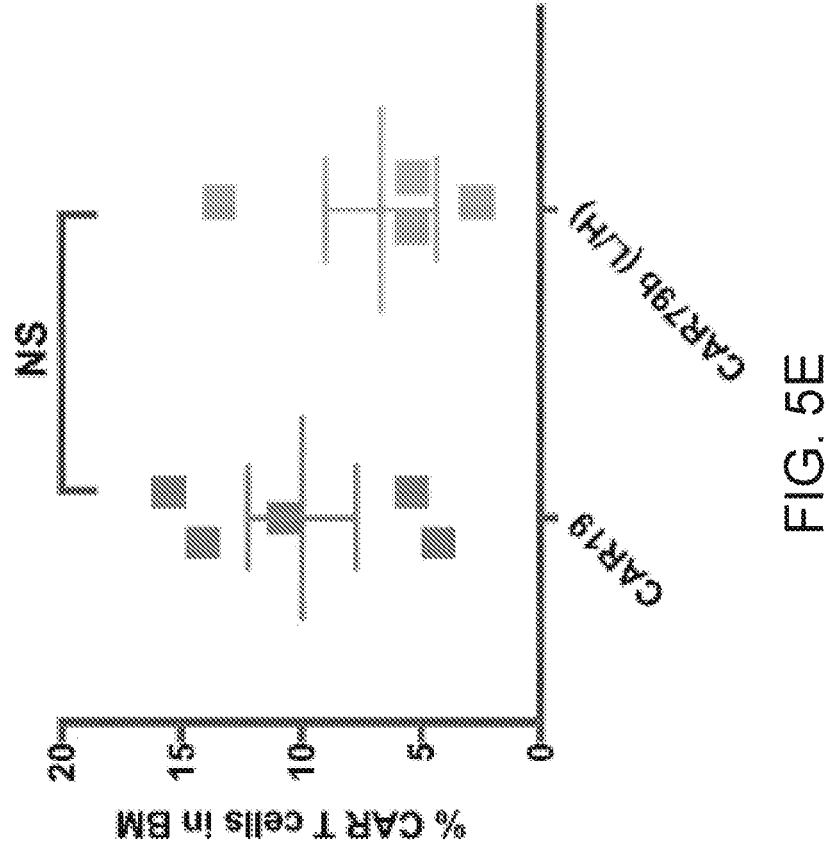

Example 4. CAR79b Eradicates MCL Tumors and Leads to Prolonged Survival In Vivo Next, we designed a series of xenograft models to test the efficacy of CAR79b (L/H) in vivo. In these experiments, we used donor-matched CAR19 and untransduced T (UTD) cells for comparison. NSG mice were intravenously injected with luciferase-positive Jeko-1 (CBG– GFP+) tumor cells, which incidentally, had a lower CD79b expression as determined by MFI compared to the PDX cells (FIG. 2A). Seven days later, tumor burden was evaluated based on BLI, and mice received a single dose of CAR79b (L/H), CAR19, or UTD cells through the tail vein (FIG. 4A). Fourteen days after CAR T cell injection, complete tumor clearance was observed for groups of mice receiving either CAR79b or CAR19 (FIG. 4B and FIG. 4C). We confirmed the persistence of CAR T cells both in peripheral blood at 14 days (FIG. 5D) and in bone marrow at 28 days post-injection (FIG. 4E). Overall, we observed no difference in tumor clearance or CAR T cell persistence between mice treated with either CAR79b or CAR19. Despite the advantage of using tumor cell lines to assess the efficacy of CAR T cells, they do not fully represent the tumor heterogeneity observed in patients. A more rigorous preclinical model to test CAR T cells is to use tumor cells directly derived from patients. Therefore, we tested the efficacy of CAR79b and CAR19 in an MCL PDX model. To do this, NSG mice were injected with luciferase-expressing MCL-PDX cells (DFBL.98848-V3). After we confirmed tumor engraftment, the mice were grouped according to BLI and injected with CAR79b, CAR19, or UTDs (FIG. 5A). Fourteen days after the CAR79b injection, we observed tumor regression, with total tumor clearance at day 21 (FIG. 5B and FIG. 5C). Mice treated with CAR19 or CAR79b survived and remained tumor-free until the end of the experiment (66 days post CAR T cell injection) (FIG. 5D). We noted persistence of a small population of CAR79b in the collected bone marrow of mice at termination day, which was similar to the results for mice treated with CAR19 (FIG. 5E). These results demonstrate the ability of CAR79b to mediate tumor clearance in different preclinical models of mantle cell lymphoma with similar efficacy as CAR19.

Figure 6A:
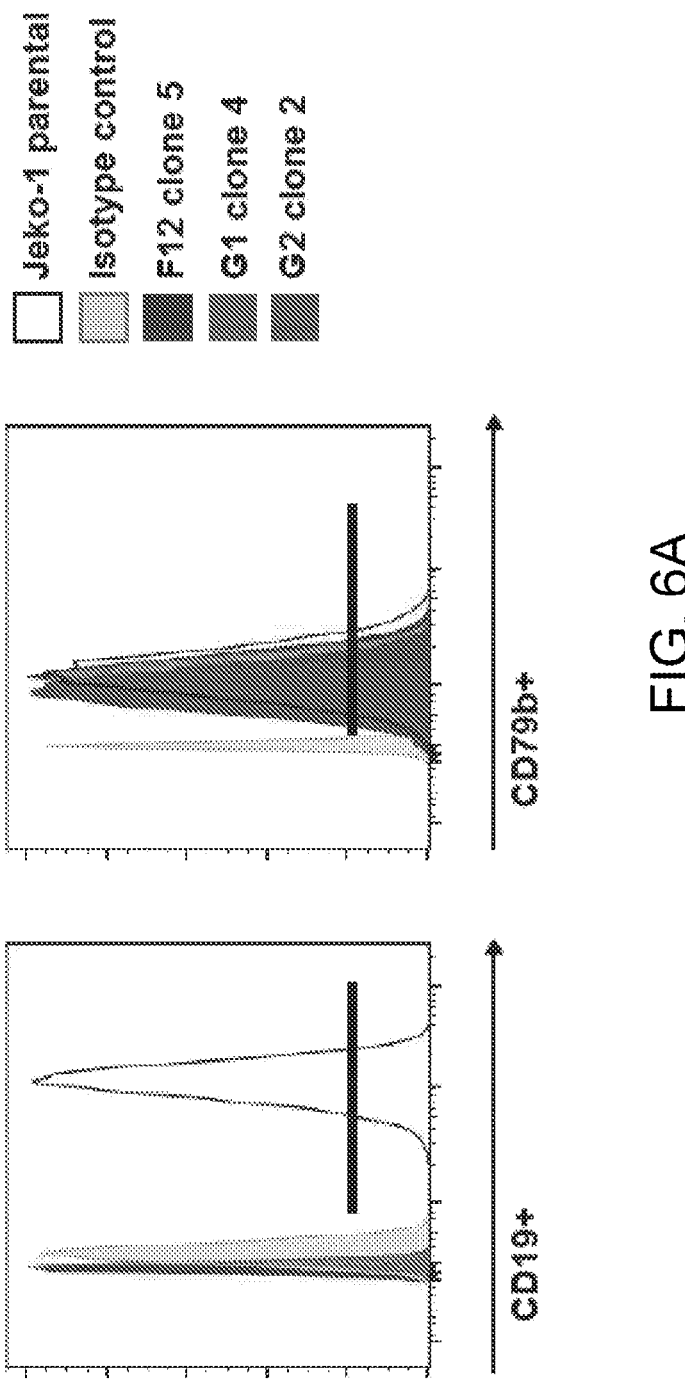
FIG. 6A-FIG. 6D show loss CD19 does not reduce CD79b surface expression.
Figure 6B:
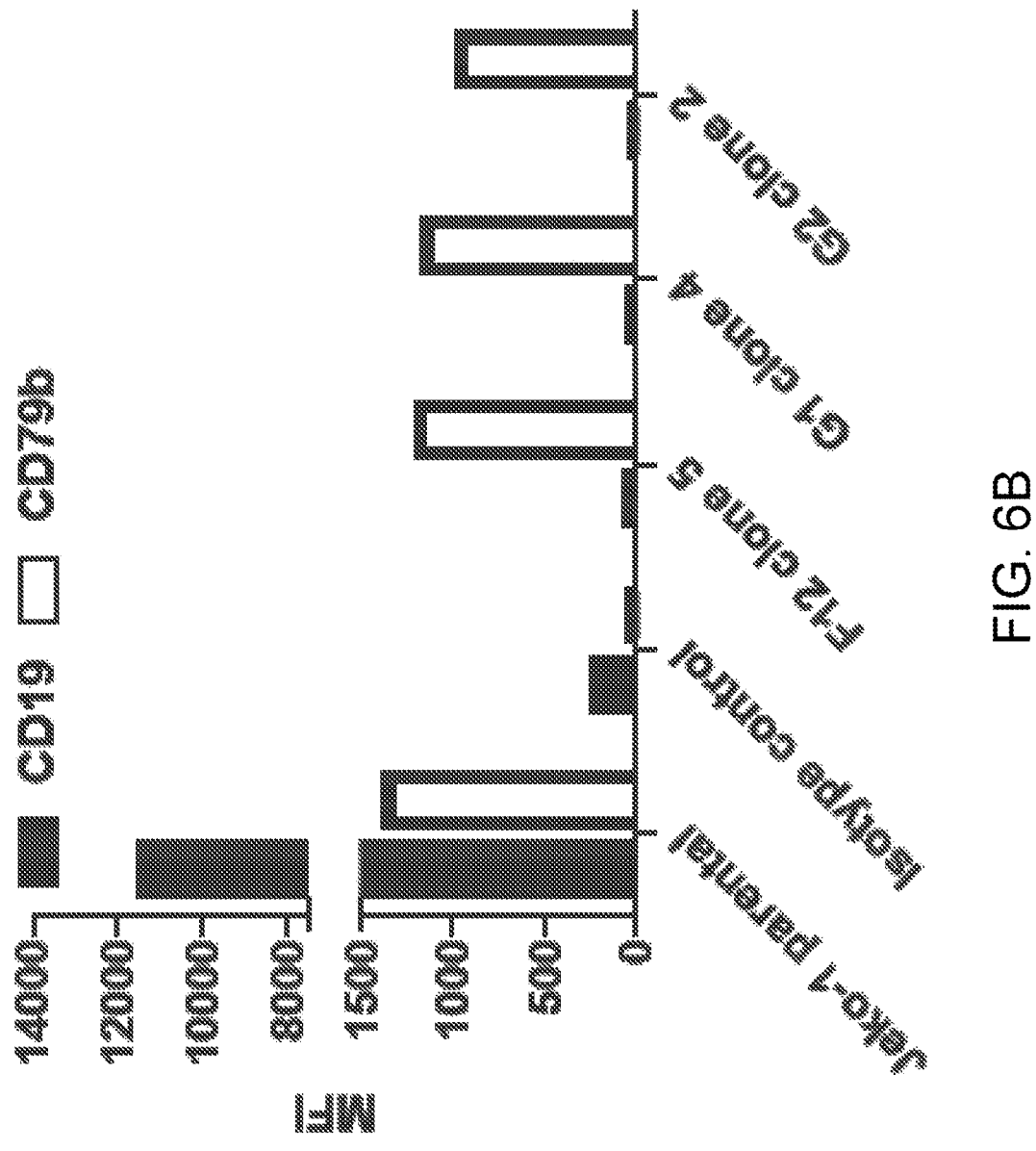
Figure 6C:
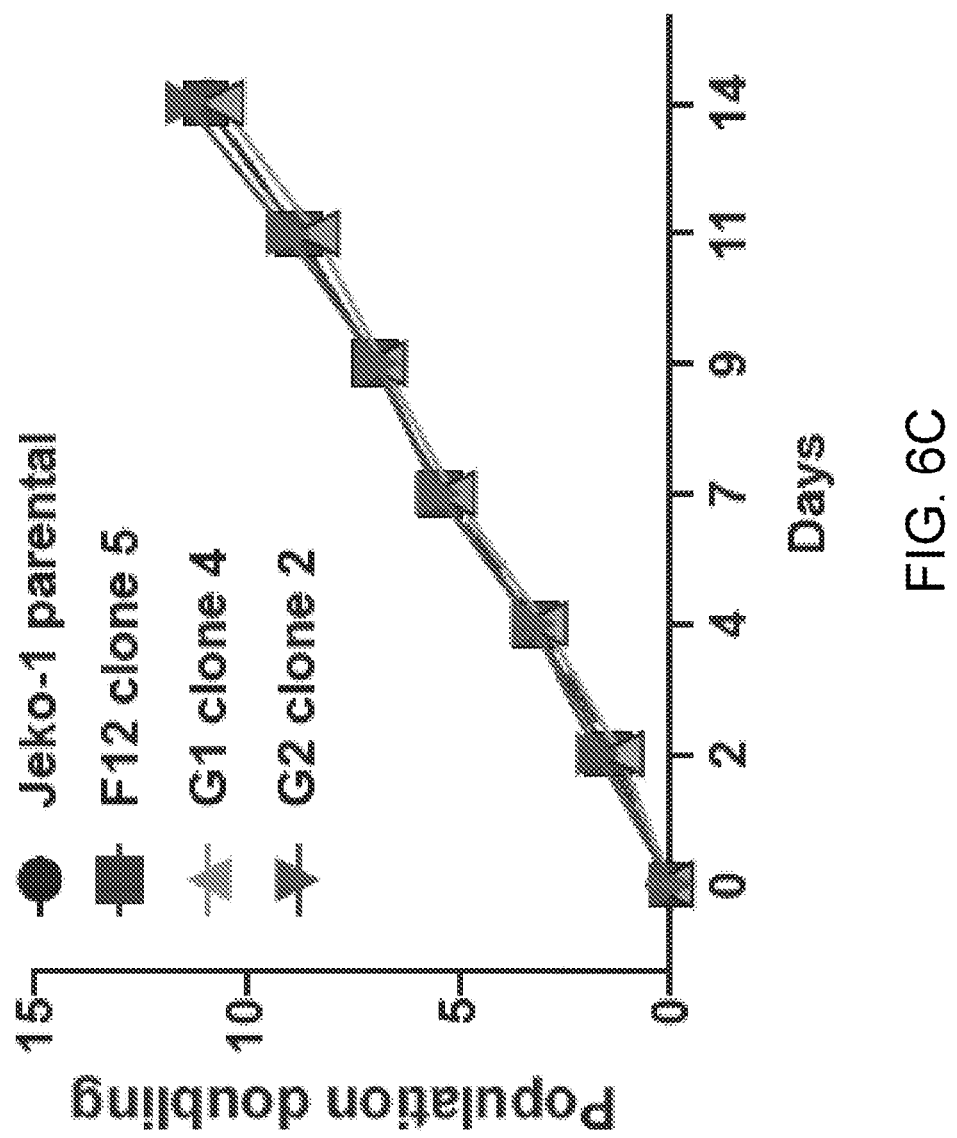
Figure 6D:
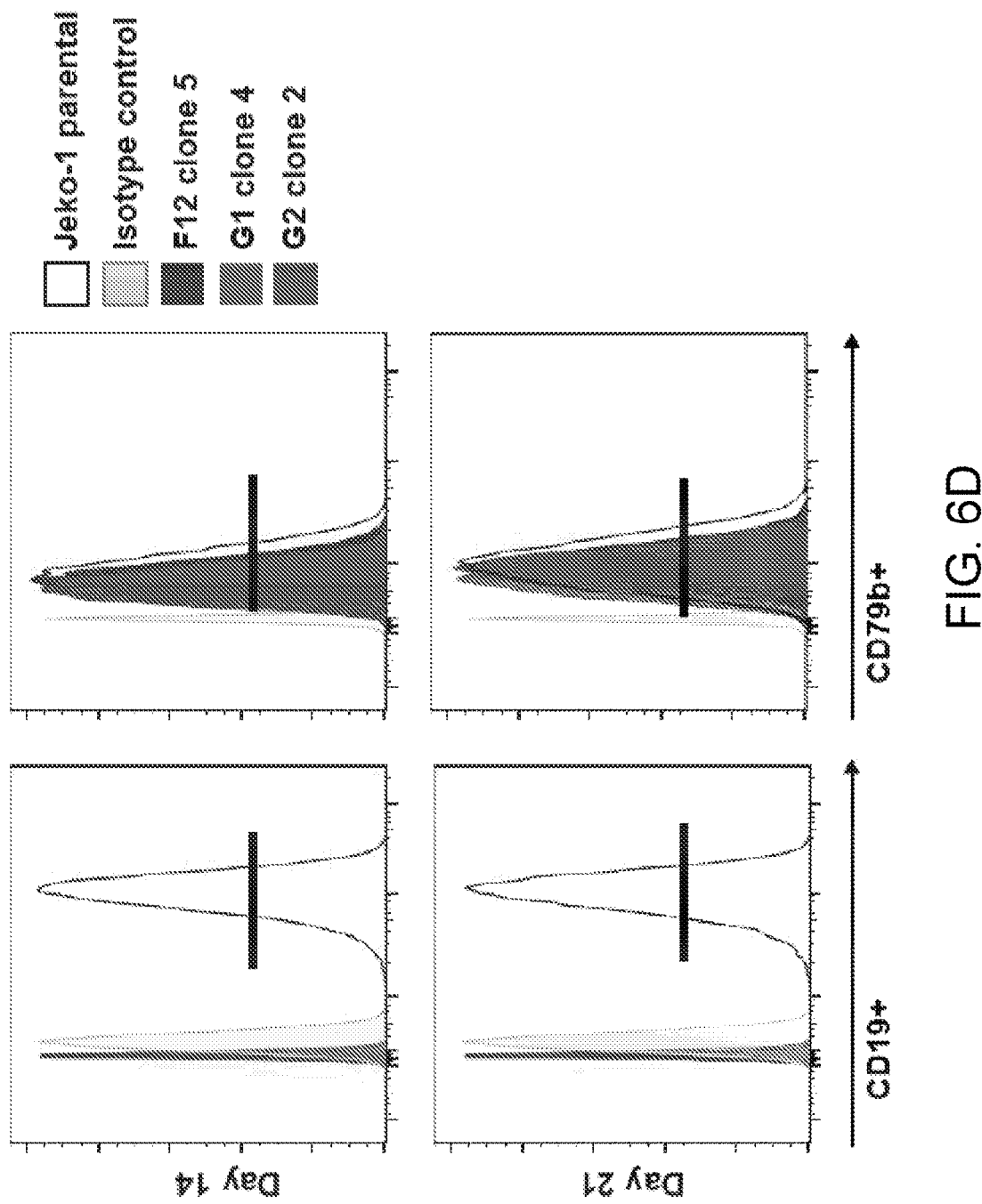
Figure 7A:
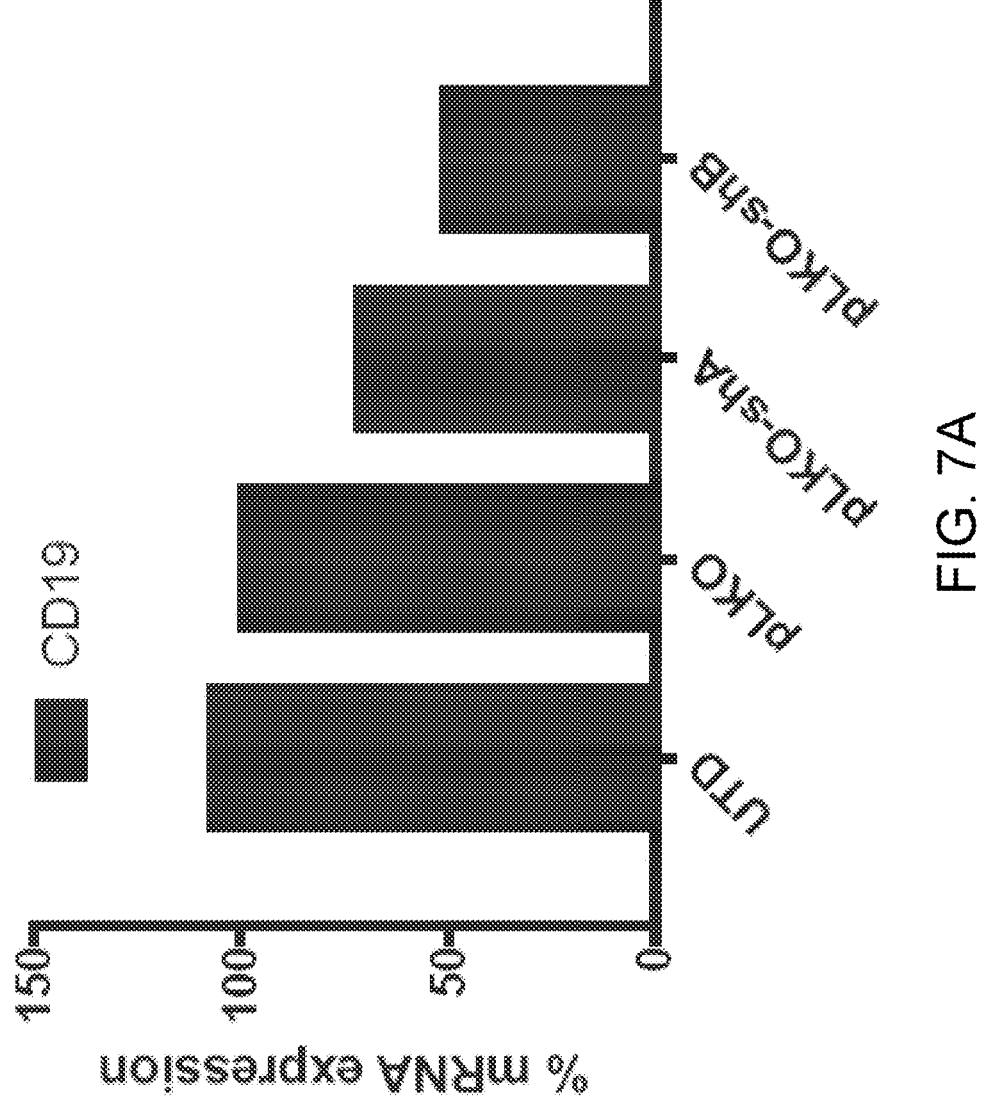
FIG. 7A-FIG. 7B show shRNA knockdown of CD19 does not reduce CD79b surface expression.
Figure 7B:
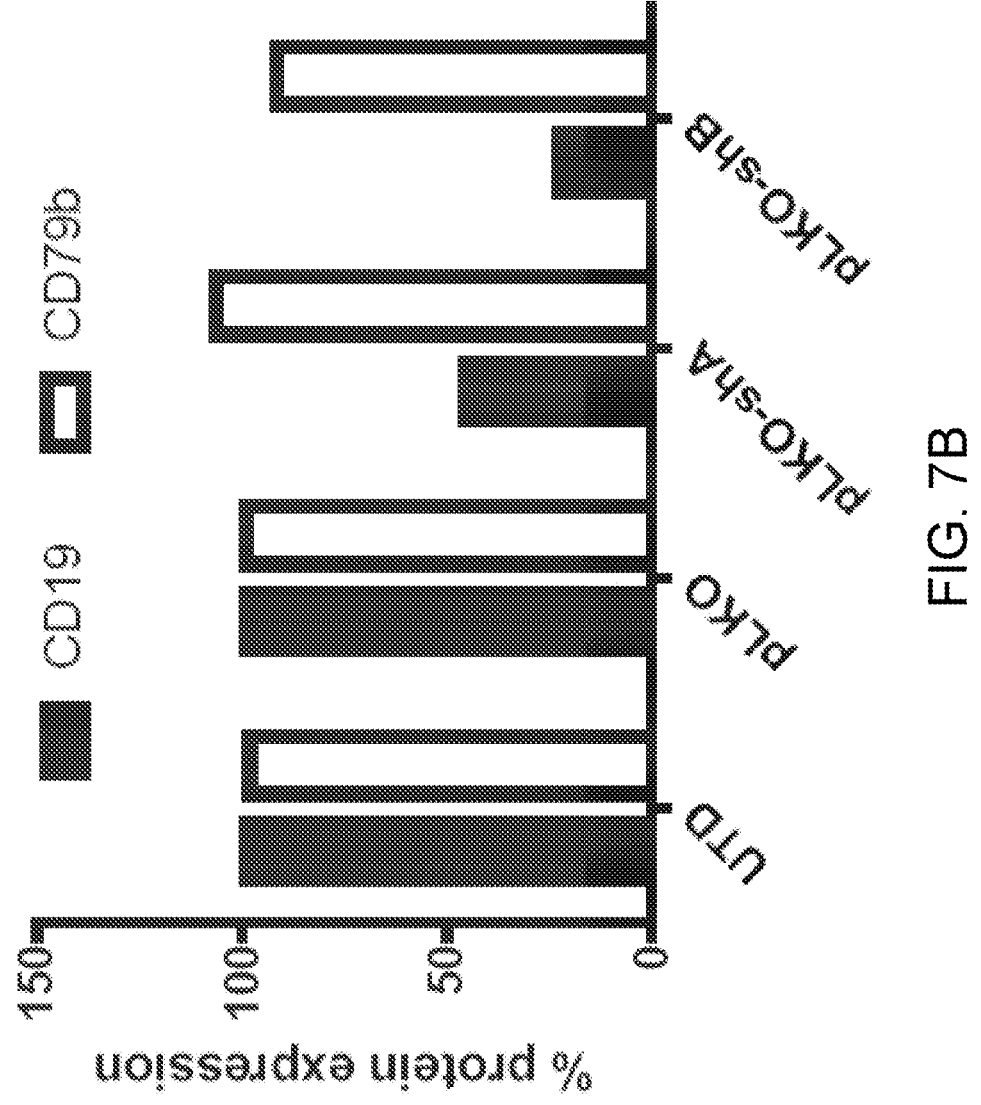

Example 5. Loss of CD19 at the DNA or RNA Level does not Reduce CD79b Surface Expression Reported loss of CD19 leading to disease relapse is a major obstacle for the curative potential of CD19-directed CAR therapy (N Engl J Med 2017; 377(26):2545-54). In ALL, an alternative splice product excluding the epitope targeted by CD19 CAR T cells has been reported as one mechanism of antigen escape and relapse (Cancer Discov 2015; 5(12):1282-95), as have frameshift mutations in the CD19 gene (Nat Med 2018; 24(10):1504-6). CD19 and BCR cross-linking lowers the threshold for B cell activation (EMBO J 2018; 37(11); Semin Immunol 1998; 10(4):267-77), thereby augmenting B cell signaling. In lymphomas, CD79b and CD19 have been proposed to form a signaling complex that promotes survival (EMBO J 2018; 37(11)). To this end, we tested whether the loss of CD19 would interfere with the surface expression of CD79b. We used CRISPR/Cas9 technology to generate CD19-negative MCL cell lines. Jeko-1 cells were stably transduced to express Cas9 protein, and then transduced with lentiviruses encoding different CD19-targeted guides. CD19-negative Jeko-1 cells were single-cell clone sorted and expanded to establish cell lines. A complete knockout of CD19 did not lead to reduction in surface CD79b expression in the generated cell lines (FIG. 1A and FIG. 6B). In addition, loss of CD19 did not alter growth kinetics in negative cell lines compared to parental Jeko-1 (FIG. 6C). Importantly, the generated CD19– negative cell lines maintained surface CD79b expression and the loss of CD19 during a prolonged culture period (FIG. 6D). Similar findings were observed using a CD19 shRNA knock-down approach, whereby the downregulation of CD19 did not reduce CD79b expression in Jeko-1 cells (FIG. 7A and FIG. 7B). Together these data indicate no immediate relationship between CD19 and CD79b surface expression, leading us to hypothesize that the loss of CD19 in patients having received CAR19 therapy will not influence surface CD79b expression. Collectively, these results further strengthen CD79b as a potential target for CAR therapy in patients relapsed with CD19-negative lymphoma.

Example 6. CAR79b eradicate CD19-negative MCL tumor in vivo

Figure 8A:
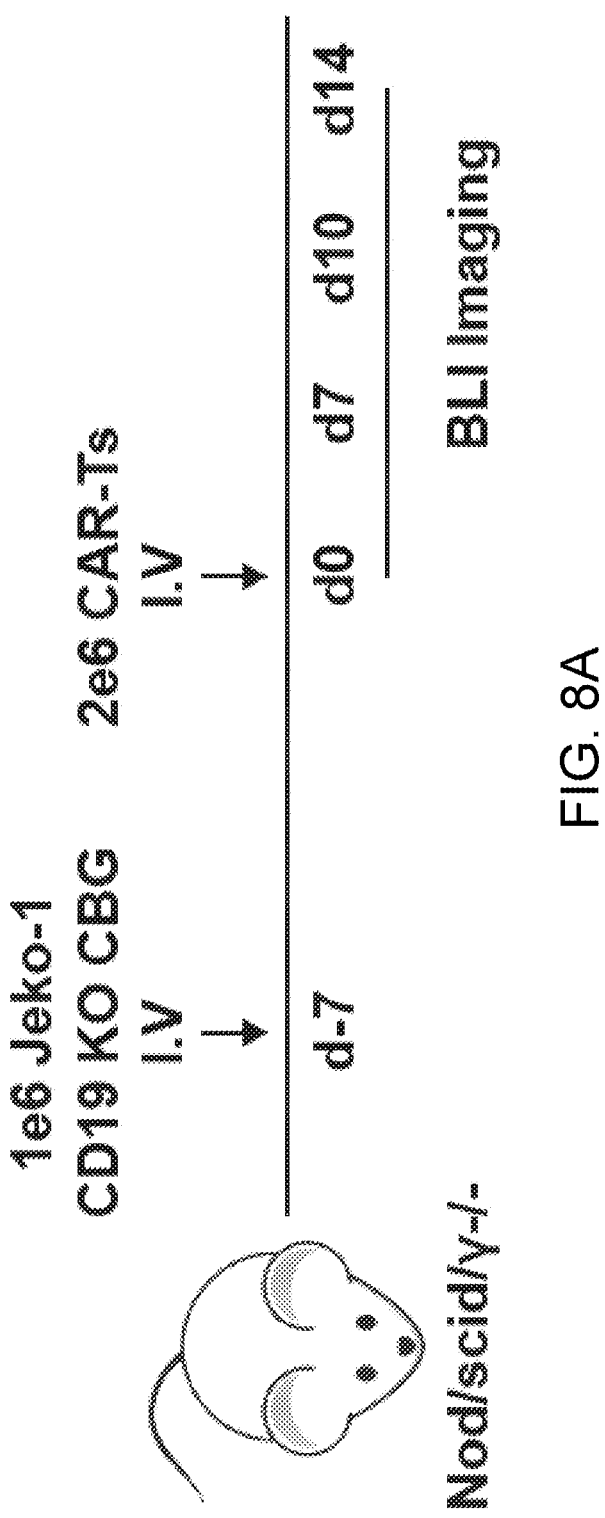
FIG. 8A-FIG. 8C show CD79b CAR T cells eradicate a CD19 negative MCL xenograft tumor.
Figure 8B:
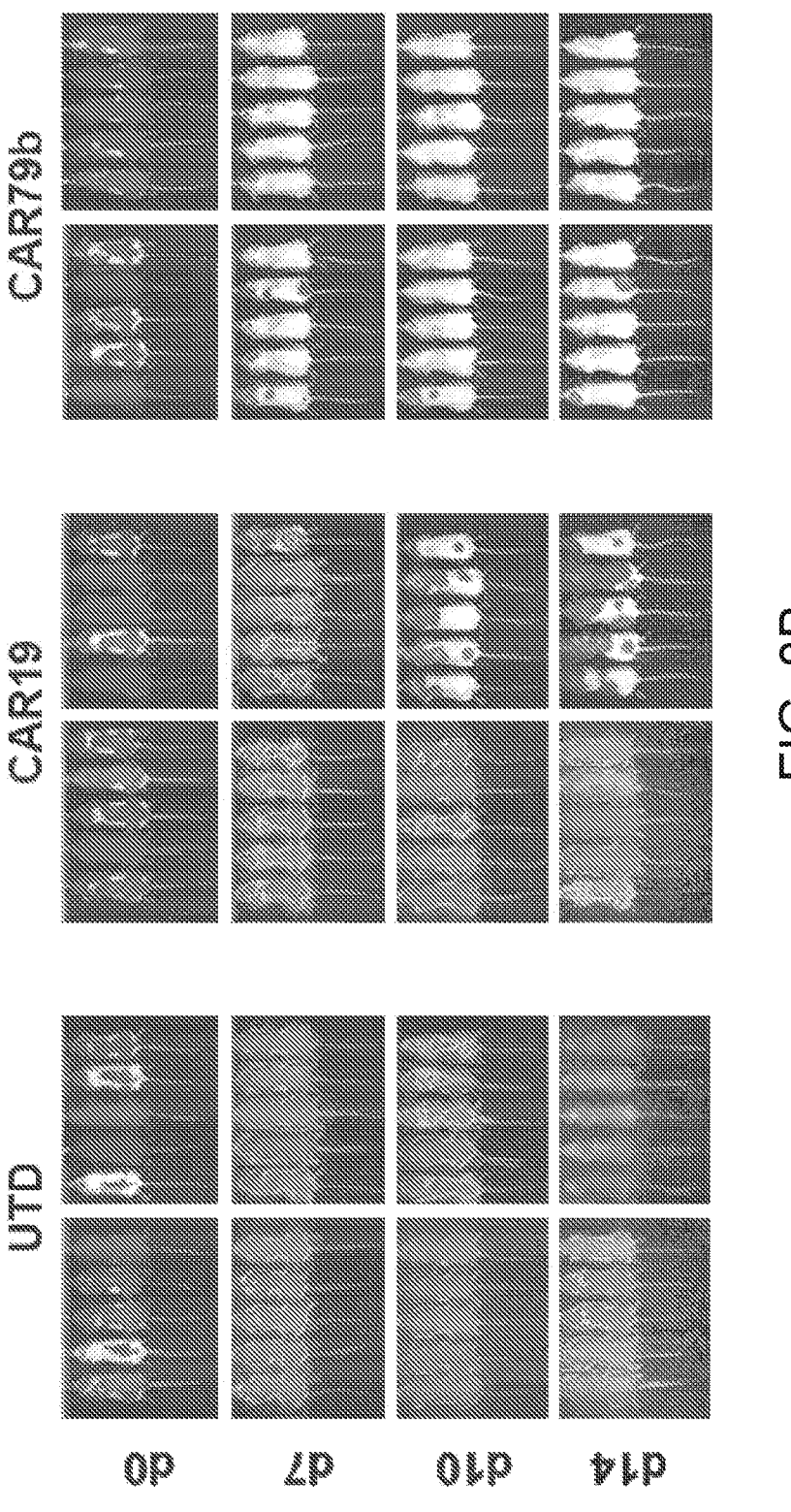
Figure 8C:
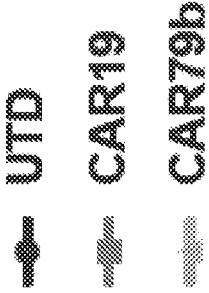
Figure 8C:
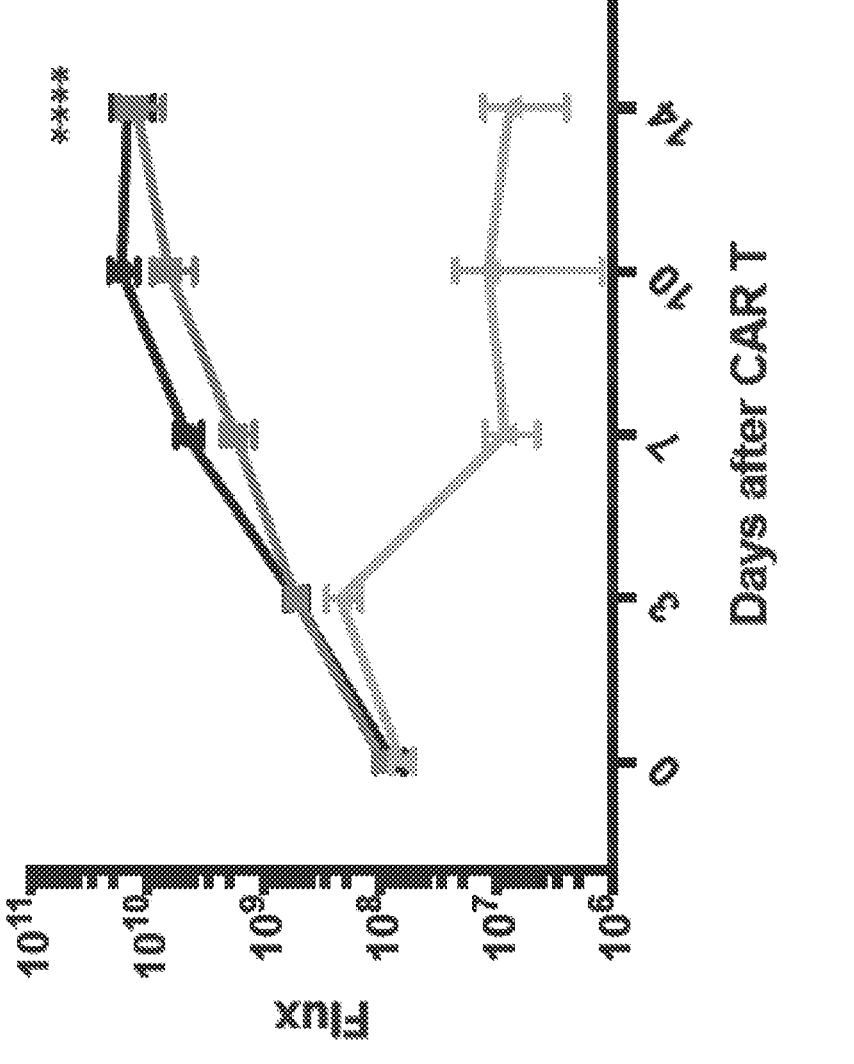

Next, we proceeded to test anti-lymphoma activity of CAR79b T cells against CD19-negative Jeko-1 cells in vivo. NSG mice were engrafted with CD19-negative Jeko-1 cells (F12 clone and subsequently injected with a single dose of CAR19, CAR79b, or UTDs (FIG. 8A). A significant reduction in tumor burden was detectable only in the CAR79b group, starting at day 7 post-treatment, and was maintained for at least 14 days (FIG. 8A and FIG. 8C). At day 14 post CAR T cell injection, we detected allogeneic response of T cells from the UTD and CAR19 groups, which may be related to constitutive expression of Cas9, since allogeneic responses at these time points were not observed in non-Cas9-expressing Jeko-1 xenografts. Due to the strong allogenicity of the CD19-negative Jeko-1 cells, further experiments with the CD19– negative Jeko-1 lines required termination at day 14.

Example 7a. Chimeric Antigen Receptors Targeting CD79b and CD19

Figure 9A:
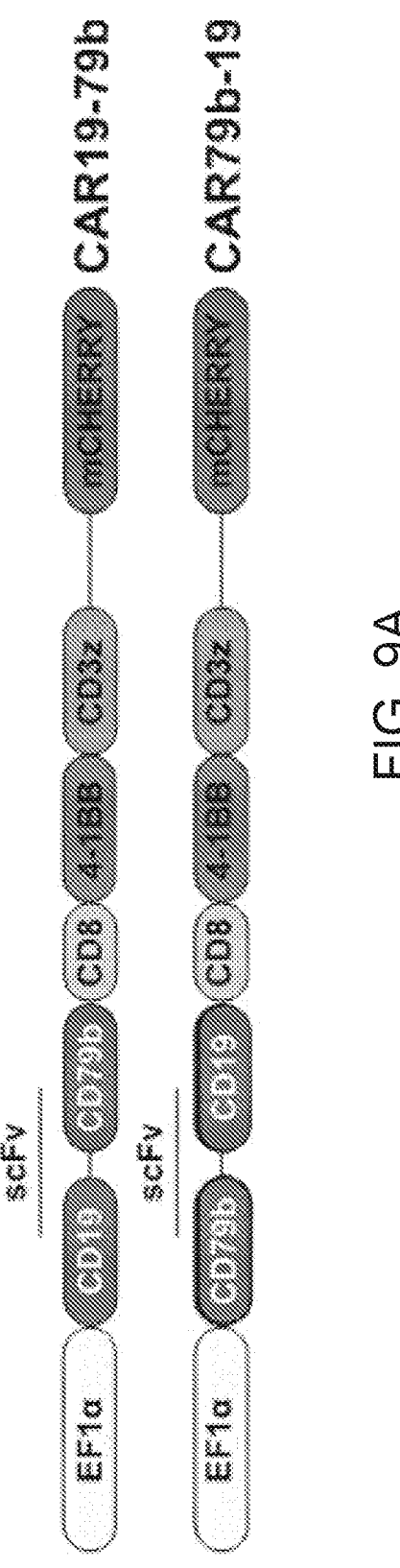
FIG. 9A-FIG. 9G show efficacy of CAR constructs.
Figure 9B:
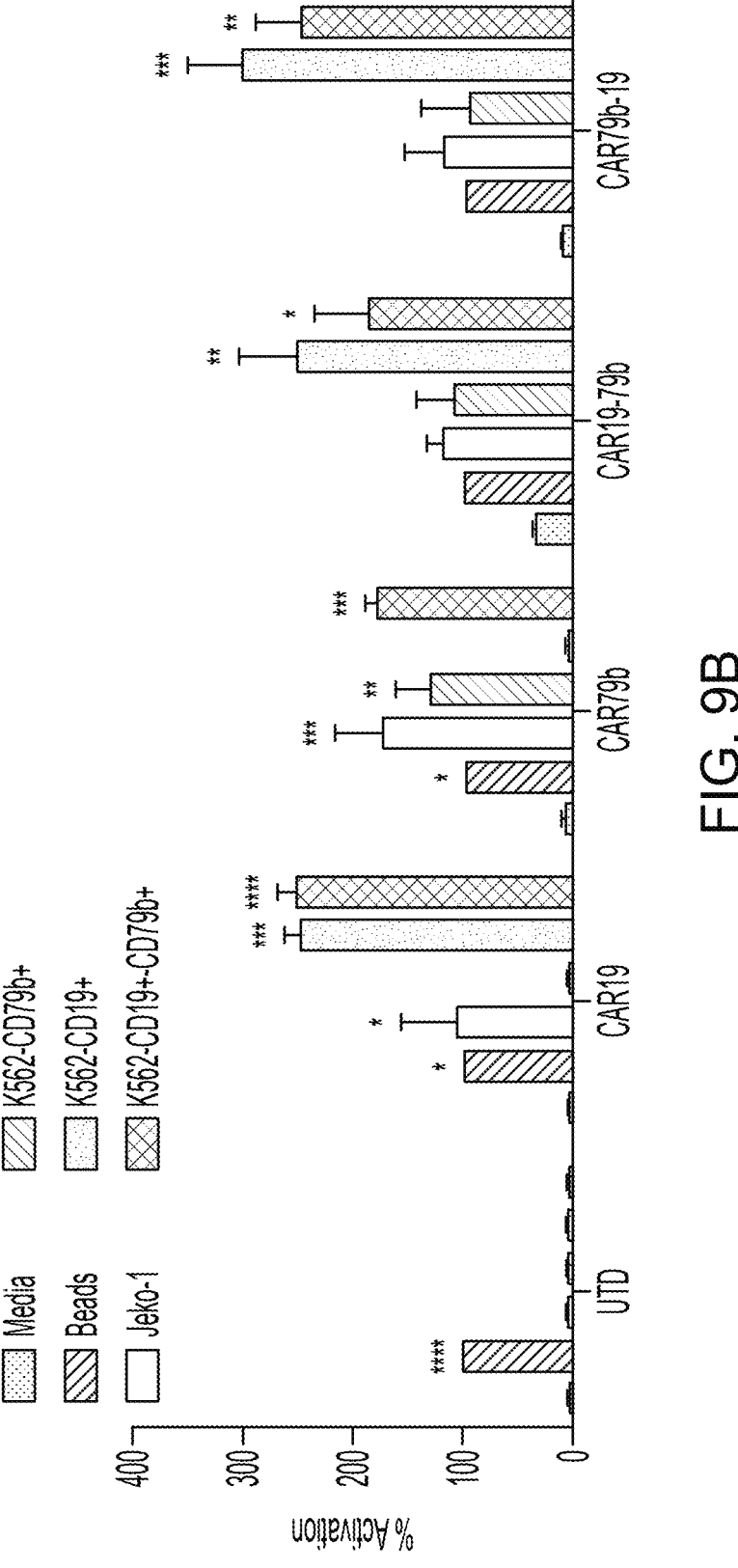
Figure 9C:
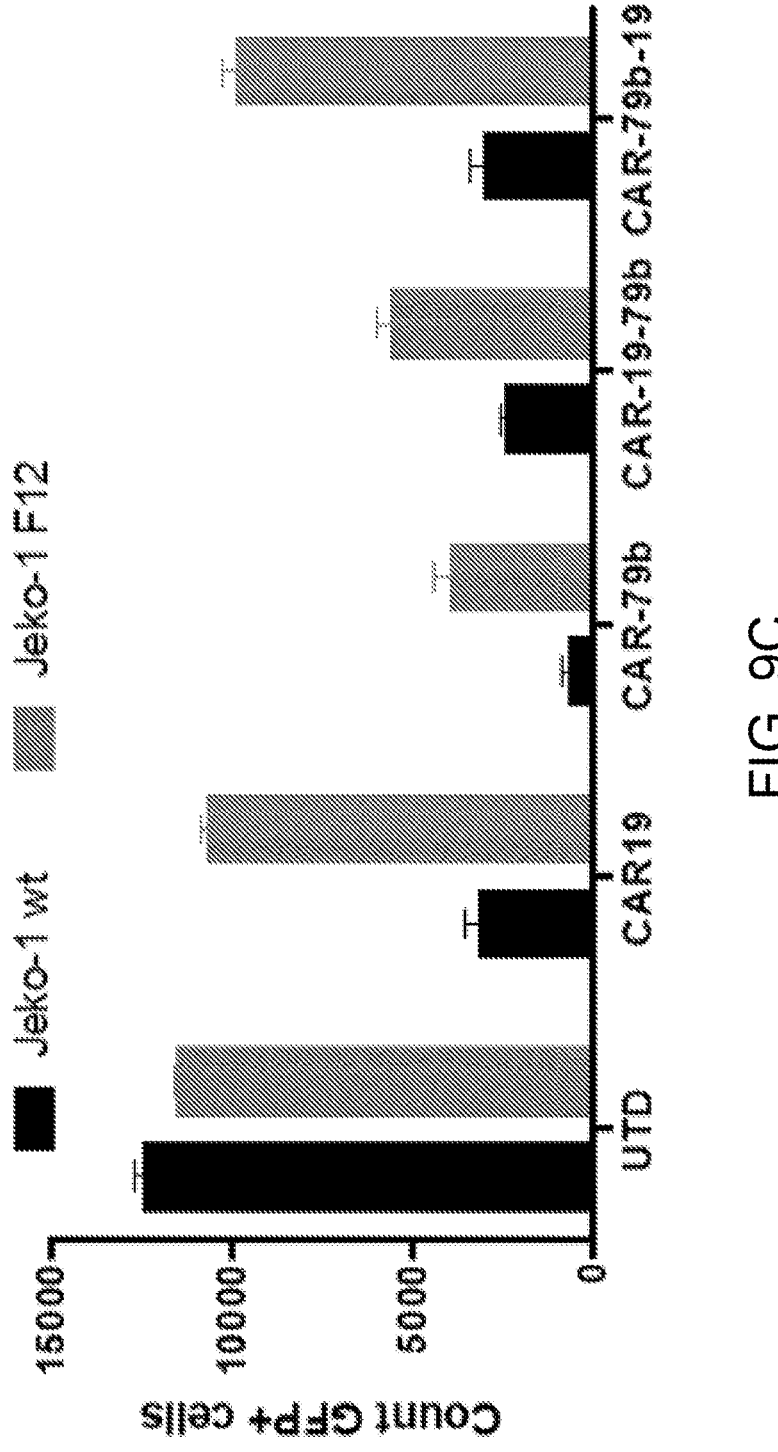
Figure 9D:
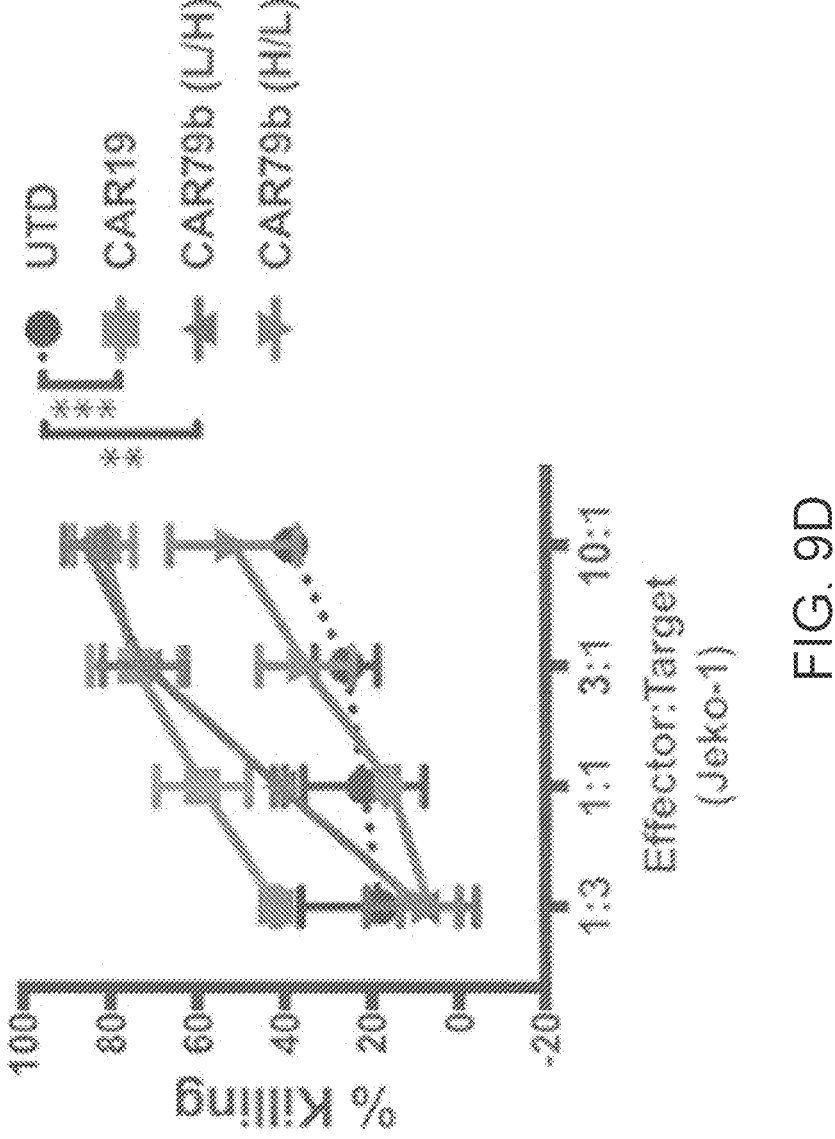
Figure 9E:
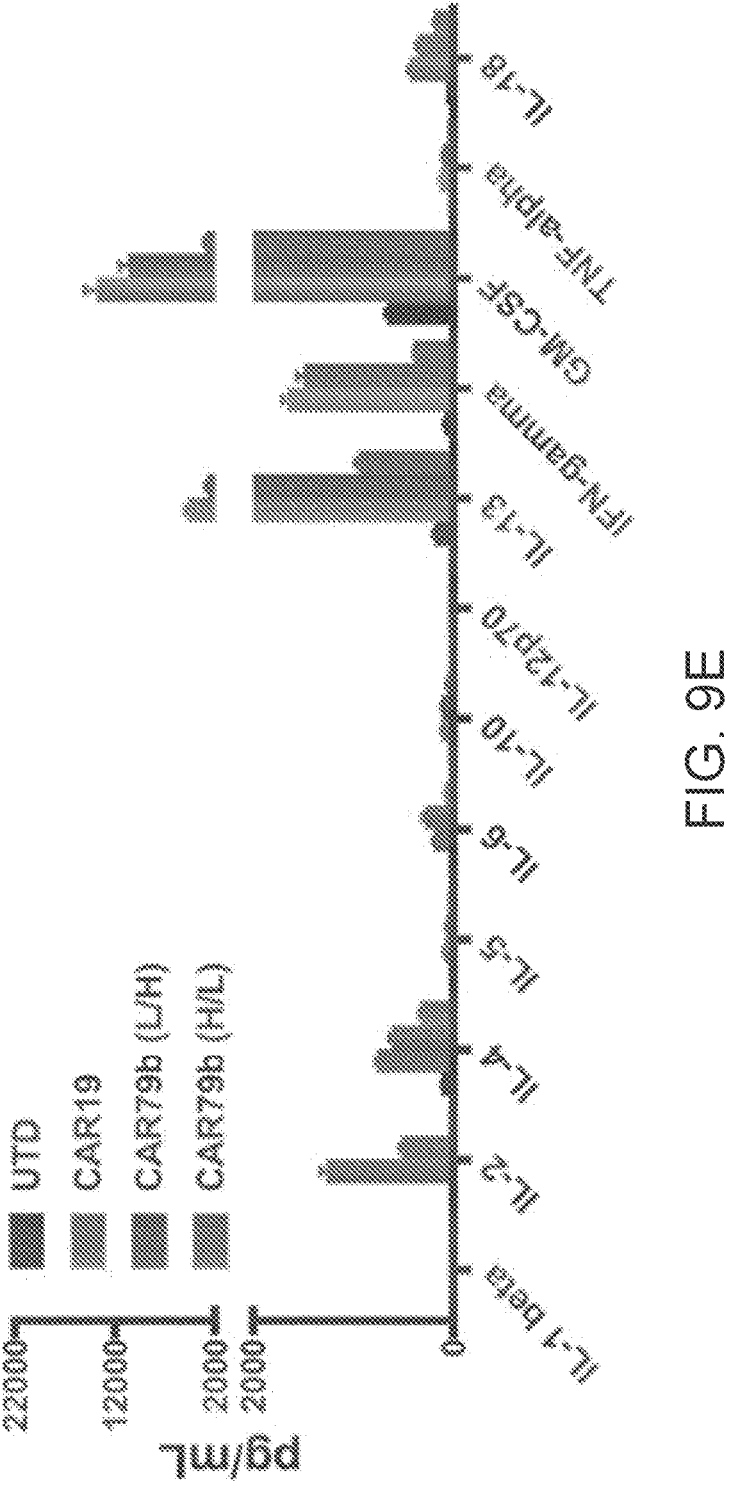
Figures 9F, 9G:
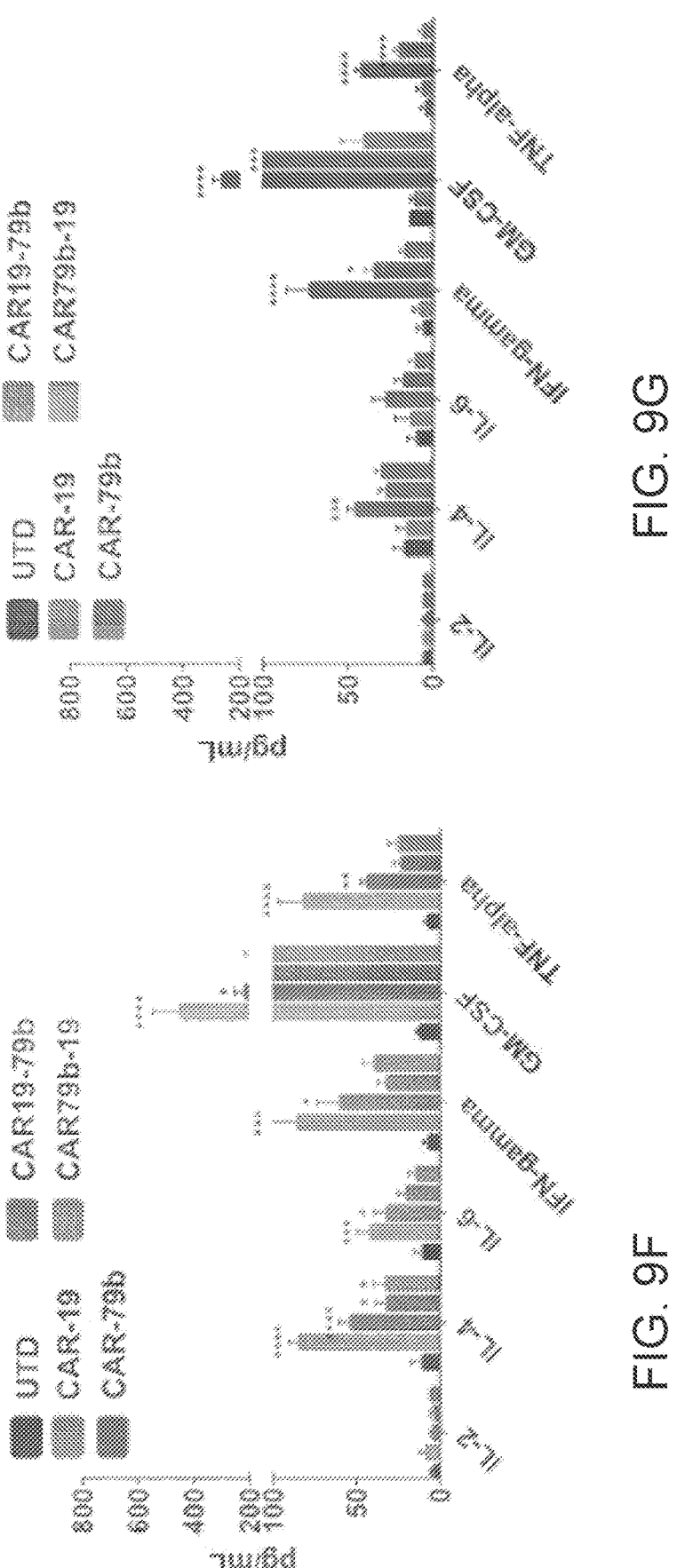
Figure 10A:
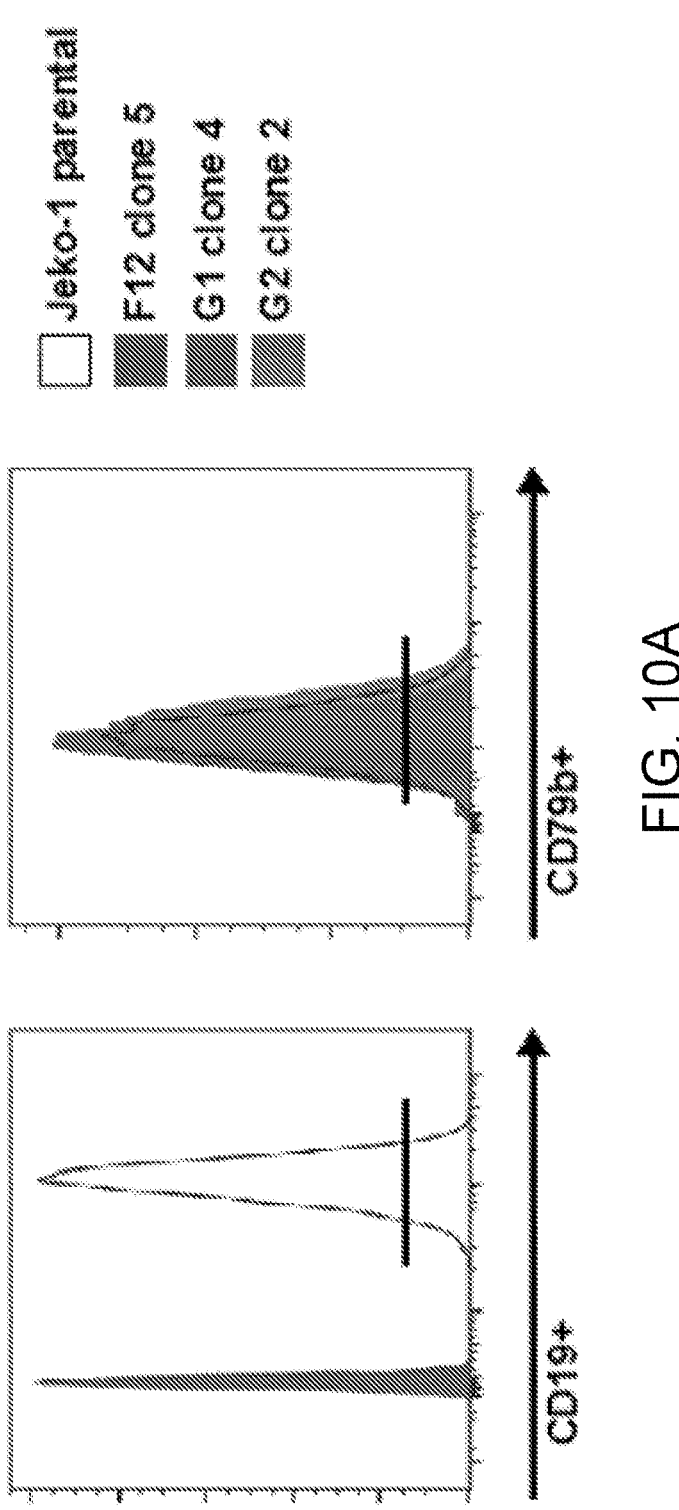
FIG. 10A and FIG. 10B are a series of graphs showing surface expression of CD79b and CD19 on Jeko-1 cell lines.
Figure 10C:
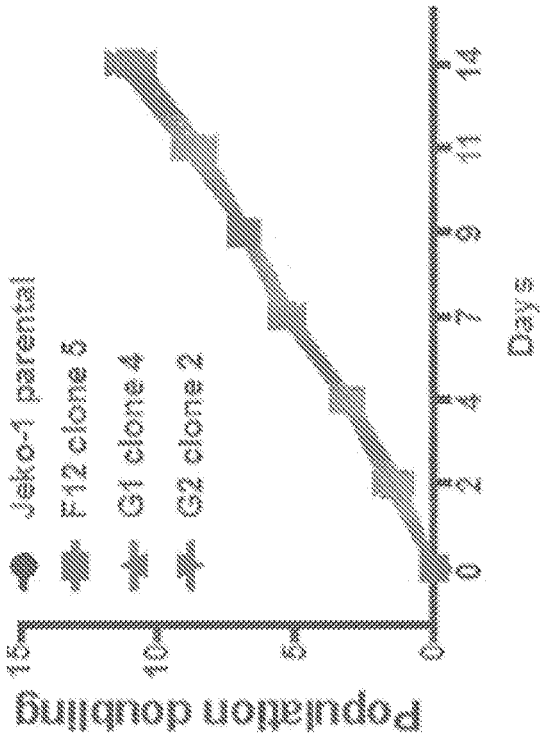
FIG. 10C shows the growth curve of the indicated Jeko-1 cell lines, demonstrating the lack of impact of CD19 knock out.
Figure 10B:
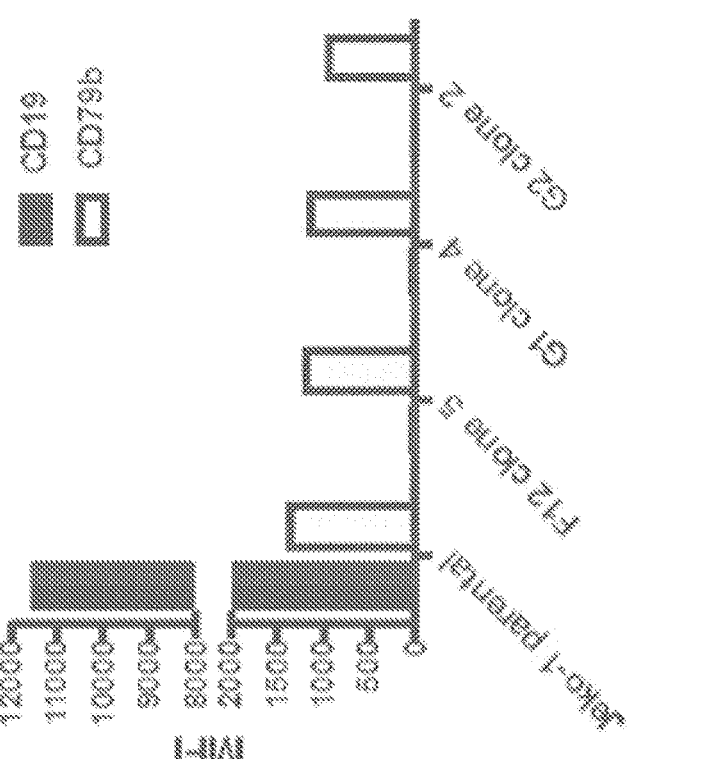
Figure 10D:
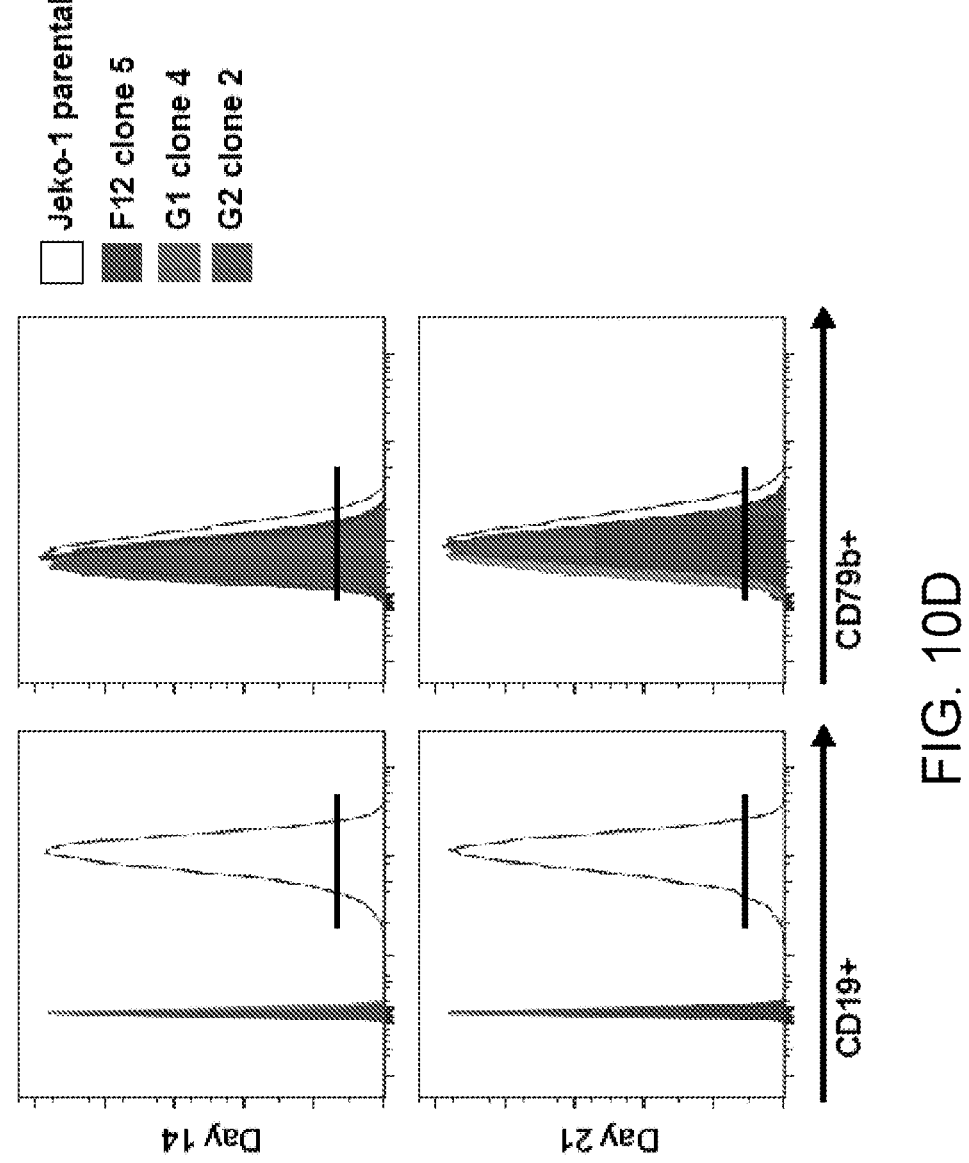
FIG. 10D indicates the stability of expression of CD19 and CD79b overtime in the Jeko-1 lines indicated.
Figure 11:
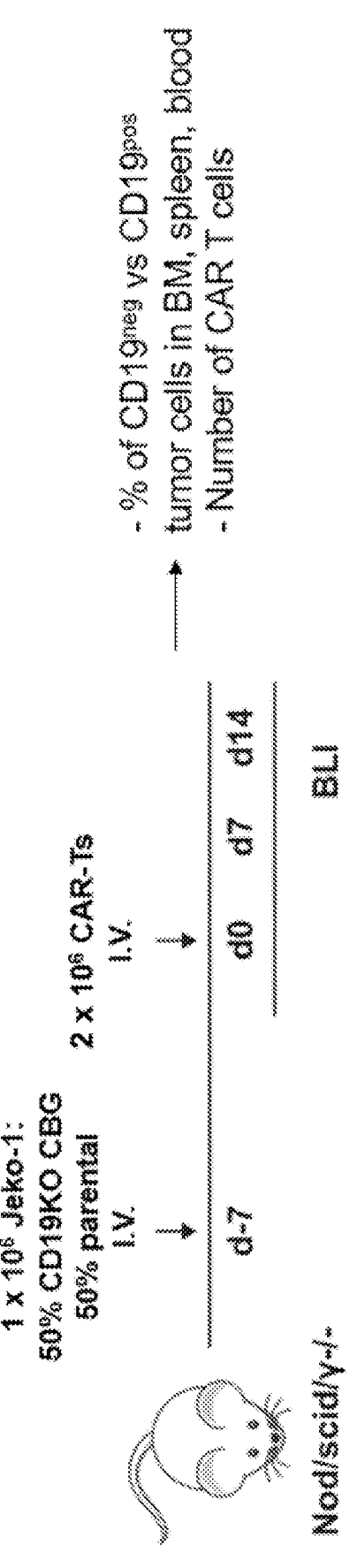
FIG. 11 is a schematic diagram showing the experimental design of an in vivo CD19 antigen escape model.

Two bispecific CARs targeting CD79b and CD19 were designed alternating the order of the CD19 scFv and the CD79b scFv, as shown in FIG. 9A. In one construct, the CD19 scFv is positioned N-terminal to the CD79b scFv (CAR19-79b (SEQ ID NO: 1)), while in the other, the CD79b scFv is positioned N-terminal to the CD19 scFv (CAR79b-19 (SEQ ID NO: 2)). T cells expressing anti-CD79b CAR and anti-CD79b/CD19 CARs were shown to be activated in response to stimulation (FIG. 9B). The CAR T cells demonstrated potent effector functions in vitro (FIG. 9C-FIG. 9G). Furthermore, it was demonstrated that loss of CD19 does not reduce CD79b surface expression (FIG. 10A-FIG. 10D). The design of an in vivo experiment testing the effector function of the CAR T cells is detailed in FIG. 11.

Example 7b. CAR79b Shows Efficacy In Vitro in a Tandem Format with CAR19

Figure 12A:
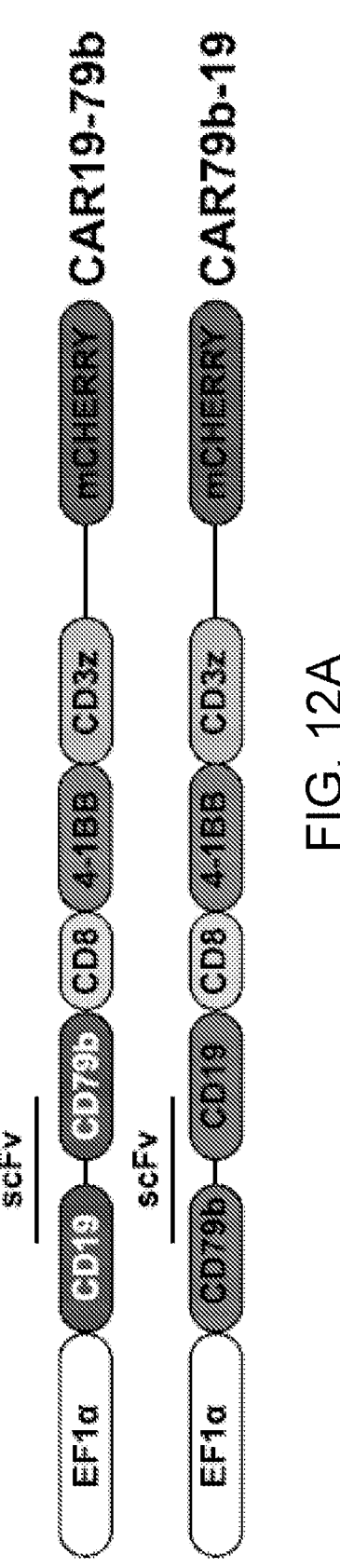
FIG. 12A-FIG. 12E show CD79b or CD79b-CD19 tan-dem CAR T cells show in vivo efficacy against heteroge-neous tumors with variable CD19 expression.
Figure 13A:
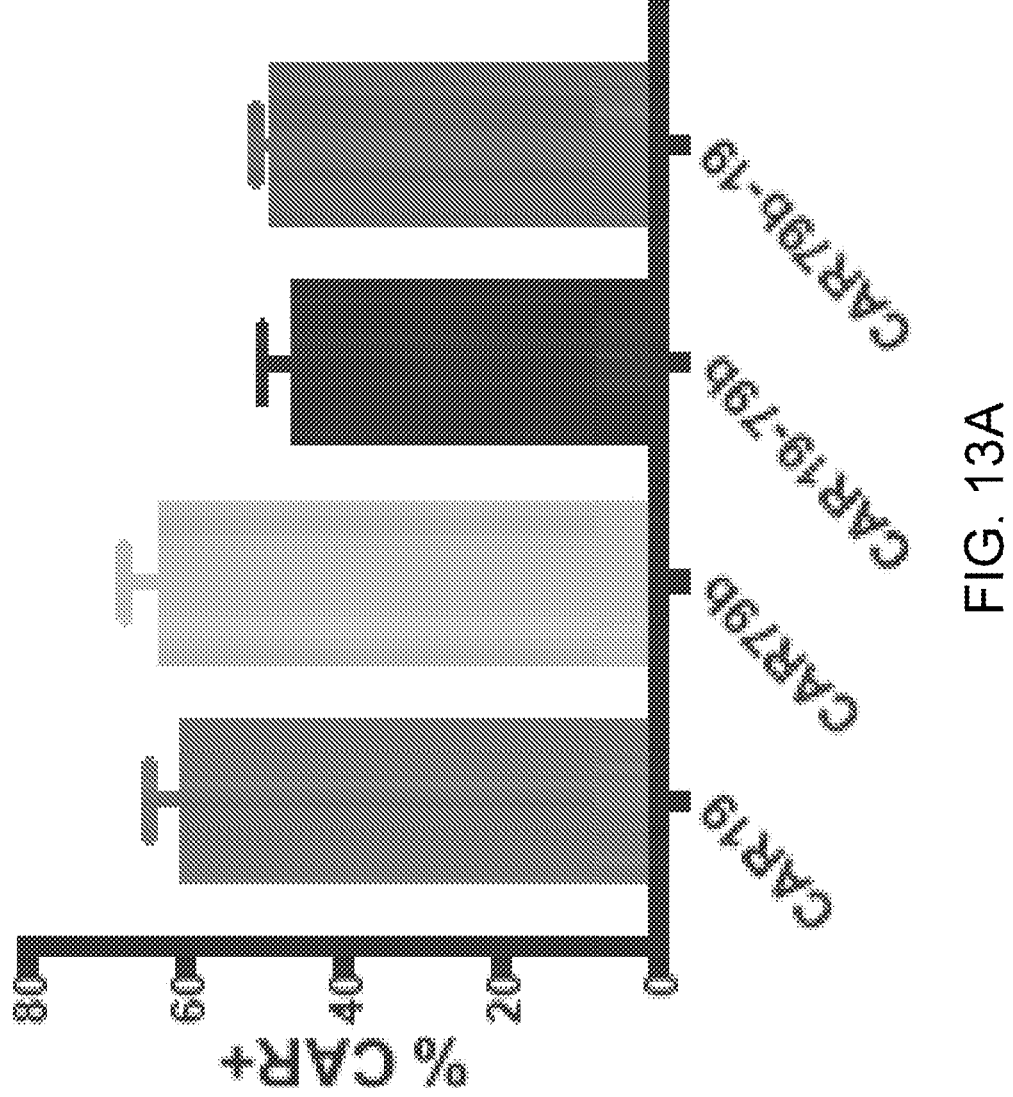
FIG. 13A-FIG. 13E show transduction efficiency and In vitro efficacy of tandem CAR T cells.
Figure 13B:
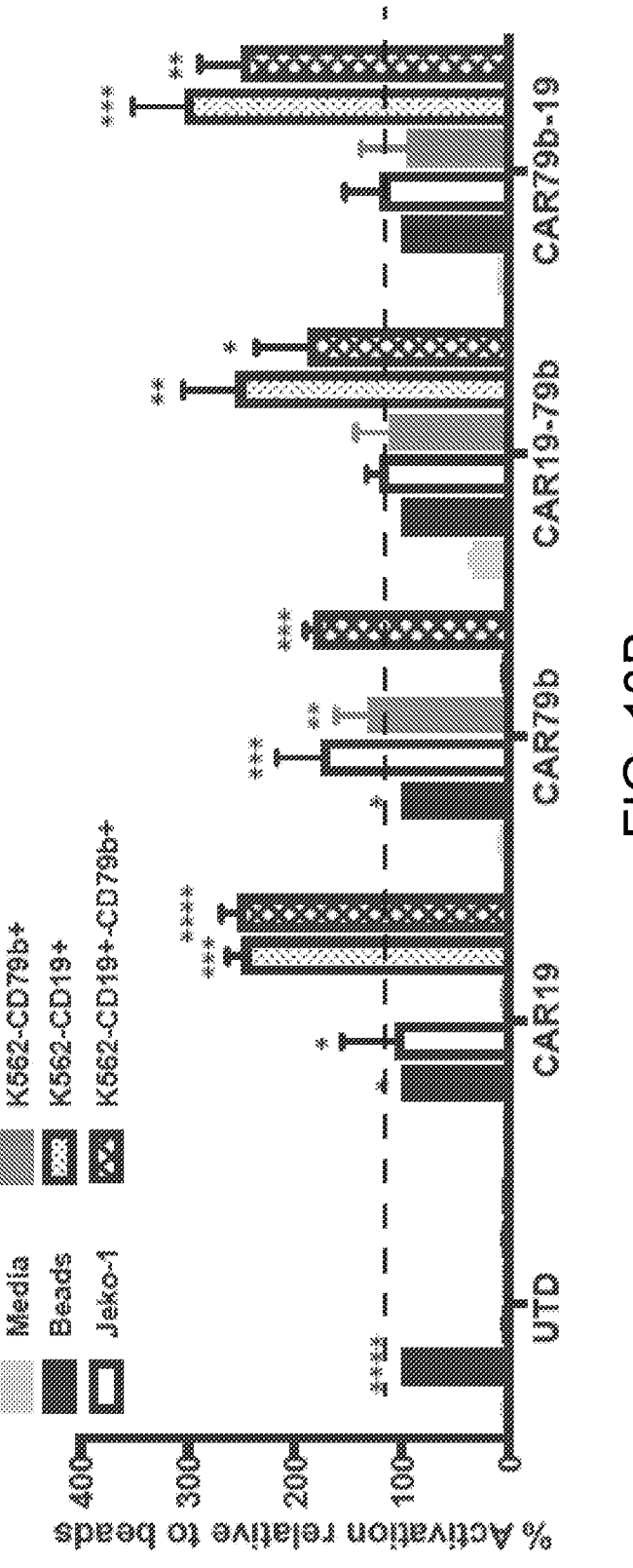
Figure 13C:
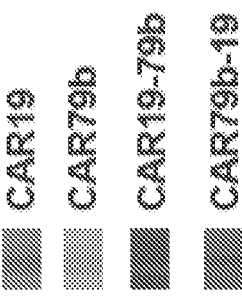
Figure 13C:
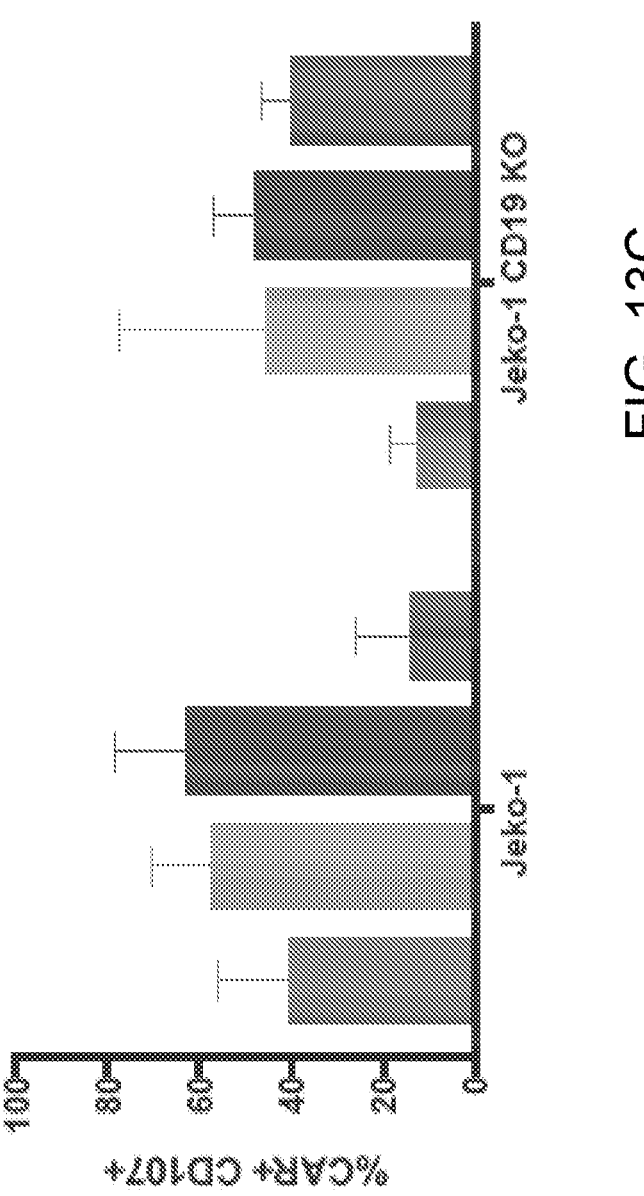
Figures 13D, 13E:
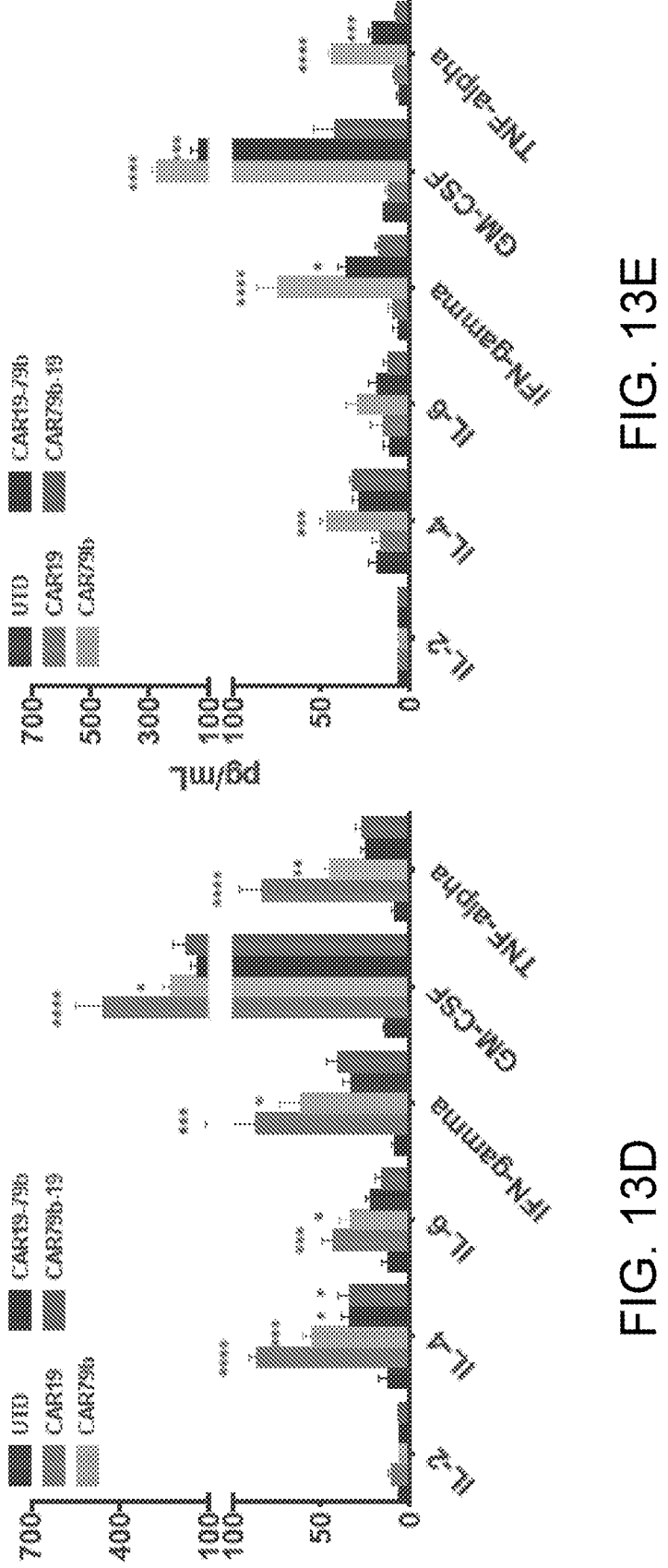

One strategy to prevent relapse with CD19-negative disease is to target heterogeneous tumors with CARs that target multiple antigens simultaneously. Therefore, we designed two second-generation tandem CARs targeting both CD79b and CD19 (FIG. 12A). No difference in transduction efficiency of human T cells from multiple donors was observed among the different tandem CAR constructs, but transduction efficiency of tandem bispecific CARs was slightly lower than the monospecific CARs, likely due to the size of the transgene (FIG. 13A). Using the Jurkat-NFAT reporter assay, we observed antigen-specific activation of our tandem CAR T cells in response to K562–CD79b+, K562–CD19+, and K562– CD19-CD79b+ cells (FIG. 13B), thus demonstrating the ability of the tandem CARs to recognize both CD19 and CD79b. Degranulation of tandem CAR T cells in response to CD19-negative tumors was evaluated after five hours of co-culture with tumor cells (FIG. 13C). All CAR T cells expressed surface CD107a when incubated with parental Jeko-1 cells. While the tandem CAR T cells maintained the ability to degranulate in response to the CD19-negative tumor, Jeko-1 (F12 clone 5), a clear reduction was seen for CAR19 in response to these cells. The CAR79b-CD19 tandem CAR seemed to have reduced degranulation against the parental Jeko-1 cells in this assay. Next, we evaluated the ability of the tandem CAR T cells to produce cytokines in response to stimulation with Jeko-1 (FIG. 13D). In general, the level of Th1 cytokine production was higher for CAR19 and CAR79b than for the tandem CAR19-79b and CAR79b-19 compared to UTDs. When the tandem CAR T cells were stimulated with CD19– negative Jeko-1 cells, we detected higher levels of cytokines in the cell culture medium for CAR19-79b than CAR79b-19 (FIG. 13E). As expected, no cytokine production by CAR19 in response to the CD19-negative Jeko-1 cell line was detected. The ability of CAR79b to secrete effector cytokines in response to the CD19-negative Jeko-1 cell line was retained. In conclusion, these results demonstrate the ability of the tandem CAR T cells to maintain their effector functions independent of CD19 antigen expression, but there was not necessarily a clear advantage of one tandem CAR format over the other.

Figure 12B:
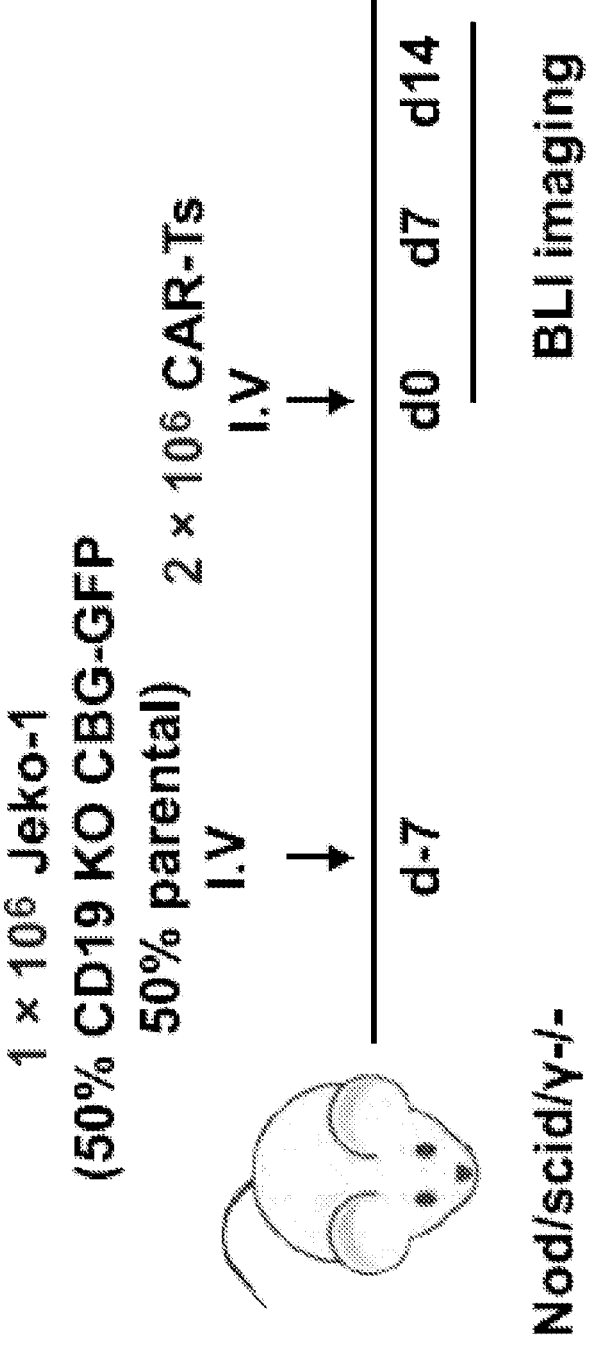
Figure 12C:
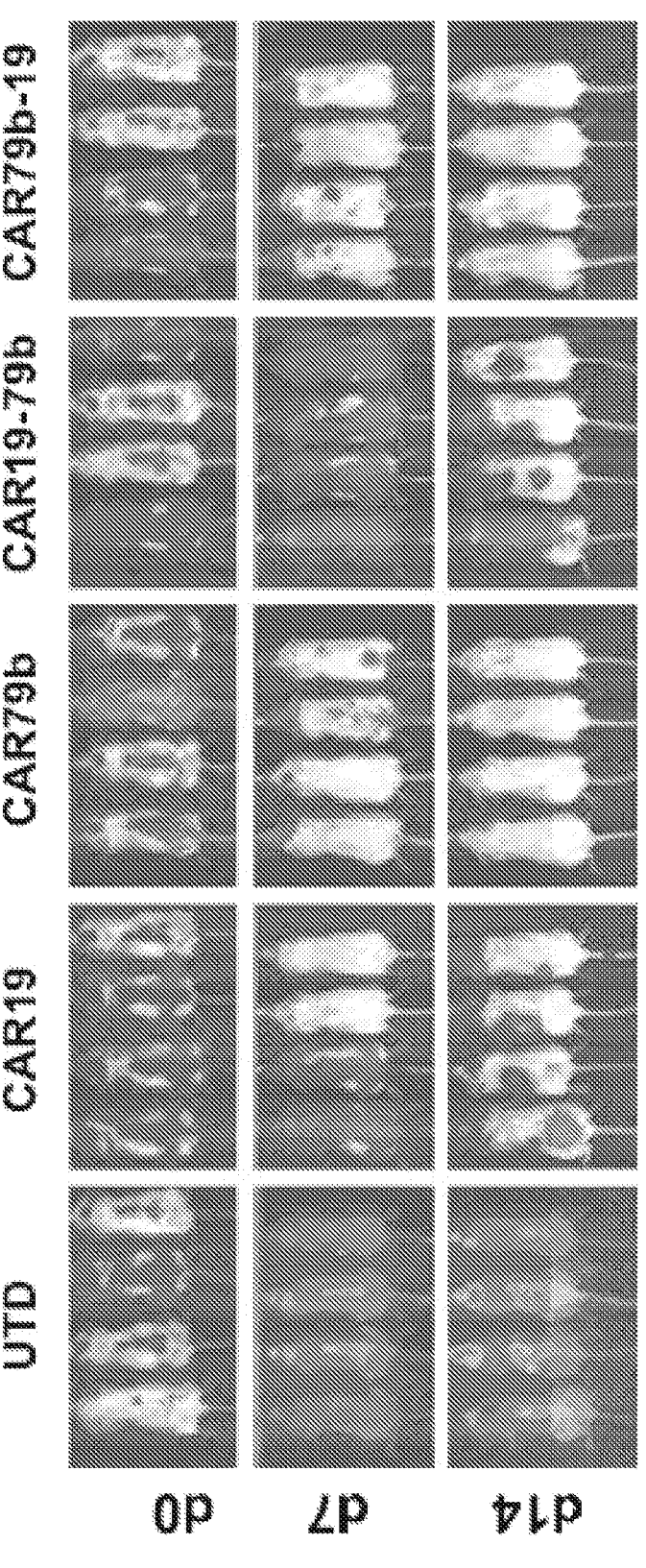
Figure 12D:
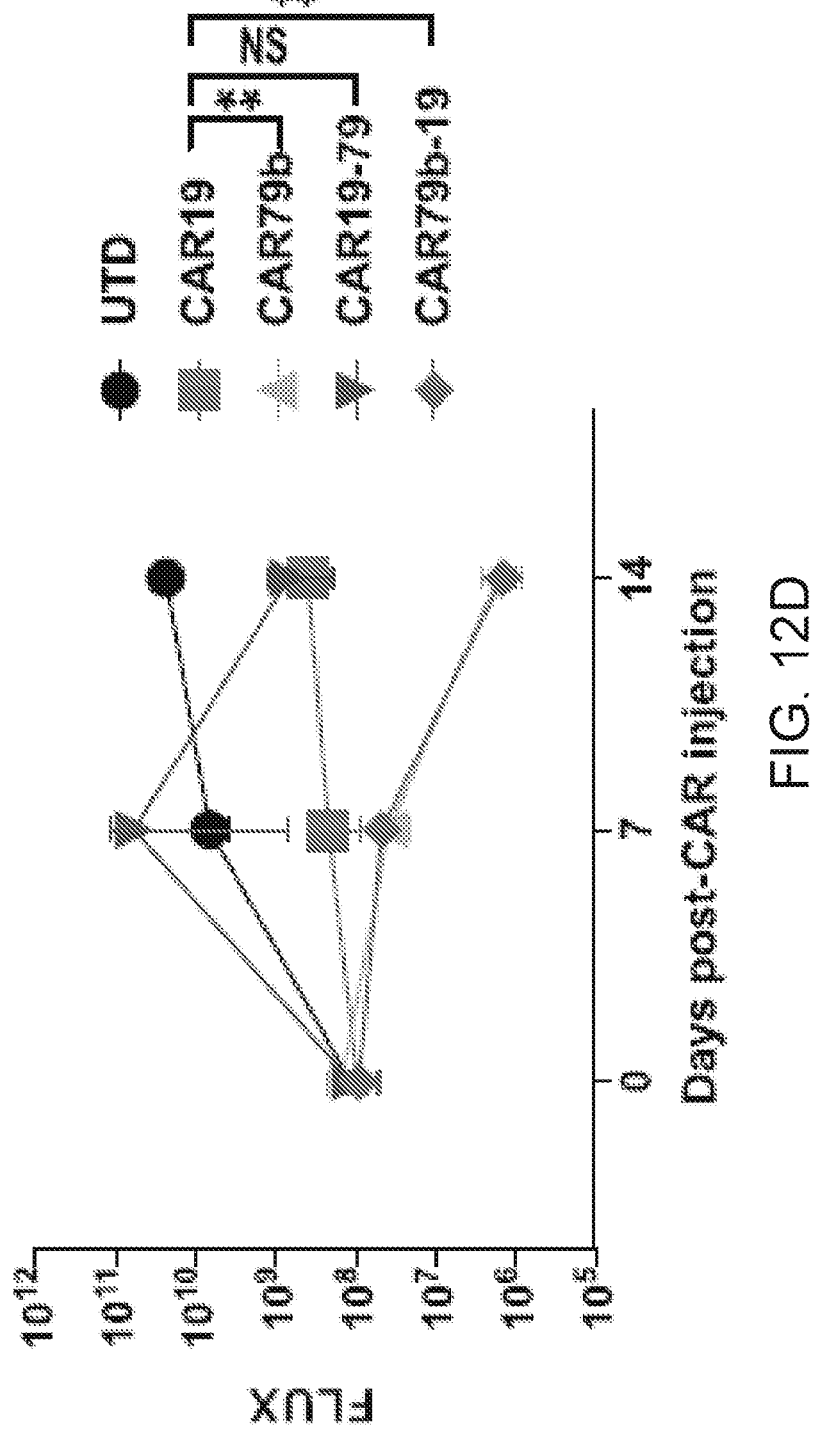
Figure 12E:
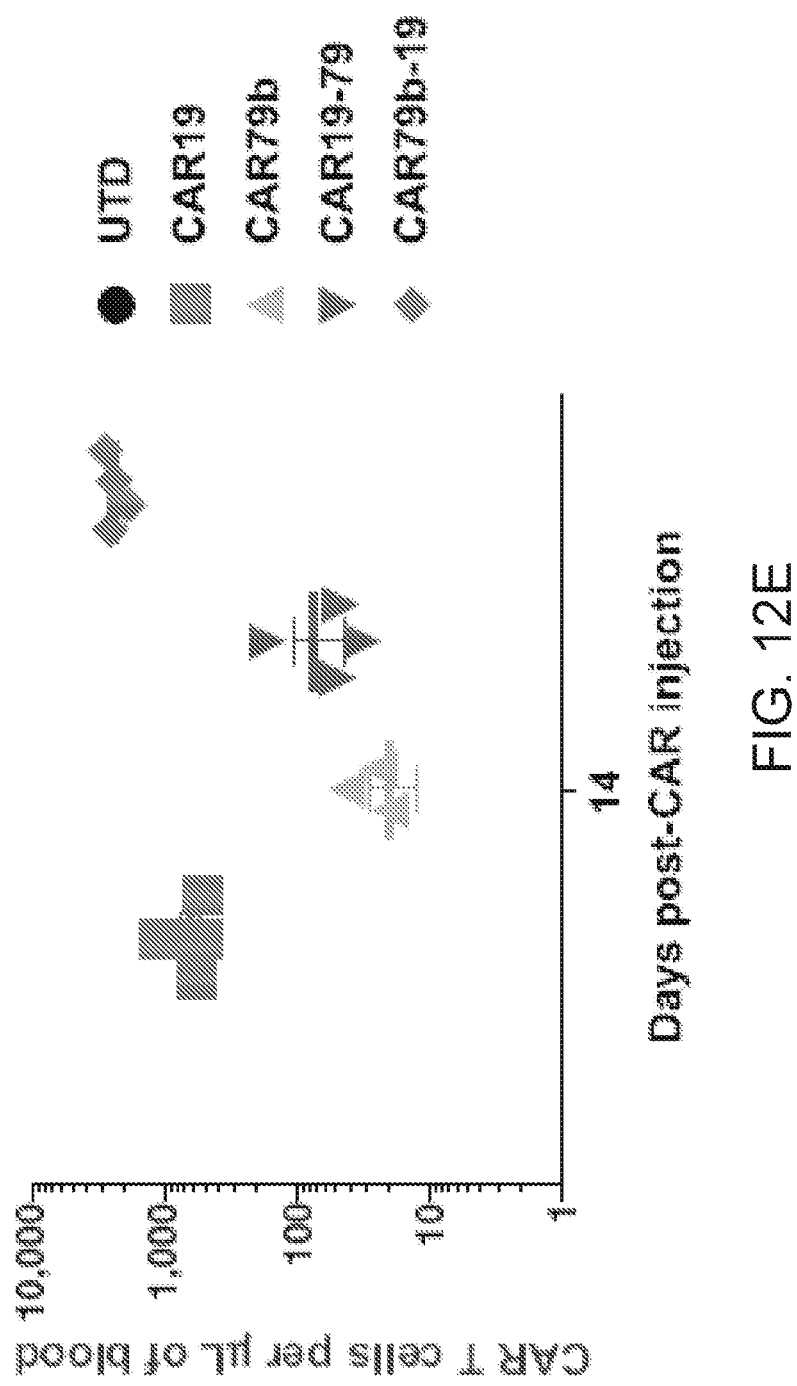

Example 8. CAR79b-CD19 Eradicates CD19-Negative MCL Tumors In Vivo within Mixed Tumors Next, we sought to test the ability of the tandem CAR T cells to lyse CD19-negative tumors in the context of a heterogeneous tumor in a xenograft model. We used a 1:1 mix of parental Jeko-1 and CD19– negative Jeko-1 cells as tumors, and tested CAR19, CAR79b, and the two tandem CARs, CAR19-79b and CAR79b-19, as treatment. Donor-matched untransduced T cells were used as controls for allogeneic effects. Briefly, NSG mice received an intravenous injection of a 1:1 mixture of tumor cells; at day 7, when tumors were established based on BLI, mice were re-grouped and received a single dose of UTD's, CAR19, CAR79b, CAR19-79b or CAR79b-19 (FIG. 12B). Seven days post CAR T cell injection, we noted a reduction in tumor burden for CAR79b and CAR79b-19 compared to CAR19 and CAR19-79b, which was maintained through day 14 (FIG. 12C and FIG. 12D). We detected the presence of CAR T cells in peripheral blood in all CAR treatment groups 14 days post CAR T cell injection (FIG. 12E). Taken together, these data demonstrate that CAR79b and CAR79b-19, but not CAR19-79b, could lyse CD19– negative lymphoma within a heterogeneous tumor.

Figure 14A:
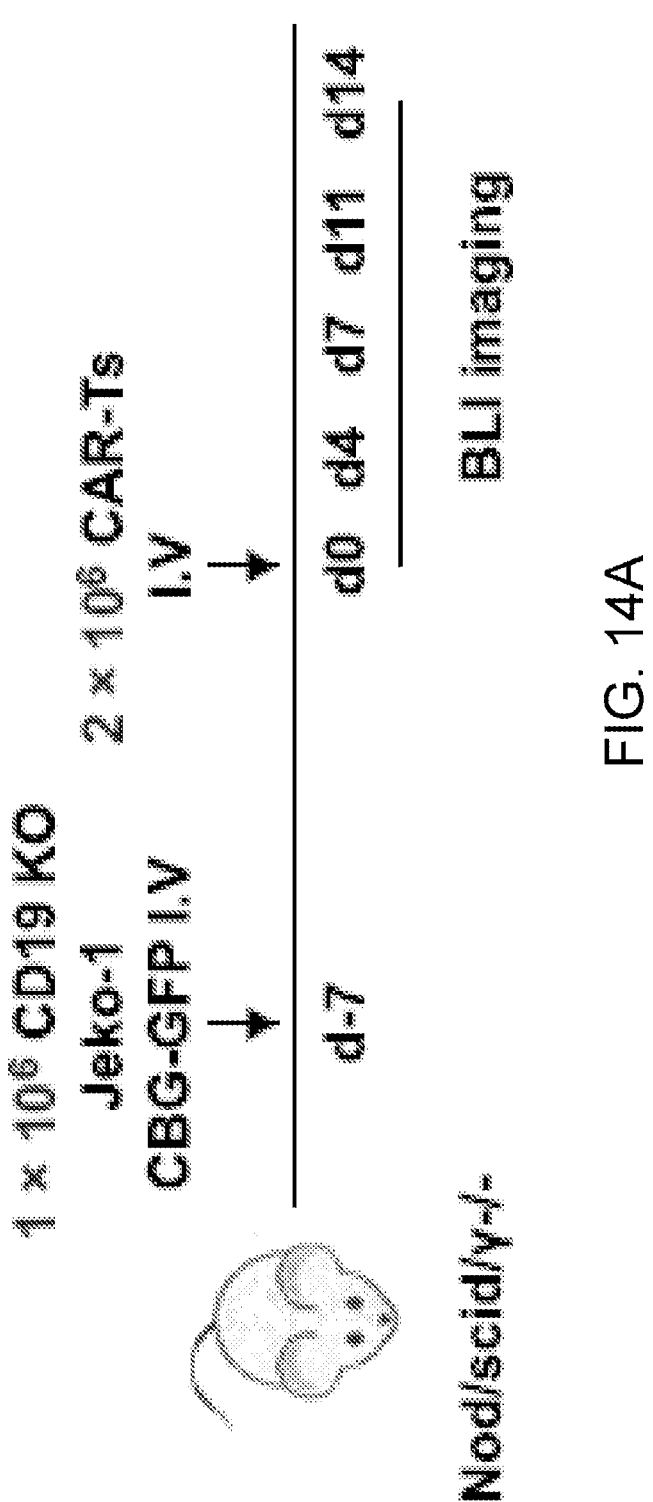
FIG. 14A-FIG. 14C show both CAR79b and CAR79b-19 T cells eradicate CD19− "relapsed" tumors in vivo.
Figure 14B:
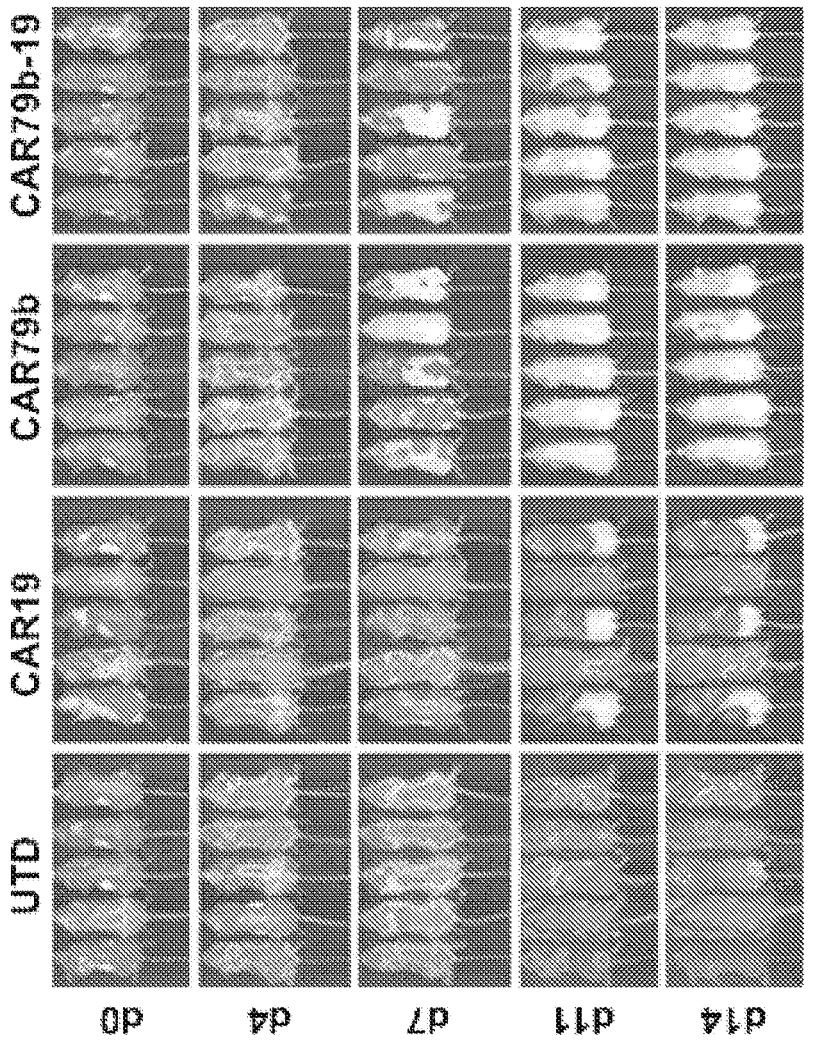
Figure 14C:
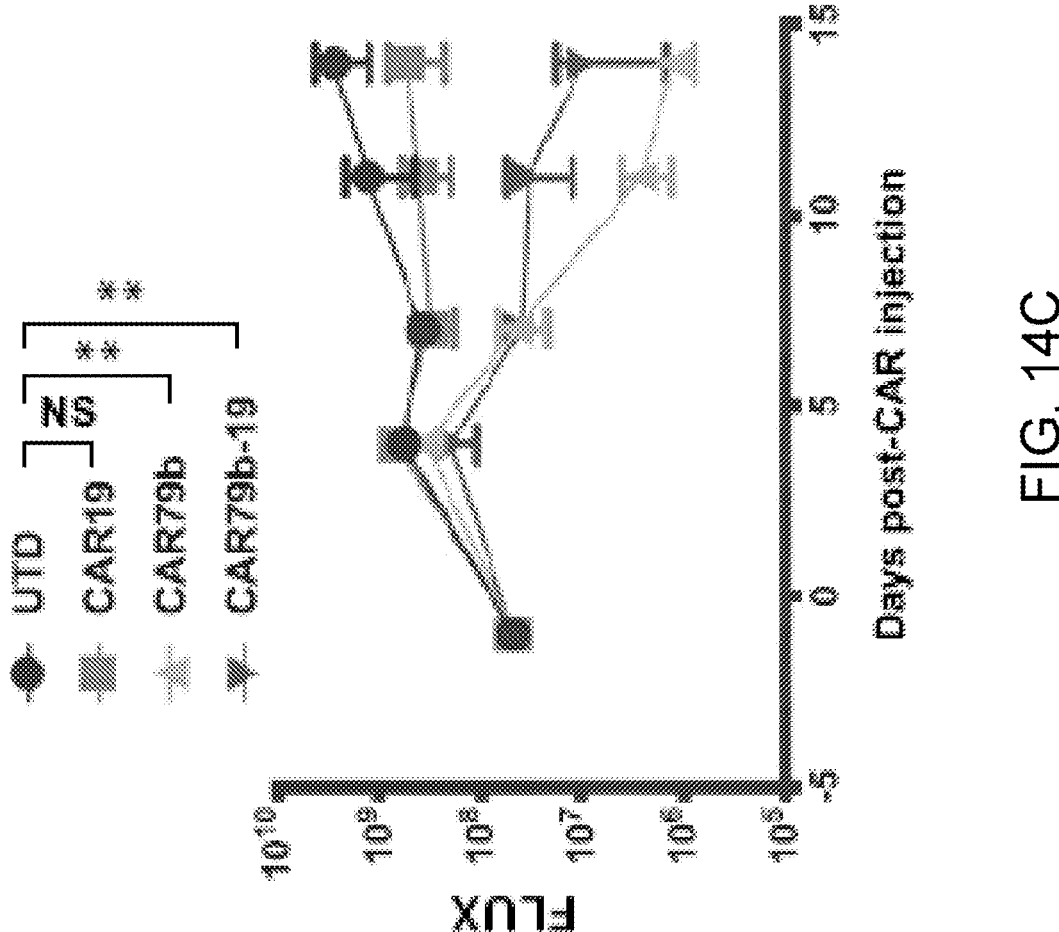
Figure 15A:
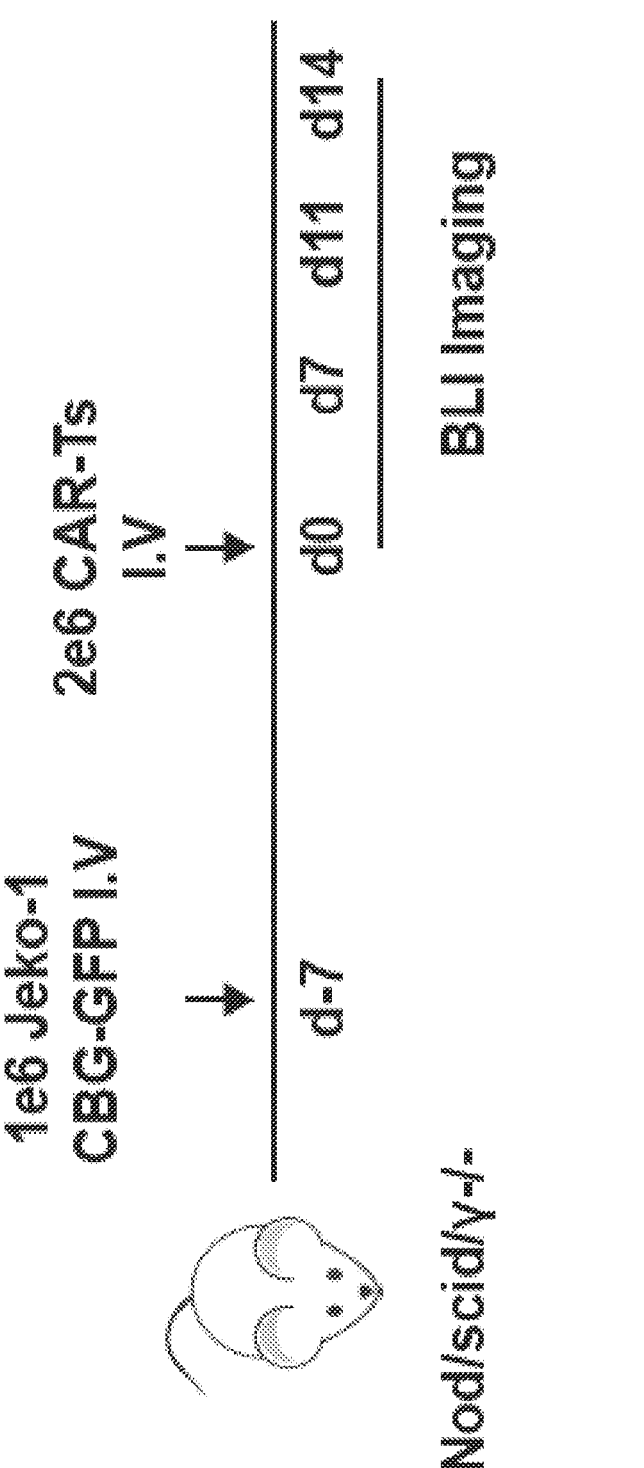
FIG. 15A-FIG. 15D show CD79b and CAR79b-19 CAR T cells clear MCL CD79b+CD19+"upfront" tumors in vivo.
Figure 15B:
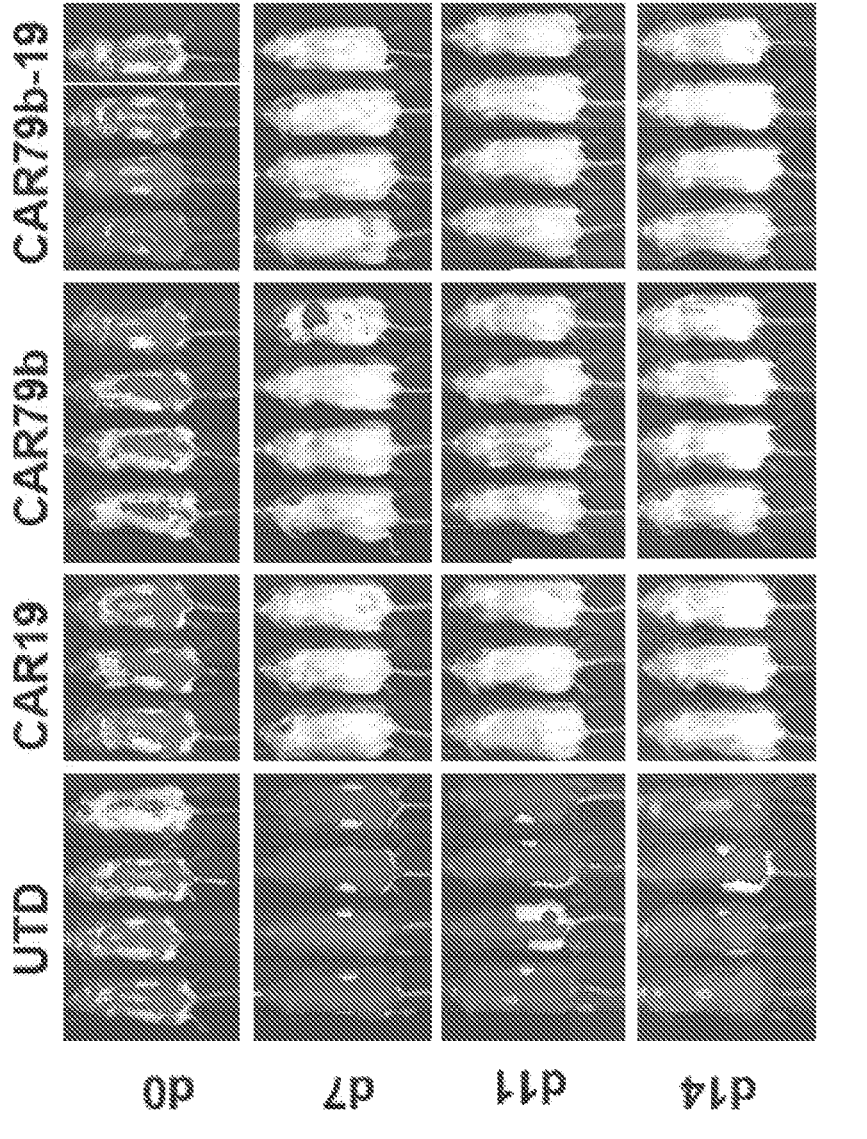
Figure 15C:
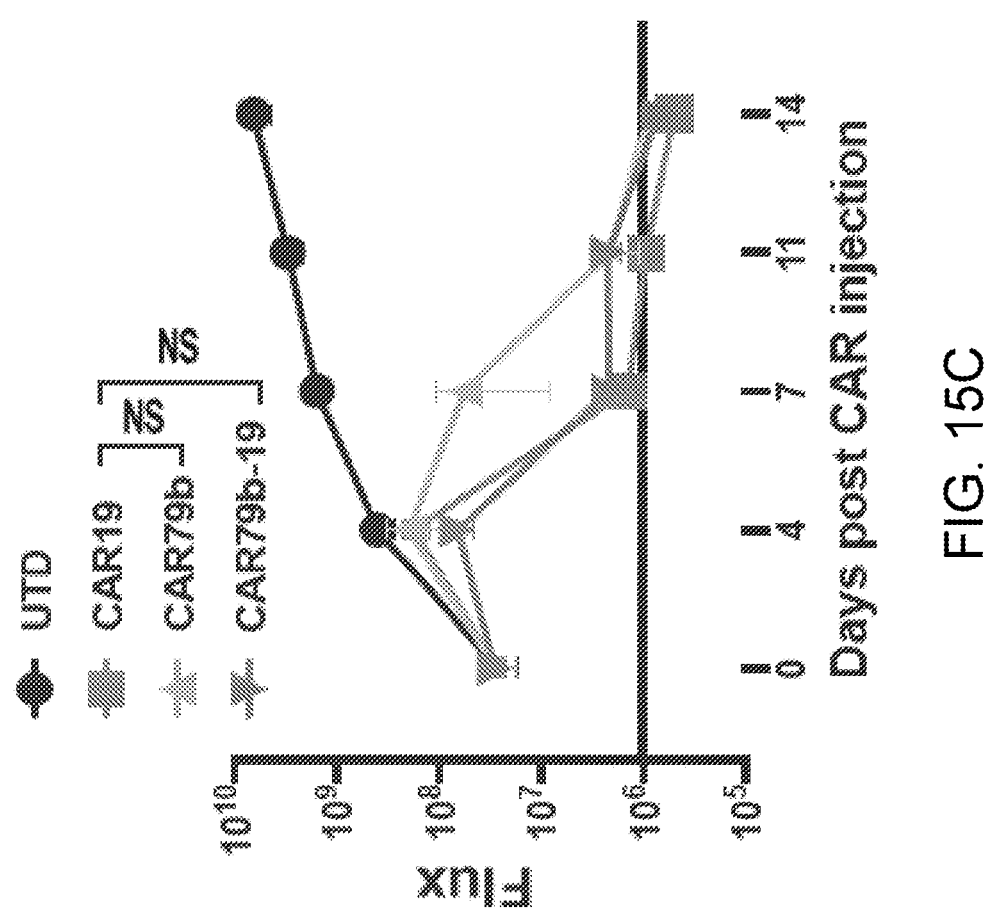
Figure 15D:
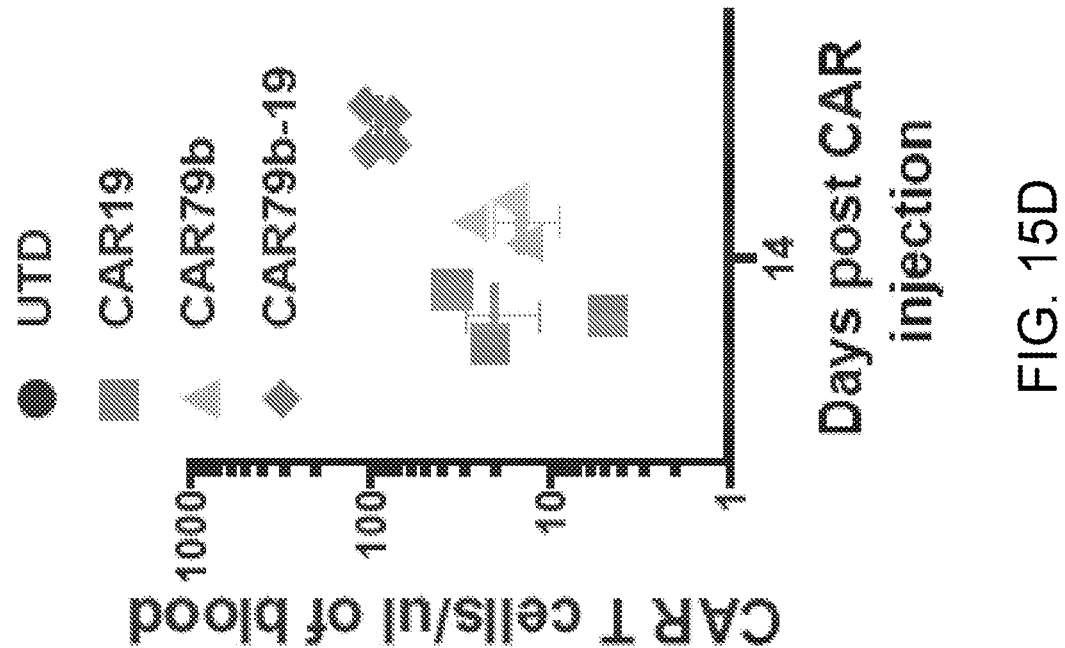
Figure 16A:
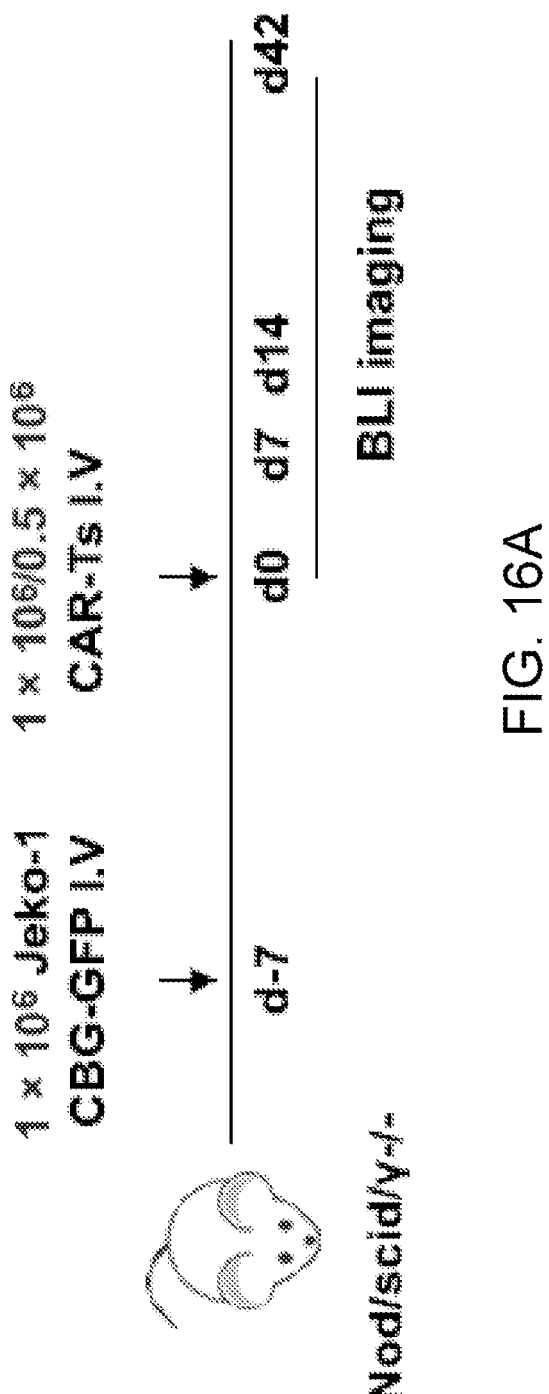
FIG. 16A-FIG. 16C show CAR79b-19 T cells eradicate MCL tumors at a lower dose compared to CAR79b.
Figure 16B:
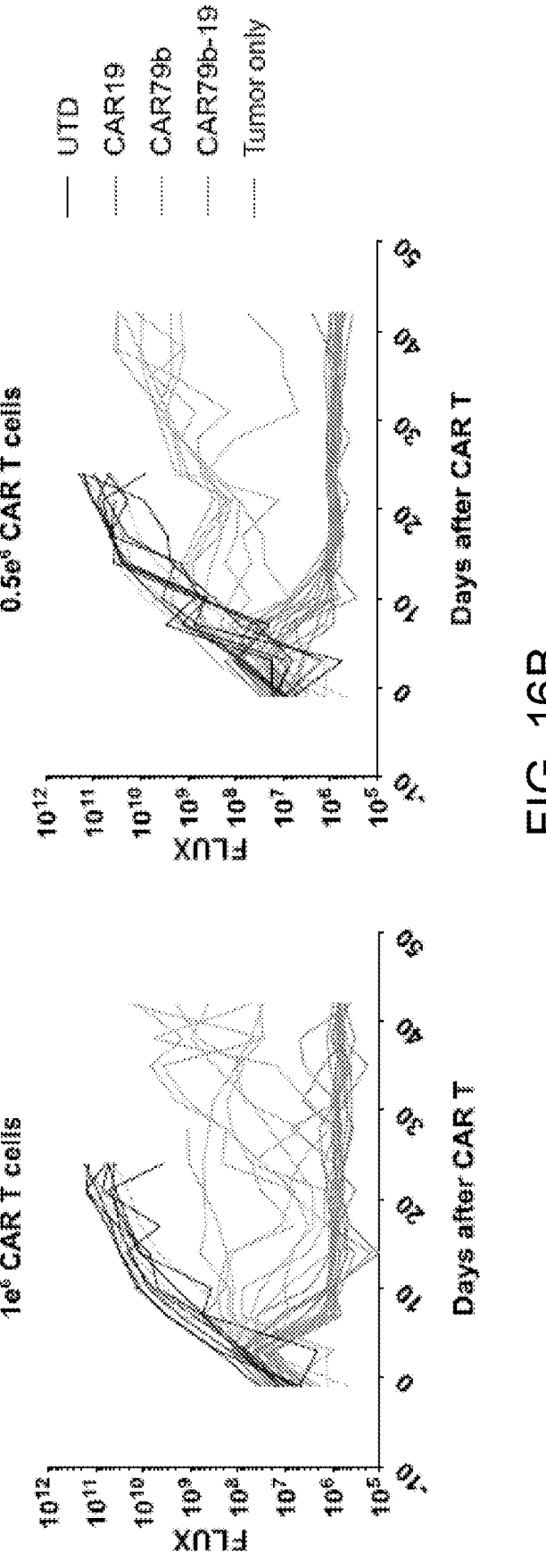
Figure 16C:
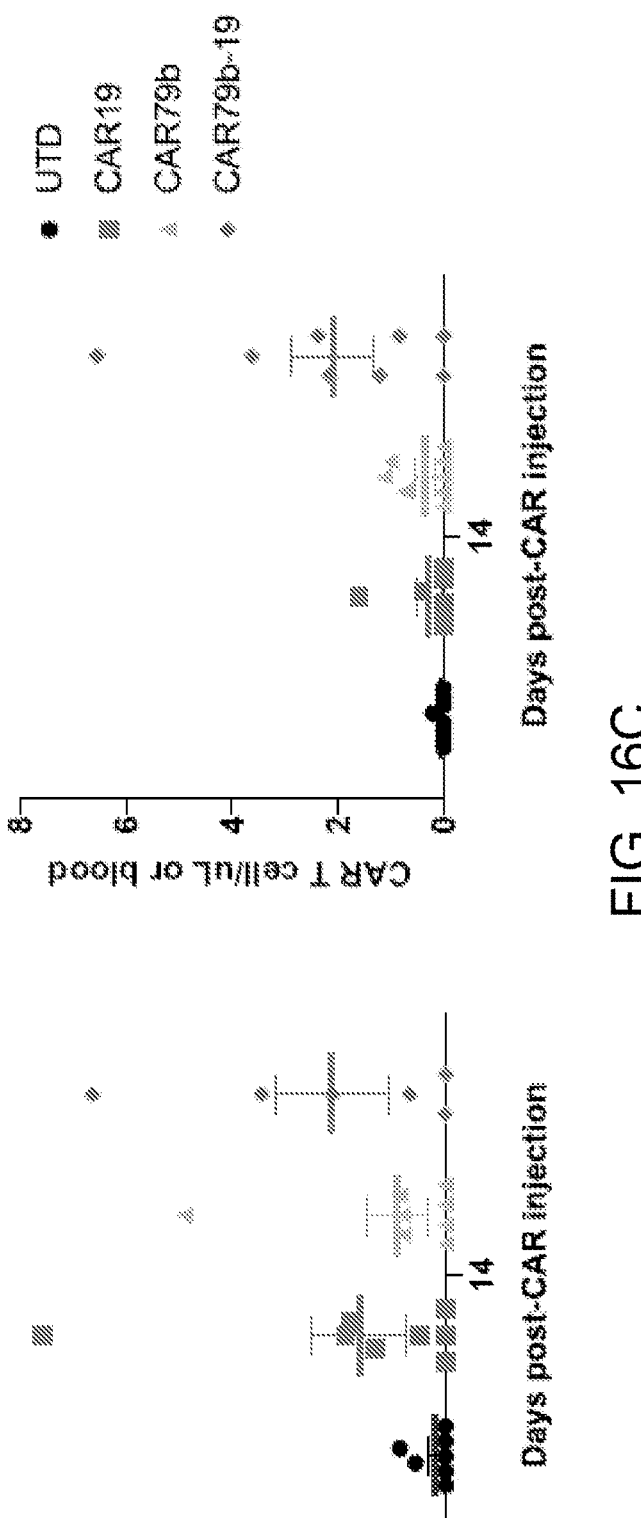

Example 9. CAR79b-CD19 CAR T Cells are Effective Against Pure CD19-Negative "Relapsed" Lymphoma and CD19+CD79b+ "Upfront" Lymphoma In order to test whether tandem bispecific CARs were still effective compared to monospecific CARs targeting CD79b in the CD19-negative relapse setting, we engrafted NSG mice intravenously with CD19-negative Jeko-1 cells one week before intravenous injection of CAR T cells, using donor-matched UTD and CAR19 serving as controls (FIG. 14A). We observed that CAR79b and CAR79b-19 both cleared tumor by day 14, though monospecific targeting with CAR79b cleared tumor a few days earlier (FIG. 14B and FIG. 14C). Next, to test whether monospecific or bispecific CARs would be equally effective in the "upfront" setting, we engrafted NSG mice with the parental Jeko-1 cells and compared treatment with CAR19, CAR79b, and CAR79b-19 to donor-matched UTD (FIG. 15A). CAR79b-19 and CAR-19 cleared the tumors by day 7, followed by CAR79b at day 11 of treatment (FIG. 15A and FIG. 15C). We confirmed the presence of CAR T cells in peripheral blood at day 14 (FIG. 16C).

Finally, we used a stress model to better evaluate and compare the efficacy of monospecific CD79b and bispecific CAR T cells targeting CD19 and CD79b. We injected $1\times10^6$ Jeko-1 cells into NSG mice followed by treatment with $1\times10^6$ or $0.5\times10^6$ UTD, CAR19 or CAR79b, CAR79b-19 bispecific T cells (FIG. 16A). CAR19 and CAR79b-19 could still induce complete remission at both lower doses of T cells. CAR79b T cells delayed tumor progression but they were insufficient to achieve tumor eradication despite evident tumor remission at early time points (FIG. 16B). We were able to detect CAR T cells in the blood at day 14 in some of the mice, which is perhaps explained by the lower dose of CAR T cells injected (FIG. 16C). Interestingly, the presence of CAR T cells in the blood did not correlate with clearance of the tumor, as it does in human subjects.

Collectively, these results indicate that tandem CAR79b-19 T cells have the potential to treat both CD19-negative relapsed tumors that may have recurred after CD19-targeted therapies, as well as to treat tumors that still retain CD19 expression, as most B cell lymphomas would prior to treatment with CD19− targeted therapies.

Example 10: Materials and Methods

Cell Lines and Culture

The human cell lines Jeko-1, JVM-2 and Granta-519 (MCL), SuDHL-4 and SuDHL-6 (DLBCL), Raji and Daudi (Burkitt's lymphoma), and MM.1s (Multiple Myeloma) were obtained from American Type Culture Collection (ATCC) and cultured in accordance with the supplier's recommendations. Parental K562 were purchased from ATCC and modified to express CD19 (K562–CD19+), CD79b (K562– CD79b+), or CD19 and CD79b (K562–CD19+CD79b+). For some assays, cell lines were transduced to express a click-beetle luciferase and green fluorescent protein (CBG-GFP+). CBG-GFP+ cells were sorted on a FACSAria (BD) and new cultures established.

Mantle Cell Lymphoma Patient Samples

Blood from six patients diagnosed with MCL was collected after written informed consent was obtained at the Haematology-Pathology Research Laboratory, Odense University Hospital, approved by The Regional Committees on Health Research Ethics for Southern Denmark in accordance with the Declaration of Helsinki. Peripheral blood mononuclear cells (PBMCs) were separated by Ficoll gradient centrifugation at diagnosis and cryopreserved until further analysis.

Flow Cytometry

Cells were stained with antibodies against phenotypic markers, run on a Fortessa X-20 (Becton Dickinson) or FACSCanto (Becton Dickinson) and data analyzed using FlowJo software (Tree Star) or Flow logic (Inivai technologies). The following antibodies, purchased from BD Bioscience and BioLegend, were used: BV421-CD19 (Clone HIB19), APC-CD19 (Clone 4G7), BB515-CD79b (Clone 3A2-2E7), PE-Cy7-CD79b (Clone CB3-1), PercPCy5.5-CD3 (Clone UCHT1), BUV395-CD3 (Clone UCTH1), PE-Cy7-kappa (G20-193), Alexa647-lambda (Clone JDC-12), PE-CD5 (UCHT2), APC-H7-CD20 (Clone 2H7), BV605-CD45 (Clone 2D1), and CD107a-AF700 (Clone H4A3). Cells were stained for 15 minutes in Hank's Balanced Salt Solution (HBSS) supplemented with 2% FBS. 7AAD or DAPI was used to exclude dead cells prior to acquisition.

CRISPR/Cas9 Knockout

Jeko-1 CBG-GFP+ cells were transduced with Cas9 lentivirus and selected with blasticidin. Three CD19 guides from the Brunello library (Nat Biotechnol 2016; 34(2):184-91) were purchased from the Broad Institute as lentiviruses and used to transduce Jeko-1 CBG-GFP+ Cas9 cells. Following puromycin selection, CD19-negative cells were single-cell sorted and further expanded for use in in vitro and in vivo assays.

CAR Constructs

Two second-generation anti-CD79b CARs, with either a light-heavy (CAR79b (L/H)) or a heavy-light (CAR79b (H/L)) single-chain variable fragment (scFv) configuration, were synthesized and cloned into a third-generation lentiviral backbone under control of the human EF1α promoter. All CARs included a CD8 hinge/transmembrane domain, 4-1 BB and CD3(intracellular domains, a T2A skip element, and an mCherry fluorescent protein as a reporter gene for transduction efficiency.

Transduction and Expansion of Human T Cells

Purified human T cells (STEMCELL Technologies, catalog #15061) from Leuko Paks of healthy donors were obtained from the Massachusetts General Hospital (MGH) blood bank under an IRB-exempt protocol in accordance with the U.S. Common Rule. For T cell expansion, T cells were activated (day 0) with anti-CD3/CD28-coated Dynabeads (Life Technologies, Catalog #111.32D) at a 3:1 bead-to-cell ratio. 24 hours after activation, T cells were lentivirally transduced to express the CAR construct. T cells were grown in RPMI media supplemented with 10% fetal bovine serum (FBS), penicillin, streptomycin (P/S), and 20 IU/mL of recombinant human IL-2. Cultures were maintained at $0.5e^6$ cells per mL and generally passaged every other day. For functional testing, cells were cryopreserved at day 9/10 of culture and directly used afterthawing.

Cytotoxicity, Activation, and Cytokine Assays

For all functional testing, different groups of CAR T cells were normalized for CAR expression by adding donor-matched and activated untransduced T cells. For cytotoxicity assays, CAR T cells were co-cultured with CBG-GFP+ target cells overnight at various ratios as indicated in each experiment. The percent specific killing was calculated based on luminescence measured with a Synergy Neo2 luminescence microplate reader (BioTek). For activation, Jurkat reporter (NFAT-luciferase) T cells transduced with CAR constructs were co-cultured overnight with target cells at a 1:1 ratio. Luciferase activity was used to measure percent specific activation using the Synergy Neo2 plate reader. For the analysis of cytokine production, CAR T cells were co-cultured overnight with target cells at a 1:1 ratio. Cell culture supernatants were collected and technical duplicates analyzed for level of cytokines, using a multiplex Luminex array (Luminex Corp., FLEXMAP 3D) in accordance with the manufacturer's instructions. All assays were performed in biological duplicates or more in each experiment, as indicated by N, which corresponds to the number of healthy donor T cells tested.

In Vivo Studies

All animal experiments were performed in accordance with Federal and Institutional Animal Care and Use Committee (IACUC) requirements under an MGH-approved protocol. Animals were caged in groups with free access to food and water. NOD-SCID-γ chain–/– (NSG) mice (Jackson Laboratories) were engrafted with Jeko-1 CBG-GFP+ or patient-derived tumor cells at the cell number and route of administration specified in each experiment. Cryopreserved CAR T cells were normalized for CAR expression by the addition of activated untransduced donor-matched T cells and given as a single intravenous (IV) injection after tumor engraftment was established by bioluminescent imaging (BLI). To estimate the tumor burden, mice were imaged using an AMI spectra imaging apparatus after receiving an intraperitoneal (IP) injection of D-Luciferin (30 mg/mL). Images were analyzed with IDL software version 4.3.1. Animal welfare—including body weight, appearance, and tumor burden—was regularly monitored and animals were euthanized when they met pre-specified end points defined by the IACUC.

Statistical Analysis

Statistical analysis was performed using GraphPad Prism 7 software. A t test was performed when comparing two groups and a one-way analysis of variance (ANOVA) or a two-way ANOVA test, as appropriate, when comparing multiple groups. A p-value <0.05 was considered statistically significant.

CD19 shRNA Knockdown pLKO.1 vectors with two different shRNA inserts specific for CD19 (MISSION shRNA, Sigma) as well as empty vector were packed in HEK293T cells into lentiviral particles, which were concentrated using PEG-6000. On day 1, 10e6 Jeko-1 cells were transduced with 50 ul 100× concentrated virus in the presence of 5 μg/ml polybrene for 24 h. On day 5, transduction efficiency was analyzed with flow cytometry, and selection with 0.4 μg/ml puromycin was initiated. After 11 days of selection, CD19 and CD79b expression was analyzed again using flow cytometry and SYBR green qPCR.

SYBR Green qPCR

RNA was isolated from jeko-1 cells with RNeasy minikit (Qiagen). cDNA was synthesized using Maxima H Minus Reverse Transcriptase (Thermo Scientific). QuantiTect SYBR green PCR kit (Qiagen) was used for qPCR, which was run on a StepOnePlus Real Time PCR System (Applied Biosystems). CD19 forward primer: 5'AGGGAGA-TAACGCTGTGCTG-3' (SEQ ID NO: 30), CD19 reverse primer: 5'-AGAAGGGTTTAAGCGGGGAC-3' (SEQ ID NO: 31), PUM1 forward primer: 5'-GTACTGTCCCCAC-GATCGGA-3' (SEQ ID NO: 32), and PUM1 reverse primer: 5-'TGCATCCCTTGGGCCAA ATC-3' (SEQ ID NO: 33).

Example 11: Summary

CD19 CAR T cell therapy has been highly efficacious as treatment of a variety of B cell malignancies, leading to recent approval by the FDA of two CD19-directed CAR T cell products, axicabtagene ciloleucel and tisagenlecleucel for r/r DLBCL. Despite the overall success rate, reports of patients relapsing with CD19-negative disease after CD19-directed CAR therapy are now emerging (N Engl J Med 2017; 377(26):2545-54; Cancer Discov 2015; 5(12):1282-95; Blood 2016; 127(20):2406-10). This constitutes a significant obstacle for CD19– directed therapies, and efforts to target additional antigens are becoming increasingly important. Trials targeting the B cell antigen CD22 in B-cell ALL are already underway, but it has been noted that serial targeting of single antigens can result in serial antigen escape (Nat Med 2018; 24(1):20-8). To avoid antigen escape, CARs targeting both CD19 and CD22 simultaneously are also in clinical development (J Immunother Cancer 2017; 5:42; Mol Ther Oncolytics 2018; 11:127-37). Unfortunately, CD22 expression is often lost in more mature B cell malignancies like lymphomas (Am J Clin Pathol 2010; 134(1):127-38; Cytometry B Clin Cytom 2011; 80(2):83-90), making alternative antigen targets necessary.

The BCR consists of membrane-bound immunoglobulin and a transmembrane heterodimer consisting of CD79a and CD79b. The cytoplasmic tails of CD79a and CD79b contain an immunoreceptor tyrosine-based activation motif (ITAM), important for propagating signals within the B cell upon antigen ligation. Because of its signal-transducing properties, CD79b is an important mediator of development and maintenance of mature B cells. Its expression is restricted to the B cell compartment and lymphoid tissues, including bone marrow, tonsils, appendix, lymph nodes, and spleen, as well as most types of lymphoma (Appl Immunohistochem Mol Morphol 2001; 9(2):97-106; Haematologica 1999; 84(5):413-8; Leukemia 1996; 10(12):1966-70). Many B cell lymphomas require continuous BCR signaling for their tumor growth, and several reports have established somatic mutations affecting the ITAM region of CD79b as a mechanism for enhanced tumorigenicity (EMBO J 2018; 37(11): pii: e97980; Hum Pathol 2014; 45(3):556-64; Leuk Lymphoma 2015; 56(7):2141-5; ISRN Oncol 2013; 2013: 252318). Indeed, different drug modalities targeting CD79b have been shown to be effective and well tolerated (Leukemia 2015; 29(7):1578-86; Lancet Oncol 2015; 16(6):704-15; Blood 2009; 114(13):2721-9; The American Society of Hematology, Blood 2014; 124(4507)) In an abstract presented at the American Association for Cancer Research in 2017, an anti-CD79b/CD3 BiTE showed inhibition of tumor growth in a humanized lymphoma xenograft mouse model. Encouragingly, an anti-cynoCD79b/CD3 BiTE was tested in a cynomolgusmonkey model and was associated with an acceptable safety profile. The antibody-drug conjugate polatuzumab vedotin, directed against CD79b, was tested in a phase 1 dose escalation trial in cohorts of patients diagnosed with NHL or CLL (Lancet Oncol 2015; 16(6):704-15). Objective responses were noted in 23 of 42 NHL patients, including responses in indolent NHL, DLBCL, and MCL. No objective responses were observed in the CLL cohort, potentially owing to the fact that CD79b surface expression is often downregulated or absent in this patient group (Haematologica 1999; 84(5):413-8; Am J Clin Pathol 1997; 108(4):378-82). Collectively, these observations support CD79b as a potential target in lymphoma for CAR T cell therapy.

The loss of CD19 has been reported in up to 30% of patients treated with CD19-CAR T cells (N Engl J Med 2017; 377(26):2545-54; Cancer Discov 2015; 5(12):1282-95; Blood 2016; 127(20):2406-10; Haematologica 2018; 103(5):e215-e8; Comput Struct Biotechnol J 2016; 14:357-62). Based on this, we hypothesized that potential antigen escape could be overcome or prevented by alternative or multiple antigen targeting. Therefore, we designed and validated the efficacy of a novel CAR construct directed against CD79b. First, we confirmed the expression of CD79b in a cohort of MCL patients. We noted some variability in the surface expression of CD79b. However, our Jeko-1 cells had lower CD79b expression as measured by MFI compared to our PDX, and yet was still responsive to the CAR79b cells. Nevertheless, selection of patients whose tumors have strong and uniform expression of CD79b may be a useful approach for early clinical testing. In the present study, we demonstrated that T cells engineered to express a second-generation CAR directed against CD79b had the ability to eradicate CD79b-expressing tumors. The anti-CD79b CAR bearing the L/H configuration showed particularly superior antitumor efficacy compared to its H/L counterpart. Importantly, the CD79b CAR T cells showed compatible efficacy to the CD19 CAR T cells used as the current gold standard within the field.

CD19 has been shown to function as a co-receptor for the BCR by reducing the threshold for B cell signaling. In addition, CD79b and CD19 have been shown to form an alternative B cell signaling module that, via continuous ITAM/PI3K signaling, can promote the survival of lymphomas (EMBO J 2018; 37(11)). Therefore, we sought to investigate if the loss of CD19 would modulate the surface expression of CD79b. We used CRISPR/Cas9 to generate CD19-negative Jeko-1 cells. Knocking out CD19 led to the loss of CD19 without altering the level of CD79b expression on the cell surface. Similar results were observed in a Burkitt's lymphoma cell line model, where CRISPR/Cas9-mediated knockout of CD19 in Ramos cells did not reduce the expression of surface CD79b (EMBO J 2018; 37(11):pii: e97980). Collectively, our results demonstrate no immediate correlation between the loss of CD19 and CD79b surface expression. Although we realize that these data are based on tumor cell lines and therefore should be interpreted with caution, they do support the hypothesis that CD79b surface expression will be retained in patients who relapse with CD19-negative disease after CD19-targeted therapy. In ALL, resistance to CAR-19 can be mediated by the production of alternative CD19 transcripts lacking the epitope targeted by the CAR. This truncated version of CD19 failed to trigger CAR T cell killing but partly rescued defects in cell proliferation and pre-BCR signaling associated with CD19 loss (Cancer Discov 2015; 5(12):1282-95). CD19 loss has also now been demonstrated at the genomic level, occurring via frameshift mutations (Nat Med 2018; 24(10): 1504-6). Whether CD19 expression loss in lymphoma is due to frameshift or splicing variants of CD19 remains to be established. In both genomic and RNA models of CD19 loss, we were able to demonstrate that CD79b expression was not affected. Furthermore, CD79b-directed CAR T cells, in both a monospecific and bi-specific confirmation with anti-CD19, were able to induce regression of CD19-negative tumor cells in vivo. Unfortunately, one weakness of our study is that our CD19-negative lymphoma tumors also expressed Cas9, and we observed that allogeneic effects against Cas9-expressing tumor cells reduced the usable timelines of our in vivo experiments. Immunogenicity in the general population against Cas9 was recently described (Nat Med 2019; 25(2): 249-54).

Because it is likely that loss of CD19 reflects the selective pressure on the antigen exerted by CAR T cells, one strategy to prevent this problem is the development of novel CARs directed against multiple surface antigens. Therefore, we designed and validated the efficacy of a tandem CAR bearing scFvs directed against CD79b and CD19. We showed that one specific configuration of tandem CAR T cells showed in vivo antitumor activity against CD19-negative lymphoma, whereas CAR19 or a different configuration of the tandem CAR did not. Unfortunately, xenograft models of lymphoma are not adequate models in which to rigorously test the hypothesis that tandem CARs can prevent antigen escape. Although some xenograft models of leukemia can be used to model CD19 escape, such pre-B cell acute lymphoblastic leukemia models would also be expected to lack CD79b expression (Leukemia 1996; 10(5): 769-73). Models of lymphoma that spontaneously result in antigen escape would be beneficial to the field.

In conclusion, CD79b represents a new target for the treatment of B-cell lymphoma. We report potent efficacy of monospecific CD79b and bispecific CD79b-CD19 CAR T cells in vitro and in xenograft models of lymphoma. CAR T cells targeting CD79b, particularly in combination with simultaneous targeting of CD19, could offer a new therapeutic option for patients who have CD19-negative recurrence of their lymphoma, or who have not had prior treatment with CD19-directed therapy, in the hopes of preventing recurrence.

Example 12. Sequences

Bispecific CARs
CAR19-79b (SEQ ID NO: 1): anti-CD19 scFv (SEQ ID NO: 6 (amino acids 1-247 of SEQ ID NO: 1)); linker (SEQ ID NO: 7 (amino acids 248-267 of SEQ ID NO: 1)); anti-CD79b (L/H) scFv (SEQ ID NO: 10 (amino acids 268-516 of SEQ ID NO: 1)); CD8 hinge/transmembrane (SEQ ID NO: 11 (amino acids 517-585 of SEQ ID NO: 1)); 4-1BB co-stimulatory domain (SEQ ID NO: 12 (amino acids 586-

627 of SEQ ID NO: 1)); and CD3(signaling domain (SEQ ID NO: 13 (amino acids 628-739 of SEQ ID NO: 1))

```
                                        (SEQ ID NO: 1)
EIVMTQSPATLSLSPGERATLSCRASQDISKYLNWYQQKPGQAPRLLIY

HTSRLHSGIPARFSGSGSGTDYTLTISSLQPEDFAVYFCQQGNTLPYTF

GQGTKLEIKGGGGSGGGGSGGGGSGGGGSQVQLQESGPGLVKPSETLSL

TCTVSGVSLPDYGVSWIRQPPGKGLEWIGVIWGSETTYYQSSLKSRVTI

SKDNSKNQVSLKLSSVTAADTAVYYCAKHYYYGGSYAMDYWGQGTLVTV

SSGGGGSGGGGSGGGGSGGGGSDIQLTQSPSSLSASVGDRVTITCKASQ

SVDYEGDSFLNWYQQKPGKAPKLLIYAASNLESGVPSRFSGSGSGIDFT

LTISSLQPEDFATYYCQQSNEDPLTFGQGTKVEIKRGGGGSGGGGSGGG

GSGGGGSEVQLVESGGGLVQPGGSLRLSCAASGYTFSSYWIEWVRQAPG

KGLEWIGEILPGGGDTNYNEIFKGRATFSADTSKNTAYLQMNSLRAEDT

AVYYCTRRVPIRLDYWGQGTLVTVSSTTTPAPRPPTPAPTIASQPLSLR

PEACRPAAGGAVHTRGLDFACDIYIWAPLAGTCGVLLLSLVITLYCKRG

RKKLLYIFKQPFMRPVQTTQEEDGCSCRFPEEEEGGCELRVKFSRSADA

PAYQQGQNQLYNELNLGRREEYDVLDKRRGRDPEMGGKPRRKNPQEGLY

NELQKDKMAEAYSEIGMKGERRRGKGHDGLYQGLSTATKDTYDALHMQA

LPPR
```

Anti-CD19 scFv (amino acids 1-247 of SEQ ID NO: 1)

```
                                        (SEQ ID NO: 6)
EIVMTQSPATLSLSPGERATLSCRASQDISKYLNWYQQKPGQAPRLLIY

HTSRLHSGIPARFSGSGSGTDYTLTISSLQPEDFAVYFCQQGNTLPYTF

GQGTKLEIKGGGGSGGGGSGGGGSGGGGSQVQLQESGPGLVKPSETLSL

TCTVSGVSLPDYGVSWIRQPPGKGLEWIGVIWGSETTYYQSSLKSRVTI

SKDNSKNQVSLKLSSVTAADTAVYYCAKHYYYGGSYAMDYWGQGTLVTV

SS
```

Linker (amino acids 248-267 of SEQ ID NO: 1)

```
                                        (SEQ ID NO: 7)
        GGGGSGGGGSGGGGSGGGGS
```

Anti-CD79b (L/H) scFv (amino acids 268-516 of SEQ ID NO: 1)

```
                                        (SEQ ID NO: 10)
DIQLTQSPSSLSASVGDRVTITCKASQSVDYEGDSFLNWYQQKPGKAPKL

LIYAASNLESGVPSRFSGSGSGIDFTLTISSLQPEDFATYYCQQSNEDPL

TFGQGTKVEIKRGGGGSGGGGSGGGGSGGGGSEVQLVESGGGLVQPGGSL

RLSCAASGYTFSSYWIEWVRQAPGKGLEWIGEILPGGGDTNYNEIFKGRA

TFSADTSKNTAYLQMNSLRAEDTAVYYCTRRVPIRLDYWGQGTLVTVSS
```

CD8 hinge/transmembrane domain (amino acids 517-585 of SEQ ID NO: 1)

```
                                      (SEQ ID NO: 11)
TTTPAPRPPTPAPTIASQPLSLRPEACRPAAGGAVHTRGLDFACDIYIWA
PLAGTCGVLLLSLVITLYC
```

4-1BB co-stimulatory domain (amino acids 586-627 of SEQ ID NO: 1)

```
                                      (SEQ ID NO: 12)
    KRGRKKLLYIFKQPFMRPVQTTQEEDGCSCRFPEEEEGGCEL
```

CD3 signaling domain (amino acids 628-739 of SEQ ID NO: 1)

```
                                      (SEQ ID NO: 13)
RVKFSRSADAPAYQQGQNQLYNELNLGRREEYDVLDKRRGRDPEMGGKPRR
KNPQEGLYNELQKDKMAEAYSEIGMKGERRRGKGHDGLYQGLSTATKDTYD
ALHMQALPPR
```

CAR79b-19 (SEQ ID NO: 2): anti-CD79b (L/H) scFv (SEQ ID NO: 10 (amino acids 1-249 of SEQ ID NO: 2)); linker (SEQ ID NO: 7 (amino acids 250-269 of SEQ ID NO: 2)); anti-CD19 scFv (SEQ ID NO: 6 (amino acids 270-516 of SEQ ID NO: 2)); CD8 hinge/transmembrane (SEQ ID NO: 11 (amino acids 517-585 of SEQ ID NO: 2)); 4-1BB co-stimulatory domain (SEQ ID NO: 12 (amino acids 586-627 of SEQ ID NO: 2)); and CD3(signaling domain (SEQ ID NO: 13 (amino acids 628-739 of SEQ ID NO: 2))

```
                                       (SEQ ID NO: 2)
DIQLTQSPSSLSASVGDRVTITCKASQSVDYEGDSFLNWYQQKPGKAPKLL

IYAASNLESGVPSRFSGSGSGIDFTLTISSLQPEDFATYYCQQSNEDPLTF

GQGTKVEIKRGGGGSGGGGSGGGGSGGGGSEVQLVESGGGLVQPGGSLRLS

CAASGYTFSSYWIEWVRQAPGKGLEWIGEILPGGGDTNYNEIFKGRATFSA

DTSKNTAYLQMNSLRAEDTAVYYCTRRVPIRLDYWGQGTLVTVSSGGGGSG

GGGSGGGGSGGGGSEIVMTQSPATLSLSPGERATLSCRASQDISKYLNWYQ

QKPGQAPRLLIYHTSRLHSGIPARFSGSGSGTDYTLTISSLQPEDFAVYFC

QQGNTLPYTFGQGTKLEIKGGGGSGGGGSGGGGSGGGGSQVQLQESGPGLV

KPSETLSLTCTVSGVSLPDYGVSWIRQPPGKGLEWIGVIWGSETTYYQSSL

KSRVTISKDNSKNQVSLKLSSVTAADTAVYYCAKHYYYGGSYAMDYWGQGT

LVTVSSTTTPAPRPPTPAPTIASQPLSLRPEACRPAAGGAVHTRGLDFACD

IYIWAPLAGTCGVLLLSLVITLYCKRGRKKLLYIFKQPFMRPVQTTQEEDG

CSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHD

GLYQGLSTATKDTYDALHMQALPPR
```

Anti-CD79b (L/H) scFv (amino acids 1-249 of SEQ ID NO: 2)

```
                                      (SEQ ID NO: 10)
DIQLTQSPSSLSASVGDRVTITCKASQSVDYEGDSFLNWYQQKPGKAPKLL

IYAASNLESGVPSRFSGSGSGIDFTLTISSLQPEDFATYYCQQSNEDPLTF

GQGTKVEIKRGGGGSGGGGSGGGGSGGGGSEVQLVESGGGLVQPGGSLRLS
```

```
CAASGYTFSSYWIEWVRQAPGKGLEWIGEILPGGGDTNYNEIFKGRATFSA

DTSKNTAYLQMNSLRAEDTAVYYCTRRVPIRLDYWGQGTLVTVSS
```

Linker (amino acids 250-269 of SEQ ID NO: 2)

```
                                       (SEQ ID NO: 7)
         GGGGSGGGGSGGGGSGGGGS
```

Anti-CD19 scFv (amino acids 270-516 of SEQ ID NO: 2)

```
                                       (SEQ ID NO: 6)
EIVMTQSPATLSLSPGERATLSCRASQDISKYLNWYQQKPGQAPRLLIYHT

SRLHSGIPARFSGSGSGTDYTLTISSLQPEDFAVYFCQQGNTLPYTFGQGT

KLEIKGGGGSGGGGSGGGGSGGGGSQVQLQESGPGLVKPSETLSLTCTVSG

VSLPDYGVSWIRQPPGKGLEWIGVIWGSETTYYQSSLKSRVTISKDNSKNQ

VSLKLSSVTAADTAVYYCAKHYYYGGSYAMDYWGQGTLVTVSS
```

CD8 hinge/transmembrane domain (amino acids 517-585 of SEQ ID NO: 2)

```
                                      (SEQ ID NO: 11)
TTTPAPRPPTPAPTIASQPLSLRPEACRPAAGGAVHTRGLDFACDIYIWAP
LAGTCGVLLLSLVITLYC
```

4-1 BB co-stimulatory domain (amino acids 586-627 of SEQ ID NO: 2)

```
                                      (SEQ ID NO: 12)
    KRGRKKLLYIFKQPFMRPVQTTQEEDGCSCRFPEEEEGGCEL
```

CD3 signaling domain (amino acids 628-739 of SEQ ID NO: 2)

```
                                      (SEQ ID NO: 13)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

Anti-CD19/CD79b CAR (SEQ ID NO: 14): anti-CD19 scFv (SEQ ID NO: 6 (amino acids 1-247 of SEQ ID NO: 14)); linker (SEQ ID NO: 7 (amino acids 248-267 of SEQ ID NO: 14)); anti-CD79b (L/H) scFv (SEQ ID NO: 17 (amino acids 268-516 of SEQ ID NO: 14)); CD8 hinge/transmembrane (SEQ ID NO: 11 (amino acids 517-585 of SEQ ID NO: 14)); 4-1BB co-stimulatory domain (SEQ ID NO: 12 (amino acids 586-627 of SEQ ID NO: 14)); and CD3(signaling domain (SEQ ID NO: 13 (amino acids 628-739 of SEQ ID NO: 14))

```
                                      (SEQ ID NO: 14)
EIVMTQSPATLSLSPGERATLSCRASQDISKYLNWYQQKPGQAPRLLIYH

TSRLHSGIPARFSGSGSGTDYTLTISSLQPEDFAVYFCQQGNTLPYTFGQ

GTKLEIKGGGGSGGGGSGGGGSGGGGSQVQLQESGPGLVKPSETLSLTCT

VSGVSLPDYGVSWIRQPPGKGLEWIGVIWGSETTYYQSSLKSRVTISKDN

SKNQVSLKLSSVTAADTAVYYCAKHYYYGGSYAMDYWGQGTLVTVSSGGG

GSGGGGSGGGGSGGGGSDIQLTQSPSSLSASVGDRVTITCKASQSVDYEG
```

-continued

DSFLNWYQQKPGKAPKLLIYAASNLESGVPSRFSGSGSGTDFTLTISSIQ

PEDFATYYCQQSNEDPLTFGQGTKVEIKRGGGGSGGGGSGGGGSGGGGSE

VQLVESGGGLVQPGGSLRLSCAASGYTFSSYWIEWVRQAPGKGLEWIGEI

LPGGGDTNYNEIFKGRATFSADTSKNTAYLQMNSLRAEDTAVYYCTRRVP

IRLDYWGQGTLVTVSSTTTPAPRPPTPAPTIASQPLSLRPEACRPAAGGA

VHTRGLDFACDIYIWAPLAGTCGVLLLSLVITLYCKRGRKKLLYIFKQPF

MRPVQTTQEEDGCSCRFPEEEEGGCELRVKFSRSADAPAYQQGQNQLYNE

LNLGRREEYDVLDKRRGRDPEMGGKPRRKNPQEGLYNELQKDKMAEAYSE

IGMKGERRRGKGHDGLYQGLSTATKDTYDALHMQALPPR

Anti-CD19 scFv (amino acids 1-247 of SEQ ID NO: 14)

(SEQ ID NO: 6)

EIVMTQSPATLSLSPGERATLSCRASQDISKYLNWYQQKPGQAPPLLIYH

TSRLHSGIPARFSGSGSGTDYTLTISSLQPEDFAVYFCQQGNTLPYTFGQ

GTKLEIKGGGGSGGGGSGGGGSGGGGSGGGGSQVQLQESGPGLVKPSETLSLTCT

VSGVSLPDYGVSWIRQPPGKGLEWIGVIWGSETTYYQSSLKSRVTISKDN

SKNQVSLKLSSVTAADTAVYYCAKHYYYGGSYAMDYWGQGTLVTVSS

Linker (amino acids 248-267 of SEQ ID NO: 14)

(SEQ ID NO: 7)

GGGGSGGGGSGGGGSGGGGS

Anti-CD79b (L/H) scFv (amino acids 268-516 of SEQ ID NO: 14)

(SEQ ID NO: 17)

DIQLTQSPSSLSASVGDRVTITCKASQSVDYEGDSFLNWYQQKPGKAPKL

LIYAASNLESGVPSRFSGSGSGTDFTLTISSIQPEDFATYYCQQSNEDPL

TFGQGTKVEIKRGGGGSGGGGSGGGGSGGGGSEVQLVESGGGLVQPGGSL

RLSCAASGYTFSSYWIEWVRQAPGKGLEWIGEILPGGGDTNYNE1FKGRA

TFSADTSKNTAYLQMNSLRAEDTAVYYCTRRVPIRLDYWGQGTLVTVSS

CD8 hinge/transmembrane domain (amino acids 517-585 of SEQ ID NO: 14)

(SEQ ID NO: 11)

TTTPAPRPPTPAPTIASQPLSLRPEACRPAAGGAVHTRGLDFACDIYIWA

PLAGTCGVLLLSLVITLYC 4-1BB co-stimulatory domain (amino acids 586-627 of SEQ ID NO: 14)

(SEQ ID NO: 12)

KRGRKKLLYIFKQPFMRPVQTTQEEDGCSCRFPEEEEGGCEL

CD3 signaling domain (amino acids 628-739 of SEQ ID NO: 14)

(SEQ ID NO: 13)

RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

Anti-CD79b/CD19 CAR (SEQ ID NO: 15): anti-CD79b (L/H) scFv (SEQ ID NO: 17 (amino acids 1-249 of SEQ ID NO: 15)); linker (SEQ ID NO: 7 (amino acids 250-269 of SEQ ID NO: 15)); anti-CD19 scFv (SEQ ID NO: 6 (amino acids 270-516 of SEQ ID NO: 15)); CD8 hinge/transmembrane (SEQ ID NO: 11 (amino acids 517-585 of SEQ ID NO: 15)); 4-1BB co-stimulatory domain (SEQ ID NO: 12 (amino acids 586-627 of SEQ ID NO: 15)); and CD3 (signaling domain (SEQ ID NO: 13 (amino acids 628-739 of SEQ ID NO: 15))

(SEQ ID NO: 15)

DIQLTQSPSSLSASVGDRVTITCKASQSVDYEGDSFLNWYQQKPGKAPKL

LIYAASNLESGVPSRFSGSGSGTDFTLTISSIQPEDFATYYCQQSNEDPL

TFGQGTKVEIKRGGGGSGGGGSGGGGSGGGGSEVQLVESGGGLVQPGGSL

RLSCAASGYTFSSYWIEWVRQAPGKGLEWIGEILPGGGDTNYNEIFKGRA

TFSADTSKNTAYLQMNSLRAEDTAVYYCTRRVPIRLDYWGQGTLVTVSSG

GGGSGGGGSGGGGSGGGGSEIVMTQSPATLSLSPGERATLSCRASQDISK

YLNWYQQKPGQAPRLLIYHTSRLHSGIPARFSGSGSGTDYTLTISSLQPE

DFAVYFCQQGNTLPYTFGQGTKLEIKGGGGSGGGGSGGGGSGGGGSQVQL

QESGPGLVKPSETLSLTCTVSGVSLPDYGVSWIRQPPGKGLEWIGVIWGS

ETTYYQSSLKSRVTISKDNSKNQVSLKLSSVTAADTAVYYCAKHYYYGGS

YAMDYWGQGTLVTVSSTTTPAPRPPTPAPTIASQPLSLRPEACRPAAGGA

VHTRGLDFACDIYIWAPLAGTCGVLLLSLVITLYCKRGRKKLLYIFKQPF

MRPVQTTQEEDGCSCRFPEEEEGGCELRVKFSRSADAPAYQQGQNQLYNE

LNLGRREEYDVLDKRRGRDPEMGGKPRRKNPQEGLYNELQKDKMAEAYSE

IGMKGERRRGKGHDGLYQGLSTATKDTYDALHMQALPPR

Anti-CD79b (L/H) scFv (amino acids 1-249 of SEQ ID NO: 15)

(SEQ ID NO: 17)

DIQLTQSPSSLSASVGDRVTITCKASQSVDYEGDSFLNWYQQKPGKAPKL

LIYAASNLESGVPSRFSGSGSGTDFTLTISSIQPEDFATYYCQQSNEDPL

TFGQGTKVEIKRGGGGSGGGGSGGGGSGGGGSEVQLVESGGGLVQPGGSL

RLSCAASGYTFSSYWIEWVRQAPGKGLEWIGEILPGGGDTNYNE1FKGRA

TFSADTSKNTAYLQMNSLRAEDTAVYYCTRRVPIRLDYWGQGTLVTVSS

Linker (amino acids 250-269 of SEQ ID NO: 15)

```
                                    (SEQ ID NO: 7)
            GGGGSGGGGSGGGGSGGGGS
```

Anti-CD19 scFv (amino acids 270-516 of SEQ ID NO: 15)
PGP-45 DNA

```
                                    (SEQ ID NO: 6)
EIVMTQSPATLSLSPGERATLSCRASQDISKYLNWYQQKPGQAPRLLIYH

TSRLHSGIPARFSGSGSGTDYTLTISSLQPEDFAVYFCQQGNTLPYTFGQ

GTKLEIKGGGGSGGGGSGGGGSGGGGSQVQLQESGPGLVKPSETLSLTCT

VSGVSLPDYGVSWIRQPPGKGLEWIGVIWGSETTYYQSSLKSRVTISKDN

SKNQVSLKLSSVTAADTAVYYCAKHYYYGGSYAMDYWGQGTLVTVSS
```

CD8 hinge/transmembrane domain (amino acids 517-585 of SEQ ID NO: 15)

```
                                    (SEQ ID NO: 11)
TTTPAPRPPTPAPTIASQPLSLRPEACRPAAGGAVHTRGLDFACDIYIWA

PLAGTCGVLLLSLVITLYC
```

4-1BB co-stimulatory domain (amino acids 586-627 of SEQ ID NO: 15)

```
                                    (SEQ ID NO: 12)
    KRGRKKLLYIFKQPFMRPVQTTQEEDGCSCRFPEEEEGGCEL
```

CD3 signaling domain (amino acids 628-739 of SEQ ID NO: 15)

```
                                    (SEQ ID NO: 13)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

CD79b CARs
pMGH73 (SEQ ID NO: 18): anti-CD79b (L/H) scFv (VL (SEQ ID NO: 16 (amino acids 1-112 of SEQ ID NO: 18))—linker (SEQ ID NO: 7 (amino acids 113-132 of SEQ ID NO: 18))—VH (SEQ ID NO: 9 (amino acids 133-249 of SEQ ID NO: 18))); CD8 hinge/transmembrane domain (SEQ ID NO: 11 (amino acids 250-318 of SEQ ID NO: 18)); 4-1 BB co-stimulatory domain (SEQ ID NO: 12 (amino acids 319-360 of SEQ ID NO: 18)); and CD3(signaling domain (SEQ ID NO: 13 (amino acids 361-472 of SEQ ID NO: 18))

```
                                    (SEQ ID NO: 18)
DIQLTQSPSSLSASVGDRVTITCKASQSVDYEGDSFLNWYQQKPGKAPKL

LIYAASNLESGVPSRFSGSGSGTDFTLTISSIQPEDFATYYCQQSNEDPL

TFGQGTKVEIKRGGGGSGGGGSGGGGSGGGGSEVQLVESGGGLVQPGGSL

RLSCAASGYTFSSYWIEWVRQAPGKGLEWIGEILPGGGDTNYNEIFKGRA

TFSADTSKNTAYLQMNSLRAEDTAVYYCTRRVPIRLDYWGQGTLVTVSST

TTPAPRPPTPAPTIASQPLSLRPEACRPAAGGAVHTRGLDFACDIYIWAP

LAGTCGVLLLSLVITLYCKRGRKKLLYIFKQPFMRPVQTTQEEDGCSCRF
```

```
PEEEEGGCELRVKFSRSADAPAYQQGQNQLYNELNLGRREEYDVLDKRRG

RDPEMGGKPRRKNPQEGLYNELQKDKMAEAYSEIGMKGERRRGKGHDGLY

QGLSTATKDTYDALHMQALPPR.
```

Anti-CD79b VL (amino acids 1-112 of SEQ ID NO: 18)

```
                                    (SEQ ID NO: 16)
DIQLTQSPSSLSASVGDRVTITCKASQSVDYEGDSFLNWYQQKPGKAPKL

LIYAASNLESGVPSRFSGSGSGTDFTLTISSIQPEDFATYYCQQSNEDPL

TFGQGTKVEIKR
```

Linker (amino acids 113-132 of SEQ ID NO: 18)

```
                                    (SEQ ID NO: 7)
            GGGGSGGGGSGGGGSGGGGS
```

Anti-CD79b VH (amino acids 133-249 of SEQ ID NO: 18)

```
                                    (SEQ ID NO: 9)
EVQLVESGGGLVQPGGSLRLSCAASGYTFSSYWIEWVRQAPGKGLEWIGE

ILPGGGDTNYNEIFKGRATFSADTSKNTAYLQMNSLRAEDTAVYYCTRRV

PIRLDYWGQGTLVTVSS
```

CD8 hinge/transmembrane domain (amino acids 250-318 of SEQ ID NO: 18)

```
                                    (SEQ ID NO: 11)
TTTPAPRPPTPAPTIASQPLSLRPEACRPAAGGAVHTRGLDFACDIYIWA

PLAGTCGVLLLSLVITLYC
```

4-1BB co-stimulatory domain (amino acids 319-360 of SEQ ID NO: 18)

```
                                    (SEQ ID NO: 12)
    KRGRKKLLYIFKQPFMRPVQTTQEEDGCSCRFPEEEEGGCEL
```

CD3 signaling domain (amino acids 361-472 of SEQ ID NO: 18)

```
                                    (SEQ ID NO: 13)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
``` pMGH74 (SEQ ID NO: 19): anti-CD79b (H/L) scFv (VH (SEQ ID NO: 9 (amino acids 1-117 of SEQ ID NO: 19))—linker (SEQ ID NO: 7 (amino acids 118-137 of SEQ ID NO: 19))—VL (SEQ ID NO: 16 (amino acids 138-249 of SEQ ID NO: 19))); CD8 hinge/transmembrane domain (SEQ ID NO: 11 (amino acids 250-318 of SEQ ID NO: 19)); 4-1 BB co-stimulatory domain (SEQ ID NO: 12 (amino acids 319-360 of SEQ ID NO: 19)); and CD3ζ signaling domain (SEQ ID NO: 13 (amino acids 361-472 of SEQ ID NO: 19))

```
                                          (SEQ ID NO: 19)
MALPVTALLLPLALLLHAARPEVQLVESGGGLVQPGGSLRLSCAASGYTF

SSYWIEWVRQAPGKGLEWIGEILPGGGDTNYNEIFKGRATFSADTSKNTA

YLQMNSLRAEDTAVYYCTRRVPIRLDYWGQGTLVTVSSGGGGSGGGGSGG

GGSGGGGSDIQLTQSPSSLSASVGDRVTITCKASQSVDYEGDSFLNWYQQ

KPGKAPKLLIYAASNLESGVPSRFSGSGSGTDFTLTISSIQPEDFATYYC

QQSNEDPLTFGQGTKVEIKRTTTPAPRPPTPAPTIASQPLSLRPEACRPA

AGGAVHTRGLDFACDIYIWAPLAGTCGVLLLSLVITLYCKRGRKKLLYIF

KQPFMRPVQTTQEEDGCSCRFPEEEEGGCELRVKFSRSADAPAYQQGQNQ

LYNELNLGRREEYDVLDKRRGRDPEMGGKPRRKNPQEGLYNELQKDKMAE

AYSEIGMKGERRRGKGHDGLYQGLSTATKDTYDALHMQALPPR
```

Anti-CD79b VH (amino acids 1-117 of SEQ ID NO: 19)

```
                                          (SEQ ID NO: 9)
EVQLVESGGGLVQPGGSLRLSCAASGYTFSSYWIEWVRQAPGKGLEWIGE

ILPGGGDTNYNEIFKGRATFSADTSKNTAYLQMNSLRAEDTAVYYCTRRV

PIRLDYWGQGTLVTVSS
```

Linker (amino acids 118-137 of SEQ ID NO: 19)

```
                                          (SEQ ID NO: 7)
GGGGSGGGGSGGGGSGGGGS
```

Anti-CD79b VL (amino acids 138-249 of SEQ ID NO: 19)

```
                                          (SEQ ID NO: 16)
DIQLTQSPSSLSASVGDRVTITCKASQSVDYEGDSFLNWYQQKPGKAPKL

LIYAASNLESGVPSRFSGSGSGTDFTLTISSIQPEDFATYYCQQSNEDPL

TFGQGTKVEIKR
```

CD8 hinge/transmembrane domain (amino acids 250-318 of SEQ ID NO: 19)

```
                                          (SEQ ID NO: 11)
TTTPAPRPPTPAPTIASQPLSLRPEACRPAAGGAVHTRGLDFACDIYIWA

PLAGTCGVLLLSLVITLYC
```

4-1BB co-stimulatory domain (amino acids 319-360 of SEQ ID NO: 19)

```
                                          (SEQ ID NO: 12)
KRGRKKLLYIFKQPFMRPVQTTQEEDGCSCRFPEEEEGGCEL
```

CD3 signaling domain (amino acids 361-472 of SEQ ID NO: 19)

```
                                          (SEQ ID NO: 13)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

See also Table 1 (below).

TABLE 1

| SEQ ID NO: | Sequence | Description |
|---|---|---|
| 1 | EIVMTQSPATLSLSPGERATLSCRASQDISKYLNWYQQKPGQAPRLLIYHTS RLHSGIPARFSGSGSGTDYTLTISSLQPEDFAVYFCQQGNTLPYTFGQGTKL EIKGGGGSGGGGSGGGGSGGGGSQVQLQESGPGLVKPSETLSLTCTVSG VSLPDYGVSWIRQPPGKGLEWIGVIWGSETTYYQSSLKSRVTISKDNSKNQ VSLKLSSVTAADTAVYYCAKHYYYGGSYAMDYWGQGTLVTVSSGGGGSG GGGSGGGGSGGGGSDIQLTQSPSSLSASVGDRVTITCKASQSVDYEGDSF LNWYQQKPGKAPKLLIYAASNLESGVPSRFSGSGSGIDFTLTISSLQPEDFA TYYCQQSNEDPLTFGQGTKVEIKRGGGGSGGGGSGGGGSGGGGSEVQL VESGGGLVQPGGSLRLSCAASGYTFSSYWIEVVVRQAPGKGLEWIGEILPG GGDTNYNEIFKGRATFSADTSKNTAYLQMNSLRAEDTAVYYCTRRVPIRLD YWGQGTLVTVSSTTTPAPRPPTPAPTIASQPLSLRPEACRPAAGGAVHTRG LDFACDIYIWAPLAGTCGVLLLSLVITLYCKRGRKKLLYIFKQPFMRPVQTTQ EEDGCSCRFPEEEEGGCELRVKFSRSADAPAYQQGQNQLYNELNLGRRE EYDVLDKRRGRDPEMGGKPRRKNPQEGLYNELQKDKMAEAYSEIGMKGE RRRGKGHDGLYQGLSTATKDTYDALHMQALPPR | CAR19-79b |
| 2 | DIQLTQSPSSLSASVGDRVTITCKASQSVDYEGDSFLNWYQQKPGKAPKLLI YAASNLESGVPSRFSGSGSGIDFTLTISSLQPEDFATYYCQQSNEDPLTFGQ GTKVEIKRGGGGSGGGGSGGGGSGGGGSEVQLVESGGGLVQPGGSLRL SCAASGYTFSSYWIEWVRQAPGKGLEWIGEILPGGGDTNYNEIFKGRATFS ADTSKNTAYLQMNSLRAEDTAVYYCTRRVPIRLDYWGQGTLVTVSSGGGG SGGGGSGGGGSGGGGSEIVMTQSPATLSLSPGERATLSCRASQDISKYLN WYQQKPGQAPRLLIYHTSRLHSGIPARFSGSGSGTDYTLTISSLQPEDFAVY FCQQGNTLPYTFGQGTKLEIKGGGGSGGGGSGGGGSGGGGSQVQLQES GPGLVKPSETLSLTCTVSGVSLPDYGVSWIRQPPGKGLEWIGVIWGSETTY YQSSLKSRVTISKDNSKNQVSLKLSSVTAADTAVYYCAKHYYYGGSYAMDY WGQGTLVTVSSTTTPAPRPPTPAPTIASQPLSLRPEACRPAAGGAVHTRGL | CAR79b-19 |

TABLE 1-continued

| | Sequence Listing | |
|---|---|---|
| SEQ ID NO: | Sequence | Description |
| | DFACDIYIWAPLAGTCGVLLLSLVITLYCKRGRKKLLYIFKQPFMRPVQTTQE EDGCSCRFPEEEEGGCELRVKFSRSADAPAYQQGQNQLYNELNLGRREE YDVLDKRRGRDPEMGGKPRRKNPQEGLYNELQKDKMAEAYSEIGMKGER RRGKGHDGLYQGLSTATKDTYDALHMQALPPR | |
| 3 | MALPVTALLLPLALLLHAARP | CD8 signal sequence |
| 4 | EIVMTQSPATLSLSPGERATLSCRASQDISKYLNWYQQKPGQAPRLLIYHTS RLHSGIPARFSGSGSGTDYTLTISSLQPEDFAVYFCQQGNTLPYTFGQGTKL EIK | CD19 VL |
| 5 | QVQLQESGPGLVKPSETLSLTCTVSGVSLPDYGVSWIRQPPGKGLEWIGVI WGSETTYYQSSLKSRVTISKDNSKNQVSLKLSSVTAADTAVYYCAKHYYYG GSYAMDYWGQGTLVTVSS | CD19 VH |
| 6 | EIVMTQSPATLSLSPGERATLSCRASQDISKYLNWYQQKPGQAPRLLIYHTS RLHSGIPARFSGSGSGTDYTLTISSLQPEDFAVYFCQQGNTLPYTFGQGTKL EIKGGGGSGGGGSGGGGSGGGGSQVQLQESGPGLVKPSETLSLTCTVSG VSLPDYGVSWIRQPPGKGLEWIGVIWGSETTYYQSSLKSRVTISKDNSKNQ VSLKLSSVTAADTAVYYCAKHYYYGGSYAMDYWGQGTLVTVSS | CD19 scFv |
| 7 | GGGGSGGGGSGGGGSGGGGS | Linker |
| 8 | DIQLTQSPSSLSASVGDRVTITCKASQSVDYEGDSFLNWYQQKPGKAPKLLI YAASNLESGVPSRFSGSGSGIDFTLTISSLQPEDFATYYCQQSNEDPLTFGQ GTKVEIKR | CD79b VL |
| 9 | EVQLVESGGGLVQPGGSLRLSCAASGYTFSSYWIEWVRQAPGKGLEWIGE ILPGGGDTNYNEIFKGRATFSADTSKNTAYLQMNSLRAEDTAVYYCTRRVPI RLDYWGQGTLVTVSS | CD79b VH |
| 10 | DIQLTQSPSSLSASVGDRVTITCKASQSVDYEGDSFLNWYQQKPGKAPKLLI YAASNLESGVPSRFSGSGSGIDFTLTISSLQPEDFATYYCQQSNEDPLTFGQ GTKVEIKRGGGGSGGGGSGGGGSGGGGSEVQLVESGGGLVQPGGSLRL SCAASGYTFSSYWIEWVRQAPGKGLEWIGEILPGGGDTNYNEIFKGRATFS ADTSKNTAYLQMNSLRAEDTAVYYCTRRVPIRLDYWGQGTLVTVSS | CD79b scFv |
| 11 | TTTPAPRPPTPAPTIASQPLSLRPEACRPAAGGAVHTRGLDFACDIYIWAPL AGTCGVLLLSLVITLYC | CD8 hinge/ TM |
| 12 | KRGRKKLLYIFKQPFMRPVQTTQEEDGCSCRFPEEEEGGCEL | 4-1BB |
| 13 | RVKFSRSADAPAYQQGQNQLYNELNLGRREEYDVLDKRRGRDPEMGGKP RRKNPQEGLYNELQKDKMAEAYSEIGMKGERRRGKGHDGLYQGLSTATKD TYDALHMQALPPR | CD3ζ |
| 14 | EIVMTQSPATLSLSPGERATLSCRASQDISKYLNWYQQKPGQAPRLLIYHTS RLHSGIPARFSGSGSGTDYTLTISSLQPEDFAVYFCQQGNTLPYTFGQGTKL EIKGGGGSGGGGSGGGGSGGGGSQVQLQESGPGLVKPSETLSLTCTVSG VSLPDYGVSWIRQPPGKGLEWIGVIWGSETTYYQSSLKSRVTISKDNSKNQ VSLKLSSVTAADTAVYYCAKHYYYGGSYAMDYWGQGTLVTVSSGGGGSG GGGSGGGGSGGGGSDIQLTQSPSSLSASVGDRVTITCKASQSVDYEGDSF LNWYQQKPGKAPKLLIYAASNLESGVPSRFSGSGSGTDFTLTISSIQPEDFA TYYCQQSNEDPLTFGQGTKVEIKRGGGGSGGGGSGGGGSGGGGSEVQL VESGGGLVQPGGSLRLSCAASGYTFSSYWIEVVVRQAPGKGLEWIGEILPG GGDTNYNEIFKGRATFSADTSKNTAYLQMNSLRAEDTAVYYCTRRVPIRLD YWGQGTLVTVSSTTTPAPRPPTPAPTIASQPLSLRPEACRPAAGGAVHTRG LDFACDIYIWAPLAGTCGVLLLSLVITLYCKRGRKKLLYIFKQPFMRPVQTTQ EEDGCSCRFPEEEEGGCELRVKFSRSADAPAYQQGQNQLYNELNLGRRE EYDVLDKRRGRDPEMGGKPRRKNPQEGLYNELQKDKMAEAYSEIGMKGE RRRGKGHDGLYQGLSTATKDTYDALHMQALPPR | Anti-CD19/ CD79b CAR |
| 15 | DIQLTQSPSSLSASVGDRVTITCKASQSVDYEGDSFLNWYQQKPGKAPKLLI YAASNLESGVPSRFSGSGSGTDFTLTISSIQPEDFATYYCQQSNEDPLTFGQ GTKVEIKRGGGGSGGGGSGGGGSGGGGSEVQLVESGGGLVQPGGSLRL SCAASGYTFSSYWIEWVRQAPGKGLEWIGEILPGGGDTNYNEIFKGRATFS ADTSKNTAYLQMNSLRAEDTAVYYCTRRVPIRLDYWGQGTLVTVSSGGGG SGGGGSGGGGSGGGGSEIVMTQSPATLSLSPGERATLSCRASQDISKYLN WYQQKPGQAPRLLIYHTSRLHSGIPARFSGSGSGTDYTLTISSLQPEDFAVY FCQQGNTLPYTFGQGTKLEIKGGGGSGGGGSGGGGSGGGGSQVQLQES GPGLVKPSETLSLTCTVSGVSLPDYGVSWIRQPPGKGLEWIGVIWGSETTY YQSSLKSRVTISKDNSKNQVSLKLSSVTAADTAVYYCAKHYYYGGSYAMDY WGQGTLVTVSSTTTPAPRPPTPAPTIASQPLSLRPEACRPAAGGAVHTRGL DFACDIYIWAPLAGTCGVLLLSLVITLYCKRGRKKLLYIFKQPFMRPVQTTQE | Anti-CD79b/ CD19 CAR |

TABLE 1-continued

Sequence Listing

| SEQ ID NO: | Sequence | Description |
|---|---|---|
| | EDGCSCRFPEEEEGGCELRVKFSRSADAPAYQQGQNQLYNELNLGRREE YDVLDKRRGRDPEMGGKPRRKNPQEGLYNELQKDKMAEAYSEIGMKGER RRGKGHDGLYQGLSTATKDTYDALHMQALPPR | |
| 16 | DIQLTQSPSSLSASVGDRVTITCKASQSVDYEGDSFLNWYQQKPGKAPKLLI YAASNLESGVPSRFSGSGSGTDFTLTISSIQPEDFATYYCQQSNEDPLTFGQ GTKVEIKR | CD79b VL |
| 17 | DIQLTQSPSSLSASVGDRVTITCKASQSVDYEGDSFLNWYQQKPGKAPKLLI YAASNLESGVPSRFSGSGSGTDFTLTISSIQPEDFATYYCQQSNEDPLTFGQ GTKVEIKRGGGGSGGGGSGGGGSGGGGSEVQLVESGGGLVQPGGSLRL SCAASGYTFSSYWIEWVRQAPGKGLEWIGEILPGGGDTNYNEIFKGRATFS ADTSKNTAYLQMNSLRAEDTAVYYCTRRVPIRLDYWGQGTLVTVSS | CD79b scFv |
| 18 | DIQLTQSPSSLSASVGDRVTITCKASQSVDYEGDSFLNWYQQKPGKAPKLLI YAASNLESGVPSRFSGSGSGTDFTLTISSIQPEDFATYYCQQSNEDPLTFGQ GTKVEIKRGGGGSGGGGSGGGGSGGGGSEVQLVESGGGLVQPGGSLRL SCAASGYTFSSYWIEWVRQAPGKGLEWIGEILPGGGDTNYNEIFKGRATFS ADTSKNTAYLQMNSLRAEDTAVYYCTRRVPIRLDYWGQGTLVTVSSTTTPA PRPPTPAPTIASQPLSLRPEACRPAAGGAVHTRGLDFACDIYIWAPLAGTCG VLLLSLVITLYCKRGRKKLLYIFKQPFMRPVQTTQEEDGCSCRFPEEEEGGC ELRVKFSRSADAPAYQQGQNQLYNELNLGRREEYDVLDKRRGRDPEMGG KPRRKNPQEGLYNELQKDKMAEAYSEIGMKGERRRGKGHDGLYQGLSTAT KDTYDALHMQALPPR | pMGH73 - anti-CD79b L/H |
| 19 | EVQLVESGGGLVQPGGSLRLSCAASGYTFSSYWIEWVRQAPGKGLEWIGE ILPGGGDTNYNEIFKGRATFSADTSKNTAYLQMNSLRAEDTAVYYCTRRVPI RLDYWGQGTLVTVSSGGGGSGGGGSGGGGSGGGGSDIQLTQSPSSLSAS VGDRVTITCKASQSVDYEGDSFLNWYQQKPGKAPKLLIYAASNLESGVPSR FSGSGSGTDFTLTISSIQPEDFATYYCQQSNEDPLTFGQGTKVEIKRTTTPA PRPPTPAPTIASQPLSLRPEACRPAAGGAVHTRGLDFACDIYIWAPLAGTCG VLLLSLVITLYCKRGRKKLLYIFKQPFMRPVQTTQEEDGCSCRFPEEEEGGC ELRVKFSRSADAPAYQQGQNQLYNELNLGRREEYDVLDKRRGRDPEMGG KPRRKNPQEGLYNELQKDKMAEAYSEIGMKGERRRGKGHDGLYQGLSTAT KDTYDALHMQALPPR | pMGH74 - anti-CD79b H/L |
| 20 | GGGGSGGGGSGGGGS | (G4S)3 |
| 21 | GGGSGGGSGGGS | Gly/Ser |
| 22 | GSTSGSGKPGSGEGSTKG | Whitlow linker |
| 23 | GGSSRSSSSGGGGSGGGG | Andris- Widhopf linker |
| 24 | MALPVTALLLPLALLLHAARPEIVMTQSPATLSLSPGERATLSCRASQDISKY LNWYQQKPGQAPRLLIYHTSRLHSGIPARFSGSGSGTDYTLTISSLQPEDFA VYFCQQGNTLPYTFGQGTKLEIKGGGGSGGGGSGGGGSGGGGSQVQLQ ESGPGLVKPSETLSLTCTVSGVSLPDYGVSWIRQPPGKGLEWIGVIWGSET TYYQSSLKSRVTISKDNSKNQVSLKLSSVTAADTAVYYCAKHYYYGGSYAM DYWGQGTLVTVSSGGGGSGGGGSGGGGSGGGGSDIQLTQSPSSLSASV GDRVTITCKASQSVDYEGDSFLNWYQQKPGKAPKLLIYAASNLESGVPSRF SGSGSGIDFTLTISSLQPEDFATYYCQQSNEDPLTFGQGTKVEIKRGGGGS GGGGSGGGGSGGGGSEVQLVESGGGLVQPGGSLRLSCAASGYTFSSYWI EVVVRQAPGKGLEWIGEILPGGGDTNYNEIFKGRATFSADTSKNTAYLQMNS LRAEDTAVYYCTRRVPIRLDYWGQGTLVTVSSTTTPAPRPPTPAPTIASQPL SLRPEACRPAAGGAVHTRGLDFACDIYIWAPLAGTCGVLLLSLVITLYCKRG RKKLLYIFKQPFMRPVQTTQEEDGCSCRFPEEEEGGCELRVKFSRSADAPA YQQGQNQLYNELNLGRREEYDVLDKRRGRDPEMGGKPRRKNPQEGLYNE LQKDKMAEAYSEIGMKGERRRGKGHDGLYQGLSTATKDTYDALHMQALPP R | CAR19-79b with CD8 signal sequence |
| 25 | MALPVTALLLPLALLLHAARPDIQLTQSPSSLSASVGDRVTITCKASQSVDYE GDSFLNWYQQKPGKAPKLLIYAASNLESGVPSRFSGSGSGIDFTLTISSLQP EDFATYYCQQSNEDPLTFGQGTKVEIKRGGGGSGGGGSGGGGSGGGGS EVQLVESGGGLVQPGGSLRLSCAASGYTFSSYWIEVVVRQAPGKGLEWIGE ILPGGGDTNYNEIFKGRATFSADTSKNTAYLQMNSLRAEDTAVYYCTRRVPI RLDYWGQGTLVTVSSGGGGSGGGGSGGGGSGGGGSEIVMTQSPATLSLS PGERATLSCRASQDISKYLNWYQQKPGQAPRLLIYHTSRLHSGIPARFSGS GSGTDYTLTISSLQPEDFAVYFCQQGNTLPYTFGQGTKLEIKGGGGSGGGG SGGGGSGGGGSQVQLQESGPGLVKPSETLSLTCTVSGVSLPDYGVSWIRQ PPGKGLEWIGVIWGSETTYYQSSLKSRVTISKDNSKNQVSLKLSSVTAADTA VYYCAKHYYYGGSYAMDYWGQGTLVTVSSTTTPAPRPPTPAPTIASQPLSL | CAR79b-19 with CD8 signal sequence |

TABLE 1-continued

| | Sequence Listing | |
|---|---|---|

| SEQ ID NO: | Sequence | Description |
|---|---|---|
| | RPEACRPAAGGAVHTRGLDFACDIYIWAPLAGTCGVLLLSLVITLYCKRGRK KLLYIFKQPFMRPVQTTQEEDGCSCRFPEEEEGGCELRVKFSRSADAPAYQ QGQNQLYNELNLGRREEYDVLDKRRGRDPEMGGKPRRKNPQEGLYNELQ KDKMAEAYSEIGMKGERRRGKGHDGLYQGLSTATKDTYDALHMQALPPR | |
| 26 | MALPVTALLLPLALLLHAARPEIVMTQSPATLSLSPGERATLSCRASQDISKY LNWYQQKPGQAPRLLIYHTSRLHSGIPARFSGSGSGTDYTLTISSLQPEDFA VYFCQQGNTLPYTFGQGTKLEIKGGGGSGGGGSGGGGSGGGGSQVQLQ ESGPGLVKPSETLSLTCTVSGVSLPDYGVSWIRQPPGKGLEWIGVIWGSET TYYQSSLKSRVTISKDNSKNQVSLKLSSVTAADTAVYYCAKHYYYGGSYAM DYWGQGTLVTVSSGGGGSGGGGSGGGGSGGGGSDIQLTQSPSSLSASV GDRVTITCKASQSVDYEGDSFLNWYQQKPGKAPKLLIYAASNLESGVPSRF SGSGSGTDFTLTISSIQPEDFATYYCQQSNEDPLTFGQGTKVEIKRGGGGS GGGGSGGGGSGGGGSEVQLVESGGGLVQPGGSLRLSCAASGYTFSSYWI EVVVRQAPGKGLEWIGEILPGGGDTNYNEIFKGRATFSADTSKNTAYLQMNS LRAEDTAVYYCTRRVPIRLDYWGQGTLVTVSSTTTPAPRPPTPAPTIASQPL SLRPEACRPAAGGAVHTRGLDFACDIYIWAPLAGTCGVLLLSLVITLYCKRG RKKLLYIFKQPFMRPVQTTQEEDGCSCRFPEEEEGGCELRVKFSRSADAPA YQQGQNQLYNELNLGRREEYDVLDKRRGRDPEMGGKPRRKNPQEGLYNE LQKDKMAEAYSEIGMKGERRRGKGHDGLYQGLSTATKDTYDALHMQALPP R | Anti-CD19/ CD79b CAR with CD8 signal sequence |
| 27 | MALPVTALLLPLALLLHAARPDIQLTQSPSSLSASVGDRVTITCKASQSVDYE GDSFLNWYQQKPGKAPKLLIYAASNLESGVPSRFSGSGSGTDFTLTISSIQP EDFATYYCQQSNEDPLTFGQGTKVEIKRGGGGSGGGGSGGGGSGGGGS EVQLVESGGGLVQPGGSLRLSCAASGYTFSSYWIEVVVRQAPGKGLEWIGE ILPGGGDTNYNEIFKGRATFSADTSKNTAYLQMNSLRAEDTAVYYCTRRVPI RLDYWGQGTLVTVSSGGGGSGGGGSGGGGSGGGGSEIVMTQSPATLSLS PGERATLSCRASQDISKYLNWYQQKPGQAPRLLIYHTSRLHSGIPARFSGS GSGTDYTLTISSLQPEDFAVYFCQQGNTLPYTFGQGTKLEIKGGGGSGGGG SGGGGSGGGGSQVQLQESGPGLVKPSETLSLTCTVSGVSLPDYGVSWIRQ PPGKGLEWIGVIWGSETTYYQSSLKSRVTISKDNSKNQVSLKLSSVTAADTA VYYCAKHYYYGGSYAMDYWGQGTLVTVSSTTTPAPRPPTPAPTIASQPLSL RPEACRPAAGGAVHTRGLDFACDIYIWAPLAGTCGVLLLSLVITLYCKRGRK KLLYIFKQPFMRPVQTTQEEDGCSCRFPEEEEGGCELRVKFSRSADAPAYQ QGQNQLYNELNLGRREEYDVLDKRRGRDPEMGGKPRRKNPQEGLYNELQ KDKMAEAYSEIGMKGERRRGKGHDGLYQGLSTATKDTYDALHMQALPPR | Anti-CD79b/ CD19 CAR with CD8 signal sequence |
| 28 | MALPVTALLLPLALLLHAARPDIQLTQSPSSLSASVGDRVTITCKASQSVDYE GDSFLNWYQQKPGKAPKLLIYAASNLESGVPSRFSGSGSGTDFTLTISSIQP EDFATYYCQQSNEDPLTFGQGTKVEIKRGGGGSGGGGSGGGGSGGGGS EVQLVESGGGLVQPGGSLRLSCAASGYTFSSYWIEVVVRQAPGKGLEWIGE ILPGGGDTNYNEIFKGRATFSADTSKNTAYLQMNSLRAEDTAVYYCTRRVPI RLDYWGQGTLVTVSSTTTPAPRPPTPAPTIASQPLSLRPEACRPAAGGAVH TRGLDFACDIYIWAPLAGTCGVLLLSLVITLYCKRGRKKLLYIFKQPFMRPVQ TTQEEDGCSCRFPEEEEGGCELRVKFSRSADAPAYQQGQNQLYNELNLGR REEYDVLDKRRGRDPEMGGKPRRKNPQEGLYNELQKDKMAEAYSEIGMK GERRRGKGHDGLYQGLSTATKDTYDALHMQALPPR | pMGH73 - anti-CD79b L/H with CD8 signal sequence |
| 29 | MALPVTALLLPLALLLHAARPEVQLVESGGGLVQPGGSLRLSCAASGYTFSS YWIEVVVRQAPGKGLEWIGEILPGGGDTNYNEIFKGRATFSADTSKNTAYLQ MNSLRAEDTAVYYCTRRVPIRLDYWGQGTLVTVSSGGGGSGGGGSGGGG SGGGGSDIQLTQSPSSLSASVGDRVTITCKASQSVDYEGDSFLNWYQQKP GKAPKLLIYAASNLESGVPSRFSGSGSGTDFTLTISSIQPEDFATYYCQQSN EDPLTFGQGTKVEIKRTTTPAPRPPTPAPTIASQPLSLRPEACRPAAGGAVH TRGLDFACDIYIWAPLAGTCGVLLLSLVITLYCKRGRKKLLYIFKQPFMRPVQ TTQEEDGCSCRFPEEEEGGCELRVKFSRSADAPAYQQGQNQLYNELNLGR REEYDVLDKRRGRDPEMGGKPRRKNPQEGLYNELQKDKMAEAYSEIGMK GERRRGKGHDGLYQGLSTATKDTYDALHMQALPPR | pMGH74 - anti-CD79b H/L with CD8 signal sequence |
| 30 | 5'-AGGGAGATAACGCTGTGCTG-3' | CD19 forward primer |
| 31 | 5'-AGAAGGGTTTAAGCGGGGAC-3' | CD19 reverse primer |

TABLE 1-continued

| | Sequence Listing | |
|---|---|---|
| SEQ ID NO: | Sequence | Description |
| 32 | 5'-GTACTGTCCCCACGATCGGA-3 | PUM1 Forward primer |
| 33 | 5-'TGCATCCCTTGGGCCAA ATC-3' | PUM1 reverse primer |

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method for treating a patient suffering from a cancer, the method comprising administering to the patient a therapeutically effective amount of an anti-cancer therapy comprising a chimeric antigen receptor (CAR) comprising an extracellular domain comprising a CD79b-binding domain and a CD19-binding domain, wherein the CAR comprises an amino acid sequence having at least 90% sequence identity to the amino acid sequence of SEQ ID NO: 1, 2, 24, or 25.

2. The method of claim 1, wherein the CAR comprises the amino acid sequence of SEQ ID NO: 1, 2, 24, or 25.

3. The method of claim 1, wherein the cancer is a lymphoma or a leukemia.

4. The method of claim 3, wherein the cancer is mantle cell lymphoma (MCL), diffuse large B-cell lymphoma (DLBCL), primary mediastinal B-cell lymphoma (PMBCL), chronic lymphocytic leukemia (CLL), small lymphocytic lymphoma (SLL), follicular lymphoma, or transformed follicular lymphoma.

5. The method of claim 3, wherein the cancer comprises cells expressing CD19.

6. The method of claim 3, wherein the cancer comprises cells expressing CD79b.

7. The method of claim 1, wherein the CAR comprises an amino acid sequence having at least 92% sequence identity to the amino acid sequence of SEQ ID NO: 1, 2, 24, or 25.

8. The method of claim 1, wherein the CAR comprises an amino acid sequence having at least 95% sequence identity to the amino acid sequence of SEQ ID NO: 1, 2, 24, or 25.

9. The method of claim 1, wherein the CAR comprises an amino acid sequence having at least 98% sequence identity to the amino acid sequence of SEQ ID NO: 1, 2, 24, or 25.

10. The method of claim 1, wherein the CAR comprises an amino acid sequence having at least 99% sequence identity to the amino acid sequence of SEQ ID NO: 1, 2, 24, or 25.

11. The method of claim 1, wherein the CAR consists of the amino acid sequence of SEQ ID NO: 1, 2, 24, or 25.

* * * * *

SEQUENCE LISTING

<160> NUMBER OF SEQ ID NOS: 33

<210> SEQ ID NO 1
<211> LENGTH: 739
<212> TYPE: PRT
<213> ORGANISM: Artificial Sequence
<220> FEATURE:
<223> OTHER INFORMATION: Synthetic Construct

<400> SEQUENCE: 1

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Gln Ser Ser Leu Lys Ser
            180                 185                 190

Arg Val Thr Ile Ser Lys Asp Asn Ser Lys Asn Gln Val Ser Leu Lys
            195                 200                 205

Leu Ser Ser Val Thr Ala Ala Asp Thr Ala Val Tyr Tyr Cys Ala Lys
    210                 215                 220
```

-continued

```
His Tyr Tyr Tyr Gly Gly Ser Tyr Ala Met Asp Tyr Trp Gly Gln Gly
225                 230                 235                 240

Thr Leu Val Thr Val Ser Ser Gly Gly Gly Gly Ser Gly Gly Gly Gly
            245                 250                 255

Ser Gly Gly Gly Gly Ser Gly Gly Gly Gly Ser Asp Ile Gln Leu Thr
            260                 265                 270

Gln Ser Pro Ser Ser Leu Ser Ala Ser Val Gly Asp Arg Val Thr Ile
        275                 280                 285

Thr Cys Lys Ala Ser Gln Ser Val Asp Tyr Glu Gly Asp Ser Phe Leu
        290                 295                 300

Asn Trp Tyr Gln Gln Lys Pro Gly Lys Ala Pro Lys Leu Leu Ile Tyr
305                 310                 315                 320

Ala Ala Ser Asn Leu Glu Ser Gly Val Pro Ser Arg Phe Ser Gly Ser
            325                 330                 335

Gly Ser Gly Ile Asp Phe Thr Leu Thr Ile Ser Ser Leu Gln Pro Glu
            340                 345                 350

Asp Phe Ala Thr Tyr Tyr Cys Gln Gln Ser Asn Glu Asp Pro Leu Thr
        355                 360                 365

Phe Gly Gln Gly Thr Lys Val Glu Ile Lys Arg Gly Gly Gly Gly Ser
    370                 375                 380

Gly Gly Gly Gly Ser Gly Gly Gly Gly Ser Gly Gly Gly Gly Ser Glu
385                 390                 395                 400

Val Gln Leu Val Glu Ser Gly Gly Gly Leu Val Gln Pro Gly Gly Ser
            405                 410                 415

Leu Arg Leu Ser Cys Ala Ala Ser Gly Tyr Thr Phe Ser Ser Tyr Trp
        420                 425                 430

Ile Glu Trp Val Arg Gln Ala Pro Gly Lys Gly Leu Glu Trp Ile Gly
        435                 440                 445

Glu Ile Leu Pro Gly Gly Gly Asp Thr Asn Tyr Asn Glu Ile Phe Lys
    450                 455                 460

Gly Arg Ala Thr Phe Ser Ala Asp Thr Ser Lys Asn Thr Ala Tyr Leu
465                 470                 475                 480

Gln Met Asn Ser Leu Arg Ala Glu Asp Thr Ala Val Tyr Tyr Cys Thr
            485                 490                 495

Arg Arg Val Pro Ile Arg Leu Asp Tyr Trp Gly Gln Gly Thr Leu Val
            500                 505                 510

Thr Val Ser Ser Thr Thr Thr Pro Ala Pro Arg Pro Pro Thr Pro Ala
        515                 520                 525

Pro Thr Ile Ala Ser Gln Pro Leu Ser Leu Arg Pro Glu Ala Cys Arg
    530                 535                 540

Pro Ala Ala Gly Gly Ala Val His Thr Arg Gly Leu Asp Phe Ala Cys
545                 550                 555                 560

Asp Ile Tyr Ile Trp Ala Pro Leu Ala Gly Thr Cys Gly Val Leu Leu
            565                 570                 575

Leu Ser Leu Val Ile Thr Leu Tyr Cys Lys Arg Gly Arg Lys Lys Leu
            580                 585                 590

Leu Tyr Ile Phe Lys Gln Pro Phe Met Arg Pro Val Gln Thr Thr Gln
        595                 600                 605

Glu Glu Asp Gly Cys Ser Cys Arg Phe Pro Glu Glu Glu Glu Gly Gly
    610                 615                 620

Cys Glu Leu Arg Val Lys Phe Ser Arg Ser Ala Asp Ala Pro Ala Tyr
625                 630                 635                 640

Gln Gln Gly Gln Asn Gln Leu Tyr Asn Glu Leu Asn Leu Gly Arg Arg
```

```
                    645                 650                 655

Glu Glu Tyr Asp Val Leu Asp Lys Arg Arg Gly Arg Asp Pro Glu Met
                660                 665                 670

Gly Gly Lys Pro Arg Arg Lys Asn Pro Gln Glu Gly Leu Tyr Asn Glu
                675                 680                 685

Leu Gln Lys Asp Lys Met Ala Glu Ala Tyr Ser Glu Ile Gly Met Lys
            690                 695                 700

Gly Glu Arg Arg Arg Gly Lys Gly His Asp Gly Leu Tyr Gln Gly Leu
705                 710                 715                 720

Ser Thr Ala Thr Lys Asp Thr Tyr Asp Ala Leu His Met Gln Ala Leu
                725                 730                 735

Pro Pro Arg

<210> SEQ ID NO 2
<211> LENGTH: 739
<212> TYPE: PRT
<213> ORGANISM: Artificial Sequence
<220> FEATURE:
<223> OTHER INFORMATION: Synthetic Construct

<400> SEQUENCE: 2

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
                20                  25                  30

Gly Asp Ser Phe Leu Asn Trp Tyr Gln Gln Lys Pro Gly Lys Ala Pro
            35                  40                  45

Lys Leu Leu Ile Tyr Ala Ala Ser Asn Leu Glu Ser Gly Val Pro Ser
        50                  55                  60

Arg Phe Ser Gly Ser Gly Ser Gly Ile Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
                100                 105                 110

Gly Gly Gly Gly Ser Gly Gly Gly Gly Ser Gly Gly Gly Gly Ser Gly
            115                 120                 125

Gly Gly Gly Ser Glu Val Gln Leu Val Glu Ser Gly Gly Gly Leu Val
        130                 135                 140

Gln Pro Gly Gly Ser Leu Arg Leu Ser Cys Ala Ala Ser Gly Tyr Thr
145                 150                 155                 160

Phe Ser Ser Tyr Trp Ile Glu Trp Val Arg Gln Ala Pro Gly Lys Gly
                165                 170                 175

Leu Glu Trp Ile Gly Glu Ile Leu Pro Gly Gly Gly Asp Thr Asn Tyr
                180                 185                 190

Asn Glu Ile Phe Lys Gly Arg Ala Thr Phe Ser Ala Asp Thr Ser Lys
            195                 200                 205

Asn Thr Ala Tyr Leu Gln Met Asn Ser Leu Arg Ala Glu Asp Thr Ala
        210                 215                 220

Val Tyr Tyr Cys Thr Arg Arg Val Pro Ile Arg Leu Asp Tyr Trp Gly
225                 230                 235                 240

Gln Gly Thr Leu Val Thr Val Ser Ser Gly Gly Gly Gly Ser Gly Gly
                245                 250                 255

Gly Gly Ser Gly Gly Gly Gly Ser Gly Gly Gly Gly Ser Glu Ile Val
            260                 265                 270
```

-continued

```
Met Thr Gln Ser Pro Ala Thr Leu Ser Leu Ser Pro Gly Glu Arg Ala
        275             280             285

Thr Leu Ser Cys Arg Ala Ser Gln Asp Ile Ser Lys Tyr Leu Asn Trp
    290             295             300

Tyr Gln Gln Lys Pro Gly Gln Ala Pro Arg Leu Leu Ile Tyr His Thr
305             310             315             320

Ser Arg Leu His Ser Gly Ile Pro Ala Arg Phe Ser Gly Ser Gly Ser
            325             330             335

Gly Thr Asp Tyr Thr Leu Thr Ile Ser Ser Leu Gln Pro Glu Asp Phe
            340             345             350

Ala Val Tyr Phe Cys Gln Gln Gly Asn Thr Leu Pro Tyr Thr Phe Gly
            355             360             365

Gln Gly Thr Lys Leu Glu Ile Lys Gly Gly Gly Gly Ser Gly Gly Gly
    370             375             380

Gly Ser Gly Gly Gly Gly Ser Gly Gly Gly Gly Ser Gln Val Gln Leu
385             390             395             400

Gln Glu Ser Gly Pro Gly Leu Val Lys Pro Ser Glu Thr Leu Ser Leu
                405             410             415

Thr Cys Thr Val Ser Gly Val Ser Leu Pro Asp Tyr Gly Val Ser Trp
            420             425             430

Ile Arg Gln Pro Pro Gly Lys Gly Leu Glu Trp Ile Gly Val Ile Trp
            435             440             445

Gly Ser Glu Thr Thr Tyr Tyr Gln Ser Ser Leu Lys Ser Arg Val Thr
    450             455             460

Ile Ser Lys Asp Asn Ser Lys Asn Gln Val Ser Leu Lys Leu Ser Ser
465             470             475             480

Val Thr Ala Ala Asp Thr Ala Val Tyr Tyr Cys Ala Lys His Tyr Tyr
            485             490             495

Tyr Gly Gly Ser Tyr Ala Met Asp Tyr Trp Gly Gln Gly Thr Leu Val
            500             505             510

Thr Val Ser Ser Thr Thr Thr Pro Ala Pro Arg Pro Pro Thr Pro Ala
            515             520             525

Pro Thr Ile Ala Ser Gln Pro Leu Ser Leu Arg Pro Glu Ala Cys Arg
    530             535             540

Pro Ala Ala Gly Gly Ala Val His Thr Arg Gly Leu Asp Phe Ala Cys
545             550             555             560

Asp Ile Tyr Ile Trp Ala Pro Leu Ala Gly Thr Cys Gly Val Leu Leu
            565             570             575

Leu Ser Leu Val Ile Thr Leu Tyr Cys Lys Arg Gly Arg Lys Lys Leu
            580             585             590

Leu Tyr Ile Phe Lys Gln Pro Phe Met Arg Pro Val Gln Thr Thr Gln
    595             600             605

Glu Glu Asp Gly Cys Ser Cys Arg Phe Pro Glu Glu Glu Glu Gly Gly
    610             615             620

Cys Glu Leu Arg Val Lys Phe Ser Arg Ser Ala Asp Ala Pro Ala Tyr
625             630             635             640

Gln Gln Gly Gln Asn Gln Leu Tyr Asn Glu Leu Asn Leu Gly Arg Arg
                645             650             655

Glu Glu Tyr Asp Val Leu Asp Lys Arg Arg Gly Arg Asp Pro Glu Met
            660             665             670

Gly Gly Lys Pro Arg Arg Lys Asn Pro Gln Glu Gly Leu Tyr Asn Glu
    675             680             685
```

```
Leu Gln Lys Asp Lys Met Ala Glu Ala Tyr Ser Glu Ile Gly Met Lys
    690             695             700

Gly Glu Arg Arg Arg Gly Lys Gly His Asp Gly Leu Tyr Gln Gly Leu
705             710             715             720

Ser Thr Ala Thr Lys Asp Thr Tyr Asp Ala Leu His Met Gln Ala Leu
                725             730             735

Pro Pro Arg

<210> SEQ ID NO 3
<211> LENGTH: 21
<212> TYPE: PRT
<213> ORGANISM: Artificial Sequence
<220> FEATURE:
<223> OTHER INFORMATION: Synthetic Construct

<400> SEQUENCE: 3

Met Ala Leu Pro Val Thr Ala Leu Leu Leu Pro Leu Ala Leu Leu Leu
1               5               10              15

His Ala Ala Arg Pro
            20

<210> SEQ ID NO 4
<211> LENGTH: 107
<212> TYPE: PRT
<213> ORGANISM: Artificial Sequence
<220> FEATURE:
<223> OTHER INFORMATION: Synthetic Construct

<400> SEQUENCE: 4

Glu Ile Val Met Thr Gln Ser Pro Ala Thr Leu Ser Leu Ser Pro Gly
1               5               10              15

Glu Arg Ala Thr Leu Ser Cys Arg Ala Ser Gln Asp Ile Ser Lys Tyr
            20              25              30

Leu Asn Trp Tyr Gln Gln Lys Pro Gly Gln Ala Pro Arg Leu Leu Ile
        35              40              45

Tyr His Thr Ser Arg Leu His Ser Gly Ile Pro Ala Arg Phe Ser Gly
    50              55              60

Ser Gly Ser Gly Thr Asp Tyr Thr Leu Thr Ile Ser Ser Leu Gln Pro
65              70              75              80

Glu Asp Phe Ala Val Tyr Phe Cys Gln Gln Gly Asn Thr Leu Pro Tyr
                85              90              95

Thr Phe Gly Gln Gly Thr Lys Leu Glu Ile Lys
            100             105

<210> SEQ ID NO 5
<211> LENGTH: 120
<212> TYPE: PRT
<213> ORGANISM: Artificial Sequence
<220> FEATURE:
<223> OTHER INFORMATION: Synthetic Construct

<400> SEQUENCE: 5

Gln Val Gln Leu Gln Glu Ser Gly Pro Gly Leu Val Lys Pro Ser Glu
1               5               10              15

Thr Leu Ser Leu Thr Cys Thr Val Ser Gly Val Ser Leu Pro Asp Tyr
            20              25              30

Gly Val Ser Trp Ile Arg Gln Pro Pro Gly Lys Gly Leu Glu Trp Ile
        35              40              45

Gly Val Ile Trp Gly Ser Glu Thr Thr Tyr Tyr Gln Ser Ser Leu Lys
    50              55              60
```

```
Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Leu Val Thr Val Ser Ser
        115                 120

<210> SEQ ID NO 6
<211> LENGTH: 247
<212> TYPE: PRT
<213> ORGANISM: Artificial Sequence
<220> FEATURE:
<223> OTHER INFORMATION: Synthetic Construct

<400> SEQUENCE: 6

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
                20                  25                  30

Leu Asn Trp Tyr Gln Gln Lys Pro Gly Gln Ala Pro Arg Leu Leu Ile
            35                  40                  45

Tyr His Thr Ser Arg Leu His Ser Gly Ile Pro Ala Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
                100                 105                 110

Gly Gly Gly Gly Ser Gly Gly Gly Gly Ser Gly Gly Gly Gly Ser Gln
            115                 120                 125

Val Gln Leu Gln Glu Ser Gly Pro Gly Leu Val Lys Pro Ser Glu Thr
        130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Gln Ser Ser Leu Lys Ser
                180                 185                 190

Arg Val Thr Ile Ser Lys Asp Asn Ser Lys Asn Gln Val Ser Leu Lys
            195                 200                 205

Leu Ser Ser Val Thr Ala Ala Asp Thr Ala Val Tyr Tyr Cys Ala Lys
        210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
            245

<210> SEQ ID NO 7
<211> LENGTH: 20
<212> TYPE: PRT
<213> ORGANISM: Artificial Sequence
<220> FEATURE:
<223> OTHER INFORMATION: Synthetic Construct
```

-continued

```
<400> SEQUENCE: 7

Gly Gly Gly Gly Ser Gly Gly Gly Gly Ser Gly Gly Gly Gly Ser Gly
1               5                   10                  15

Gly Gly Gly Ser
            20

<210> SEQ ID NO 8
<211> LENGTH: 112
<212> TYPE: PRT
<213> ORGANISM: Artificial Sequence
<220> FEATURE:
<223> OTHER INFORMATION: Synthetic Construct

<400> SEQUENCE: 8

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Ile Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

<210> SEQ ID NO 9
<211> LENGTH: 117
<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser
        115

<210> SEQ ID NO 10
<211> LENGTH: 249
<212> TYPE: PRT
<213> ORGANISM: Artificial Sequence
<220> FEATURE:
```

-continued

<223> OTHER INFORMATION: Synthetic Construct

<400> SEQUENCE: 10

```
Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Ile Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

Gly Gly Gly Gly Ser Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Ala Ala Ser Gly Tyr Thr
145                 150                 155                 160

Phe Ser Ser Tyr Trp Ile Glu Trp Val Arg Gln Ala Pro Gly Lys Gly
                165                 170                 175

Leu Glu Trp Ile Gly Glu Ile Leu Pro Gly Gly Gly Asp Thr Asn Tyr
            180                 185                 190

Asn Glu Ile Phe Lys Gly Arg Ala Thr Phe Ser Ala Asp Thr Ser Lys
            195                 200                 205

Asn Thr Ala Tyr Leu Gln Met Asn Ser Leu Arg Ala Glu Asp Thr Ala
    210                 215                 220

Val Tyr Tyr Cys Thr Arg Arg Val Pro Ile Arg Leu Asp Tyr Trp Gly
225                 230                 235                 240

Gln Gly Thr Leu Val Thr Val Ser Ser
                245
```

<210> SEQ ID NO 11
<211> LENGTH: 69
<212> TYPE: PRT
<213> ORGANISM: Artificial Sequence
<220> FEATURE:
<223> OTHER INFORMATION: Synthetic Construct

<400> SEQUENCE: 11

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65
```

<210> SEQ ID NO 12

-continued

```
<211> LENGTH: 42
<212> TYPE: PRT
<213> ORGANISM: Artificial Sequence
<220> FEATURE:
<223> OTHER INFORMATION: Synthetic Construct

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 13
<211> LENGTH: 112
<212> TYPE: PRT
<213> ORGANISM: Artificial Sequence
<220> FEATURE:
<223> OTHER INFORMATION: Synthetic Construct

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 739
<212> TYPE: PRT
<213> ORGANISM: Artificial Sequence
<220> FEATURE:
<223> OTHER INFORMATION: Synthetic Construct

<400> SEQUENCE: 14

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110
```

-continued

```
Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Gln Ser Ser Leu Lys Ser
                180                 185                 190

Arg Val Thr Ile Ser Lys Asp Asn Ser Lys Asn Gln Val Ser Leu Lys
            195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser Gly Gly Gly Gly Ser Gly Gly Gly Gly
                245                 250                 255

Ser Gly Gly Gly Gly Ser Gly Gly Gly Gly Ser Asp Ile Gln Leu Thr
                260                 265                 270

Gln Ser Pro Ser Ser Leu Ser Ala Ser Val Gly Asp Arg Val Thr Ile
            275                 280                 285

Thr Cys Lys Ala Ser Gln Ser Val Asp Tyr Glu Gly Asp Ser Phe Leu
    290                 295                 300

Asn Trp Tyr Gln Gln Lys Pro Gly Lys Ala Pro Lys Leu Leu Ile Tyr
305                 310                 315                 320

Ala Ala Ser Asn Leu Glu Ser Gly Val Pro Ser Arg Phe Ser Gly Ser
                325                 330                 335

Gly Ser Gly Thr Asp Phe Thr Leu Thr Ile Ser Ser Ile Gln Pro Glu
                340                 345                 350

Asp Phe Ala Thr Tyr Tyr Cys Gln Gln Ser Asn Glu Asp Pro Leu Thr
            355                 360                 365

Phe Gly Gln Gly Thr Lys Val Glu Ile Lys Arg Gly Gly Gly Gly Ser
    370                 375                 380

Gly Gly Gly Gly Ser Gly Gly Gly Gly Ser Gly Gly Gly Gly Ser Glu
385                 390                 395                 400

Val Gln Leu Val Glu Ser Gly Gly Gly Leu Val Gln Pro Gly Gly Ser
                405                 410                 415

Leu Arg Leu Ser Cys Ala Ala Ser Gly Tyr Thr Phe Ser Ser Tyr Trp
            420                 425                 430

Ile Glu Trp Val Arg Gln Ala Pro Gly Lys Gly Leu Glu Trp Ile Gly
            435                 440                 445

Glu Ile Leu Pro Gly Gly Gly Asp Thr Asn Tyr Asn Glu Ile Phe Lys
    450                 455                 460

Gly Arg Ala Thr Phe Ser Ala Asp Thr Ser Lys Asn Thr Ala Tyr Leu
465                 470                 475                 480

Gln Met Asn Ser Leu Arg Ala Glu Asp Thr Ala Val Tyr Tyr Cys Thr
                485                 490                 495

Arg Arg Val Pro Ile Arg Leu Asp Tyr Trp Gly Gln Gly Thr Leu Val
                500                 505                 510

Thr Val Ser Ser Thr Thr Thr Pro Ala Pro Arg Pro Pro Thr Pro Ala
            515                 520                 525

Pro Thr Ile Ala Ser Gln Pro Leu Ser Leu Arg Pro Glu Ala Cys Arg
```

-continued

```
          530              535              540

Pro Ala Ala Gly Gly Ala Val His Thr Arg Gly Leu Asp Phe Ala Cys
545              550              555              560

Asp Ile Tyr Ile Trp Ala Pro Leu Ala Gly Thr Cys Gly Val Leu Leu
                 565              570              575

Leu Ser Leu Val Ile Thr Leu Tyr Cys Lys Arg Gly Arg Lys Lys Leu
                 580              585              590

Leu Tyr Ile Phe Lys Gln Pro Phe Met Arg Pro Val Gln Thr Thr Gln
                 595              600              605

Glu Glu Asp Gly Cys Ser Cys Arg Phe Pro Glu Glu Glu Glu Gly Gly
         610              615              620

Cys Glu Leu Arg Val Lys Phe Ser Arg Ser Ala Asp Ala Pro Ala Tyr
625              630              635              640

Gln Gln Gly Gln Asn Gln Leu Tyr Asn Glu Leu Asn Leu Gly Arg Arg
                 645              650              655

Glu Glu Tyr Asp Val Leu Asp Lys Arg Arg Gly Arg Asp Pro Glu Met
                 660              665              670

Gly Gly Lys Pro Arg Arg Lys Asn Pro Gln Glu Gly Leu Tyr Asn Glu
                 675              680              685

Leu Gln Lys Asp Lys Met Ala Glu Ala Tyr Ser Glu Ile Gly Met Lys
                 690              695              700

Gly Glu Arg Arg Arg Gly Lys Gly His Asp Gly Leu Tyr Gln Gly Leu
705              710              715              720

Ser Thr Ala Thr Lys Asp Thr Tyr Asp Ala Leu His Met Gln Ala Leu
                 725              730              735

Pro Pro Arg

<210> SEQ ID NO 15
<211> LENGTH: 739
<212> TYPE: PRT
<213> ORGANISM: Artificial Sequence
<220> FEATURE:
<223> OTHER INFORMATION: Synthetic Construct

<400> SEQUENCE: 15

Asp Ile Gln Leu Thr Gln Ser Pro Ser Ser Leu Ser Ala Ser Val Gly
1               5               10              15

Asp Arg Val Thr Ile Thr Cys Lys Ala Ser Gln Ser Val Asp Tyr Glu
                 20              25              30

Gly Asp Ser Phe Leu Asn Trp Tyr Gln Gln Lys Pro Gly Lys Ala Pro
         35              40              45

Lys Leu Leu Ile Tyr Ala Ala Ser Asn Leu Glu Ser Gly Val Pro Ser
    50              55              60

Arg Phe Ser Gly Ser Gly Ser Gly Thr Asp Phe Thr Leu Thr Ile Ser
65              70              75              80

Ser Ile Gln Pro Glu Asp Phe Ala Thr Tyr Tyr Cys Gln Gln Ser Asn
                 85              90              95

Glu Asp Pro Leu Thr Phe Gly Gln Gly Thr Lys Val Glu Ile Lys Arg
                 100             105             110

Gly Gly Gly Gly Ser Gly Gly Gly Gly Ser Gly Gly Gly Gly Ser Gly
         115             120             125

Gly Gly Gly Ser Glu Val Gln Leu Val Glu Ser Gly Gly Gly Leu Val
    130             135             140

Gln Pro Gly Gly Ser Leu Arg Leu Ser Cys Ala Ala Ser Gly Tyr Thr
145             150             155             160
```

-continued

Phe Ser Ser Tyr Trp Ile Glu Trp Val Arg Gln Ala Pro Gly Lys Gly
                165                 170                 175

Leu Glu Trp Ile Gly Glu Ile Leu Pro Gly Gly Gly Asp Thr Asn Tyr
            180                 185                 190

Asn Glu Ile Phe Lys Gly Arg Ala Thr Phe Ser Ala Asp Thr Ser Lys
            195                 200                 205

Asn Thr Ala Tyr Leu Gln Met Asn Ser Leu Arg Ala Glu Asp Thr Ala
        210                 215                 220

Val Tyr Tyr Cys Thr Arg Arg Val Pro Ile Arg Leu Asp Tyr Trp Gly
225                 230                 235                 240

Gln Gly Thr Leu Val Thr Val Ser Ser Gly Gly Gly Ser Gly Gly
            245                 250                 255

Gly Gly Ser Gly Gly Gly Gly Ser Gly Gly Gly Gly Ser Glu Ile Val
            260                 265                 270

Met Thr Gln Ser Pro Ala Thr Leu Ser Leu Ser Pro Gly Glu Arg Ala
        275                 280                 285

Thr Leu Ser Cys Arg Ala Ser Gln Asp Ile Ser Lys Tyr Leu Asn Trp
        290                 295                 300

Tyr Gln Gln Lys Pro Gly Gln Ala Pro Arg Leu Leu Ile Tyr His Thr
305                 310                 315                 320

Ser Arg Leu His Ser Gly Ile Pro Ala Arg Phe Ser Gly Ser Gly Ser
            325                 330                 335

Gly Thr Asp Tyr Thr Leu Thr Ile Ser Ser Leu Gln Pro Glu Asp Phe
            340                 345                 350

Ala Val Tyr Phe Cys Gln Gln Gly Asn Thr Leu Pro Tyr Thr Phe Gly
            355                 360                 365

Gln Gly Thr Lys Leu Glu Ile Lys Gly Gly Gly Gly Ser Gly Gly Gly
        370                 375                 380

Gly Ser Gly Gly Gly Gly Ser Gly Gly Gly Gly Ser Gln Val Gln Leu
385                 390                 395                 400

Gln Glu Ser Gly Pro Gly Leu Val Lys Pro Ser Glu Thr Leu Ser Leu
            405                 410                 415

Thr Cys Thr Val Ser Gly Val Ser Leu Pro Asp Tyr Gly Val Ser Trp
            420                 425                 430

Ile Arg Gln Pro Pro Gly Lys Gly Leu Glu Trp Ile Gly Val Ile Trp
        435                 440                 445

Gly Ser Glu Thr Thr Tyr Tyr Gln Ser Ser Leu Lys Ser Arg Val Thr
        450                 455                 460

Ile Ser Lys Asp Asn Ser Lys Asn Gln Val Ser Leu Lys Leu Ser Ser
465                 470                 475                 480

Val Thr Ala Ala Asp Thr Ala Val Tyr Tyr Cys Ala Lys His Tyr Tyr
            485                 490                 495

Tyr Gly Gly Ser Tyr Ala Met Asp Tyr Trp Gly Gln Gly Thr Leu Val
            500                 505                 510

Thr Val Ser Ser Thr Thr Thr Pro Ala Pro Arg Pro Pro Thr Pro Ala
            515                 520                 525

Pro Thr Ile Ala Ser Gln Pro Leu Ser Leu Arg Pro Glu Ala Cys Arg
        530                 535                 540

Pro Ala Ala Gly Gly Ala Val His Thr Arg Gly Leu Asp Phe Ala Cys
545                 550                 555                 560

Asp Ile Tyr Ile Trp Ala Pro Leu Ala Gly Thr Cys Gly Val Leu Leu
            565                 570                 575

-continued

```
Leu Ser Leu Val Ile Thr Leu Tyr Cys Lys Arg Gly Arg Lys Lys Leu
            580                 585                 590

Leu Tyr Ile Phe Lys Gln Pro Phe Met Arg Pro Val Gln Thr Thr Gln
            595                 600                 605

Glu Glu Asp Gly Cys Ser Cys Arg Phe Pro Glu Glu Glu Glu Gly Gly
            610                 615                 620

Cys Glu Leu Arg Val Lys Phe Ser Arg Ser Ala Asp Ala Pro Ala Tyr
625                 630                 635                 640

Gln Gln Gly Gln Asn Gln Leu Tyr Asn Glu Leu Asn Leu Gly Arg Arg
                645                 650                 655

Glu Glu Tyr Asp Val Leu Asp Lys Arg Arg Gly Arg Asp Pro Glu Met
                660                 665                 670

Gly Gly Lys Pro Arg Arg Lys Asn Pro Gln Glu Gly Leu Tyr Asn Glu
            675                 680                 685

Leu Gln Lys Asp Lys Met Ala Glu Ala Tyr Ser Glu Ile Gly Met Lys
            690                 695                 700

Gly Glu Arg Arg Arg Gly Lys Gly His Asp Gly Leu Tyr Gln Gly Leu
705                 710                 715                 720

Ser Thr Ala Thr Lys Asp Thr Tyr Asp Ala Leu His Met Gln Ala Leu
                725                 730                 735

Pro Pro Arg
```

```
<210> SEQ ID NO 16
<211> LENGTH: 112
<212> TYPE: PRT
<213> ORGANISM: Artificial Sequence
<220> FEATURE:
<223> OTHER INFORMATION: Synthetic Construct

<400> SEQUENCE: 16

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
            35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Ile Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110
```

```
<210> SEQ ID NO 17
<211> LENGTH: 249
<212> TYPE: PRT
<213> ORGANISM: Artificial Sequence
<220> FEATURE:
<223> OTHER INFORMATION: Synthetic Construct

<400> SEQUENCE: 17

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30
```

-continued

```
Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Ile Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

Gly Gly Gly Gly Ser Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Ala Ala Ser Gly Tyr Thr
145                 150                 155                 160

Phe Ser Ser Tyr Trp Ile Glu Trp Val Arg Gln Ala Pro Gly Lys Gly
                165                 170                 175

Leu Glu Trp Ile Gly Glu Ile Leu Pro Gly Gly Gly Asp Thr Asn Tyr
            180                 185                 190

Asn Glu Ile Phe Lys Gly Arg Ala Thr Phe Ser Ala Asp Thr Ser Lys
            195                 200                 205

Asn Thr Ala Tyr Leu Gln Met Asn Ser Leu Arg Ala Glu Asp Thr Ala
    210                 215                 220

Val Tyr Tyr Cys Thr Arg Arg Val Pro Ile Arg Leu Asp Tyr Trp Gly
225                 230                 235                 240

Gln Gly Thr Leu Val Thr Val Ser Ser
                245
```

```
<210> SEQ ID NO 18
<211> LENGTH: 472
<212> TYPE: PRT
<213> ORGANISM: Artificial Sequence
<220> FEATURE:
<223> OTHER INFORMATION: Synthetic Construct

<400> SEQUENCE: 18
```

```
Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Ile Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

Gly Gly Gly Gly Ser Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140
```

-continued

```
Gln Pro Gly Gly Ser Leu Arg Leu Ser Cys Ala Ala Ser Gly Tyr Thr
145                 150                 155                 160

Phe Ser Ser Tyr Trp Ile Glu Trp Val Arg Gln Ala Pro Gly Lys Gly
                165                 170                 175

Leu Glu Trp Ile Gly Glu Ile Leu Pro Gly Gly Gly Asp Thr Asn Tyr
            180                 185                 190

Asn Glu Ile Phe Lys Gly Arg Ala Thr Phe Ser Ala Asp Thr Ser Lys
        195                 200                 205

Asn Thr Ala Tyr Leu Gln Met Asn Ser Leu Arg Ala Glu Asp Thr Ala
    210                 215                 220

Val Tyr Tyr Cys Thr Arg Arg Val Pro Ile Arg Leu Asp Tyr Trp Gly
225                 230                 235                 240

Gln Gly Thr Leu Val Thr Val Ser Ser Thr Thr Thr Pro Ala Pro Arg
                245                 250                 255

Pro Pro Thr Pro Ala Pro Thr Ile Ala Ser Gln Pro Leu Ser Leu Arg
                260                 265                 270

Pro Glu Ala Cys Arg Pro Ala Ala Gly Gly Ala Val His Thr Arg Gly
            275                 280                 285

Leu Asp Phe Ala Cys Asp Ile Tyr Ile Trp Ala Pro Leu Ala Gly Thr
    290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350

Glu Glu Glu Gly Gly Cys Glu Leu Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470
```

```
<210> SEQ ID NO 19
<211> LENGTH: 472
<212> TYPE: PRT
<213> ORGANISM: Artificial Sequence
<220> FEATURE:
<223> OTHER INFORMATION: Synthetic Construct

<400> SEQUENCE: 19
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30
```

-continued

```
Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
        50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
                100                 105                 110

Val Thr Val Ser Ser Gly Gly Gly Gly Ser Gly Gly Gly Gly Ser Gly
                115                 120                 125

Gly Gly Gly Ser Gly Gly Gly Gly Ser Asp Ile Gln Leu Thr Gln Ser
        130                 135                 140

Pro Ser Ser Leu Ser Ala Ser Val Gly Asp Arg Val Thr Ile Thr Cys
145                 150                 155                 160

Lys Ala Ser Gln Ser Val Asp Tyr Glu Gly Asp Ser Phe Leu Asn Trp
                165                 170                 175

Tyr Gln Gln Lys Pro Gly Lys Ala Pro Lys Leu Leu Ile Tyr Ala Ala
                180                 185                 190

Ser Asn Leu Glu Ser Gly Val Pro Ser Arg Phe Ser Gly Ser Gly Ser
                195                 200                 205

Gly Thr Asp Phe Thr Leu Thr Ile Ser Ser Ile Gln Pro Glu Asp Phe
        210                 215                 220

Ala Thr Tyr Tyr Cys Gln Gln Ser Asn Glu Asp Pro Leu Thr Phe Gly
225                 230                 235                 240

Gln Gly Thr Lys Val Glu Ile Lys Arg Thr Thr Thr Pro Ala Pro Arg
                245                 250                 255

Pro Pro Thr Pro Ala Pro Thr Ile Ala Ser Gln Pro Leu Ser Leu Arg
                260                 265                 270

Pro Glu Ala Cys Arg Pro Ala Ala Gly Gly Ala Val His Thr Arg Gly
                275                 280                 285

Leu Asp Phe Ala Cys Asp Ile Tyr Ile Trp Ala Pro Leu Ala Gly Thr
        290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
                340                 345                 350

Glu Glu Glu Gly Gly Cys Glu Leu Arg Val Lys Phe Ser Arg Ser Ala
                355                 360                 365

Asp Ala Pro Ala Tyr Gln Gln Gly Gln Asn Gln Leu Tyr Asn Glu Leu
        370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
                420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
```

```
            450                 455                 460

His Met Gln Ala Leu Pro Pro Arg
465                 470

<210> SEQ ID NO 20
<211> LENGTH: 15
<212> TYPE: PRT
<213> ORGANISM: Artificial Sequence
<220> FEATURE:
<223> OTHER INFORMATION: Synthetic Construct

<400> SEQUENCE: 20

Gly Gly Gly Gly Ser Gly Gly Gly Gly Ser Gly Gly Gly Gly Ser
1               5                   10                  15

<210> SEQ ID NO 21
<211> LENGTH: 12
<212> TYPE: PRT
<213> ORGANISM: Artificial Sequence
<220> FEATURE:
<223> OTHER INFORMATION: Synthetic Construct

<400> SEQUENCE: 21

Gly Gly Gly Ser Gly Gly Gly Ser Gly Gly Gly Ser
1               5                   10

<210> SEQ ID NO 22
<211> LENGTH: 18
<212> TYPE: PRT
<213> ORGANISM: Artificial Sequence
<220> FEATURE:
<223> OTHER INFORMATION: Synthetic Construct

<400> SEQUENCE: 22

Gly Ser Thr Ser Gly Ser Gly Lys Pro Gly Ser Gly Glu Gly Ser Thr
1               5                   10                  15

Lys Gly

<210> SEQ ID NO 23
<211> LENGTH: 18
<212> TYPE: PRT
<213> ORGANISM: Artificial Sequence
<220> FEATURE:
<223> OTHER INFORMATION: Synthetic Construct

<400> SEQUENCE: 23

Gly Gly Ser Ser Arg Ser Ser Ser Ser Gly Gly Gly Gly Ser Gly Gly
1               5                   10                  15

Gly Gly

<210> SEQ ID NO 24
<211> LENGTH: 760
<212> TYPE: PRT
<213> ORGANISM: Artificial Sequence
<220> FEATURE:
<223> OTHER INFORMATION: Synthetic Construct

<400> SEQUENCE: 24

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45
```

-continued

```
Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Ser Gly
    130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
            165                 170                 175

Leu Pro Asp Tyr Gly Val Ser Trp Ile Arg Gln Pro Pro Gly Lys Gly
        180                 185                 190

Leu Glu Trp Ile Gly Val Ile Trp Gly Ser Glu Thr Thr Tyr Tyr Gln
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
            245                 250                 255

Tyr Trp Gly Gln Gly Thr Leu Val Thr Val Ser Ser Gly Gly Gly Gly
        260                 265                 270

Ser Gly Gly Gly Gly Ser Gly Gly Gly Gly Ser Gly Gly Gly Gly Ser
    275                 280                 285

Asp Ile Gln Leu Thr Gln Ser Pro Ser Ser Leu Ser Ala Ser Val Gly
    290                 295                 300

Asp Arg Val Thr Ile Thr Cys Lys Ala Ser Gln Ser Val Asp Tyr Glu
305                 310                 315                 320

Gly Asp Ser Phe Leu Asn Trp Tyr Gln Gln Lys Pro Gly Lys Ala Pro
            325                 330                 335

Lys Leu Leu Ile Tyr Ala Ala Ser Asn Leu Glu Ser Gly Val Pro Ser
        340                 345                 350

Arg Phe Ser Gly Ser Gly Ser Gly Ile Asp Phe Thr Leu Thr Ile Ser
        355                 360                 365

Ser Leu Gln Pro Glu Asp Phe Ala Thr Tyr Tyr Cys Gln Gln Ser Asn
    370                 375                 380

Glu Asp Pro Leu Thr Phe Gly Gln Gly Thr Lys Val Glu Ile Lys Arg
385                 390                 395                 400

Gly Gly Gly Gly Ser Gly Gly Gly Gly Ser Gly Gly Gly Ser Gly
            405                 410                 415

Gly Gly Gly Ser Glu Val Gln Leu Val Glu Ser Gly Gly Gly Leu Val
        420                 425                 430

Gln Pro Gly Gly Ser Leu Arg Leu Ser Cys Ala Ala Ser Gly Tyr Thr
        435                 440                 445

Phe Ser Ser Tyr Trp Ile Glu Trp Val Arg Gln Ala Pro Gly Lys Gly
    450                 455                 460
```

```
Leu Glu Trp Ile Gly Glu Ile Leu Pro Gly Gly Gly Asp Thr Asn Tyr
465             470             475             480

Asn Glu Ile Phe Lys Gly Arg Ala Thr Phe Ser Ala Asp Thr Ser Lys
                485             490             495

Asn Thr Ala Tyr Leu Gln Met Asn Ser Leu Arg Ala Glu Asp Thr Ala
                500             505             510

Val Tyr Tyr Cys Thr Arg Arg Val Pro Ile Arg Leu Asp Tyr Trp Gly
                515             520             525

Gln Gly Thr Leu Val Thr Val Ser Ser Thr Thr Thr Pro Ala Pro Arg
        530             535             540

Pro Pro Thr Pro Ala Pro Thr Ile Ala Ser Gln Pro Leu Ser Leu Arg
545             550             555             560

Pro Glu Ala Cys Arg Pro Ala Ala Gly Gly Ala Val His Thr Arg Gly
                565             570             575

Leu Asp Phe Ala Cys Asp Ile Tyr Ile Trp Ala Pro Leu Ala Gly Thr
                580             585             590

Cys Gly Val Leu Leu Leu Ser Leu Val Ile Thr Leu Tyr Cys Lys Arg
        595             600             605

Gly Arg Lys Lys Leu Leu Tyr Ile Phe Lys Gln Pro Phe Met Arg Pro
        610             615             620

Val Gln Thr Thr Gln Glu Glu Asp Gly Cys Ser Cys Arg Phe Pro Glu
625             630             635             640

Glu Glu Glu Gly Gly Cys Glu Leu Arg Val Lys Phe Ser Arg Ser Ala
                645             650             655

Asp Ala Pro Ala Tyr Gln Gln Gly Gln Asn Gln Leu Tyr Asn Glu Leu
                660             665             670

Asn Leu Gly Arg Arg Glu Glu Tyr Asp Val Leu Asp Lys Arg Arg Gly
        675             680             685

Arg Asp Pro Glu Met Gly Gly Lys Pro Arg Arg Lys Asn Pro Gln Glu
        690             695             700

Gly Leu Tyr Asn Glu Leu Gln Lys Asp Lys Met Ala Glu Ala Tyr Ser
705             710             715             720

Glu Ile Gly Met Lys Gly Glu Arg Arg Arg Gly Lys Gly His Asp Gly
                725             730             735

Leu Tyr Gln Gly Leu Ser Thr Ala Thr Lys Asp Thr Tyr Asp Ala Leu
                740             745             750

His Met Gln Ala Leu Pro Pro Arg
        755             760
```

<210> SEQ ID NO 25
<211> LENGTH: 760
<212> TYPE: PRT
<213> ORGANISM: Artificial Sequence
<220> FEATURE:
<223> OTHER INFORMATION: Synthetic Construct

<400> SEQUENCE: 25

```
Met Ala Leu Pro Val Thr Ala Leu Leu Leu Pro Leu Ala Leu Leu Leu
1               5               10              15

His Ala Ala Arg Pro Asp Ile Gln Leu Thr Gln Ser Pro Ser Ser Leu
                20              25              30

Ser Ala Ser Val Gly Asp Arg Val Thr Ile Thr Cys Lys Ala Ser Gln
        35              40              45

Ser Val Asp Tyr Glu Gly Asp Ser Phe Leu Asn Trp Tyr Gln Gln Lys
        50              55              60
```

-continued

```
Pro Gly Lys Ala Pro Lys Leu Leu Ile Tyr Ala Ala Ser Asn Leu Glu
65                  70                  75                  80

Ser Gly Val Pro Ser Arg Phe Ser Gly Ser Gly Ser Gly Ile Asp Phe
                85                  90                  95

Thr Leu Thr Ile Ser Ser Leu Gln Pro Glu Asp Phe Ala Thr Tyr Tyr
            100                 105                 110

Cys Gln Gln Ser Asn Glu Asp Pro Leu Thr Phe Gly Gln Gly Thr Lys
        115                 120                 125

Val Glu Ile Lys Arg Gly Gly Gly Ser Gly Gly Gly Gly Ser Gly
    130                 135                 140

Gly Gly Gly Ser Gly Gly Gly Ser Glu Val Gln Leu Val Glu Ser
145                 150                 155                 160

Gly Gly Gly Leu Val Gln Pro Gly Gly Ser Leu Arg Leu Ser Cys Ala
                165                 170                 175

Ala Ser Gly Tyr Thr Phe Ser Ser Tyr Trp Ile Glu Trp Val Arg Gln
            180                 185                 190

Ala Pro Gly Lys Gly Leu Glu Trp Ile Gly Glu Ile Leu Pro Gly Gly
        195                 200                 205

Gly Asp Thr Asn Tyr Asn Glu Ile Phe Lys Gly Arg Ala Thr Phe Ser
    210                 215                 220

Ala Asp Thr Ser Lys Asn Thr Ala Tyr Leu Gln Met Asn Ser Leu Arg
225                 230                 235                 240

Ala Glu Asp Thr Ala Val Tyr Tyr Cys Thr Arg Arg Val Pro Ile Arg
                245                 250                 255

Leu Asp Tyr Trp Gly Gln Gly Thr Leu Val Thr Val Ser Ser Gly Gly
            260                 265                 270

Gly Gly Ser Gly Gly Gly Gly Ser Gly Gly Gly Gly Ser Gly Gly Gly
        275                 280                 285

Gly Ser Glu Ile Val Met Thr Gln Ser Pro Ala Thr Leu Ser Leu Ser
    290                 295                 300

Pro Gly Glu Arg Ala Thr Leu Ser Cys Arg Ala Ser Gln Asp Ile Ser
305                 310                 315                 320

Lys Tyr Leu Asn Trp Tyr Gln Gln Lys Pro Gly Gln Ala Pro Arg Leu
                325                 330                 335

Leu Ile Tyr His Thr Ser Arg Leu His Ser Gly Ile Pro Ala Arg Phe
            340                 345                 350

Ser Gly Ser Gly Ser Gly Thr Asp Tyr Thr Leu Thr Ile Ser Ser Leu
        355                 360                 365

Gln Pro Glu Asp Phe Ala Val Tyr Phe Cys Gln Gln Gly Asn Thr Leu
    370                 375                 380

Pro Tyr Thr Phe Gly Gln Gly Thr Lys Leu Glu Ile Lys Gly Gly Gly
385                 390                 395                 400

Gly Ser Gly Gly Gly Gly Ser Gly Gly Gly Gly Ser Gly Gly Gly Gly
                405                 410                 415

Ser Gln Val Gln Leu Gln Glu Ser Gly Pro Gly Leu Val Lys Pro Ser
            420                 425                 430

Glu Thr Leu Ser Leu Thr Cys Thr Val Ser Gly Val Ser Leu Pro Asp
        435                 440                 445

Tyr Gly Val Ser Trp Ile Arg Gln Pro Pro Gly Lys Gly Leu Glu Trp
    450                 455                 460

Ile Gly Val Ile Trp Gly Ser Glu Thr Thr Tyr Tyr Gln Ser Ser Leu
465                 470                 475                 480

Lys Ser Arg Val Thr Ile Ser Lys Asp Asn Ser Lys Asn Gln Val Ser
```

-continued

```
            485                 490                 495
Leu Lys Leu Ser Ser Val Thr Ala Ala Asp Thr Ala Val Tyr Tyr Cys
            500                 505                 510

Ala Lys His Tyr Tyr Tyr Gly Gly Ser Tyr Ala Met Asp Tyr Trp Gly
            515                 520                 525

Gln Gly Thr Leu Val Thr Val Ser Ser Thr Thr Thr Pro Ala Pro Arg
        530                 535                 540

Pro Pro Thr Pro Ala Pro Thr Ile Ala Ser Gln Pro Leu Ser Leu Arg
545                 550                 555                 560

Pro Glu Ala Cys Arg Pro Ala Ala Gly Gly Ala Val His Thr Arg Gly
                565                 570                 575

Leu Asp Phe Ala Cys Asp Ile Tyr Ile Trp Ala Pro Leu Ala Gly Thr
                580                 585                 590

Cys Gly Val Leu Leu Leu Ser Leu Val Ile Thr Leu Tyr Cys Lys Arg
                595                 600                 605

Gly Arg Lys Lys Leu Leu Tyr Ile Phe Lys Gln Pro Phe Met Arg Pro
            610                 615                 620

Val Gln Thr Thr Gln Glu Glu Asp Gly Cys Ser Cys Arg Phe Pro Glu
625                 630                 635                 640

Glu Glu Glu Gly Gly Cys Glu Leu Arg Val Lys Phe Ser Arg Ser Ala
                645                 650                 655

Asp Ala Pro Ala Tyr Gln Gln Gly Gln Asn Gln Leu Tyr Asn Glu Leu
                660                 665                 670

Asn Leu Gly Arg Arg Glu Glu Tyr Asp Val Leu Asp Lys Arg Arg Gly
            675                 680                 685

Arg Asp Pro Glu Met Gly Gly Lys Pro Arg Arg Lys Asn Pro Gln Glu
        690                 695                 700

Gly Leu Tyr Asn Glu Leu Gln Lys Asp Lys Met Ala Glu Ala Tyr Ser
705                 710                 715                 720

Glu Ile Gly Met Lys Gly Glu Arg Arg Arg Gly Lys Gly His Asp Gly
                725                 730                 735

Leu Tyr Gln Gly Leu Ser Thr Ala Thr Lys Asp Thr Tyr Asp Ala Leu
            740                 745                 750

His Met Gln Ala Leu Pro Pro Arg
            755                 760
```

```
<210> SEQ ID NO 26
<211> LENGTH: 760
<212> TYPE: PRT
<213> ORGANISM: Artificial Sequence
<220> FEATURE:
<223> OTHER INFORMATION: Synthetic Construct

<400> SEQUENCE: 26

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
        50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
```

-continued

```
                    85                    90                    95
Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gly
        130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
            165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Gln
            195                 200                 205

Ser Ser Leu Lys Ser Arg Val Thr Ile Ser Lys Asp Asn Ser Lys Asn
        210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
            245                 250                 255

Tyr Trp Gly Gln Gly Thr Leu Val Thr Val Ser Ser Gly Gly Gly Gly
            260                 265                 270

Ser Gly Gly Gly Gly Ser Gly Gly Gly Gly Ser Gly Gly Gly Gly Ser
        275                 280                 285

Asp Ile Gln Leu Thr Gln Ser Pro Ser Ser Leu Ser Ala Ser Val Gly
    290                 295                 300

Asp Arg Val Thr Ile Thr Cys Lys Ala Ser Gln Ser Val Asp Tyr Glu
305                 310                 315                 320

Gly Asp Ser Phe Leu Asn Trp Tyr Gln Gln Lys Pro Gly Lys Ala Pro
            325                 330                 335

Lys Leu Leu Ile Tyr Ala Ala Ser Asn Leu Glu Ser Gly Val Pro Ser
            340                 345                 350

Arg Phe Ser Gly Ser Gly Ser Gly Thr Asp Phe Thr Leu Thr Ile Ser
            355                 360                 365

Ser Ile Gln Pro Glu Asp Phe Ala Thr Tyr Tyr Cys Gln Gln Ser Asn
        370                 375                 380

Glu Asp Pro Leu Thr Phe Gly Gln Gly Thr Lys Val Glu Ile Lys Arg
385                 390                 395                 400

Gly Gly Gly Gly Ser Gly Gly Gly Gly Ser Gly Gly Gly Gly Ser Gly
            405                 410                 415

Gly Gly Gly Ser Glu Val Gln Leu Val Glu Ser Gly Gly Gly Leu Val
            420                 425                 430

Gln Pro Gly Gly Ser Leu Arg Leu Ser Cys Ala Ala Ser Gly Tyr Thr
        435                 440                 445

Phe Ser Ser Tyr Trp Ile Glu Trp Val Arg Gln Ala Pro Gly Lys Gly
    450                 455                 460

Leu Glu Trp Ile Gly Glu Ile Leu Pro Gly Gly Gly Asp Thr Asn Tyr
465                 470                 475                 480

Asn Glu Ile Phe Lys Gly Arg Ala Thr Phe Ser Ala Asp Thr Ser Lys
            485                 490                 495

Asn Thr Ala Tyr Leu Gln Met Asn Ser Leu Arg Ala Glu Asp Thr Ala
            500                 505                 510
```

-continued

```
Val Tyr Tyr Cys Thr Arg Arg Val Pro Ile Arg Leu Asp Tyr Trp Gly
        515                 520                 525

Gln Gly Thr Leu Val Thr Val Ser Ser Thr Thr Thr Pro Ala Pro Arg
    530                 535                 540

Pro Pro Thr Pro Ala Pro Thr Ile Ala Ser Gln Pro Leu Ser Leu Arg
545                 550                 555                 560

Pro Glu Ala Cys Arg Pro Ala Ala Gly Gly Ala Val His Thr Arg Gly
                565                 570                 575

Leu Asp Phe Ala Cys Asp Ile Tyr Ile Trp Ala Pro Leu Ala Gly Thr
                580                 585                 590

Cys Gly Val Leu Leu Leu Ser Leu Val Ile Thr Leu Tyr Cys Lys Arg
                595                 600                 605

Gly Arg Lys Lys Leu Leu Tyr Ile Phe Lys Gln Pro Phe Met Arg Pro
        610                 615                 620

Val Gln Thr Thr Gln Glu Glu Asp Gly Cys Ser Cys Arg Phe Pro Glu
625                 630                 635                 640

Glu Glu Glu Gly Gly Cys Glu Leu Arg Val Lys Phe Ser Arg Ser Ala
                645                 650                 655

Asp Ala Pro Ala Tyr Gln Gln Gly Gln Asn Gln Leu Tyr Asn Glu Leu
                660                 665                 670

Asn Leu Gly Arg Arg Glu Glu Tyr Asp Val Leu Asp Lys Arg Arg Gly
        675                 680                 685

Arg Asp Pro Glu Met Gly Gly Lys Pro Arg Arg Lys Asn Pro Gln Glu
        690                 695                 700

Gly Leu Tyr Asn Glu Leu Gln Lys Asp Lys Met Ala Glu Ala Tyr Ser
705                 710                 715                 720

Glu Ile Gly Met Lys Gly Glu Arg Arg Arg Gly Lys Gly His Asp Gly
                725                 730                 735

Leu Tyr Gln Gly Leu Ser Thr Ala Thr Lys Asp Thr Tyr Asp Ala Leu
            740                 745                 750

His Met Gln Ala Leu Pro Pro Arg
        755                 760
```

<210> SEQ ID NO 27
<211> LENGTH: 760
<212> TYPE: PRT
<213> ORGANISM: Artificial Sequence
<220> FEATURE:
<223> OTHER INFORMATION: Synthetic Construct

<400> SEQUENCE: 27

```
Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Leu
            20                  25                  30

Ser Ala Ser Val Gly Asp Arg Val Thr Ile Thr Cys Lys Ala Ser Gln
        35                  40                  45

Ser Val Asp Tyr Glu Gly Asp Ser Phe Leu Asn Trp Tyr Gln Gln Lys
    50                  55                  60

Pro Gly Lys Ala Pro Lys Leu Leu Ile Tyr Ala Ala Ser Asn Leu Glu
65                  70                  75                  80

Ser Gly Val Pro Ser Arg Phe Ser Gly Ser Gly Ser Gly Thr Asp Phe
                85                  90                  95

Thr Leu Thr Ile Ser Ser Ile Gln Pro Glu Asp Phe Ala Thr Tyr Tyr
            100                 105                 110
```

-continued

```
Cys Gln Gln Ser Asn Glu Asp Pro Leu Thr Phe Gly Gln Gly Thr Lys
        115                 120                 125

Val Glu Ile Lys Arg Gly Gly Gly Ser Gly Gly Gly Gly Ser Gly
    130                 135                 140

Gly Gly Gly Ser Gly Gly Gly Gly Ser Glu Val Gln Leu Val Glu Ser
145                 150                 155                 160

Gly Gly Gly Leu Val Gln Pro Gly Gly Ser Leu Arg Leu Ser Cys Ala
                165                 170                 175

Ala Ser Gly Tyr Thr Phe Ser Ser Tyr Trp Ile Glu Trp Val Arg Gln
                180                 185                 190

Ala Pro Gly Lys Gly Leu Glu Trp Ile Gly Glu Ile Leu Pro Gly Gly
                195                 200                 205

Gly Asp Thr Asn Tyr Asn Glu Ile Phe Lys Gly Arg Ala Thr Phe Ser
        210                 215                 220

Ala Asp Thr Ser Lys Asn Thr Ala Tyr Leu Gln Met Asn Ser Leu Arg
225                 230                 235                 240

Ala Glu Asp Thr Ala Val Tyr Tyr Cys Thr Arg Arg Val Pro Ile Arg
                245                 250                 255

Leu Asp Tyr Trp Gly Gln Gly Thr Leu Val Thr Val Ser Ser Gly Gly
                260                 265                 270

Gly Gly Ser Gly Gly Gly Gly Ser Gly Gly Gly Gly Ser Gly Gly Gly
        275                 280                 285

Gly Ser Glu Ile Val Met Thr Gln Ser Pro Ala Thr Leu Ser Leu Ser
        290                 295                 300

Pro Gly Glu Arg Ala Thr Leu Ser Cys Arg Ala Ser Gln Asp Ile Ser
305                 310                 315                 320

Lys Tyr Leu Asn Trp Tyr Gln Gln Lys Pro Gly Gln Ala Pro Arg Leu
                325                 330                 335

Leu Ile Tyr His Thr Ser Arg Leu His Ser Gly Ile Pro Ala Arg Phe
                340                 345                 350

Ser Gly Ser Gly Ser Gly Thr Asp Tyr Thr Leu Thr Ile Ser Ser Leu
        355                 360                 365

Gln Pro Glu Asp Phe Ala Val Tyr Phe Cys Gln Gln Gly Asn Thr Leu
        370                 375                 380

Pro Tyr Thr Phe Gly Gln Gly Thr Lys Leu Glu Ile Lys Gly Gly Gly
385                 390                 395                 400

Gly Ser Gly Gly Gly Gly Ser Gly Gly Gly Gly Ser Gly Gly Gly Gly
                405                 410                 415

Ser Gln Val Gln Leu Gln Glu Ser Gly Pro Gly Leu Val Lys Pro Ser
        420                 425                 430

Glu Thr Leu Ser Leu Thr Cys Thr Val Ser Gly Val Ser Leu Pro Asp
        435                 440                 445

Tyr Gly Val Ser Trp Ile Arg Gln Pro Pro Gly Lys Gly Leu Glu Trp
    450                 455                 460

Ile Gly Val Ile Trp Gly Ser Glu Thr Thr Tyr Tyr Gln Ser Ser Leu
465                 470                 475                 480

Lys Ser Arg Val Thr Ile Ser Lys Asp Asn Ser Lys Asn Gln Val Ser
                485                 490                 495

Leu Lys Leu Ser Ser Val Thr Ala Ala Asp Thr Ala Val Tyr Tyr Cys
        500                 505                 510

Ala Lys His Tyr Tyr Tyr Gly Gly Ser Tyr Ala Met Asp Tyr Trp Gly
        515                 520                 525
```

```
Gln Gly Thr Leu Val Thr Val Ser Ser Thr Thr Thr Pro Ala Pro Arg
    530             535             540

Pro Pro Thr Pro Ala Pro Thr Ile Ala Ser Gln Pro Leu Ser Leu Arg
545             550             555             560

Pro Glu Ala Cys Arg Pro Ala Ala Gly Gly Ala Val His Thr Arg Gly
            565             570             575

Leu Asp Phe Ala Cys Asp Ile Tyr Ile Trp Ala Pro Leu Ala Gly Thr
            580             585             590

Cys Gly Val Leu Leu Leu Ser Leu Val Ile Thr Leu Tyr Cys Lys Arg
            595             600             605

Gly Arg Lys Lys Leu Leu Tyr Ile Phe Lys Gln Pro Phe Met Arg Pro
    610             615             620

Val Gln Thr Thr Gln Glu Glu Asp Gly Cys Ser Cys Arg Phe Pro Glu
625             630             635             640

Glu Glu Glu Gly Gly Cys Glu Leu Arg Val Lys Phe Ser Arg Ser Ala
            645             650             655

Asp Ala Pro Ala Tyr Gln Gln Gly Gln Asn Gln Leu Tyr Asn Glu Leu
            660             665             670

Asn Leu Gly Arg Arg Glu Glu Tyr Asp Val Leu Asp Lys Arg Arg Gly
            675             680             685

Arg Asp Pro Glu Met Gly Gly Lys Pro Arg Arg Lys Asn Pro Gln Glu
    690             695             700

Gly Leu Tyr Asn Glu Leu Gln Lys Asp Lys Met Ala Glu Ala Tyr Ser
705             710             715             720

Glu Ile Gly Met Lys Gly Glu Arg Arg Arg Gly Lys Gly His Asp Gly
            725             730             735

Leu Tyr Gln Gly Leu Ser Thr Ala Thr Lys Asp Thr Tyr Asp Ala Leu
            740             745             750

His Met Gln Ala Leu Pro Pro Arg
    755             760
```

<210> SEQ ID NO 28
<211> LENGTH: 493
<212> TYPE: PRT
<213> ORGANISM: Artificial Sequence
<220> FEATURE:
<223> OTHER INFORMATION: Synthetic Construct

<400> SEQUENCE: 28

```
Met Ala Leu Pro Val Thr Ala Leu Leu Leu Pro Leu Ala Leu Leu Leu
1               5               10              15

His Ala Ala Arg Pro Asp Ile Gln Leu Thr Gln Ser Pro Ser Ser Leu
            20              25              30

Ser Ala Ser Val Gly Asp Arg Val Thr Ile Thr Cys Lys Ala Ser Gln
            35              40              45

Ser Val Asp Tyr Glu Gly Asp Ser Phe Leu Asn Trp Tyr Gln Gln Lys
    50              55              60

Pro Gly Lys Ala Pro Lys Leu Leu Ile Tyr Ala Ala Ser Asn Leu Glu
65              70              75              80

Ser Gly Val Pro Ser Arg Phe Ser Gly Ser Gly Ser Gly Thr Asp Phe
            85              90              95

Thr Leu Thr Ile Ser Ser Ile Gln Pro Glu Asp Phe Ala Thr Tyr Tyr
            100             105             110

Cys Gln Gln Ser Asn Glu Asp Pro Leu Thr Phe Gly Gln Gly Thr Lys
            115             120             125
```

-continued

```
Val Glu Ile Lys Arg Gly Gly Gly Ser Gly Gly Gly Ser Gly
    130             135             140

Gly Gly Gly Ser Gly Gly Gly Gly Ser Glu Val Gln Leu Val Glu Ser
145             150             155             160

Gly Gly Gly Leu Val Gln Pro Gly Gly Ser Leu Arg Leu Ser Cys Ala
                165             170             175

Ala Ser Gly Tyr Thr Phe Ser Ser Tyr Trp Ile Glu Trp Val Arg Gln
            180             185             190

Ala Pro Gly Lys Gly Leu Glu Trp Ile Gly Glu Ile Leu Pro Gly Gly
            195             200             205

Gly Asp Thr Asn Tyr Asn Glu Ile Phe Lys Gly Arg Ala Thr Phe Ser
    210             215             220

Ala Asp Thr Ser Lys Asn Thr Ala Tyr Leu Gln Met Asn Ser Leu Arg
225             230             235             240

Ala Glu Asp Thr Ala Val Tyr Tyr Cys Thr Arg Arg Val Pro Ile Arg
                245             250             255

Leu Asp Tyr Trp Gly Gln Gly Thr Leu Val Thr Val Ser Ser Thr Thr
            260             265             270

Thr Pro Ala Pro Arg Pro Pro Thr Pro Ala Pro Thr Ile Ala Ser Gln
            275             280             285

Pro Leu Ser Leu Arg Pro Glu Ala Cys Arg Pro Ala Ala Gly Gly Ala
    290             295             300

Val His Thr Arg Gly Leu Asp Phe Ala Cys Asp Ile Tyr Ile Trp Ala
305             310             315             320

Pro Leu Ala Gly Thr Cys Gly Val Leu Leu Leu Ser Leu Val Ile Thr
                325             330             335

Leu Tyr Cys Lys Arg Gly Arg Lys Lys Leu Leu Tyr Ile Phe Lys Gln
            340             345             350

Pro Phe Met Arg Pro Val Gln Thr Thr Gln Glu Glu Asp Gly Cys Ser
            355             360             365

Cys Arg Phe Pro Glu Glu Glu Glu Gly Gly Cys Glu Leu Arg Val Lys
    370             375             380

Phe Ser Arg Ser Ala Asp Ala Pro Ala Tyr Gln Gln Gly Gln Asn Gln
385             390             395             400

Leu Tyr Asn Glu Leu Asn Leu Gly Arg Arg Glu Glu Tyr Asp Val Leu
            405             410             415

Asp Lys Arg Arg Gly Arg Asp Pro Glu Met Gly Gly Lys Pro Arg Arg
            420             425             430

Lys Asn Pro Gln Glu Gly Leu Tyr Asn Glu Leu Gln Lys Asp Lys Met
            435             440             445

Ala Glu Ala Tyr Ser Glu Ile Gly Met Lys Gly Glu Arg Arg Arg Gly
    450             455             460

Lys Gly His Asp Gly Leu Tyr Gln Gly Leu Ser Thr Ala Thr Lys Asp
465             470             475             480

Thr Tyr Asp Ala Leu His Met Gln Ala Leu Pro Pro Arg
            485             490
```

<210> SEQ ID NO 29
<211> LENGTH: 493
<212> TYPE: PRT
<213> ORGANISM: Artificial Sequence
<220> FEATURE:
<223> OTHER INFORMATION: Synthetic Construct

<400> SEQUENCE: 29

-continued

```
Met Ala Leu Pro Val Thr Ala Leu Leu Leu Pro Leu Ala Leu Leu Leu
1                5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Gly Tyr
        35                  40                  45

Thr Phe Ser Ser Tyr Trp Ile Glu Trp Val Arg Gln Ala Pro Gly Lys
    50                  55                  60

Gly Leu Glu Trp Ile Gly Glu Ile Leu Pro Gly Gly Gly Asp Thr Asn
65                  70                  75                  80

Tyr Asn Glu Ile Phe Lys Gly Arg Ala Thr Phe Ser Ala Asp Thr Ser
                85                  90                  95

Lys Asn Thr Ala Tyr Leu Gln Met Asn Ser Leu Arg Ala Glu Asp Thr
            100                 105                 110

Ala Val Tyr Tyr Cys Thr Arg Arg Val Pro Ile Arg Leu Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Gly Gly Gly Gly Ser Asp Ile
145                 150                 155                 160

Gln Leu Thr Gln Ser Pro Ser Ser Leu Ser Ala Ser Val Gly Asp Arg
                165                 170                 175

Val Thr Ile Thr Cys Lys Ala Ser Gln Ser Val Asp Tyr Glu Gly Asp
            180                 185                 190

Ser Phe Leu Asn Trp Tyr Gln Gln Lys Pro Gly Lys Ala Pro Lys Leu
        195                 200                 205

Leu Ile Tyr Ala Ala Ser Asn Leu Glu Ser Gly Val Pro Ser Arg Phe
    210                 215                 220

Ser Gly Ser Gly Ser Gly Thr Asp Phe Thr Leu Thr Ile Ser Ser Ile
225                 230                 235                 240

Gln Pro Glu Asp Phe Ala Thr Tyr Tyr Cys Gln Gln Ser Asn Glu Asp
                245                 250                 255

Pro Leu Thr Phe Gly Gln Gly Thr Lys Val Glu Ile Lys Arg Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
```

-continued

```
              420               425                430

Lys Asn Pro Gln Glu Gly Leu Tyr Asn Glu Leu Gln Lys Asp Lys Met
        435               440               445

Ala Glu Ala Tyr Ser Glu Ile Gly Met Lys Gly Glu Arg Arg Arg Gly
    450               455               460

Lys Gly His Asp Gly Leu Tyr Gln Gly Leu Ser Thr Ala Thr Lys Asp
465               470               475               480

Thr Tyr Asp Ala Leu His Met Gln Ala Leu Pro Pro Arg
                485               490

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
agggagataa cgctgtgctg                                            20

<210> SEQ ID NO 31
<211> LENGTH: 20
<212> TYPE: DNA
<213> ORGANISM: Artificial Sequence
<220> FEATURE:
<223> OTHER INFORMATION: Synthetic Construct

<400> SEQUENCE: 31
agaagggttt aagcggggac                                            20

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct

<400> SEQUENCE: 32
gtactgtccc cacgatcgga                                            20

<210> SEQ ID NO 33
<211> LENGTH: 20
<212> TYPE: DNA
<213> ORGANISM: Artificial Sequence
<220> FEATURE:
<223> OTHER INFORMATION: Synthetic Construct

<400> SEQUENCE: 33
tgcatccctt gggccaaatc                                            20
```